(12) United States Patent
Guo et al.

(10) Patent No.: US 7,087,614 B2
(45) Date of Patent: Aug. 8, 2006

(54) PYRIMIDINE INHIBITORS OF PHOSPHODIESTERASE (PDE) 7

(75) Inventors: Junqing Guo, Princeton, NJ (US); Joseph Barbosa, Lambertville, NJ (US); William John Pitts, Newtown, PA (US); Marianne Carlsen, Yardley, PA (US); Claude Quesnelle, Brossard (CA); Marco Dodier, Ste-Catherine (CA)

(73) Assignee: Bristol-Myers Squibb Co., Princeton, NJ (US)

( * ) Notice: Subject to any disclaimer, the term of this patent is extended or adjusted under 35 U.S.C. 154(b) by 354 days.

(21) Appl. No.: 10/173,442

(22) Filed: Jun. 17, 2002

(65) Prior Publication Data

US 2003/0162802 A1 Aug. 28, 2003

Related U.S. Application Data

(60) Provisional application No. 60/368,752, filed on Mar. 29, 2002, provisional application No. 60/355,141, filed on Feb. 8, 2002, provisional application No. 60/299,287, filed on Jun. 19, 2001.

(51) Int. Cl.
*A61K 31/513* (2006.01)
*A61K 31/506* (2006.01)
*A61K 31/505* (2006.01)
*C07D 43/02* (2006.01)
*C07D 277/42* (2006.01)

(52) U.S. Cl. .............. 514/269; 514/275; 514/252.14; 544/295; 544/320; 544/323; 544/324

(58) Field of Classification Search ............ 514/342, 514/340, 269, 275, 252.14; 544/333, 335, 544/295, 320, 323, 324
See application file for complete search history.

(56) References Cited

U.S. PATENT DOCUMENTS

| | | | |
|---|---|---|---|
| 4,876,252 A | 10/1989 | Torley et al. | 514/224.8 |
| 5,330,989 A | 7/1994 | Soll et al. | 514/258 |
| 5,530,000 A | 6/1996 | Sanfilippo et al. | 514/252 |
| 5,863,924 A | 1/1999 | Berger et al. | 514/275 |
| 6,593,326 B1 * | 7/2003 | Bradbury et al. | 514/235.8 |
| 6,596,746 B1 * | 7/2003 | Das et al. | 514/370 |

FOREIGN PATENT DOCUMENTS

| | | |
|---|---|---|
| WO | WO 98/18782 | 5/1998 |
| WO | 00-62778 | * 10/2000 |
| WO | WO 00/76980 | 12/2000 |
| WO | WO 01/17995 | 3/2001 |
| WO | WO 01/47897 | 7/2001 |
| WO | WO 01/55148 | 8/2001 |

OTHER PUBLICATIONS

Beyer, H., and Hantschel, H., Chem. Ber., 95, pp. 902-906 (1962).
Nakata A. et al., clin. Exp. Immunol., 2002, vol. 128, pp. 460-466.
Paul, R. et al., J. Med. Chem., 1993, vol. 36, No. 19, pp. 2716-2725.

* cited by examiner

*Primary Examiner*—James O. Wilson
*Assistant Examiner*—Tamthom N. Truong
(74) *Attorney, Agent, or Firm*—Laurelee A. Duncan

(57) ABSTRACT

Pyrimidine phosphodiesterase 7 (PDE 7) inhibitors of the following formula wherein $R^1$, $R^2$, Z, J and L are described herein, and analogs thereof are provided which are useful in treating T-cell mediated diseases.

7 Claims, No Drawings

PYRIMIDINE INHIBITORS OF PHOSPHODIESTERASE (PDE) 7

This application claims priority to U.S. Provisional Application Ser. No. 60/299,287 filed Jun. 19, 2001, U.S. Provisional Application Ser. No. 60/355,141 filed Feb. 8, 2002, and U.S. Provisional Application Ser. No. 60/368,752 filed Mar. 29, 2002. The entirety of each of these applications is incorporated herein by reference.

FIELD OF THE INVENTION

The present invention relates to pyrimidine inhibitors of phosphodiesterase 7 (PDE 7) (including both selective inhibitors of PDE 7, and dual inhibitors of PDE 7 and phosphodiesterase 4), pharmaceutical compositions containing these inhibitors, and the use of these inhibitors in the treatment of leukocyte activation-associated or leukocyte-activation mediated disease and inflammatory diseases either alone or in combination with other therapeutic agents.

BACKGROUND OF THE INVENTION

Phosphodiesterases (PDEs) hydrolyze the second messenger molecules cAMP and cGMP to affect cellular signaling. At least 11 families of PDEs exist, some of which (PDE3,4,7,8) are specific for cAMP, and others (PDE5,6,9) for cGMP. Further family members (PDE1,2,10,11) have dual specificity. A recent publication demonstrated a role for PDE7 in the activation and/or proliferation of T cells (Li, Yee and Beavo, Science 283:848–851, 1999). Resting T lymphocytes express mainly PDE3 and PDE4. However, upon activation, T cells dramatically upregulate PDE7 and appear to rely on this isozyme for regulation of cAMP levels. Removal of the ability to upregulate the production of PDE7 protein by anti-sense oligonucleotides inhibited the proliferation and IL-2 production along with the maintenance of high concentrations of intracellular cAMP in CD3×CD28 stimulated T cells.

A PDE7 inhibitor is defined herein as a compound for which the $IC_{50}$ of the compound in a PDE7 inhibition assay is less than 20 micromolar (preferably less than 10 micromolar, more preferably less than 5 micromolar, most preferably less than 1 micromolar). The PDE7 $IC_{50}$ of a selective PDE7 inhibitor should be less than one-tenth the IC50 of said compound in all of the following PDE assays: PDE1, PDE3 and PDE4 (more preferably the PDE7 $IC_{50}$ of a selective PDE7 inhibitor should be less than one-twentieth the $IC_{50}$ of said compound in the following PDE assays: PDE1 and PDE3, most preferably the PDE7 $IC_{50}$ of a selective PDE7 inhibitor should be less than one-hundreth the $IC_{50}$ of said compound in a PDE3 assay).

Several isoforms of PDE1 have been identified and are distributed in heart, lung, and kidney tissue, as well as in circulating blood cells and smooth muscle cells. PDE1 inhibitors have demonstrated potent vasodilator activity. Such activity would represent an undesirable side effect in a therapeutic agent with the utilities listed in this patent for a PDE7 inhibitor. The PDE3 family of enzymes are distributed in several tissues including the heart liver, and platelets. PDE3 inhibitors have demonstrated potent cardiac iotropic activity. Such activity would represent an undesirable side effect in a therapeutic agent with the utilities listed in this patent for a PDE7 inhibitor. Several isoforms of PDE4 exist, and these are expressed in a wide variety of tissues including heart, kidney, brain, the gastrointestinal track and circulating blood cells. PDE4 inhibitors have demonstrated clinical utility for COPD, and have also been suggested to have utility for rheumatoid arthritis, and multiple sclerosis, and to possess anti-inflammatory activity. The utility of PDE4 inhibitors has been limited to some extent by their propensity to cause emesis. As such there are circumstances where it would be desirable to develop PDE7 inhibitors, which have a degree of selectivity against PDE. A selective inhibitor of PDE7 is expected to have broad application as an immunosuppressant in T cell-mediated diseases. PDE7 inhibitors will act at a different stage of the T cell signaling process compared to current immunosuppressants by inhibiting a very early stage of the T cell activation cascade. A selective inhibitor of PDE7 is also expected to have a decreased potential for clinically significant side effects compared to current immunosuppressants, therefore the primary disease indications are solid organ transplantation (SOT) and rheumatoid arthritis. Additional indications may include IBD, psoriasis, asthma and lupus.

A dual PDE7-PDE4 inhibitor (PDE4/7 or PDE7/4) is defined herein as any compound which has an IC50 in both a PDE7 and a PDE4 inhibition assay of less than 20 micromolar (preferably less than 10 micromolar, and more preferably less than 5 micromolar and most preferably less than 1 micromolar), and an IC50 in a PDE3 inhibition assay which is at least 10 times higher than the IC50 of the compound in the PDE7 assay (more preferably at least 20 times higher than the IC50 of the compound in the PDE7 assay, and most preferably at least 100 times higher than the IC50 of the compound in the PDE7 assay). A dual PDE4/7 inhibitor should have a ratio of inhibition or PDE7 IC50 divided by PDE4 IC50 of between one-tenth and 100. Inhibitors that exhibit such a ratio of inhibition include those that inhibit PDE3, PDE4 and PDE7 as described above, and further inhibit PDE1 at an IC50 at least 10 times higher than the IC50 of the compound in a PDE7 assay (more preferably at least 20 times higher than the IC50 of the compound in the PDE7 assay, and most preferably at least 100 times higher than the IC50 of the compound in the PDE7 assay). Preferred dual PDE7-PDE4 inhibitors further include those compounds that inhibit PDE3, PDE4 and PDE7 as described above, and further suppress both T cell proliferation, and TNF-alpha secretion from either THP-1 monocytes or human peripheral blood mononuclear cells at a level of less than 20 micromolar.

"Leukocyte activation" is defined herein as any or all of leukocyte (T cell, monocyte macrophage, neutrophil etc.) cell proliferation, cytokine production, adhesion protein expression, and production of inflammatory mediators. This is mediated in part by the action of PDE4 and/or PDE7 depending on the particular leukocyte under consideration.

Examples of leukocyte activation associated or leukocyte activation mediated disorders include transplant rejection, graph verses host disease, and autoimmune disorders, such as rheumatoid arthritis, multiple sclerosis, juvenile diabetes, COPD, asthma, and inflammatory bowel disease, T-cell mediated hypersensitivity diseases, ischemic or reperfusion injury, and T-cell proliferative disorders.

Dual PDE4/7 inhibitors would be expected to block the T cell component of a disease as well as possess anti-inflammatory activity. Thus a dual PDE4/7 inhibitor which is not significantly limited by emesis, may be more effective than either a selective PDE4 inhibitor or a selective PDE7 inhibitor in a variety of disease states such as rheumatoid arthritis, asthma, COPD and multiple sclerosis.

Development of either selective PDE7 inhibitors, or dual PDE7-PDE4 inhibitors will yield novel classes of therapeutics and have a novel mechanism of action by maintaining high levels of intracellular cAMP. These inhibitors would target a major unmet medical need in an area where current therapies possess significant toxicity.

Two PDE7 genes have been identified. PDE7A (EC 3.1.4.17) has two isoforms generated by alternate splicing; PDE7A1 restricted mainly to T cells and the brain, and PDE7A2 for which mRNA is expressed in a number of cell types including muscle cells. The isoforms have different sequence at the amino termini, and it is thought that this portion of each molecule is likely to be important for cellular localization of the enzyme. However, the catalytic domain of each PDE7A enzyme is identical (Han, P., Zhu, X. and Michaeli, T. *Alternative splicing of the high affinity cAMP-specific phosphodiesterase (PDE7A) mRNA in human skeletal muscle and heart. J. Biol. Chem.* 272 (26), 16152–16157 (1997)). Although abundant PDE7A2 mRNA has been identified, the presence of active enzyme in tissues is controversial, as no convincing data shows PDE7A2 protein in situ in the adult. PDE7B (EC 3.1.4.17), a second PDE7 gene family member, has approximately 70% homology to PDE7A in the enzymatic core (Sasaki, T., Kotera, J., Yuasa, K. and Omori, K. *Identification of human PDE7B, a cAMP-specific phosphodiesterase Biochem. Biophys. Res. Commun.* 271 (3), 575–583 (2000)). Two patents from Cold Spring Harbor Labs (U.S. Pat. No. 5,527,896 and U.S. Pat. No. 5,977,305) cover the methods of preparation and use of recombinant PDE7A protein. A recent publication describes moderately active PDE7 inhibitors (J. Med Chem. Vol. 43, 683 (2000)). WO 00/68230 discloses certain 1,9 dihydro-purin-6-ones derivatives as PDE7 inhibitors.

SUMMARY OF THE INVENTION

The present invention provides pyrimidine compounds of the following formula (I), their enantiomers, diastereomers, tautomers and pharmaceutically acceptable salts, prodrugs and solvates thereof, for use as PDE7 inhibitors and dual PDE4/7 inhibitors:

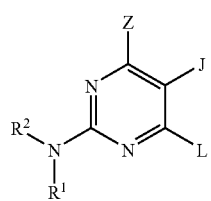
(I)

wherein
$R^1$ is H or alkyl;
$R^2$ is
(a) heteroaryl, or heterocyclo, either of which may be optionally substituted with one to three groups $T^1$, $T^2$, $T^3$;
(b) aryl substituted with one to three groups $T^1$, $T^2$, $T^3$ provided that at least one of $T^1$, $T^2$, $T^3$ is other than H; or
(c) aryl fused to a heteroaryl or heterocyclo ring wherein the combined ring system may be optionally substituted with one to three groups $T^1$, $T^2$, $T^3$;

Z is
(a) —$OR^4$, —$C(O)R^4$, —$C(O)OR^4$, —$SR^4$, —$NR^3R^4$, —$C(O)NR^3R^4$, —$NR^3SO_2R^{4c}$ halogen, nitro, haloalkyl; or (b) alkyl, aryl, heteroaryl, heterocyclo, or cycloalkyl any of which may be optionally substituted with one to three groups $T^{1a}$, $T^{2a}$ $T^{3a}$;

J is
(a) hydrogen, halo, —$OR^{4a}$, or
(b) alkyl, alkenyl, or alkynyl any of which may be optionally substituted with one to three groups $T^{1b}$, $T^{2b}$ or $T^{3b}$;

L is
(a) hydrogen, —$OR^{4b}$, —$C(O)R^{4b}$, —$C(O)OR^{4b}$, —$SR^{4b}$, —$NR^5R^6$, —$C(O)NR^5R^6$, —$NR^5SO_2R^{4d}$, halogen, haloalkyl, nitro, or
(b) alkyl, aryl, heteroaryl, heterocyclo, or cycloalkyl any of which may be optionally substituted with one to three groups $T^{1c}$, $T^{2c}$ or $T^{3c}$;

$R^3$ and $R^4$ are independently H, alkyl, alkenyl, aryl, (aryl)alkyl, heteroaryl, (heteroaryl)alkyl, cycloalkyl, (cycloalkyl)alkyl, heterocylo or (heterocyclo)alkyl any of which may be optionally substituted with one to three groups $T^{1a}$, $T^{2a}$ or $T^{3a}$;

or $R^3$ and $R^4$ together with the nitrogen atom to which they are attached may combine to form a 4 to 8 membered heterocyclo ring optionally substituted with one to three groups $T^{1a}$, $T^{2a}$ or $T^{3a}$;

$R^{4a}$ is hydrogen, alkyl, alkenyl, aryl, heteroaryl, (aryl)alkyl, (heteroaryl)alkyl, heterocylo, (heterocyclo)alkyl, cycloalkyl or (cycloalkyl)alkyl any of which may be optionally substituted with one to three groups $T^{1b}$, $T^{2b}$ or $T^{3b}$;

$R^{4b}$ is hydrogen, alkyl, alkenyl, aryl, heteroaryl, (aryl)alkyl, (heteroaryl)alkyl, heterocylo, (heterocyclo)alkyl, cycloalkyl or (cycloalkyl)alkyl any of which may be optionally substituted with one to three groups $T^{1c}$, $T^{2c}$ or $T^{3c}$;

$R^{4c}$ and $R^{4d}$ are independently alkyl, alkenyl, aryl, (aryl)alkyl, heteroaryl, (heteroaryl)alkyl, cycloalkyl, (cycloalkyl)alkyl, heterocylo or (heterocyclo)alkyl any of which may be optionally substituted with one to three groups $T^{1a}$, $T^{2a}$ or $T^{3a}$;

$R^5$ and $R^6$ are independently H, alkyl, alkenyl, aryl, (aryl)alkyl, heteroaryl, (heteroaryl)alkyl, cycloalkyl, (cycloalkyl)alkyl, heterocylo or (heterocyclo)alkyl any of which may be optionally independently substituted where valance allows with one to three groups $T^{1c}$, $T^{2c}$ or $T^{3c}$;

or $R^5$ and $R^6$ together with the nitrogen atom to which they are attached may combine to form a 4 to 8-membered heterocyclo ring optionally substituted with one to three groups $T^{1c}$, $T^{2c}$ or $T^{3c}$;

$T^{1-1c}$, $T^{2-2c}$, and $T^{3-3c}$ are are each independently
(1) hydrogen or $T^6$, where $T^6$ is
  (i) alkyl, (hydroxy)alkyl, (alkoxy)alkyl, alkenyl, alkynyl, cycloalkyl, (cycloalkyl)alkyl, cycloalkenyl, (cycloalkenyl)alkyl, aryl, (aryl)alkyl, heterocyclo, (heterocylco)alkyl, heteroaryl, or (heteroaryl)alkyl;
  (ii) (ii) a group (i) which is itself substituted by one or more of the same or different groups (i); or
  (iii) (iii) a group (i) or (ii) which is independently substituted by one or more (preferably 1 to 3) of the following groups (2) to (13) of the definition of $T^{1-1c}$, $T^{2-2c}$ and $T^{3-3c}$,
(2) —OH or —$OT^6$,
(3) —SH or —$ST^6$,
(4) —$C(O)_tH$, —$C(O)_tT^6$, or —O—$C(O)T^6$, where t is 1 or 2;
(5) —$SO_3H$, —$S(O)_tT^6$, or $S(O)_tN(T^9)T^6$,
(6) halo,
(7) cyano, (8) nitro,
(9) -$T^4$-$NT^7T^8$,
(10) -$T^4$-$N(T^9)$-$T^5$-$NT^7T^8$,
(11) -$T^4$-$N(T^{10})$-$T^5$-$T^6$,
(12) -$T^4$-$N(T^{10})$-$T^5$-H,
(13) oxo, $T^4$ and $T^5$ are each independently
  (1) a single bond,
  (2) -$T^{11}$-S(O)$_t$-$T^{12}$-,
  (3) -$T^{11}$-C(O)-$T^{12}$-,
  (4) -$T^{11}$-C(S)-$T^{12}$-,
  (5) -$T^{11}$-O-$T^{12}$-,
  (6) -$T^{11}$-S-$T^{12}$-,
  (7) -$T^{11}$-O—C(O)-$T^{12}$-,
  (8) -$T^{11}$-C(O)—O-$T^{12}$-,
  (9) -$T^{11}$-C(=$NT^{9a}$)-$T^{12}$-, or
  (10) -$T^{11}$-C(O)—C(O)-$T^{12}$—

$T^7$, $T^8$, $T^9$, $T^{9a}$ and $T^{10}$
  (1) are each independently hydrogen or a group provided in the definition of $T^6$, or
  (2) $T^7$ and $T^8$ may together be alkylene or alkenylene, completing a 3- to 8-membered saturated or unsaturated ring together with the atoms to which they are attached, which ring is unsubstituted or substituted with one or more groups listed in the description of $T^{1-1c}$, $T^{2-2c}$ and $T^{3-3c}$, or
  (3) $T^7$ or $T^8$, together with $T^9$, may be alkylene or alkenylene completing a 3- to 8-membered saturated or unsaturated ring together with the nitrogen atoms to which they are attached, which ring is unsubstituted or substituted with one or more groups listed in the description of $T^{1-1c}$, $T^{2-2c}$ and $T^{3-3c}$, or
  (4) $T^7$ and $T^8$ or $T^9$ and $T^{10}$ together with the nitrogen atom to which they are attached may combine to form a group —N=$CT^{13}T^{14}$ where $T^{13}$ and $T^{14}$ are each independently H or a group provided in the definition of $T^6$; and $T^{11}$ and $T^{12}$ are each independently
  (1) a single bond,
  (2) alkylene,
  (3) alkenylene, or
  (4) alkynylene.

Preferred compounds of Formula I include those wherein:

Z is
  (a) halogen, alkoxy, haloalkyl, —$NR^3R^4$, —C(O)$OR^4$, —C(O)$NR^3R^4$;
  (b) aryl or heteroaryl either of which may be optionally substituted with one or more $T^{1a}$, $T^{2a}$, $T^{3a}$ (especially cyano, optionally substituted alkyl, (hydroxy)alkyl, —OH, —$OT^6$, —$ST^6$, —SO$_t$$T^6$, —CO$_t$H, —CO$_t$$T^6$, -$T^4NT^7T^8$, or -$T^4N(T^{10})$-$T^5$-$T^6$);
  (c) optionally substituted alkyl (especially substituted with one or more —OH, —CO$_t$H, —CO$_t$$T^6$, -$T^4$-$NT^7T^8$, -$T^4$-$N(T^{10})$-$T^5$-H, or; -$T^4$-$N(T^{10})$-$T^5$-$T^6$);

J is
  (a) H, or
  (b) alkyl or alkenyl either of which may be optionally substituted (especially with one or more —OH, —$OT^6$, —CO$_t$H, or —CO$_t$$T^6$);

L is
  (a) H;
  (b) halogen, alkoxy, haloalkyl, —$NR^5R^6$, —C(O)$OR^{4b}$, —C(O)$NR^5R^6$;
  (c) aryl or heteroaryl either of which may be optionally substituted with one or more $T^{1c}$, $T^{2c}$, $T^{3c}$ (especially cyano, optionally substituted alkyl, (hydroxy)alkyl, —OH, —$OT^6$, —$ST^6$, —SO$_t$$T^6$, —CO$_t$H, —CO$_t$$T^6$, -$T^4NT^7T^8$, or -$T^4N(T^{10})$-$T^5$-$T^6$); or
  (d) optionally substituted alkyl (especially substituted with one or more —OH, —CO$_t$H, —CO$_t$$T^6$, -$T^4$-$NT^7T^8$, -$T^4$-$N(T^{10})$-$T^5$—H, or; -$T^4$-$N(T^{10})$-$T^5$-$T^6$);

$R^1$ is H or alkyl;

$R^2$ is
  (a) heteroaryl (more preferably thiazolyl or oxazolyl) optionally substituted with one to three groups $T^1$, $T^2$, $T^3$, preferably including H, alkyl, haloalkyl, halo, heteroaryl, cyano, C(O)$_t$$T^6$, $OT^6$, -$T^4NT^7T^8$;
  (b) aryl substituted with one to three groups $T^1$, $T^2$, $T^3$ (preferably including heteroaryl (preferably, imidazolyl, oxazolyl, or thiazolyl any of which may be further optionally substituted), cyano, C(O)$_t$$T^6$, S(O)$_t$N($T^9$)$T^6$, halo alkyl, and haloalkyl); or
  (c) aryl fused to a heterocyclo ring (e.g., 2,3-dihydro-1H-indole bound through the aryl ring, quinolyl bound through the aryl ring (especially quinol-6-yl), quinazolinyl bound through the aryl ring (especially quinazolin-7-yl), cinnolinyl bound through the aryl ring (especially cinnolin-6-yl), isoqinolinyl bound through the aryl ring (especially isoquinol-6-yl), and phthalazinyl bound through the aryl ring (especially phthalazin-6-yl)) wherein the combined ring system may be optionally substituted with one to three groups $T^1$, $T^2$, $T^3$ (especially halo, OH, $OT^6$, alkyl, —CO$_t$H, —CO$_t$$T^6$, or —C(O)$NT^7T^8$);

$R^3$ is H or optionally substituted alkyl (especially substituted with one or more —OH, or —$OT^6$);

$R^4$ is
  (a) hydrogen;
  (b) (aryl)alkyl where the aryl group is optionally independently substituted with one or more groups $T^{1a}$, $T^{2a}$, $T^{3a}$ (especially optionally substituted alkyl, halo, cyano, nitro, (hydroxy)alkyl, —OH, —$OT^6$, —$ST^6$, —CO$_t$H, —CO$_t$$T^6$, —SO$_3$H, —SO$_t$$T^6$, —SO$_t$N($T^9$)($T^6$), -$T^4NT^7T^8$, -$T^4$-$N(T^{10})$-$T^5$-$T^6$, heterocyclo, or heteroaryl);
  (c) (heteroaryl)alky where the heteroaryl group is optionally independently substituted with one or more groups $T^{1a}$, $T^{2a}$, $T^{3a}$ (especially optionally substituted alkyl, halo, cyano, nitro, (hydroxy)alkyl, —OH, —$OT^6$, —$ST^6$, —CO$_t$H, —CO$_t$$T^6$, —SO$_3$H, —SO$_t$$T^6$, —SO$_t$N($T^9$)($T^6$), -$T^4NT^7T^8$, -$T^4$-$N(T^{10})$-$T^5$-$T^6$, heterocyclo, or heteroaryl);
  (d) (heterocyclo)alkyl where the heterocyclo group is optionally independently substituted with one or more groups $T^{1a}$, $T^{2a}$, $T^{3a}$ (especially optionally substituted alkyl, halo, cyano, nitro, oxo, (hydroxy)alkyl, —OH, —$OT^6$, —$ST^6$, —CO$_t$H, —CO$_t$$T^6$, —SO$_3$H, —SO$_t$$T^6$, —SO$_t$N($T^9$)($T^6$), —$T^4NT^7T^8$, -$T^4$-$N(T^{10})$-$T^5$-$T^6$, heterocyclo, or heteroaryl);
  (e) alkyl optionally independently substituted with one or more groups $T^{1a}$, $T^{2a}$, $T^{3a}$ (especially —OH, —$OT^6$, —CO$_t$H, —CO$_t$$T^6$, -$T^4NT^7T^8$ or -$T^4$-$N(T^{10})$-$T^5$-$T^6$);
  (f) heterocyclo optionally independently substituted with one or more groups $T^{1a}$, $T^{2a}$, $T^{3a}$ (especially optionally substituted alkyl, optionally substituted aryl, optionally substituted heteroaryl, optionally substituted aralkyl, optionaly subsituted heterocyclo, cyano, —OH, —$OT^6$, —CO$_t$H, —CO$_t$$T^6$, oxo, hydroxy(alkyl), (alkoxy)alkyl, -$T^4$-$N(T^{10})$-$T^5$-$T^6$, or -$T^4$-$NT^7T^8$);

or $R^3$ and $R^4$ together with the nitrogen atom to which they are attached combine to form a 4 to 8-membered heterocyclo ring (especially pyrrolidinyl, piperadinyl, piperazinyl, morpholinyl, diazapanyl or 1,4-dioxa-8-azaspiro[4.5]

decan-8-yl) optionally substituted with one to three groups $T^{1a}$, $T^{2a}$, $T^{3a}$ (especially optionally substituted alkyl, optionally substituted aryl, optionally substituted heteroaryl, optionally substituted aralkyl, optionaly subsituted heterocyclo, cyano, —OH, —OT$^6$, —CO$_t$H, —CO$_t$T$^6$, oxo, hydroxy(alkyl), (alkoxy)alkyl, -T$^4$-N(T$^{10}$)-T$^5$-T$^6$, or -T$^4$-NT$^7$T$^8$);

$R^5$ is hydrogen or alkyl;

$R^6$ is
- (a) hydrogen;
- (b) (aryl)alkyl where the aryl group is optionally independently substituted with one or more groups $T^{1c}$, $T^{2c}$, $T^{3c}$ (especially optionally substituted alkyl, halo, cyano, nitro, (hydroxy)alkyl, —OH, —OT$^6$, —ST$^6$, —CO$_t$H, —CO$_t$T$^6$, —SO$_3$H, —SO$_t$T$^6$, —SO$_t$N(T$^9$)(T$^6$), -T$^4$-N(T$^{10}$)-T$^5$-T$^6$, heterocyclo, or heteroaryl);
- (c) (heteroaryl)alky where the heteroaryl group is optionally independently substituted with one or more groups $T^{1c}$, $T^{2c}$, $T^{3c}$ (especially optionally substituted alkyl, halo, cyano, nitro, (hydroxy)alkyl, —OH, —OT$^6$, —ST$^6$, —CO$_t$H, —CO$_t$T$^6$, —SO$_3$H, —SO$_t$T$^6$, —SO$_t$N(T$^9$)(T$^6$), -T$^4$-N(T$^{10}$)-T$^5$-T$^6$, heterocyclo, or heteroaryl);
- (d) (heterocyclo)alkyl where the heterocyclo group is optionally independently substituted with one or more groups $T^{1c}$, $T^{2c}$, $T^{3c}$ (especially optionally substituted alkyl, halo, cyano, nitro, oxo, (hydroxy)alkyl, —OH, —OT$^6$, —ST$^6$, —CO$_t$H, —CO$_t$T$^6$, —SO$_3$H, —SO$_t$T$^6$, —SO$_t$N(T$^9$)(T$^6$), -T$^4$-N(T$^{10}$)-T$^5$-T$^6$, heterocyclo, or heteroaryl);
- (e) alkyl optionally independently substituted with one or more groups $T^{1c}$, $T^{2c}$, $T^{3c}$ (especially —OH, —OT$^6$, —CO$_t$H, —CO$_t$H$^6$, -T$^4$NT$^7$T$^8$ or -T$^4$-N(T$^{10}$)-T$^5$-T$^6$);
- (f) heterocyclo optionally independently substituted with one or more groups $T^{1c}$, $T^{2c}$, $T^{3c}$ (especially optionally substituted alkyl, optionally substituted aryl, optionally substituted heteroaryl, optionally substituted aralkyl, optionaly subsituted heterocyclo, cyano, —OH, —OT$^6$, —CO$_t$H, —CO$_t$T$^6$, oxo, hydroxy(alkyl), (alkoxy)alkyl, -T$^4$-N(T$^{10}$)-T$^5$-T$^6$, or -T$^4$-NT$^7$T$^8$);

or $R^5$ and $R^6$ together with the nitrogen atom to which they are attached combine to form a 4 to 8-membered heterocyclo ring (especially pyrrolidinyl, piperadinyl, piperazinyl, morpholinyl, diazapanyl or 1,4-dioxa-8-azaspiro[4.5]decan-8-yl) optionally substituted with one to three groups $T^{1c}$, $T^{2c}$, $T^{3c}$ (especially optionally substituted alkyl, optionally substituted aryl, optionally substituted heteroaryl, optionally substituted aralkyl, optionaly subsituted heterocyclo, cyano, —OH, —OT$^6$, —CO$_t$H, —CO$_t$T$^6$, oxo, hydroxy(alkyl), (alkoxy)alkyl, -T$^4$-N(T$^{10}$)-T$^5$-T$^6$, or -T$^4$-NT$^7$T$^8$).

More preferred compounds of the present invention include compounds wherein:

Z is
- (a) halogen, alkoxy, haloalkyl, —NR$^3$R$^4$, —C(O)OR$^4$, —C(O)NR$^3$R$^4$;
- (b) aryl or heteroaryl either of which may be optionally substituted with one or more $T^{1a}$, $T^{2a}$, $T^{3a}$ selected from cyano, optionally substituted alkyl, (hydroxy)alkyl, —OH, —OT$^6$, —ST$^6$, —SO$_t$T$^6$, —CO$_t$H, —CO$_t$T$^6$, -T$^4$NT$^7$T$^8$, or -T$^4$N(T$^{10}$)-T$^5$-T$^6$, where $T^4$ is a bond or —C(O)—;

$T^5$ is —C(O)—, or —C(O)O—;

$T^6$ is alkyl or haloalkyl;

$T^7$ and $T^8$ are independently H;
  alkyl optiontionally substituted with cycloalkyl, heteroaryl, hydroxy or —NT$^7$T$^8$;
  cycloalkyl; or
  aryl optionally substituted with halogen;

or $T^7$ and $T^8$ together with the nitrogen atom to which they are attached combine to form a heterocyclo ring optionally substituted with (hydroxy)alkyl, CO$_t$H or CO$_t$T$^6$ $T^{10}$ is hydrogen;

- (c) alkyl optionally substituted with one or more —OH, —CO$_t$H, —CO$_t$T$^6$, -T$^4$-NT$^7$T$^8$, -T$^4$-N(T$^{10}$)-T$^5$-H, or; -T$^4$-N(T$^{10}$)-T$^5$-T$^6$ where $T^4$ is —C(O)—;

$T^5$ is -alkylene-O—;

$T^6$ is alkyl;

$T^7$ and $T^8$ are independently H, alkyl, cycloalkyl, aryl, (aryl)alkyl (optionally substituted as described in the definition of $R^4$), or heterocyclo (optionally substituted as described in the definition of $R^3$ and $R^4$ combining to form a heterocyclo ring); and $T^{10}$ is H;

J is
- (a) H, or
- (b) alkyl or alkenyl either of which may be optionally substituted with one or more —OH, —OT$^6$, —CO$_t$H, or —CO$_t$T$^6$, where $T^6$ is alkyl;

L is
- (a) H;
- (b) halogen, alkoxy, haloalkyl, —NR$^5$R$^6$, —C(O)OR$^{4b}$, —C(O)NR$^5$R$^6$;
- (c) aryl or heteroaryl either of which may be optionally substituted with one or more $T^{1c}$, $T^{2c}$, $T^{3c}$ selected from cyano, optionally substituted alkyl (especially substituted with CO$_t$H or CO$_t$T$^6$), (hydroxy)alkyl, —OH, —OT$^6$, —ST$^6$, —SO$_t$T$^6$, —CO$_t$H, —CO$_t$T$^6$, -T$^4$NT$^7$T$^8$, or -T$^4$N(T$^{10}$)-T$^5$-T$^6$, where $T^4$ is a bond or —C(O)—;

$T^5$ is —C(O)—, or —C(O)O—;

$T^6$ is alkyl or haloalkyl;

$T^7$ and $T^8$ are independently H;
  alkyl optiontionally substituted with cycloalkyl, heteroaryl, hydroxy or —NT$^7$T$^8$;
  cycloalkyl; or
  aryl optionally substituted with halogen;

or $T^7$ and $T^8$ together with the nitrogen atom to which they are attached combine to form a heterocyclo ring optionally substituted with (hydroxy)alkyl, CO$_t$H or CO$_t$T$^6$ $T^{10}$ is hydrogen;

- (d) alkyl optionally substituted with one or more —OH, —CO$_t$H, —CO$_t$T$^6$, -T$^4$-NT$^7$T$^8$, -T$^4$-N(T$^{10}$)-T$^5$-H, or; -T$^4$-N(T$^{10}$)-T$^5$-T$^6$ where $T^4$ is —(O)—;

$T^5$ is -alkylene-O—;

$T^6$ is alkyl;

$T^7$ and $T^8$ are independently H, alkyl, cycloalkyl, aryl, (aryl)alkyl (optionally substituted as described in the definition of $R^4$), or heterocyclo (optionally substituted as described in the definition of $R^3$ and $R^4$ combining to form a heterocyclo ring); and $T^{10}$ is H;

$R^1$ is H or alkyl;

$R^2$ is (a) heteroaryl (more preferably thiazolyl or oxazolyl) optionally substituted with one to three groups $T^1$, $T^2$, $T^3$, preferably including H, alkyl, haloalkyl, halo, heteroaryl, cyano, $C(O)_tT^6$, $OT^6$, $-T^4NT^7T^8$;

(b) aryl substituted with one to three groups $T^1$, $T^2$, $T^3$ (preferably including heteroaryl (preferably, imidazolyl, oxazolyl, or thiazolyl any of which may be further optionally substituted), cyano, $C(O)_tT^6$, $S(O)_tN(T^9)T^6$, halo alkyl, and haloalkyl); or (c) aryl fused to a heterocyclo ring (e.g., 2,3-dihydro-1H-indole bound through the aryl ring) wherein the combined ring system may be optionally substituted with one to three groups $T^1$, $T^2$, $T^3$ (especially halo, OH, $OT^6$, alkyl, $-CO_tH$, $-CO_tT^6$, or $-C(O)NT^7T^8$);

$R^3$ is H or optionally substituted alkyl (especially substituted with one or more $-OH$, or $-OT^6$);

$R^4$ is (a) hydrogen;

(b) (aryl)alkyl where the aryl group is optionally independently substituted with one or more groups $T^{1a}$, $T^{2a}$, $T^{3a}$ selected from optionally substituted alkyl, halo, cyano, nitro, (hydroxy)alkyl, $-OH$, $-OT^6$, $-ST^6$, $-CO_tH$, $-CO_tT^6$, $-SO_3H$, $-SO_tT^6$, $-SO_tN(T^9)(T^6)$, $-T^4NT^7T^8$, $-T^4-N(T^{10})-T^5-T^6$, heterocyclo, or heteroaryl)

where $T^4$ is a bond, $-SO_2-$, or $-C(O)-$;
$T^5$ is $-SO_2-$, or -alkylene-O—;
$T^6$ is alkyl, or cycloalkyl;
$T^7$ and $T^8$ are independently H or alkyl; and
$T^9$ and $T^{10}$ are hydrogen;

(c) (heteroaryl)alky where the heteroaryl group is optionally independently substituted with one or more groups $T^{1a}$, $T^{2a}$, $T^{3a}$ selected from optionally substituted alkyl, halo, cyano, nitro, oxo, (hydroxy)alkyl, $-OH$, $-OT^6$, $-ST^6$, $-CO_tH$, $-CO_tT^6$, $-SO_3H$, $-SO_tT^6$, $-SO_tN(T^9)(T^6)$, $-T^4NT^7T^8$, $-T^4-N(T^{10})-T^5-T^6$, heterocyclo, or heteroaryl)

where $T^4$ is a bond, $-SO_2-$, or $-C(O)-$;
$T^5$ is $-SO_2-$, or -alkylene-O—;
$T^6$ is alkyl, or cycloalkyl;
$T^7$ and $T^8$ are independently H or alkyl; and
$T^9$ and $T^{10}$ are hydrogen;

(d) (heterocyclo)alkyl where the heterocyclo group is optionally independently substituted with one or more groups $T^{1a}$, $T^{2a}$, $T^{3a}$ selected from optionally substituted alkyl, halo, cyano, nitro, (hydroxy)alkyl, $-OH$, $-OT^6$, $-ST^6$, $-CO_tH$, $-CO_tT^6$, $-SO_3H$, $-SO_tT^6$, $-T^4NT^7T^8$, $-T^4-N(T^{10})-T^5-T^6$, heterocyclo, or heteroaryl)

where $T^4$ is a bond, $-SO_2-$, or $-C(O)-$;
$T^5$ is $-SO_2-$, or -alkylene-O—;
$T^6$ is alkyl, or cycloalkyl;
$T^7$ and $T^8$ are independently H or alkyl; and
$T^9$ and $T^{10}$ are hydrogen;

(e) alkyl optionally independently substituted with one or more groups $T^{1a}$, $T^{2a}$, $T^{3a}$ selected from $-OH$, $-OT^6$, $-CO_tH$, $-CO_tT^6$, $-T^4NT^7T^8$ or $-T^4-N(T^{10})-T^5-T^6$)

where $T^4$ is a bond;
$T^5$ is $-CO)-$;
$T^6$ is alkyl;
$T^7$ and $T^8$ are independently H or alkyl; and
$T^{10}$ is hydrogen;

(f) heterocyclo optionally independently substituted with one or more groups $T^{1a}$, $T^{2a}$, $T^{3a}$ selected from optionally substituted alkyl (especially substituted with $-T^4NT^7T^8$), optionally substituted aryl (especially substituted with halogen or haloalkyl), cyano, $-OH$, $-OT^6$, $-CO_tH$, $-CO_tT^6$, oxo, hydroxy(alkyl), (alkoxy)alkyl, $-T^4-N(T^{10})-T^5-T^6$, or $-T^4-NT^7T^8$)

where $T^4$ is a bond or $-C(O)-$;
$T^5$ is $-C(O)-$, $-SO_2-$, or -alkylene-C(O)O—;
$T^6$ is alkyl, alkoxy, or heteroaryl;
$T^7$ and $T^8$ are independently H, alkyl, or cycloalkyl;
or $T^7$ and $T^8$ together with the nitrogen atom to which they are attached combine to form a an optionally substituted heterocyclo ring;

or $R^3$ and $R^4$ together with the nitrogen atom to which they are attached combine to form a heterocylco ring selected from pyrrolidinyl, piperadinyl, piperazinyl, morpholinyl, diazapanyl or 1,4-dioxa-8-azaspiro[4.5]decan-8-yl), any of which are optionally independently substituted with one to three groups $T^{1a}$, $T^{2a}$, $T^{3a}$ selected from optionally substituted alkyl (especially substituted with $-T^4NT^7T^8$), optionally substituted aryl (especially substituted with halogen or haloalkyl), cyano, $-OH$, $-OT^6$, $-CO_tH$, $-CO_tT^6$, oxo, hydroxy(alkyl), (alkoxy)alkyl, $-T^4-N(T^{10})-T^5-T^6$, or $-T^4-NT^7T^8$)

where $T^4$ is a bond or $-C(O)-$;
$T^5$ is $-C(O)-$, $-SO_2-$, or -alkylene-C(O)O—;
$T^6$ is alkyl, alkoxy, or heteroaryl;
$T^7$ and $T^8$ are independently H, alkyl, or cycloalkyl;
or $T^7$ and $T^8$ together with the nitrogen atom to which they are attached combine to form a an optionally substituted heterocyclo ring;

$R^5$ is hydrogen or alkyl;

$R^6$ is (a) hydrogen;

(b) (aryl)alkyl where the aryl group is optionally independently substituted with one or more groups $T^{1c}$, $T^{2c}$, $T^{3c}$ selected from optionally substituted alkyl, halo, cyano, nitro, (hydroxy)alkyl, $-OH$, $-OT^6$, $-ST^6$, $-CO_tH$, $-CO_tT^6$, $-SO_3H$, $-SO_tT^6$, $-SO_tN(T^9)(T^6)$, $-T^4NT^7T^8$, $-T^4-N(T^{10})-T^5T^6$ heterocyclo, or heteroaryl)

where $T^4$ is a bond, $-SO_2-$, or $-C(O)-$;
$T^5$ is $-SO_2-$, or -alkylene-O—;
$T^6$ is alkyl, or cycloalkyl;
$T^7$ and $T^8$ are independently H or alkyl; and
$T^9$ and $T^{10}$ are hydrogen;

(c) (heteroaryl)alky where the heteroaryl group is optionally independently substituted with one or more groups $T^{1c}$, $T^{2c}$, $T^{3c}$ selected from optionally substituted alkyl, halo, cyano, nitro, oxo, (hydroxy)alkyl, $-OH$, $-OT^6$, $-ST^6$, $-CO_tH$, $-CO_tT^6$, $-SO_3H$, $-SO_tT^6$, $-SO_tN(T^9)(T^6)$, $-T^4NT^7T^8$, $-T^4-N(T^{10})-T^5-T^6$, heterocyclo, or heteroaryl)

where $T^4$ is a bond, $-SO_2-$, or $-C(O)-$;
$T^5$ is $-SO_2-$, or -alkylene-O—;
$T^6$ is alkyl, or cycloalkyl;
$T^7$ and $T^8$ are independently H or alkyl; and
$T^9$ and $T^{10}$ are hydrogen;

(d) (heterocyclo)alkyl where the heterocyclo group is optionally independently substituted with one or more groups $T^{1c}$, $T^{2c}$, $T^{3c}$ selected from optionally substituted alkyl, halo, cyano, nitro, (hydroxy)alkyl, $-OH$, —OT⁶, —ST⁶, —CO₂H, —CO₂T⁶, —SO₃H, —SO₂T⁶, -T⁴NT⁷T⁸, -T⁴-N(T¹⁰)-T⁵-T⁶, heterocyclo, or heteroaryl)
where
  T⁴ is a bond, —SO₂—, or —C(O)—;
  T⁵ is —SO₂—, or -alkylene-O—;
  T⁶ is alkyl, or cycloalkyl;
  T⁷ and T⁸ are independently H or alkyl; and
  T⁹ and T¹⁰ are hydrogen;
(e) alkyl optionally independently substituted with one or more groups T¹ᶜ, T²ᶜ, T³ᶜ selected from —OH, —OT⁶, —CO₂H, —CO₂T⁶, -T⁴NT⁷T⁸ or -T⁴-N(T¹⁰)-T⁵-T⁶)
where
  T⁴ is a bond;
  T⁵ is —CO)—;
  T⁶ is alkyl;
  T⁷ and T⁸ are independently H or alkyl; and
  T¹⁰ is hydrogen;
(f) heterocyclo optionally independently substituted with one or more groups T¹ᶜ, T²ᶜ, T³ᶜ selected from optionally substituted alkyl (especially substituted with -T⁴NT⁷T⁸), optionally substituted aryl (especially substituted with halogen or haloalkyl), cyano, —OH, —OT⁶, —CO₂H, —CO₂T⁶, oxo, hydroxy(alkyl), (alkoxy)alkyl, -T⁴-N(T¹⁰)-T⁵-T⁶, or -T⁴-NT⁷T⁸)
where
  T⁴ is a bond or —C(O)—;
  T⁵ is —C(O)—, —SO₂—, or -alkylene-C(O)O—;
  T⁶ is alkyl, alkoxy, or heteroaryl;
  T⁷ and T⁸ are independently H, alkyl, or cycloalkyl;
  or T⁷ and T⁸ together with the nitrogen atom to which they are attached combine to form a an optionally substituted heterocyclo ring;
or R⁵ and R⁶ together with the nitrogen atom to which they are attached combine to form a heterocyclo ring selected from pyrrolidinyl, piperadinyl, piperazinyl, morpholinyl, diazapanyl or 1,4-dioxa-8-azaspiro[4.5]decan-8-yl), any of which are optionally independently substituted with one to three groups T¹ᵃ, T²ᵃ, T³ᵃ selected from optionally substituted alkyl (especially substituted with -T⁴NT⁷T⁸), optionally substituted aryl (especially substituted with halogen or haloalkyl), cyano, —OH, —OT⁶, —CO₂H, —CO₂T⁶, oxo, hydroxy(alkyl), (alkoxy)alkyl, -T⁴-N(T¹⁰)-T⁵-T⁶, or -T⁴-NT⁷T⁸)
where
  T⁴ is a bond or —C(O)—;
  T⁵ is —C(O)—, —SO₂—, or -alkylene-C(O)O—;
  T⁶ is alkyl, alkoxy, or heteroaryl;
  T⁷ and T⁸ are independently H, alkyl, or cycloalkyl;
  or T⁷ and T⁸ together with the nitrogen atom to which they are attached combine to form a an optionally substituted heterocyclo ring.

Preferred compounds of the present invention include compounds of Formula (II),

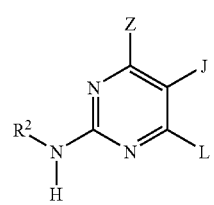

II where:
Z, J and L are as described above (including preferred groups);
R² is

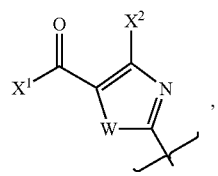 , 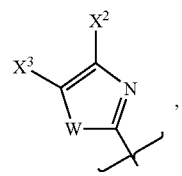 ,

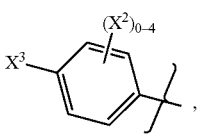 , 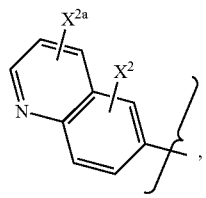 ,

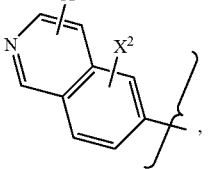 , 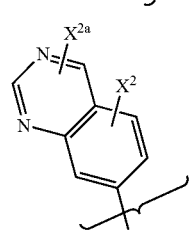 ,

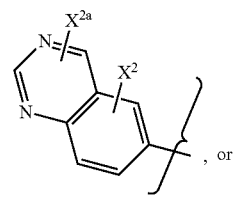 , or 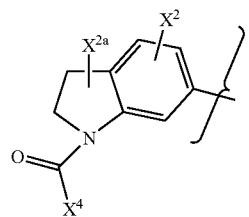 .

wherein:
W is O or S, more preferably S;
X¹ is NHT⁸ or OT⁶;
X² and X²ᵃ are independently hydrogen, halo, OT⁶, alkyl, or haloalkyl;
X³ is heteroaryl (preferably, pyrimidinyl, imidazolyl, oxazolyl, or thiazolyl any of which may be further optionally substituted), cyano, C(O)ₜT⁶, or S(O)ₜNT⁷T⁸; and
X⁴ is alkyl, haloalkyl, NHT⁸ or OT⁶.

Compounds within the scope of the Formulas I and II include dual PDE7-PDE4 inhibitors of the following Formula III:

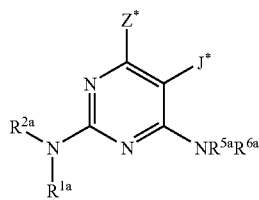

III wherein
R¹ᵃ is H or alkyl;
R²ᵃ is optionally substituted heteroaryl;
Z* is halogen, alkyl, substituted alkyl, haloalkyl, NR³ᵃR⁴ᵃ, —C(O)—N(T¹⁰)-T⁵-H, —C(O)—N(T¹⁰)-T⁵-T⁶, optionally substituted aryl or optionally substituted heteroaryl;
R³ᵃ is hydrogen or alkyl;
R⁴ᵃ is alkyl, alkoxy, optionally substituted (heteroaryl)alkyl, optionally substituted heterocylo, optionally substituted (heterocyclo)alkyl, or (aryl)alkyl wherein the aryl group is substituted with one or two groups T¹* and T²* and optionally further substituted with a group T³*;
or R³ᵃ and R⁴ᵃ together with the nitrogen atom to which they are attached may combine to form an optionally substituted heterocyclo ring;
R⁵ᵃ is optionally substituted (heteroaryl)alkyl, or (aryl)alkyl wherein the aryl group is substituted with one or two groups T¹* and T²* and optionally further substituted with a group T³*;
or R⁵ᵃ and R⁶ᵃ together with the nitrogen atom to which they are attached may combine to form an optionally substituted heterocyclo ring;
R⁶ᵃ is hydrogen or alkyl;
J* is hydrogen or alkyl;
T¹* and T²* are independently alkoxy, alkoxycarbonyl, heteroaryl SO₃H or —SO₂R⁸ᵃ where R⁸ᵃ is alkyl, amino, alkylamino or dialkylamino;
or T¹* and T²* together with the aryl ring to which they are attached may combine to form a bicyclic ring (e.g., benzodioxole);
T³* is H, alkyl, halo, haloalkyl or cyano.

Preferred compounds within Formula III are those wherein:
R¹ᵃ is H;
R²ᵃ is thiazolyl, oxazolyl, tetrahydroindolinyl, or isoxozolyl (preferably thiazolyl) any of which may be optionally substituted (preferably with one or more alkyl, alkylcarbonyl or alkoxycarbonyl groups);
Z* is halogen, alkyl, haloalkyl, NR³ᵃR⁴ᵃ, —C(O)—N(T¹⁰)-T⁵-H, or —C(O)—N(T¹⁰)-T⁵-T⁶;
R³ᵃ is hydrogen;
R⁴ᵃ is alkyl, alkoxy, haloalkyl, or optionally substituted (heterocyclo)alkyl, especially where the heterocyclo ring is morpholinyl, pyrrolidinyl or tetrahydrofuranyl;
or R³ᵃ and R⁴ᵃ together with the nitrogen atom to which they are attached may combine to form an optionally substituted heterocyclo ring, especially piperazine or piperidine or morpholine optionally substituted with one or more alkyl, (hydroxy)alkyl, hydroxy, —C(O)NT⁷T⁸, cyano, oxo, —CO_tH, or —CO_tT⁶;
R⁵ᵃ is
  a) (phenyl)alkyl where the phenyl group is substituted with one or two alkoxy, alkoxycarbonyl, heteroaryl (especially thiadiazolyl) or —SO₂R⁸ᵃ;
  b) optionally substituted (heteroaryl)alkyl; or
  c) optionally substituted (benzodioxole)alkyl, especially (1,3-benzodioxole)alkyl;
R⁶ᵃ is hydrogen;
or R⁵ᵃ and R⁶ᵃ together with the nitrogen atom to which they are attached may combine to form an optionally substituted heterocyclo ring, especially piperazine or piperidine or morpholine optionally substituted with one or more alkyl, (hydroxy)alkyl, hydroxy, —C(O)NT⁷T⁸, cyano, oxo, —CO_tH, or —CO_tT⁶; and
J* is hydrogen or alkyl.

More preferred compounds within Formula III are those wherein:
R¹ᵃ is hydrogen.
R²ᵃ is

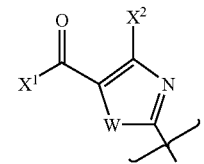

where W is O or S (preferably S), X¹ is alkoxy, and X² is alkyl;
Z* is halogen, haloalkyl, oxazolyl, phenyl (optionally substituted with heteroaryl, CO_tH or CO_tT⁶), —NR³ᵃR⁴ᵃ, or —C(O)—N(H)-alkylene-COOH;
R³ᵃ is hydrogen;
R⁴ᵃ is alkyl, optionally substituted (morpholinyl)alkyl, optionally substituted (pyrrolidinyl)alkyl, or optionally substituted (tetrahydrofuranyl)alkyl;
or R³ᵃ and R⁴ᵃ together with the nitrogen atom to which they are attached may combine to form a piperazine, piperadine or morpholine ring optionally substituted with one or more more alkyl, (hydroxy)alkyl, hydroxy, —C(O)NH₂, cyano, oxo, or —CO_talkyl;
R⁵ᵃ is
  a) (phenyl)alkyl where the phenyl group is substituted with one or more alkoxy, alkoxycarbonyl, heteroaryl (especially thiadiazolyl) or —SO₂R⁸ᵃ;
  b) (tetrazolyl)alkyl, or (pryidyl)alkyl;
  c) optionally substituted (benzodioxole)alkyl , especially (1,3-benzodioxole)alkyl;
R⁶ᵃ is hydrogen;
or R⁵ᵃ and R⁶ᵃ together with the nitrogen atom to which they are attached may combine to form an optionally substituted heterocyclo ring, especially piperazine or piperidine or morpholine optionally substituted with one or more alkyl, (hydroxy)alkyl, hydroxy, —C(O)NH₂, cyano, oxo, or —CO_talkyl; and
J* is hydrogen or alkyl.

Preferred compounds within the scope of formula III include:

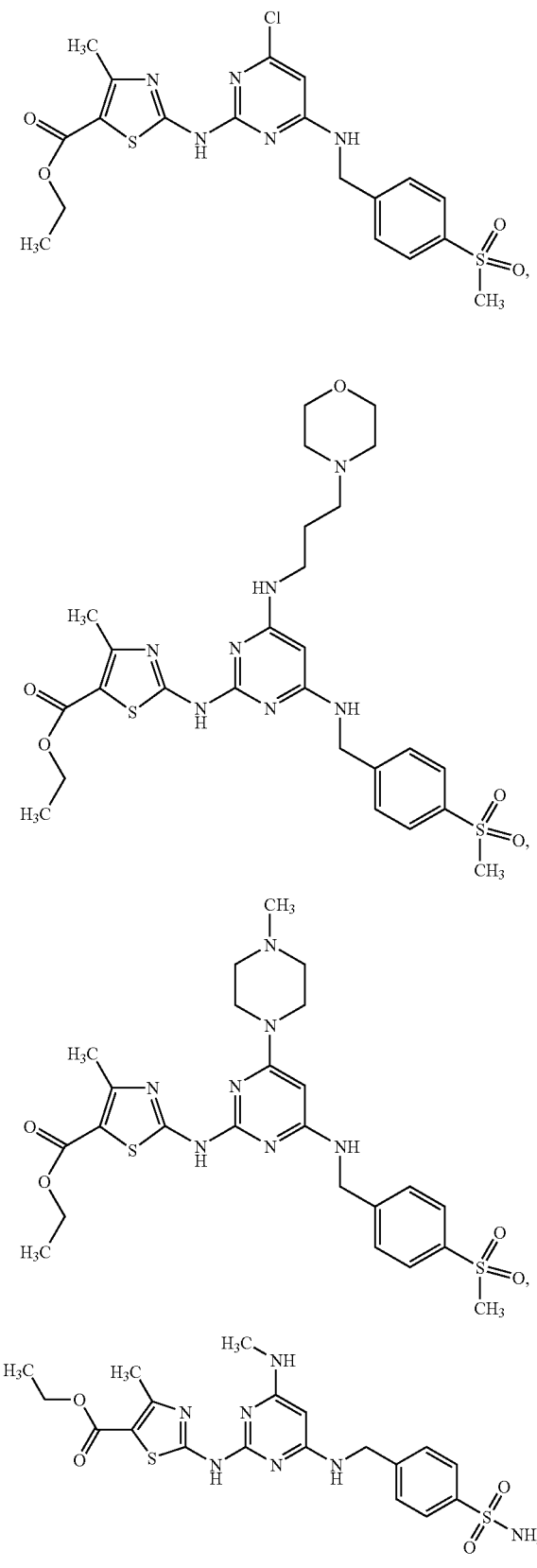
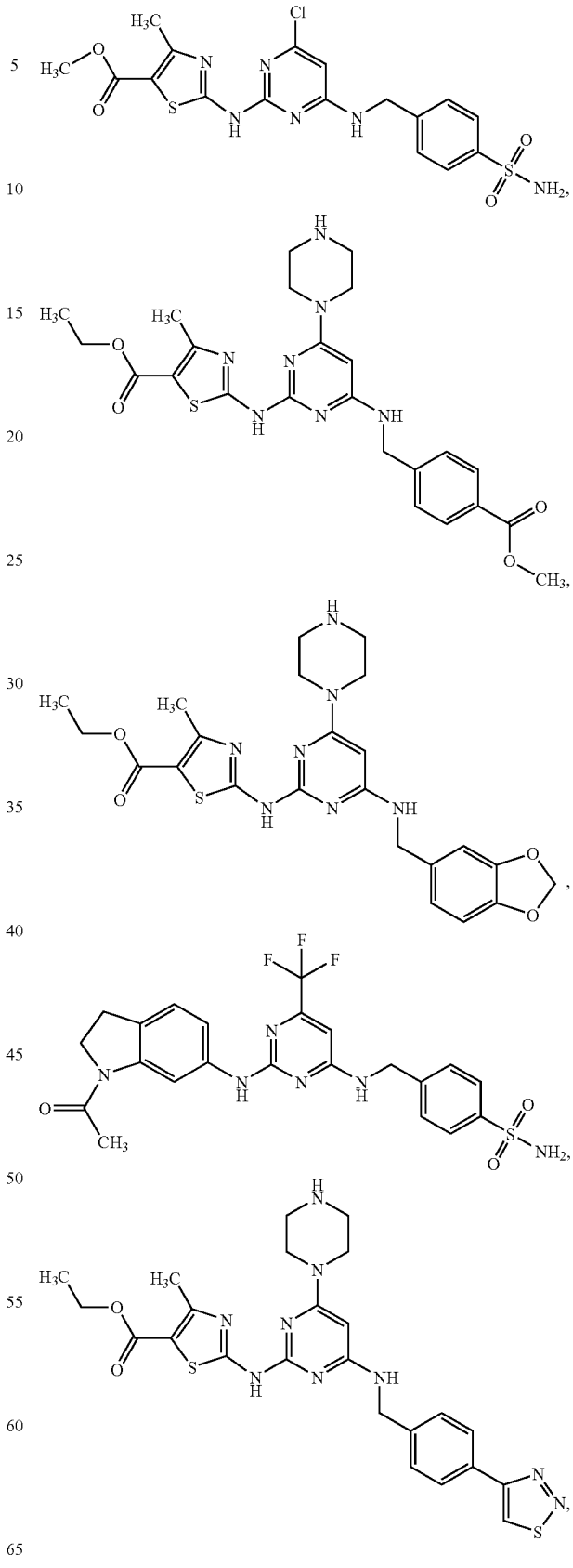

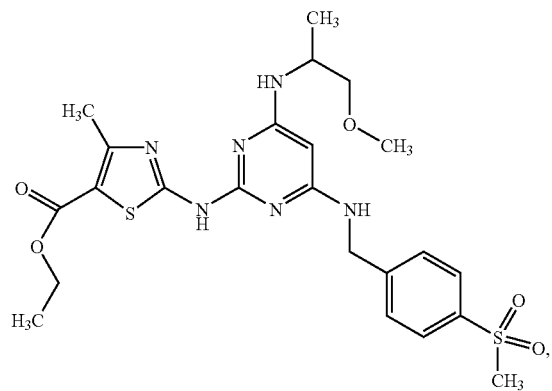
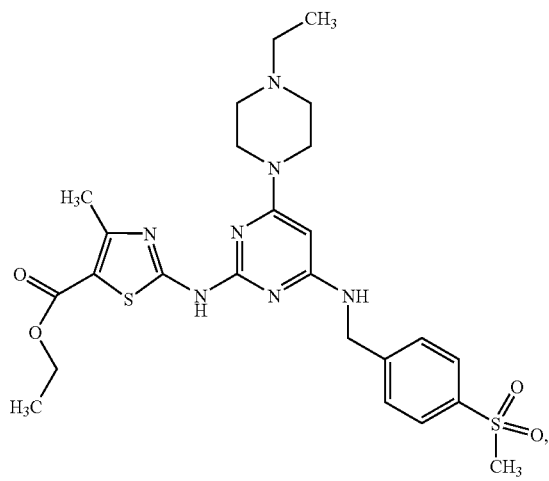
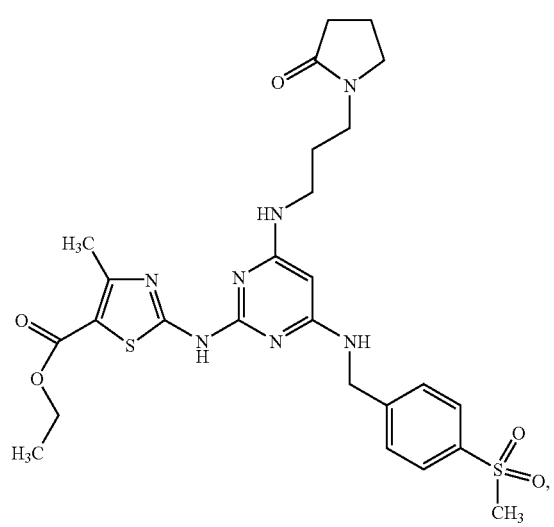
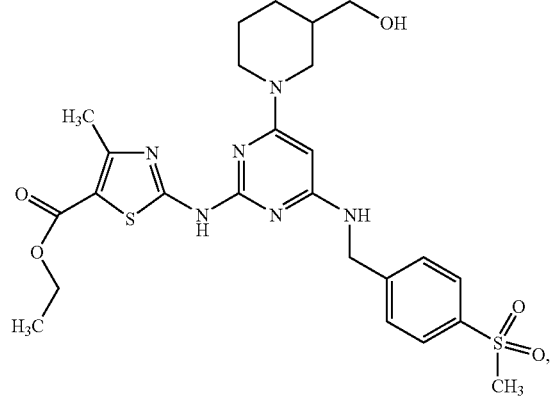
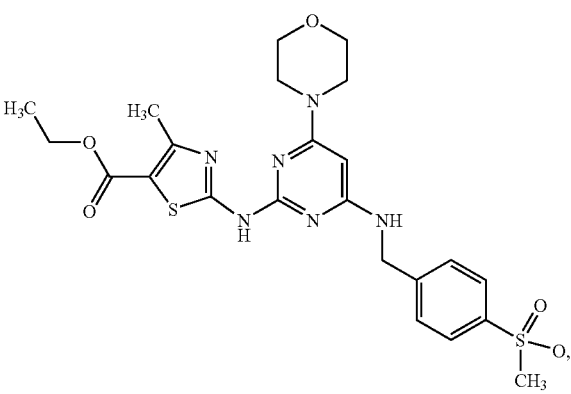

-continued
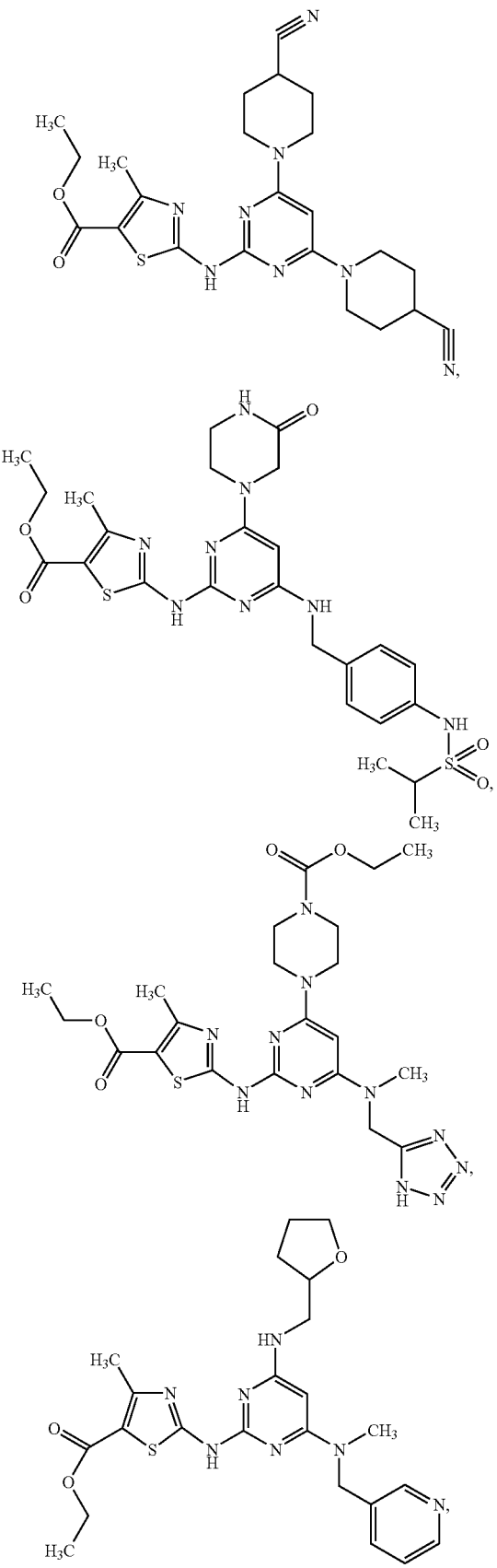
-continued
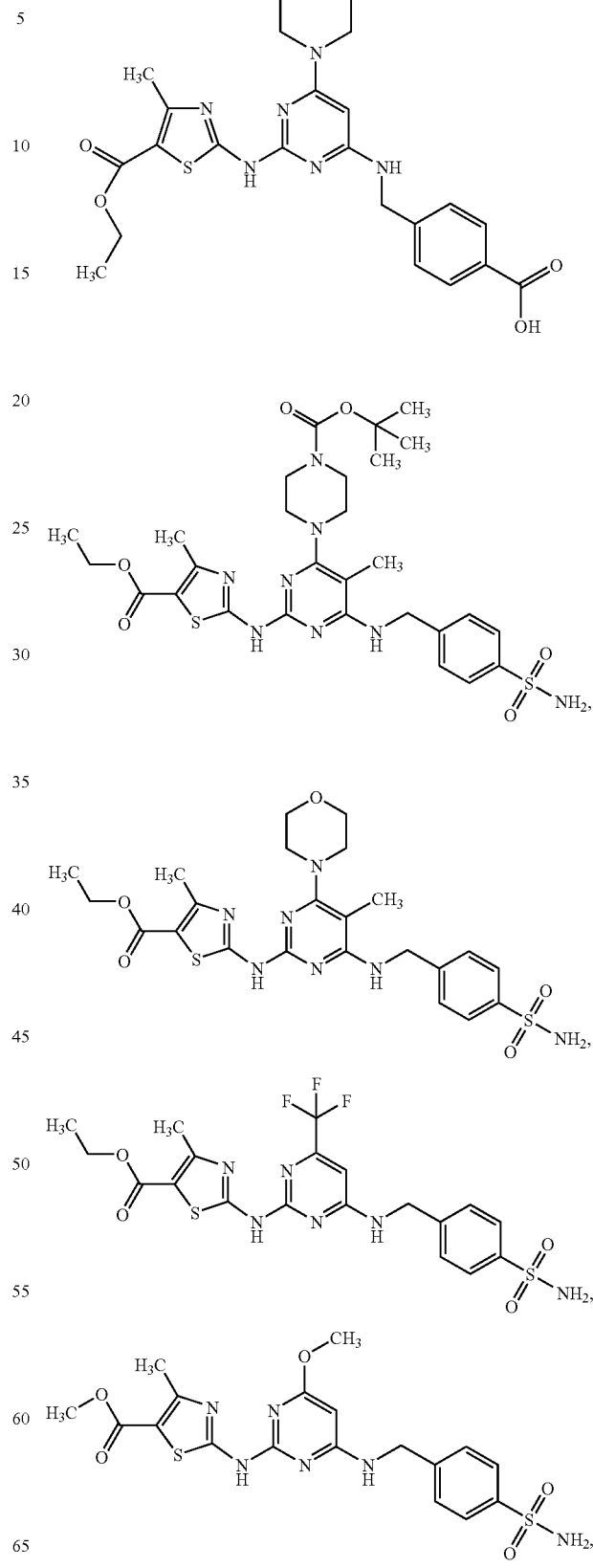

-continued

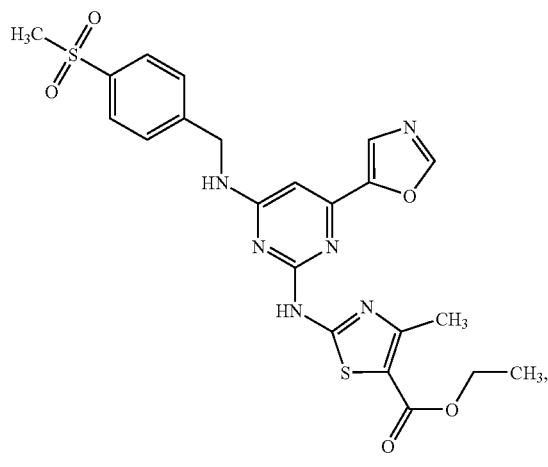

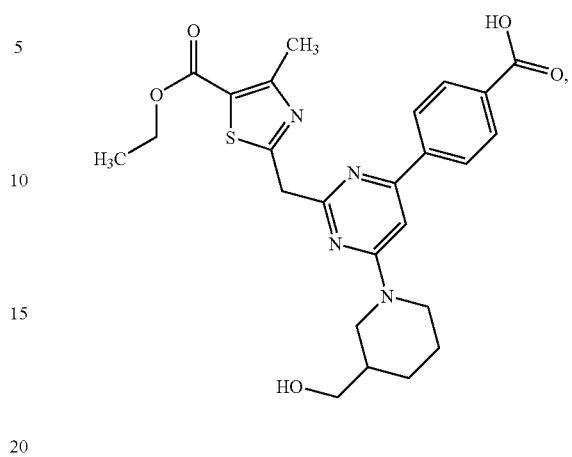

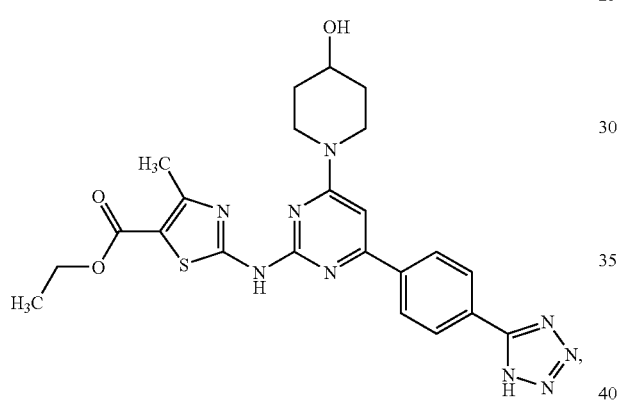

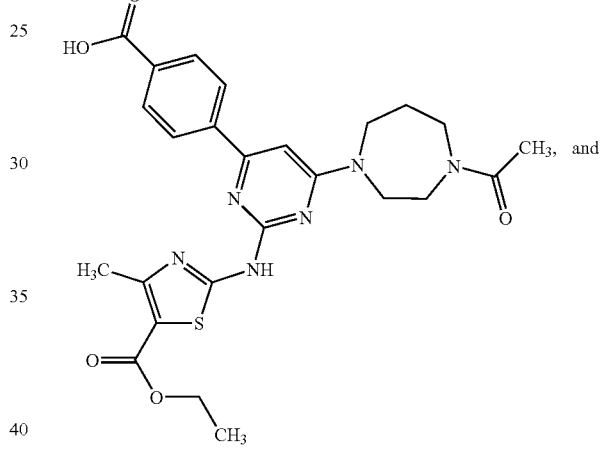

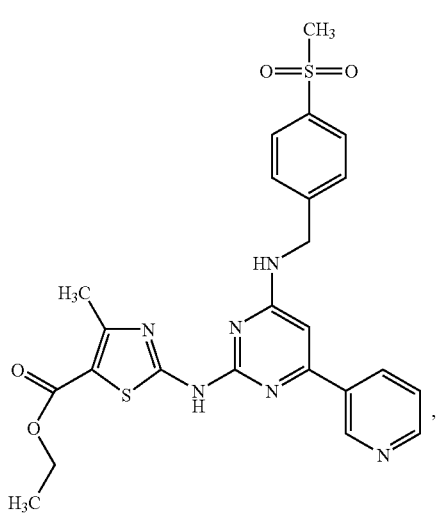

The following are definitions of the terms as used throughout this specification and claims. The initial definition provided for a group or term herein applies to that group or term throughout the present specification, individually or as part of another group, unless otherwise indicated.

The terms "alk" or "alkyl" refer to straight or branched chain hydrocarbon groups having 1 to 12 carbon atoms, preferably 1 to 8 carbon atoms, such as methyl, ethyl, n-propyl, i-propyl, n-butyl, i-butyl, t-butyl, pentyl, hexyl, heptyl, octyl, etc. Lower alkyl groups, that is, alkyl groups of 1 to 6 carbon atoms, are generally most preferred.

The term "substituted alkyl" refers to alkyl groups substituted with one or more groups listed in the definition of $T^1$, $T^2$ and $T^3$, preferably selected from halo, cyano, O—$R_7$, S—$R_7$, $NR_8R_9$, nitro, cycloalkyl, substituted cycloalkyl, oxo, aryl, substituted aryl, heterocyclo, heteroaryl, $CO_2R_7$, $S(O)R_7$, $SO_2R_7$, $SO_3R_7$, $SO_2NR_8R_9$, $C(O)NR_8R_9$, C(O) alkyl, and C(O)H.

The term "alkylene" refers to a straight chain bridge of 1 to 4 carbon atoms connected by single bonds (e.g., —$(CH_2)_x$— wherein x is 1 to 5), which may be substituted with one or more groups listed in the definition of $T^1$, $T^2$ and $T^3$.

The term "alkenyl" refers to straight or branched chain hydrocarbon groups having 2 to 12 carbon atoms, preferably 2 to 4 carbon atoms, and at least one double carbon to carbon bond (either cis or trans), such as ethenyl.

The term "substituted alkenyl" refers to an alkenyl group as defined above substituted with one or more groups listed in the definition of $T^1$, $T^2$ and $T^3$, preferably selected from halo, cyano, O—$R_7$, S—$R_7$, $NR_8R_9$, nitro, cycloalkyl, substituted cycloalkyl, oxo, aryl, substituted aryl, heterocyclo, heteroaryl, $CO_2R_7$, $S(O)R_7$, $SO_2R_7$, $SO_3R_7$, $SO_2NR_8R_9$, $C(O)NR_8R_9$, C(O)alkyl, and C(O)H.

The term "alkynyl" refers to straight or branched chain hydrocarbon group having 2 to 12 carbon atoms and one, two or three triple bonds, preferably 2 to 6 carbon atoms and one triple bond.

The term "substituted alkynyl" refers to an alkynyl group as defined above substituted with one or more groups listed in the definition of $T^1$, $T^2$ and $T^3$, preferably selected from halo, cyano, O—$R_7$, S—$R_7$, $NR_8R_9$, nitro, cycloalkyl, substituted cycloalkyl, oxo, aryl, substituted aryl, heterocyclo, heteroaryl, $CO_2R_7$, $S(O)R_7$, $SO_2R_7$, $SO_3R_7$, $SO_2NR_8R_9$, $C(O)NR_8R_9$, C(O)alkyl, and C(O)H.

The term "halo" refers to chloro, bromo, fluoro, and iodo.

The term "cycloalkyl" refers to saturated and partially unsaturated (containing 1 or 2 double bonds) cyclic hydrocarbon groups containing 1 to 3 rings, including monocyclicalkyl, bicyclicalkyl and tricyclicalkyl, containing a total of 3 to 20 carbons forming the rings, preferably 3 to 7 carbons, forming the ring and which may be fused to 1 or 2 aromatic or heterocyclo rings, which include cyclopropyl, cyclobutyl, cyclopentyl, cyclohexyl, cycloheptyl, cyclooctyl, cyclodecyl, cyclododecyl, cyclohexenyl,

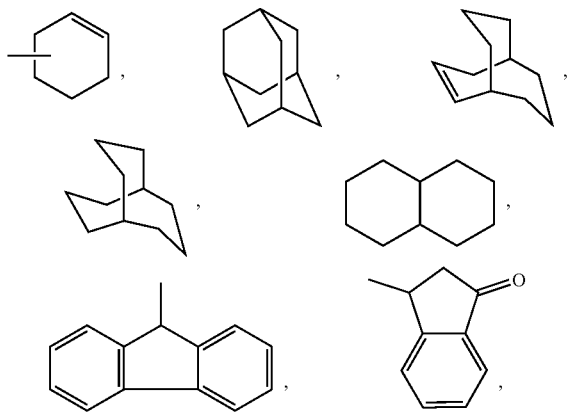

-continued

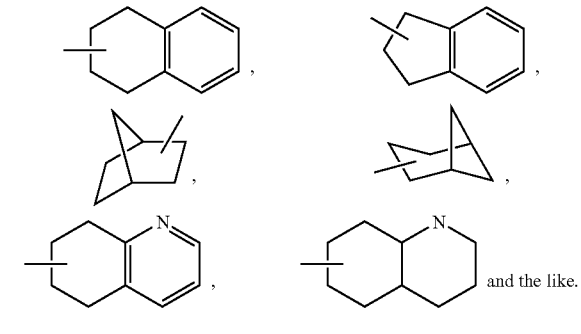

, and the like.

The term "substituted cycloalkyl" refers to such cycloalkyl group as defined above substituted with one or more groups listed in the definition of $T^1$, $T^2$ and $T^3$, preferably selected from halogen, nitro, alkyl, substituted alkyl, alkenyl, cyano, cycloalkyl, substituted cycloalkyl, aryl, substituted aryl, heterocyclo, heteroaryl, oxo, $OR_7$, $CO_2R_7$, $C(O)NR_8R_9$, $OC(O)R_7$, $OC(O)OR_7$, $OC(O)NR_8R_9$, $OCH_2CO_2R_7$, $C(O)R_7$, $NR_8R_9$, $NR_{10}C(O)R_7$, $NR_{10}C(O)OR_7$, $NR_{10}C(O)C(O)OR_7$, $NR_{10}C(O)C(O)NR_8R_9$, $NR_{10}C(O)C(O)$alkyl, $NR_{10}C(NCN)OR_7$, $NR_{10}C(O)NR_8R_9$, $NR_{10}C(NCN)NR_8R_9$, $NR_{10}C(NR_{11})NR_8R_9$, $NR_{10}SO_2NR_8R_9$, $NR_{10}SO_2R_7$, $SR_7$, $S(O)R_7$, $SO_2R_7$, $SO_3R_7$, $SO_2NR_8R_9$, $NHOR_7$, $NR_{10}NR_8R_9$, $N(COR_7)OR_{10}$, $N(CO_2R_7)OR_{10}$, $C(O)NR_{10}(CR_{12}R_{13})_rR_7$, $CO(CR_{12}R_{13})pO(CR_{14}R_{15})qCO_2R_7$, $CO(CR_{12}R_{13})rOR_7$, $CO(CR_{12}R_{13})pO(CR_{14}R_{15})qR_7$, $CO(CR_{12}R_{13})rNR_8R_9$, $OC(O)O(CR_{12}R_{13})mNR_8R_9$, $OC(O)N(CR_{12}R_{13})rR_7$, $O(CR_{12}R_{13})mNR_8R_9$, $NR_{10}C(O)(CR_{12}R_{13})rR_7$, $NR_{10}C(O)(CR_{12}R_{13})rOR_7$, $NR_{10}C(=NC)(CR_{12}R_{13})rR_7$, $NR_{10}CO(CR_{12}R_{13})rNR_8R_9$, $NR_{10}C(CR_{12}R_{13})mOR_7$, $NR_{10}(CR_{12}R_{13})rCO_2R_7$, $NR_{10}(CR_{12}R_{13})mNR_8R_9$, $NR_{10}(CR_{12}R_{13})nSO_2(CR_{14}R_{15})qR_7$, $CONR_{10}(CR_{12}R_{13})nSO_2(CR_{14}R_{15})qR_7$, $SO_2NR_{10}(CR_{12}R_{13})nCO(CR_{14}R_{15})qR_7$, and $SO_2NR_{10}(CR_{12}R_{13})mOR_7$.

The terms "ar" or "aryl" refer to aromatic homocyclic (i.e., hydrocarbon) mono-, bi- or tricyclic ring-containing groups preferably having 6 to 12 members such as phenyl, naphthyl and biphenyl, as well as such rings fused to a cycloalkyl, cycloalkenyl, heterocyclo, or heteroaryl ring. Examples include:

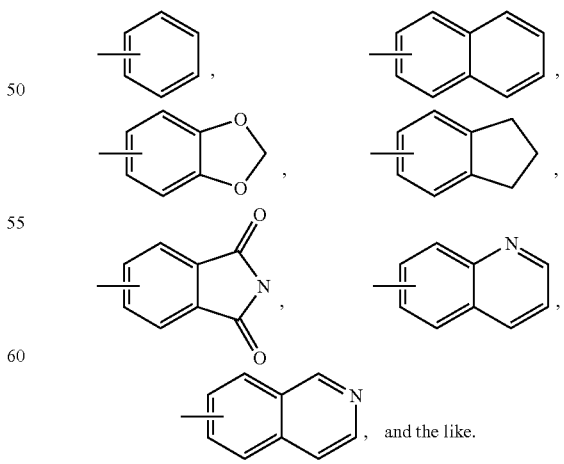

, and the like.

The term "substituted aryl" refers to such aryl groups as defined above substituted with one or more groups listed in the definition of T¹, T² and T³, preferably selected from halogen, nitro, alkyl, substituted alkyl, alkenyl, cyano, cycloalkyl, substituted cycloalkyl, aryl, substituted aryl, heterocyclo, heteroaryl, OR$_7$, CO$_2$R$_7$, C(O)NR$_8$R$_9$, OC(O)R$_7$, OC(O)OR$_7$, OC(O)NR$_8$R$_9$, OCH$_2$CO$_2$R$_7$, C(O)R$_7$, NR$_8$R$_9$, NR$_{10}$C(O)R$_7$, NR$_{10}$C(O)OR$_7$, NR$_{10}$C(O)C(O)OR$_7$, NR$_{10}$C(O)C(O)NR$_8$R$_9$, NR$_{10}$C(O)C(O)alkyl, NR$_{10}$C(NCN)OR$_7$, NR$_{10}$C(O)NR$_8$R$_9$, NR$_{10}$C(NCN)NR$_8$R$_9$, NR$_{10}$C(NR$_{11}$)NR$_8$R$_9$, NR$_{10}$SO$_2$NR$_8$R$_9$, NR$_{10}$SO$_2$R$_7$, SR$_7$, S(O)R$_7$, SO$_2$R$_7$, SO$_3$R$_7$, SO$_2$NR$_8$R$_9$, NHOR$_7$, NR$_{10}$NR$_8$R$_9$, N(COR$_7$)OR$_{10}$, N(CO$_2$R$_7$)OR$_{10}$, C(O)NR$_{10}$(CR$_{12}$R$_{13}$)$_r$R$_7$, CO(CR$_{12}$R$_{13}$)pO(CR$_{14}$R$_{15}$)qCO$_2$R$_7$, CO(CR$_{12}$R$_{13}$)rOR$_7$, CO(CR$_{12}$R$_{13}$)pO(CR$_{14}$R$_{15}$)qR$_7$, CO(CR$_{12}$R$_{13}$)rNR$_8$R$_9$, OC(O)O(CR$_{12}$R$_{13}$)mNR$_8$R$_9$, OC(O)N(CR$_{12}$R$_{13}$)rR$_7$, O(CR$_{12}$R$_{13}$)mNR$_8$R$_9$, NR$_{10}$C(O)(CR$_{12}$R$_{13}$)rR$_7$, NR$_{10}$C(O)(CR$_{12}$R$_{13}$)rOR$_7$, NR$_{10}$C(=NC)(CR$_{12}$R$_{13}$)rR$_7$, NR$_{10}$CO(CR$_{12}$R$_{13}$)rNR$_8$R$_9$, NR$_{10}$(CR$_{12}$R$_{13}$)mOR$_7$, NR$_{10}$(CR$_{12}$R$_{13}$)rCO$_2$R$_7$, NR$_{10}$(CR$_{12}$R$_{13}$)mNR$_8$R$_9$, NR$_{10}$(CR$_{12}$R$_{13}$)nSO$_2$(CR$_{14}$R$_{15}$)qR$_7$, CONR$_{10}$(CR$_{12}$R$_{13}$)nSO$_2$(CR$_{14}$R$_{15}$)qR$_7$, SO$_2$NR$_{10}$(CR$_{12}$R$_{13}$)nCO(CR$_{14}$R$_{15}$)qR$_7$, and SO$_2$NR$_{10}$(CR$_{12}$R$_{13}$)mOR$_7$ as well as pentafluorophenyl.

The terms "heterocycle", "heterocyclic", "heterocyclic group" or "heterocyclo" refer to fully saturated or partially unsaturated cyclic groups (for example, 3 to 13 member monocyclic, 7 to 17 member bicyclic, or 10 to 20 member tricyclic ring systems, preferably containing a total of 3 to 10 ring atoms) which have at least one heteroatom in at least one carbon atom-containing ring. Each ring of the heterocyclic group containing a heteroatom may have 1, 2, 3 or 4 heteroatoms selected from nitrogen atoms, oxygen atoms and/or sulfur atoms, where the nitrogen and sulfur heteroatoms may optionally be oxidized and the nitrogen heteroatoms may optionally be quaternized. The heterocyclic group may be attached at any heteroatom or carbon atom of the ring or ring system. The rings of multi-ring heterocycles may be either fused, bridged and/or joined through one or more spiro unions. Exemplary heterocyclic groups include

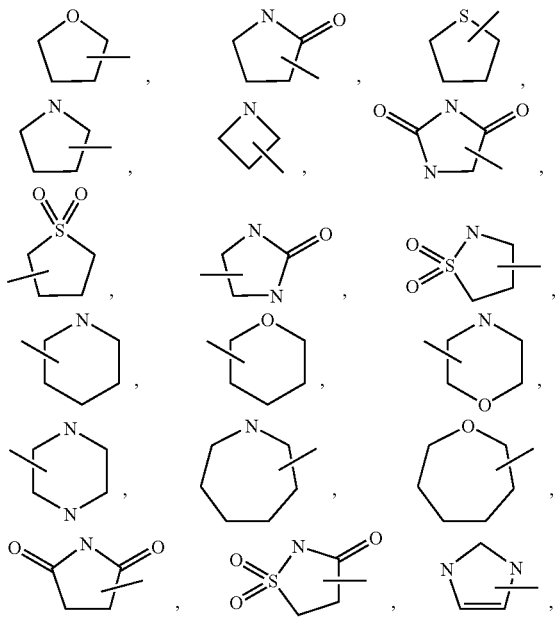

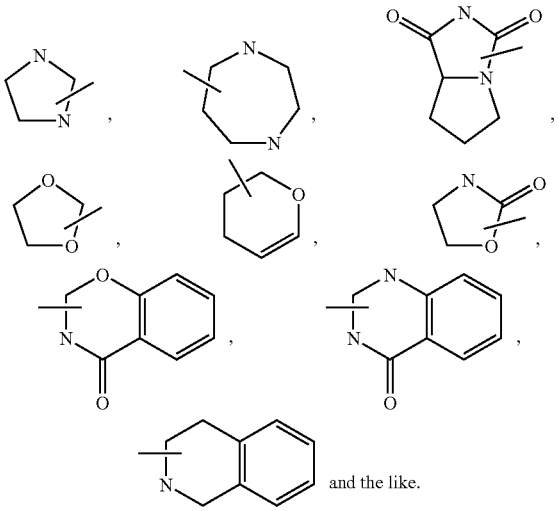

and the like.

The terms "substituted heterocycle" or "substituted heterocycle" and the like refer to such heterocylo groups as defined above substituted with one or more groups listed in the definition of T¹, T² and T³, preferably selected from halogen, nitro, alkyl, substituted alkyl, alkenyl, cyano, cycloalkyl, substituted cycloalkyl, aryl, substituted aryl, heterocyclo, heteroaryl,oxo, OR$_7$, CO$_2$R$_7$, C(O)NR$_8$R$_9$, OC(O)R$_7$, OC(O)OR$_7$, OC(O)NR$_8$R$_9$, OCH$_2$CO$_2$R$_7$, C(O)R$_7$, NR$_8$R$_9$, NR$_{10}$C(O)R$_7$, NR$_{10}$C(O)OR$_7$, NR$_{10}$C(O)C(O)OR$_7$, NR$_{10}$C(O)C(O)NR$_8$R$_9$, NR$_{10}$C(O)C(O)alkyl, NR$_{10}$C(NCN)OR$_7$, NR$_{10}$C(O)NR$_8$R$_9$, NR$_{10}$C(NCN)NR$_8$R$_9$, NR$_{10}$C(NR$_{11}$)NR$_8$R$_9$, NR$_{10}$SO$_2$NR$_8$R$_9$, NR$_{10}$SO$_2$R$_7$, SR$_7$, S(O)R$_7$, SO$_2$R$_7$, SO$_3$R$_7$, SO$_2$NR$_8$R$_9$, NHOR$_7$, NR$_{10}$NR$_8$R$_9$, N(COR$_7$)OR$_{10}$, N(CO$_2$R$_7$)OR$_{10}$, C(O)NR$_{10}$(CR$_{12}$R$_{13}$)$_r$R$_7$, CO(CR$_{12}$R$_{13}$)pO(CR$_{14}$R$_{15}$)qCO$_2$R$_7$, CO(CR$_{12}$R$_{13}$)rOR$_7$, CO(CR$_{12}$R$_{13}$)pO(CR$_{14}$R$_{15}$)qR$_7$, CO(CR$_{12}$R$_{13}$)rNR$_8$R$_9$, OC(O)O(CR$_{12}$R$_{13}$)mNR$_8$R$_9$, OC(O)N(CR$_{12}$R$_{13}$)rR$_7$, O(CR$_{12}$R$_{13}$)mNR$_8$R$_9$, NR$_{10}$C(O)(CR$_{12}$R$_{13}$)rR$_7$, NR$_{10}$C(O)(CR$_{12}$R$_{13}$)rOR$_7$, NR$_{10}$C(=NC)(CR$_{12}$R$_{13}$)rR$_7$, NR$_{10}$CO(CR$_{12}$R$_{13}$)rNR$_8$R$_9$, NR$_{10}$(CR$_{12}$R$_{13}$)mOR$_7$, NR$_{10}$(CR$_{12}$R$_{13}$)rCO$_2$R$_7$, NR$_{10}$(CR$_{12}$R$_{13}$)mNR$_8$R$_9$, NR$_{10}$(CR$_{12}$R$_{13}$)nSO$_2$(CR$_{14}$R$_{15}$)qR$_7$, CONR$_{10}$(CR$_{12}$R$_{13}$)nSO$_2$(CR$_{14}$R$_{15}$)qR$_7$, SO$_2$NR$_{10}$(CR$_{12}$R$_{13}$)nCO(CR$_{14}$R$_{15}$)qR$_7$, and SO$_2$NR$_{10}$(CR$_{12}$R$_{13}$)mOR$_7$.

The term "heteroaryl" as used herein alone or as part of another group refers to a 5- 6- or 7-membered aromatic rings containing from 1 to 4 nitrogen atoms and/or 1 or 2 oxygen or sulfur atoms provided that the ring contains at least 1 carbon atom and no more than 4 heteroatoms. The heteroaryl ring is linked through an available carbon or nitrogen atom. Also included within the definition of heteroaryl are such rings fused to a cycloalkyl, aryl, cycloheteroalkyl, or another heteroaryl ring. One, two, or three available carbon or nitrogen atoms in the heteroaryl ring can be optionally substituted with substituents listed in the description of T$_1$, T$_2$ and T$_3$. Also an available nitrogen or sulfur atom in the heteroaryl ring can be oxidized. Examples of heteroaryl rings include

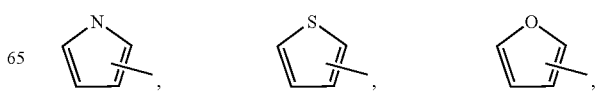

-continued
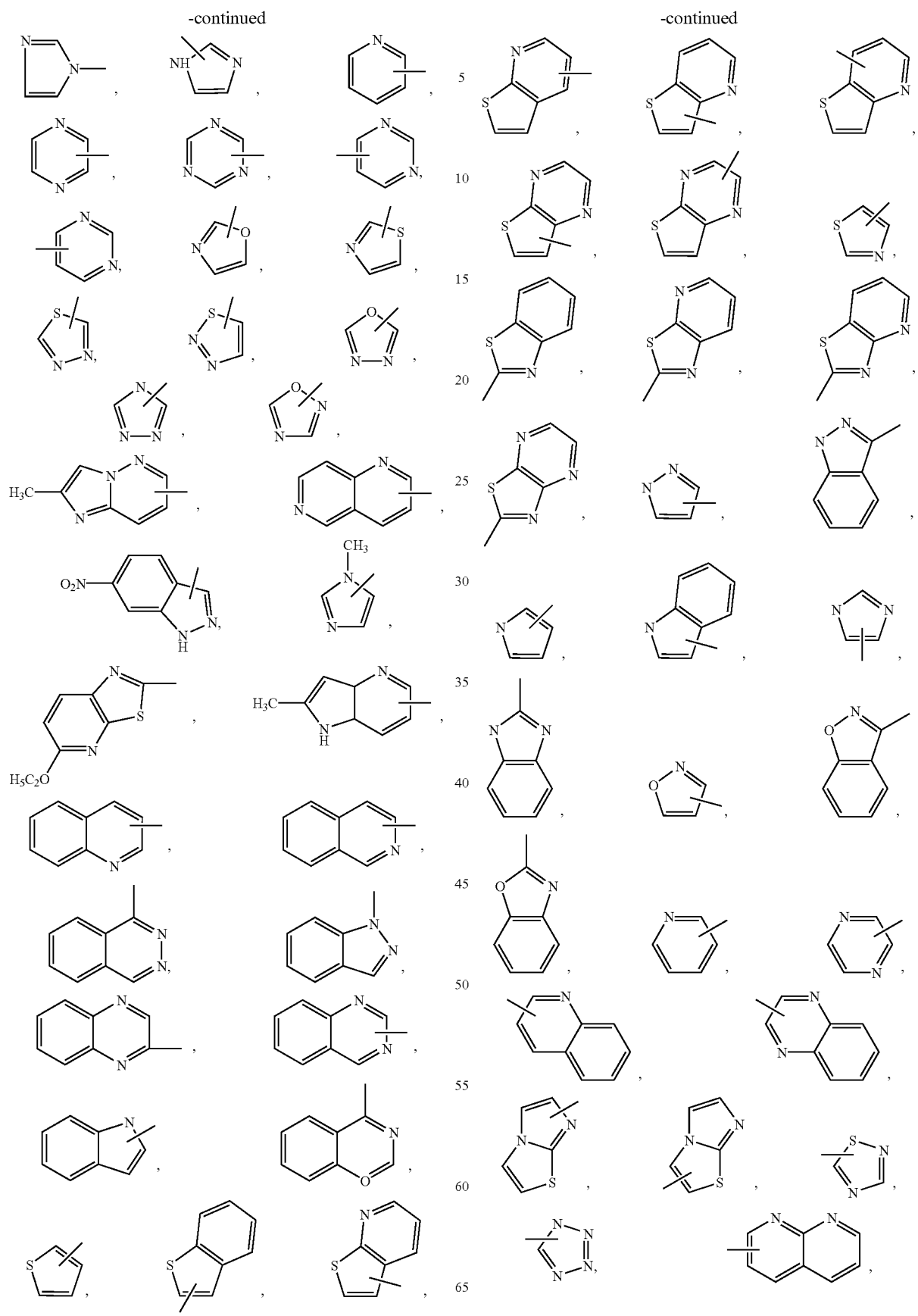

-continued

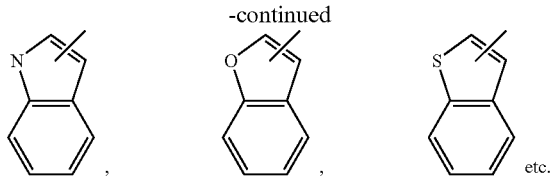

The term "substituted heteroaryl" refers to such heteroaryl groups as defined above substituted on any available atom with one or more groups listed in the definition of $T^1$, $T^2$ and $T^3$, preferably selected from" refers to such heterocylo groups as defined above substituted with one or more groups listed in the definition of $T^1$, $T^2$ and $T^3$, preferably selected from halogen, nitro, alkyl, substituted alkyl, alkenyl, cyano, cycloalkyl, substituted cycloalkyl, aryl, substituted aryl, heterocyclo, heteroaryl, $OR_7$, $CO_2R_7$, $C(O)NR_8R_9$, $OC(O)R_7$, $OC(O)OR_7$, $OC(O)NR_8R_9$, $OCH_2CO_2R_7$, $C(O)R_7$, $NR_8R_9$, $NR_{10}C(O)R_7$, $NR_{10}C(O)OR_7$, $NR_{10}C(O)C(O)OR_7$, $NR_{10}C(O)C(O)NR_8R_9$, $NR_{10}C(O)C(O)$alkyl, $NR_{10}C(NCN)OR_7$, $NR_{10}C(O)NR_8R_9$, $NR_{10}C(NCN)NR_8R_9$, $NR_{10}C(NR_{11})NR_8R_9$, $NR_{10}SO_2NR_8R_9$, $NR_{10}SO_2R_7$, $SR_7$, $S(O)R_7$, $SO_2R_7$, $SO_3R_7$, $SO_2NR_8R_9$, $NHOR_7$, $NR_{10}NR_8R_9$, $N(COR_7)OR_{10}$, $N(CO_2R_7)OR_{10}$, $C(O)NR_{10}(CR_{12}R_{13})_rR_7$, $CO(CR_{12}R_{13})pO(CR_{14}R_{15})qCO_2R_7$, $CO(CR_{12}R_{13})rOR_7$, $CO(CR_{12}R_{13})pO(CR_{14}R_{15})qR_7$, $CO(CR_{12}R_{13})rNR_8R_9$, $OC(O)O(CR_{12}R_{13})mNR_8R_9$, $OC(O)N(CR_{12}R_{13})rR_7$, $O(CR_{12}R_{13})mNR_8R_9$, $NR_{10}C(O)(CR_{12}R_{13})rR_7$, $NR_{10}C(O)(CR_{12}R_{13})rOR_7$, $NR_{10}C(=NC)(CR_{12}R_{13})rR_7$, $NR_{10}CO(CR_{12}R_{13})rNR_8R_9$, $NR_{10}(CR_{12}R_{13})mOR_7$, $NR_{10}(CR_{12}R_{13})rCO_2R_7$, $NR_{10}(CR_{12}R_{13})mNR_8R_9$, $NR_{10}(CR_{12}R_{13})nSO_2(CR_{14}R_{15})qR_7$, $CONR_1(CR_{12}R_{13})nSO_2(CR_{14}R_{15})qR_7$, $SO_2NR_{10}(CR_{12}R_{13})nCO(CR_{14}R_{15})qR_7$, and $SO_2NR_{10}(CR_{12}R_{13})mOR_7$.

$R_7$, $R_{10}$, and $R_{11}$, are independently selected from the group consisting of hydrogen, alkyl, substituted alkyl, alkenyl, alkynyl, cycloalkyl, substituted cycloalkyl, C(O)alkyl, C(O)substituted alkyl, C(O)cycloalkyl, C(O)substituted cycloalkyl, C(O)aryl, C(O)substituted aryl, C(O)Oalkyl, C(O)Osubstituted alkyl, C(O)heterocyclo, C(O)heteroaryl, aryl, substituted aryl, heterocyclo and heteroaryl.

$R_8$ and $R_9$ are independently selected from the group consisting of hydrogen, alkyl, substituted alkyl, cycloalkyl, substituted cycloalkyl, alkenyl, alkynyl, C(O)alkyl, C(O)substituted alkyl, C(O)cycloalkyl, C(O)substituted cycloalkyl, C(O)aryl, C(O)substituted aryl, C(O)Oalkyl, C(O)Osustituted alkyl, C(O)heterocyclo, C(O)heteroaryl, $S(O)_2$alkyl, $S(O)_2$substituted alkyl, $S(O)_2$cycloalkyl, $S(O)_2$substituted cycloalkyl, $S(O)_2$aryl, $S(O)_2$substituted aryl, $S(O)_2$heterocyclo, $S(O)_2$heteroaryl, aryl, substituted aryl, heterocyclo, and heteroaryl or $R_8$ and $R_9$ taken together with the nitrogen atom to which they are attached complete a heterocyclo or heteroaryl ring.

$R_{12}$ and $R_{14}$ are independently selected from hydrogen and alkyl or 1 to 4 carbons.

$R_{13}$ and $R_{15}$ are independently selected from hydrogen, alkyl of 1 to 4 carbons, and substituted alkyl or 1 to 4 carbons.

n is zero or an integer from 1 to 4.

m is an integer from 2 to 6.

p is an integer from 1 to 3.

q is zero or an integer from 1 to 3.

r is zero or an integer from 1 to 6.

$T^1$, $T^2$, and $T^3$ are are each independently (1) hydrogen or $T^6$, where $T^6$ is
 (i) alkyl, (hydroxy)alkyl, (alkoxy)alkyl, alkenyl, alkynyl, cycloalkyl, (cycloalkyl)alkyl, cycloalkenyl, (cycloalkenyl)alkyl, aryl, (aryl)alkyl, heterocyclo, (heterocylco)alkyl, heteroaryl, or (heteroaryl)alkyl;
 (ii) a group (i) which is itself substituted by one or more of the same or different groups (i); or
 (iii) a group (i) or (ii) which is independently substituted by one or more (preferably 1 to 3) of the following groups (2) to (13) of the definition of $T^1$, $T^2$ and $T^3$;
(2) —OH or —$OT^6$,
(3) —SH or —$ST^6$,
(4) —$C(O)_tH$, —$C(O)_tT^6$, or —O—$C(O)T^6$, where t is 1 or 2;
(5) —$SO_3H$, —$S(O)_tT^6$, or $S(O)_tN(T^9)T^6$,
(6) halo,
(7) cyano,
(8) nitro,
(9) -$T^4$-$NT^7T^8$,
(10) -$T^4$-$N(T^9)$-$T^5$-$NT^7T^8$,
(11) -$T^4$-$N(T^{10})$-$T^5$-$T^6$,
(12) -$T^4$-$N(T^{10})$-$T^5$-H,
(13) oxo, $T^4$ and $T^5$ are each independently
(1) a single bond,
(2) -$T^{11}$-S(O)-$T^{12}$-,
(3) -$T^{11}$-C(O)-$T^{12}$-,
(4) -$T^{11}$-C(S)-$T^{12}$-,
(5) -$T^{11}$-O-$T^{12}$-,
(6) -$T^{11}$-S-$T^{12}$-,
(7) -$T^{11}$-O—C(O)-$T^{12}$-,
(8) -$T^{11}$-C(O)—O-$T^{12}$-,
(9) -$T^{11}$-C(=$NT^{9a}$)-$T^{12}$-, or
(10) -$T^{11}$-C(O)—C(O)-$T^{12}$-

$T^7$, $T^8$, $T^9$, $T^{9a}$ and $T^{10}$
(1) are each independently hydrogen or a group provided in the definition of $T^6$, or
(2) $T^7$ and $T^8$ may together be alkylene or alkenylene, completing a 3- to 8-membered saturated or unsaturated ring together with the atoms to which they are attached, which ring is unsubstituted or substituted with one or more groups listed in the description of $T^1$, $T^2$ and $T^3$, or
(3) $T^7$ or $T^8$, together with $T^9$, may be alkylene or alkenylene completing a 3- to 8-membered saturated or unsaturated ring together with the nitrogen atoms to which they are attached, which ring is unsubstituted or substituted with one or more groups listed in the description of $T^1$, $T^2$ and $T^3$, or
(4) $T^7$ and $T^8$ or $T^9$ and $T^{10}$ together with the nitrogen atom to which they are attached may combine to form a group —N=$CT^{13}T^{14}$ where $T^{13}$ and $T^{14}$ are each independently H or a group provided in the definition of $T^6$; and $T^{11}$ and $T^{12}$ are each independently
(1) a single bond,
(2) alkylene,
(3) alkenylene, or
(4) alkynylene.

"T cell-mediated diseases" refers to any disorder or disease state in which modulation of the activity of T cells is implicated in a process which results in either a pathophysiological state or a process where the normal function of T cells is intended to be suppressed for therapeutic benefit. Examples of T cell mediated disorders include transplant rejection, graph verses host disease, and autoimmune disorders, such as rheumatoid arthritis, multiple sclerosis, juvenile diabetes, asthma, and inflammatory bowel disease, T-cell mediated hypersensitivity diseases, ischemic or reperfusion injury, and T-cell proliferative disorders.

PDE7 inhibitors in accordance with the present invention are employed, typically in the form of a pharmaceutical composition including a pharmaceutically acceptable carrier for the treatment of T-cell mediated disease. The compounds employed for this purpose are typically administered in an amount from about 0.01 to 100 mg/kg/day.

The pharmaceutical compositions comprising at least one PDE7 inhibitor may be formulated, for example, by employing conventional solid or liquid vehicles or diluents, as well as pharmaceutical additives of a type appropriate to the mode of desired administration (for example, excipients, binders, preservatives, stabilizers, flavors, etc.) according to techniques such as those well known in the art of pharmaceutical formulation.

The PDE7 inhibitors may be administered by any suitable means, for example, orally, such as in the form of tablets, capsules, granules or powders; sublingually; buccally; parenterally, such as by subcutaneous, intravenous, intramuscular, or intrasternal injection or infusion techniques (e.g., as sterile injectable aqueous or non-aqueous solutions or suspensions); nasally such as by inhalation spray; topically, such as in the form of a cream or ointment; or rectally such as in the form of suppositories; in dosage unit formulations containing non-toxic, pharmaceutically acceptable vehicles or diluents. The present compounds may, for example, be administered in a form suitable for immediate release or extended release. Immediate release or extended release may be achieved by the use of suitable pharmaceutical compositions comprising the present compounds, or, particularly in the case of extended release, by the use of devices such as subcutaneous implants or osmotic pumps. The present compounds may also be administered in the form of liposomes.

Exemplary compositions for oral administration include suspensions which may contain, for example, microcrystalline cellulose for imparting bulk, alginic acid or sodium alginate as a suspending agent, methylcellulose as a viscosity enhancer, and sweeteners or flavoring agents such as those known in the art; and immediate release tablets which may contain, for example, microcrystalline cellulose, dicalcium phosphate, starch, magnesium stearate and/or lactose and/or other excipients, binders, extenders, disintegrants, diluents and lubricants such as those known in the art. The present compounds may also be delivered through the oral cavity by sublingual and/or buccal administration. Molded tablets, compressed tablets or freeze-dried tablets are exemplary forms which may be used. Exemplary compositions include those formulating the present compound(s) with fast dissolving diluents such as mannitol, lactose, sucrose and/or cyclodextrins. Also included in such formulations may be high molecular weight excipients such as celluloses (avicel) or polyethylene glycols (PEG). Such formulations may also include an excipient to aid mucosal adhesion such as hydroxy propyl cellulose (HPC), hydroxy propyl methyl cellulose (HPMC), sodium carboxy methyl cellulose (SCMC), maleic anhydride copolymer (e.g., Gantrez), and agents to control release such as polyacrylic copolymer (e.g., Carbopol 934). Lubricants, glidants, flavors, coloring agents and stabilizers may also be added for ease of fabrication and use.

Exemplary compositions for nasal aerosol or inhalation administration include solutions in saline which may contain, for example, benzyl alcohol or other suitable preservatives, absorption promoters to enhance bioavailability, and/or other solubilizing or dispersing agents such as those known in the art.

Exemplary compositions for parenteral administration include injectable solutions or suspensions which may contain, for example, suitable non-toxic, parenterally acceptable diluents or solvents, such as mannitol, 1,3-butanediol, water, Ringer's solution, an isotonic sodium chloride solution, or other suitable dispersing or wetting and suspending agents, including synthetic mono- or diglycerides, and fatty acids, including oleic acid.

Exemplary compositions for rectal administration include suppositories which may contain, for example, a suitable non-irritating excipient, such as cocoa butter, synthetic glyceride esters or polyethylene glycols, which are solid at ordinary temperatures, but liquefy and/or dissolve in the rectal cavity to release the drug.

Exemplary compositions for topical administration include a topical carrier such as Plastibase (mineral oil gelled with polyethylene).

The effective amount of a compound employed in the present invention may be determined by one of ordinary skill in the art, and includes exemplary dosage amounts for an adult human of from about 0.01 to 100 mg/kg of body weight of active compound per day, which may be administered in a single dose or in the form of individual divided doses, such as from 1 to 4 times per day. It will be understood that the specific dose level and frequency of dosage for any particular subject may be varied and will depend upon a variety of factors including the activity of the specific compound employed, the metabolic stability and length of action of that compound, the species, age, body weight, general health, sex and diet of the subject, the mode and time of administration, rate of excretion, drug combination, and severity of the particular condition. Preferred subjects for treatment include animals, most preferably mammalian species such as humans, and domestic animals such as dogs, cats and the like, subject to inflammatory, immunological, or respiratory cell-associated disorders.

PDE7 inhibitors for use in the treatment of various T-cell mediated diseases are those covered by Formula I Compounds of Formula I include salts, prodrugs and solvates. The term "salt(s)", as employed herein, denotes acidic and/or basic salts formed with inorganic and/or organic acids and bases. Zwitterions (internal or inner salts) are included within the term "salt(s)" as used herein (and may be formed, for example, where the R substituents comprise an acid moiety such as a carboxyl group). Also included herein are quaternary ammonium salts such as alkylammonium salts. Pharmaceutically acceptable (i.e., non-toxic, physiologically acceptable) salts are preferred, although other salts are useful, for example, in isolation or purification steps which may be employed during preparation. Salts of the compounds of the formula I may be formed, for example, by reacting a compound I with an amount of acid or base, such as an equivalent amount, in a medium such as one in which the salt precipitates or in an aqueous medium followed by lyophilization.

Exemplary acid addition salts include acetates (such as those formed with acetic acid or trihaloacetic acid, for example, trifluoroacetic acid), adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides, hydrobromides, hydroiodides, 2-hydroxyethanesulfonates, lactates, maleates, methanesulfonates, 2-naphthalenesulfonates, nicotinates, nitrates, oxalates, pectinates, persulfates, 3-phenylpropionates, phosphates, picrates, pivalates, propionates, salicylates, succinates, sulfates (such as those formed with sulfuric acid), sulfonates (such as those mentioned herein), tartrates, thiocyanates, toluenesulfonates, undecanoates, and the like.

Exemplary basic salts (formed, for example, where the R substituents comprise an acidic moiety such as a carboxyl group) include ammonium salts, alkali metal salts such as sodium, lithium, and potassium salts, alkaline earth metal salts such as calcium and magnesium salts, salts with organic bases (for example, organic amines) such as benzathines, dicyclohexylamines, hydrabamines, N-methyl-D-glucamines, N-methyl-D-glucamides, t-butyl amines, and salts with amino acids such as arginine, lysine and the like. The basic nitrogen-containing groups may be quaternized with agents such as lower alkyl halides (e.g. methyl, ethyl, propyl, and butyl chlorides, bromides and iodides), dialkyl sulfates (e.g. dimethyl, diethyl, dibutyl, and diamyl sulfates), long chain halides (e.g. decyl, lauryl, myristyl and stearyl chlorides, bromides and iodides), aralkyl halides (e.g. benzyl and phenethyl bromides), and others.

Prodrugs and solvates of the compounds of the invention are also contemplated herein. The term "prodrug", as employed herein, denotes a compound which, upon administration to a subject, undergoes chemical conversion by metabolic or chemical processes to yield a compound of the Formula I, or a salt and/or solvate thereof. Solvates of the compounds of Formula I are preferably hydrates.

All stereoisomers of the present compounds, such as those which may exist due to asymmetric carbons on the R substituents of the compound of the formula I, including enantiomeric and diastereomeric forms, are contemplated within the scope of this invention. Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the IUPAC 1974 Recommendations.

The compounds of Formula I are typically employed as part of a pharmaceutical composition including a pharmaceutically acceptable carrier for the treatment of respiratory and non-respiratory diseases. The compounds employed for this purpose are typically administered in an amount of from about 0.01 to 100 mg/kg/day. The compounds of Formula I are especially effective in inhibiting the PDE7 enzyme. Additionally a subset of compounds are also effective at inhibiting PDE4.

The pharmaceutical composition comprising at least one compound of Formula I may be formulated, for example, by employing conventional solid or liquid vehicles or diluents, as well as pharmaceutical additives of a type appropriate to the mode of desired administration (for example, excipients, binders, preservatives, stabilizers, flavors, etc.) according to techniques such as those well known in the art of pharmaceutical formulation.

The compounds of Formula I may be administered by any suitable means, for example, orally, such as in the form of tablets, capsules, granules or powders; sublingually; bucally; parenterally, such as by subcutaneous, intravenous, intramuscular, or intrasternal injection or infusion techniques (e.g., as sterile injectable aqueous or non-aqueous solutions or suspensions); nasally such as by inhalation spray; topically, such as in the form of a cream or ointment; or rectally such as in the form of suppositories; in dosage unit formulations containing non-toxic, pharmaceutically acceptable vehicles or diluents. The present compounds may be based for immediate release or extended release by the use of suitable pharmaceutical compositions comprising the present compounds, or, particularly in the case of extended release, by the use of devices such as subcutaneous implants or osmotic pumps. The present compounds may also be administered liposomally.

Exemplary compositions for oral administration include suspensions which may contain, for example, microcrystalline cellulose for imparting bulk, alginic acid or sodium alginate as a suspending agent, methylcellulose as a viscosity enhancer, and sweeteners or flavoring agents such as those known in the art; and immediate release tablets which may contain, for example, microcrystalline cellulose, dicalcium phosphate, starch, magnesium stearate and/or lactose and/or other excipients, binders, extenders, disintegrants, diluents and lubricants such as those known in the art. The present compounds may also be delivered through the oral cavity by sublingual and/or buccal administration. Molded tablets, compressed tablets or freeze-dried tablets are exemplary forms which may be used. Exemplary compositions include those formulating the present compound(s) with fast dissolving diluents such as mannitol, lactose, sucrose and/or cyclodextrins. Also included in such formulations may be high molecular weight excipients such as celluloses (avicel) or polyethylene glycols (PEG). Such formulations may also include an excipient to aid mucosal adhesion such as hydroxy propyl cellulose (HPC), hydroxy propyl methyl cellulose (HPMC), sodium carboxy methyl cellulose (SCMC), maleic anhydride copolymer (e.g., Gantrez), and agents to control release such as polyacrylic copolymer (e.g., Carbopol 934). Lubricants, glidants, flavors, coloring agents and stabilizers may also be added for ease of fabrication and use.

Exemplary compositions for nasal aerosol or inhalation administration include solutions in saline which may contain, for example, benzyl alcohol or other suitable preservatives, absorption promoters to enhance bioavailability, and/or other solubilizing or dispersing agents such as those known in the art.

Exemplary compositions for parenteral administration include injectable solutions or suspensions which may contain, for example, suitable non-toxic, parenterally acceptable diluents or solvents, such as mannitol, 1,3-butanediol, water, Ringer's solution, an isotonic sodium chloride solution, or other suitable dispersing or wetting and suspending agents, including synthetic mono- or diglycerides, and fatty acids, including oleic acid.

Exemplary compositions for rectal administration include suppositories which may contain, for example, a suitable non-irritating excipient, such as cocoa butter, synthetic glyceride esters or polyethylene glycols, which are solid at ordinary temperatures, but liquefy and/or dissolve in the rectal cavity to release the drug.

Exemplary compositions for topical administration include a topical carrier such as Plastibase (mineral oil gelled with polyethylene).

The effective amount of a compound of the present invention may be determined by one of ordinary skill in the art, and includes exemplary dosage amounts for an adult human from about 0.01 to 100 mg/kg of body weight of active compound per day, which may be administered in a single dose or in the form of individual divided doses, such as from 1 to 4 times per day. It will be understood that the specific dose level and frequency of dosage for any particular subject may be varied and will depend upon a variety of factors including the activity of the specific compound employed, the metabolic stability and length of action of that compound, the species, age, body weight, general health, sex and diet of the subject, the mode and time of administration, rate of excretion, drug combination, and severity of the particular condition. Preferred subjects for treatment include animals, most preferably mammalian species such as humans, and domestic animals such as dogs, cats and the like, subject to leukocyte activation or respiratory cell-associated disorders.

METHODS OF PREPARATION

Compounds of Formula I may be prepared by reference to the methods illustrated in the following Schemes A through B. As shown therein the end product is a compound having the same structural formula as Formula I. It will be understood that any compound of Formula I may be produced by Scheme A and B by the suitable selection of appropriate substitution. Solvents, temperatures, pressures, and other reaction conditions may readily be selected by one of ordinary skill in the art. All documents cited are incorporated herein by reference in their entirety. Starting materials are commercially available or readily prepared by one of ordinary skill in the art. Constituents of compounds are as defined herein or elsewhere in the specification.

Compounds of formula I may be prepared from readily available starting materials by a number of methods known to one skilled in the art of organic chemistry and is illustrated in Scheme A1. An amine 1A is reacted with reagent 2A to provide guanidine 3A which is deprotected and freebased to yield guanidine 4A. Reaction with either a beta-keto ester 5A or a malonate 5A with heat with or without added base condenses to produce pyrimidine 6A. beta-Keto ester 5A or malonate 5A are either commercially available or readily prepared by methods well known in the literature. For examples see Advanced Organic Chemistry 3$^{rd}$ edition (1990, Plenum Press New York) Carey, F and Sundberg, R., chapter 2 section 2, and Comprehensive Organic Transformations, (1989 VCH publishers NY). This pyrimidine 6A is reacted with phosphorous oxychloride to produce intermediate pyrimidine 7A. Reaction with reagent 8A which may be an amine or an alcohol, a thiol or a sulfonamide on the presence of a suitable base to provide pyrimidines 9A, which are compounds of Formula I. In the case of pyrimidine 9A1, the chloro group may be replaced by an amine by reaction at elevated temperature, or, in some cases with the aid of a microwave apparatus, to produce pyrimidine 10 which are also compounds of Formula I.

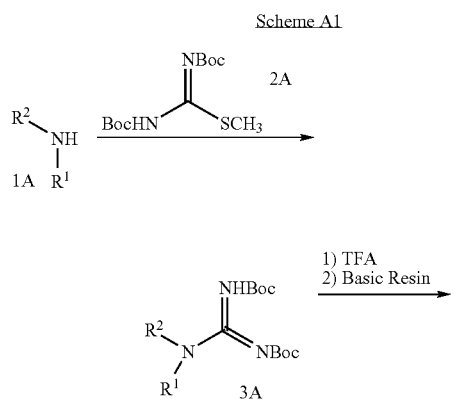

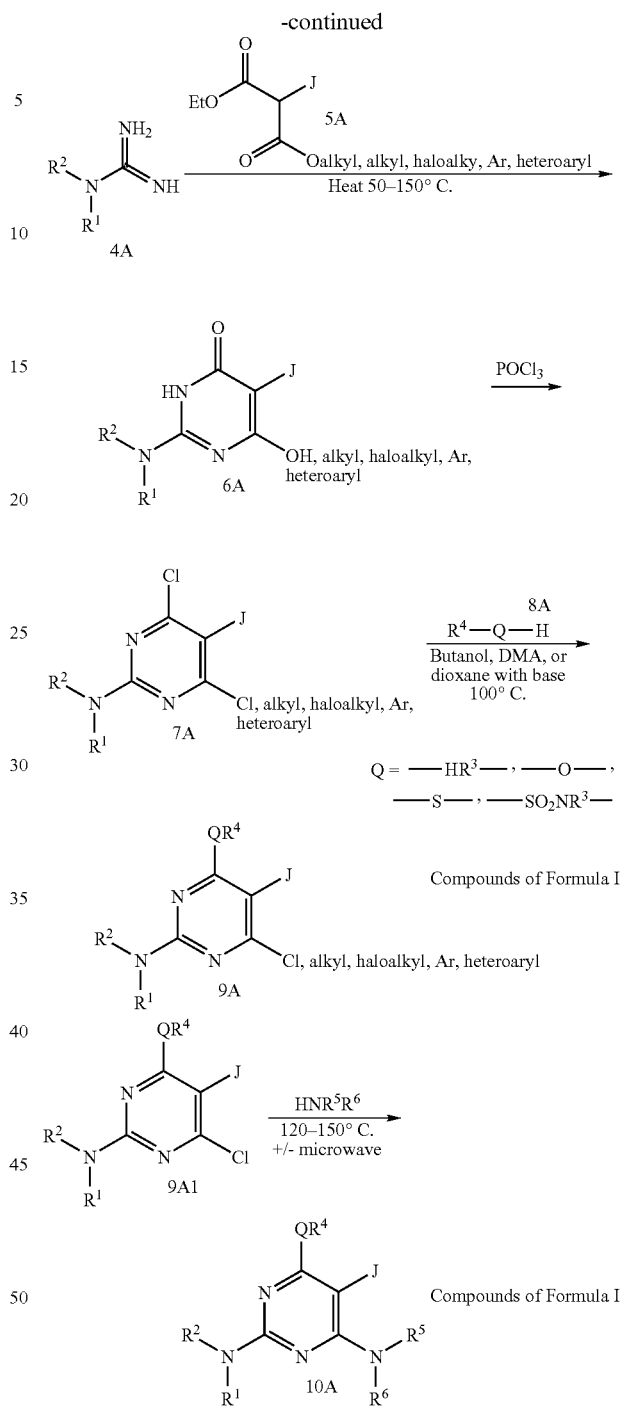

In some instances the intermediate guanidines 4A might be readily prepared by direct synthesis, an example of which is illustrated in scheme B1. alpha-Haloketone 1B is reacted with a thiobiuret such as 2B to provide the guanidine salt 3B. Intermediates 3B1 and 3B2 are of particular utility to this invention. The guanidine salt, if required nay liberated to its free base by treatment with a basic resin, or sodium hydroxide, sodium methoxide, or an amine base to provide intermediate 4B, which can be further elaborated to compounds of formula I as illustrated in scheme A1.

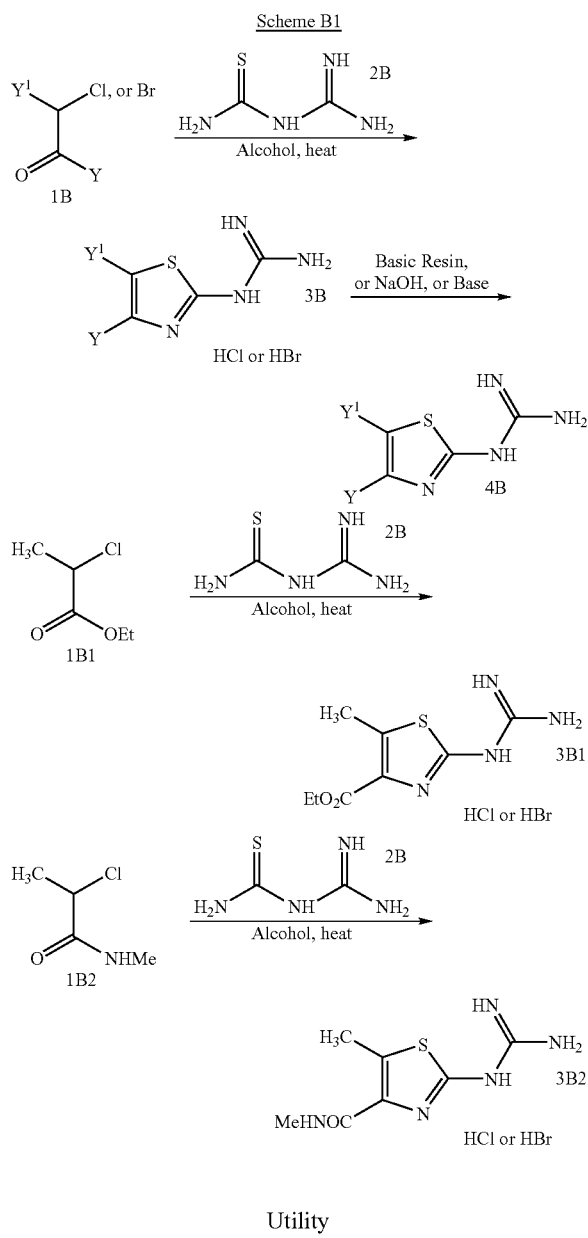

Scheme B1

Utility

Selective PDE7 inhibitors or dual PDE7-PDE4 inhibitors including compounds of formulas I, are useful in the treatment (including prevention, partial alleviation or cure) of leukocyte activation-associated disorders, which include (but are not limited to) disorders such as: transplant rejection (such as organ transplant, acute transplant, xenotransplant or heterograft or homograft such as is employed in burn treatment); protection from ischemic or reperfusion injury such as ischemic or reperfusion injury incurred during organ transplantation, myocardial infarction, stroke or other causes; transplantation tolerance induction; arthritis (such as rheumatoid arthritis, psoriatic arthritis or osteoarthritis); multiple sclerosis; respiratory and pulmonary diseases including but not limited to asthma, exercise induced asthma, chronic obstructive pulmonary disease (COPD), emphysema, bronchitis, and acute respiratory distress syndrome (ARDS); inflammatory bowel disease, including ulcerative colitis and Crohn's disease; lupus (systemic lupus erythematosis); graft vs. host disease; T-cell mediated hypersensitivity diseases, including contact hypersensitivity, delayed-type hypersensitivity, and gluten-sensitive enteropathy (Celiac disease); psoriasis; contact dermatitis (including that due to poison ivy); Hashimoto's thyroiditis; Sjogren's syndrome; Autoimmune Hyperthyroidism, such as Graves' Disease; Addison's disease (autoimmune disease of the adrenal glands); Autoimmune polyglandular disease (also known as autoimmune polyglandular syndrome); autoimmune alopecia; pernicious anemia; vitiligo; autoimmune hypopituatarism; Guillain-Barre syndrome; other autoimmune diseases; glomerulonephritis; serum sickness; uticaria; allergic diseases such as respiratory allergies (e.g., asthma, hayfever, allergic rhinitis) or skin allergies; scleracierma; mycosis fungoides; acute inflammatory and respiratory responses (such as acute respiratory distress syndrome and ishchemia/reperfusion injury); dermatomyositis; alopecia areata; chronic actinic dermatitis; eczema; Behcet's disease; Pustulosis palmoplanteris; Pyoderma gangrenum, Sezary's syndrome; atopic dermatitis; systemic schlerosis; and morphea.

The term "leukocyte activation-associated disorder" or "leukocyte activation-mediated disorder" as used herein includes each of the above referenced diseases or disorders. The compounds of the present invention are useful for treating the aforementioned exemplary disorders irrespective of their etiology.

Those present compounds which are dual PDE7/4 inhibitors may be more effective than either a selective PDE4 inhibitor or a selective PDE7 inhibitor in the above mentioned disease states, as a result of either additive or synergistic activity resulting from the combined inhibition of PDE7 and PDE4.

The present invention thus provides methods for the treatment of disorders as discussed above comprising the step of administering to a subject in need thereof of at least one selective PDE7 inhibitor or at least one dual PDE7-PDE4 inhibitor for the treatment of leukocyte activation-associated or leukocyte-activation mediated disease. Other therapeutic agents such as those described below may be employed with the compounds of the present invention. In the methods of the present invention, such other therapeutic agent(s) may be administered prior to, simultaneously with or following the administration of the compound(s) of the present invention.

The methods of treating diseases which would benefit from the inhibition of PDE7 or the inhibition of both PDE7-PDE4 by a dual agent may comprise administering compounds of Formula (I) alone or in combination with each other and/or other suitable therapeutic agents useful in treating such conditions such as: immunosuppressants such as, cyclosporins (e.g., cyclosporin A), anti-IL-1 agents, such as Anakinra, the IL-1 receptor antagonist, CTLA4-Ig, antibodies such as anti-ICAM-3, anti-IL-2 receptor (Anti-Tac), anti-CD45RB, anti-CD2, anti-CD3, anti-CD4, anti-CD80, anti-CD86, monoclonal antibody OKT3, agents blocking the interaction between CD40 and CD 154, such as antibodies specific for CD40 and/or CD154 (i.e., CD40L), fusion proteins constructed from CD40 and CD154 (CD40Ig and CD8-CD154), interferon beta, interferon gamma, methotrexate, FK506 (tacrolimus, Prograf), rapamycin (sirolimus or Rapamune)mycophenolate mofetil, leflunomide (Arava), azathioprine and cyclophosphamide, inhibitors, such as nuclear translocation inhibitors, of NF-kappa B function, such as deoxyspergualin (DSG), non-steroidal antiinflammatory drugs (NSAIDs) such as ibuprofen, cyclooxygenase-2 (COX-2) inhibitors such as celecoxib (Celebrex) and rofecoxib (Vioxx), or derivatives thereof, steroids such as prednisone or dexamethasone, gold compounds TNF-α inhibitors such as tenidap, anti-TNF antibodies or soluble TNF receptor such as etanercept (Enbrel), inhibitors of p-38 kinase such as BIRB-796, RO-3201195, VX-850, and VX-750, beta-2 agonists such as albuterol, levalbuterol (Xopenex), and salmeterol (Serevent) inhibitors of leukotriene synthesis such as montelukast (Singulair) and zariflukast (Accolate), and anticholinergic agents such as ipratropium bromide (Atrovent), PDEA inhibitors such as Arofyline, Cilomilast, Roflumilast, C-11294A, CDC-801, BAY-19-8004, Cipamfylline, SCH351591, YM-976, PD-189659, Mesiopram, Pumafentrine, CDC-998, IC-485, and KW-4490, PDE7 inhibitors such as IC242, (Lee, et. al. *PDE7A is expressed in human B-lymphocytes and is up-regulated by elevation of intracellular cAMP. Cell Signalling*, 14, 277–284, (2002)) and also include compounds disclosed in the following patent documents: WO 0068230, WO 0129049, WO 0132618, WO 0134601, WO 0136425, WO 0174786, WO 0198274, WO 0228847, U.S. Provisional Application Ser. No. 60/287,964, and U.S. Provisional Application Ser. No. 60/355,141 anti-cytokines such as anti-IL-1 mAb or IL-1 receptor agonist, anti-IL-4 or IL-4 receptor fusion proteins and PTK inhibitors such as those disclosed in the following U.S. Patents and Applications, incorporated herein by reference in their entirety: U.S Pat. No. 6,235,740, U.S. Pat. No. 6,239,133, U.S. application Ser. No. 60/065,042, filed Nov. 10, 1997, U.S. application Ser. No. 09/173,413, filed Oct. 15, 1998, and U.S. Pat. No. 5,990,109.

See the following documents and references cited therein: Hollenbaugh, D., Douthwright, J., McDonald, V., and Aruffo, A., "Cleavable CD40Ig fusion proteins and the binding to sgp39", *J. Immunol. Methods* (Netherlands), 188(1), p. 1–7 (Dec. 15, 1995); Hollenbaugh, D., Grosmaire, L. S., Kullas, C. D., Chalupny, N. J., Braesch-Andersen, S., Noelle, R. J., Stamenkovic, I., Ledbetter, J. A., and Aruffo, A., "The human T cell antigen gp39, a member of the TNF gene family, is a ligand for the CD40 receptor: expression of a soluble form of gp39 with B cell co-stimulatory activity", *EMBO J* (England), 11(12), p 4313–4321 (December 1992); and Moreland, L. W. et al., "Treatment of rheumatoid arthritis with a recombinant human tumor necrosis factor receptor (p75)-Fc fusion protein, *New England J. of Medicine*, 337(3), p. 141–147 (1997).

Compounds present invention (especially selective PDE 7 inhibitors) may also be employed in combination with PDE 4 inhibitors. Examples of selective PDE4 inhibitors currently in development, which can be used in combination with compounds of the present invention include Arofyline, Cilomilast, Roflumilast, C-11294A, CDC-801, BAY-19-8004, Cipamfylline, SCH351591, YM-976, PD-189659, Mesiopram, Pumafentrine, CDC-998, IC-485, and KW-4490.

The above other therapeutic agents, when employed in combination with the compounds of the present invention, may be used, for example, in those amounts indicated in the Physicians' Desk Reference (PDR) or as otherwise determined by one of ordinary skill in the art.

Use of the compounds of the present invention as encompassed by formula I in treating leukocyte activation-associated disorders is exemplified by, but is not limited to, treating a range of disorders such as: transplant (such as organ transplant, acute transplant, xenotransplant or heterograft or homograft (such as is employed in burn treatment)) rejection; protection from ischemic or reperfusion injury such as ischemic or reperfusion injury incurred during organ transplantation, myocardial infarction, stroke or other causes; transplantation tolerance induction; arthritis (such as rheumatoid arthritis, psoriatic arthritis or osteoarthritis); multiple sclerosis; respiratory and pulmonary diseases including but not limited to asthma, exercise induced asthma, chronic obstructive pulmonary disease (COPD), emphysema, bronchitis, and acute respiratory distress syndrome (ARDS); inflammatory bowel disease, including ulcerative colitis and Crohn's disease; lupus (systemic lupus erythematosis); graft vs. host disease; T-cell mediated hypersensitivity diseases, including contact hypersensitivity, delayed-type hypersensitivity, and gluten-sensitive enteropathy (Celiac disease); psoriasis; contact dermatitis (including that due to poison ivy); Hashimoto's thyroiditis; Sjogren's syndrome; Autoimmune Hyperthyroidism, such as Graves' Disease; Addison's disease (autoimmune disease of the adrenal glands); Autoimmune polyglandular disease (also known as autoimmune polyglandular syndrome); autoimmune alopecia; pernicious anemia; vitiligo; autoimmune hypopituatarism; Guillain-Barre syndrome; other autoimmune diseases; glomerulonephritis; serum sickness; uticaria; allergic diseases such as respiratory allergies (asthma, hayfever, allergic rhinitis) or skin allergies; scleracierma; mycosis fungoides; acute inflammatory and respiratory responses (such as acute respiratory distress syndrome and ishechemia/reperfusion injury); dermatomyositis; alopecia areata; chronic actinic dermatitis; eczema; Behcet's disease; Pustulosis palmoplanteris; Pyoderma gangrenum; Sezary's syndrome; atopic dermatitis; systemic schlerosis; and morphea.

The combined activity of the present compounds towards T-cells and other PDE7-expressing cells may be of value in the treatment of any of the aforementioned disorders. Additionally those present compounds which are dual PDE4/7 inhibitors may be more effective than either a selective PDE4 inhibitor or a selective PDE7 inhibitor in the above mentioned disease states.

In a particular embodiment, the compounds of the present invention are useful for the treatment of the aforementioned exemplary disorders irrespective of their etiology, for example, for the treatment of transplant rejection, rheumatoid arthritis, multiple sclerosis, chronic obstructive pulmonary disease, inflammatory bowel disease, lupus, graft v. host disease, T-cell mediated hypersensitivity disease, psoriasis, Hashimoto's thyroiditis, Guillain-Barre syndrome, cancer, contact dermatitis, allergic disease such as allergic rhinitis, asthma, ischemic or reperfusion injury, respiratory diseases such as asthma, COPD and bronchitis or atopic dermatitis whether or not associated with leukocyte activation.

PDE-containing Cell Lysates

Hut78 cells were grown in 10% FCS in Iscoves Modified Dulbecco's Medium (Gibco BRL-Life Technologies, Grand Island, N.Y.) with antibiotics. Cells were centrifuged and resuspended in four volumes of [40 mM Tris (pH 7.5)/50 μM EDTA/200 uM PMSF with a cocktail of Protease inhibitors (Boehringher Mannheim, Indianapolis, Ind.)] at 4C. Cells were homogenized using a Virtis homogenizer, and the lysate was centrifuged twice for 15 min at 15,000×g. Glycerol was added to a final volume of 50% for storage at −20C.

SPA Assay

Inhibition of PDE activity in Hut78 cell lysate was determined using an SPA specific for cAMP (Amersham Pharmacia Biotech, Buckinghamshire, UK) according to the manufacturers instructions with minor modifications. Enzyme assays were performed at room temperature in the presence of 50 mM Tris HCl, pH7.5, containing 8.3 mM MgCl$_2$, 1.7 mM EGTA and 0.5 mg/mL BSA. Each assay was performed in a 100 μL reaction volume in 96 well microtitre plates containing the above buffer, 0.3 ul of Hut78 cell lysate treated with 2 uM Zardaverine to inhibit PDE3 and PDE4, 0.05 uCi of [5',8-$_3$H] Adenosine 3',5'-cyclic phosphate as an ammonium salt for 20 min. The reaction was terminated by the addition of 50 μl PDE SPA beads (1 mg) water with 10 mM cold cAMP (Sigma, St. Louis Mo.). The reaction mix was allowed to settle for 20 minutes before counting in a Top Count-NXT scintillation counter (Packard BioScience, Meriden, Conn.). For individual PDE enzymes other than PDE7, the assay was essentially unchanged except that $^3$H-cyclic GMP was used as the substrate for PDE1, PDE5 and PDE6. The following PDEs/activators and enzyme sources were used: PDE1, bovine (Sigma St Louis), calmodulin; PDE2, rat kidney, cGMP; PDE3, human platelet; PDE4, rat kidney; PDE5, human platelet, and PDE6, bovine retina.

T Cell Proliferation Assay

Peripheral blood mononuclear cells (PBMC) were isolated from whole blood by density gradient centrifugation over Lymphoprep, 1.077. Cells were plated into 96 well U-bottom plates at 2.5×10$_5$ cells/well in 10% FBS RPMI 1640 (Life Technologies/Gibco-BRL) containing 10 ug/ml anti-CD3 (G19-4, Bristol-Myers Squibb P.R.I., Princeton, N.J.) and 1 ug/ml anti-CD28 (9.3, Bristol-Myers Squibb P.R.I.) in the presence and absence of inhibitors. DMSO (used as a solvent for inhibitors) was added to the medium at 0.1% final concentration. The total volume per well was 200 μL. Cells were incubated at 37C 5% CO2 for 3 days, at which time 0.5 μCi of $^3$H-thymidine was added to each well. Six hours following the addition of $^3$H-thymidine, the plates were harvested onto filter plates, 30 ul EcoLite scintillant (ICN, Costa Mesa, Calif.) was added per well, and plates read on a Top Count-NXT scintillation counter.

TNFα Secretion Assay

The ability of compounds to inhibit the production and secretion of TNFα from leukocytes was performed using either PBMC (obtained as described above) or the THP-1 cell line as a source of monocytes. Compounds were diluted in RPMI 1640 supplemented with 10% FBS and DMSO at a final concentration of 0.2%. Cells (2×10$^5$/well in U-bottom 96 well plates) were pre-incubated with compounds for 30 min at 37 C prior to addition of lipopolysaccharide (LPS) at a final concentration of 6.25 ng/ml in a total volume of 200 μL. After 4 h at 37C, 50 μL of supernatant was carefully aspirated for detection of soluble TNFα. Soluble TNFα was detected by ELISA developed by R&D Systems (Minneapolis, Minn.) according to the manufacturers instructions.

EXAMPLES

The following examples illustrate preferred embodiments of the present invention and do not limit the scope of the present invention which is defined in the claims. Abbreviations employed in the Examples are defined below. Compounds of the Examples are identified by the example and step in which they are prepared (e.g., "A1.1" denotes the title compound of step 1 of Example A1), or by the example only where the compound is the title compound of the example (for example, "A2" denotes the title compound of Example A2).

| Abbreviations | |
|---|---|
| Ac | Acetyl |
| AcOH | Acetic acid |
| aq. | Aqueous |
| CDI | Carbonyldiimidazole |
| Bn | Benzyl |
| Bu | Butyl |
| Boc or BOC | tert-butoxycarbonyl |
| DMAP | Dimethylaminopyridine |
| DMA | N,N-Dimethylacetamide |
| DMF | dimethylformamide |
| DMSO | Dimethylsulfoxide |
| EDC | 1-(3-Dimethylaminopropyl)-3-ethylcarbodiimide hydrochloride |
| EtOAc | Ethyl acetate |
| Et | Ethyl |
| EtOH | Ethanol |
| H | Hydrogen |
| h | Hours |
| i | iso |
| HPLC | High pressure liquid chromatography |
| HOAc | Acetic acid |
| Lawesson's Reagent | [2,4-bis(4-methoxyphenyl)-1,3-dithia-2,4-diphosphetane-2-4-disufide |
| LC | liquid chromatography |
| Me | Methyl |
| MeOH | Methanol |
| min. | Minutes |
| M$^+$ | (M + H)$^+$ |
| M$^{+1}$ | (M + H)$^+$ |
| MS | Mass spectrometry |
| n | normal |
| ON | over night |
| Pd/C | Palladium on carbon |
| Ph | Phenyl |
| Pr | Propyl |
| Ret Time | Retention time |
| rt or RT | Room temperature |
| sat. | Saturated |
| S-Tol-BINAP | (S)-(−)-2,2'-Bis(di-p-tolylphosphino)-1,1'-binapthyl |
| t | tert |
| TFA | Trifluoroacetic acid |
| THF | Tetrahydrofuran |
| YMC | YMC Inc, Wilmington, NC 28403 |

HPLC conditions used to determine retention times; 2 min gradient 0–100% B in A(A; 0.1% TFA in 90/10 water/methanol; B; 0.1% TFA in 10/90 water/methanol) using a YMC turbopack column at with a detection wavelength of 220 nanometeres or 254 nanometers.

Examples A1

2-[[4-[[[4-(Aminosulfonyl)phenyl]methyl]amino]-6-(4-methyl-1-piperazinyl)-2-pyrimidinyl]amino]-4-methyl-5-thiazolecarboxylic acid ethyl ester

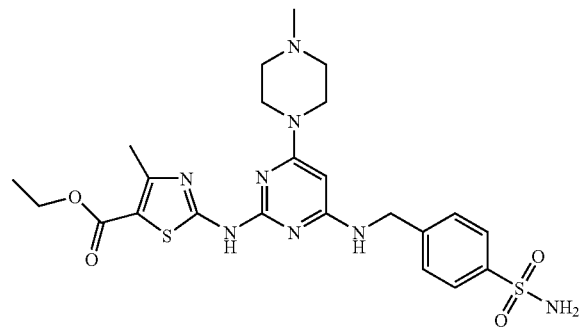

A1.1: 2-[(Aminoiminomethyl)amino]-4-methyl-5-thiazolecarboxylic acid ethyl ester

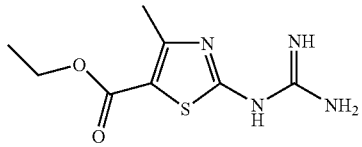

A solution of 2-imino-4-thiobiuret (20.0 g, 0.17 mol), 2-chloroacetoacetate (28 g, 0.17 mol) in ethanol (500 mL) was heated to 100° C. for 4 hours. The reaction mixture was concentrated to half volume and poured into 1 liter of 1N NaOH. The white solid which precipitated out was collected by filtration and dried under vacuum to yield A1.1 (30.5 g, 79%). $^1$H-NMR (DMSO-$d_6$) δ: 4.22 (2H, q, J=7 Hz), 2.50 (3H, merge with DMSO), 1.26 (3H, t, J=7 Hz). HPLC: 97.7%, ret. time=1.619 min., LC/MS (M+H)$^+$=229.

A1.2: 2-[(4-6(1H,5H)-pyrimidinedion-2-yl)amino]-4-methyl-5-thiazolecarboxylic acid ethyl ester

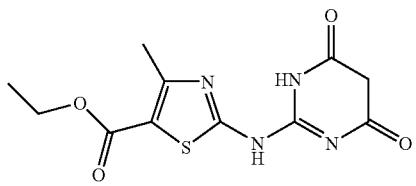

To a solution of A1.1 (5.7 g, 25 mmol) in ethanol (250 mL) was added 21% sodium ethoxide in ethanol (7.75 mL, 25 mmol). The reaction mixture was heated in an oil bath at 100° C. for 15 minutes during which time most, but not all, of the material had dissolved, and Diethylmalonate (3.8 g, 25 mmol) was added. The reaction mixture was maintained in an oil bath to 100° C. for 2 hours. An additional 4 mL of 21% sodium ethoxide in ethanol and additional 2 mL of diethylmalonate were added and the reaction mixture refluxed for an additional 2 hours after which HPLC analysis indicated only a trace amount of starting material remained. The reaction mixture was allowed to cool to room temperature and the copious crystals which precipitated out were collected by filtration and dried to yield A1.2 solvated with 1 molecule of ethanol (7.6 g, 89% based on solvate). $^1$H-NMR (DMSO-$d_6$) δ: 9.75 (1H, br s) 4.45 (1H, t, J=4 Hz), 4.14 (2H, q, J=7 Hz), 3.45 (2H, m) 2.56 (3H, s), 1.29(3H, t, J=7 Hz). 1.05(3H, t, J=7 Hz), HPLC: 91.5%, ret. time=2.836 min., LC/MS (M+H)$^+$=297.

A1.3: 2-[(4-6-Dichloropyrimidin-2-yl)amino]-4-methyl-5-thiazolecarboxylic acid ethyl ester

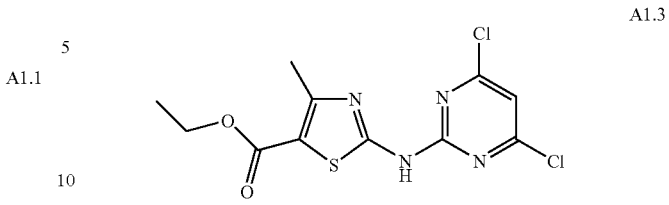

A suspension of A1.2 (7.6 g, 22 mmol) in POCl$_3$ (54 ml) was heated at 100° C. for 16 hours and then it was cooled down to RT which was poured into 500 g of ice. After the ice melted the solid was collected by filtration and triturated with hot methanol. The solid was then dried under vacuum to yield. A1.3 (6.2 g, 84%). $^1$H-NMR (DMSO-$d_6$) δ: 7.55 (1H, s), 4.27 (2H, q, J=7 Hz), 2.56 (3H, s), 1.29 (3H, t, J=7 Hz). HPLC: 97%, ret. time=3.929 min., LC/MS (M+H)$^+$=333.

A1.4: 2-[[4-[[[4-(Aminosulfonyl)phenyl]methyl]amino]-6-chloro-2-pyrimidinyl]amino]-4-methyl-5-thiazolecarboxylic acid ethyl ester

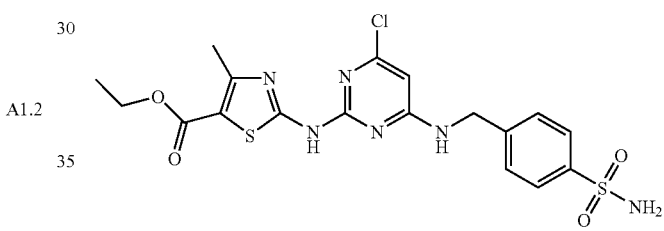

A suspension solution of A1.3 (33 mg, 0.1 mmol), p-aminomethyl-benzenesulfonamide•HCl (24 mg, 0.106 mmol) and diisopropylethylamine (58 mg, 0.45 mmol) in n-butanol (2 mL) was heated to 105° C. for 2 hours and then it was cooled down to RT. The solid was precipitated out which was collected with filtration to yield A1.4 (31.8 mg, 66%). $^1$H-NMR (DMSO-$d_6$) δ: 7.77 (2H, d, J=8 Hz), 7.52 (2H, d, J=8 Hz), 7.31 (2H, s), 6.27 (1H, s), 4.81 (2H, m), 4.22 (2H, q, J=7 Hz), 2.50 (3H, merge with DMSO), 1.26 (3H, t, J=7 Hz). HPLC: 96%, ret. time=3.232 min., LC/MS (M+H)$^+$=483.

A1.5: 2-[[4-[[[4-(Aminosulfonyl)phenyl]methyl]amino]-6-(4-methyl-1-piperazinyl)-2-pyrimidinyl]amino]-4-methyl-5-thiazolecarboxylic acid ethyl ester A solution of A1.4 (21.8 mg, 0.045 mmol) and 1-methylpiperazine (90 mg, 0.9 mmol) in dimethylacetamide (0.5 ml) was heated to 120 to 130° C. for half an hour. The reaction mixture was concentrated to yield a crude product which was added 1 mL of methanol and stirred for 20 minutes. The solid was precipitated out which was collected with filtration to yield A1 (12.5 mg, 51%). $^1$H-NMR (DMSO-$d_6$) δ: 11.17 (1H, s), 7.75 (2H, d, J=8 Hz), 7.50 (2H, d, J=8 Hz), 7.28 (2H, s), 5.40 (1H, s), 4.65 (2H, m), 4.19 (2H, q, J=7 Hz), 3.48 (4H, m), 3.17 (3H, d, J=5 Hz), 2.50 (3H, merge with DMSO), 2.10–2.50 (4H, m), 1.26 (3H, t, J=7 Hz). HPLC: 88.3%, ret. time=1.979 min., LC/MS (M+H)$^+$=547.

Example A2

2-[[4-[[(3,4-Dimethoxyphenyl)methyl]amino]-6-(1-piperazinyl)-2-pyrimidinyl]amino]-4-methyl-5-thiazolecarboxylic acid ethyl ester trifluoroacetate salt

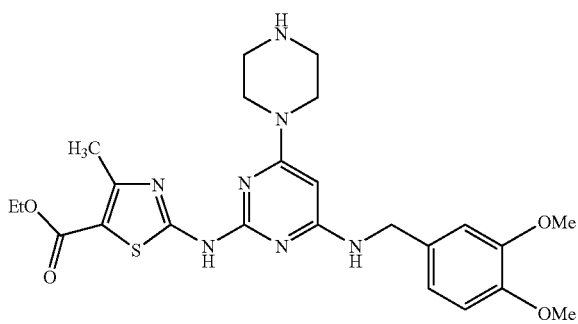

A2.1: 2-[[4-chloro-6-(4-tertbutyloxycarbonyl-1-piperazinyl)-2-pyrimidinyl]amino]-4-methyl-5-thiazolecarboxylic acid ethyl ester

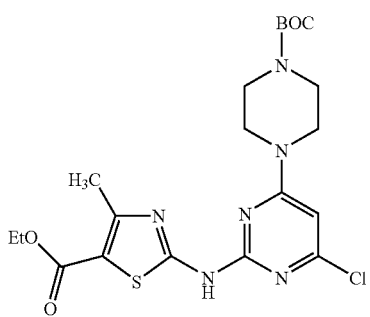

A suspension solution of A1.3 (800 mg, 2.4 mmol), 1-tert-butoxycarbonylpiperazine (470 mg, 2.5 mmol) and diisopropylethylamine (1.8 ml, 10.6 mmol) in n-butanol (16 mL) was heated to 105° C. for 3 hours. After cooling to room temperature, the precipitated solid was collected by filtration and washed with methanol to yield A2.1 (1.1 g, 94%). $^1$H-NMR (DMSO-$d_6$) δ: 6.61 (1H, s), 4.22 (2H, q, J=7 Hz), 3.75 (1H, br. s), 3.45 (4H, br. s),3.30 (4H, br. s), 2.50 (3H, merge with DMSO), 1.43 (9H, s), 1.28 (3H, t, J=7 Hz). HPLC: 95%, ret. time=3.320 min., LC/MS (M+H)$^+$=483.

A2.2: 2-[[4-[[(3,4-Dimethoxyphenyl)methyl]amino]-6-(4-tertbutyloxycarbonyl-1-piperazinyl)-2-pyrimidinyl]amino]-4-methyl-5-thiazolecarboxylic acid ethyl ester

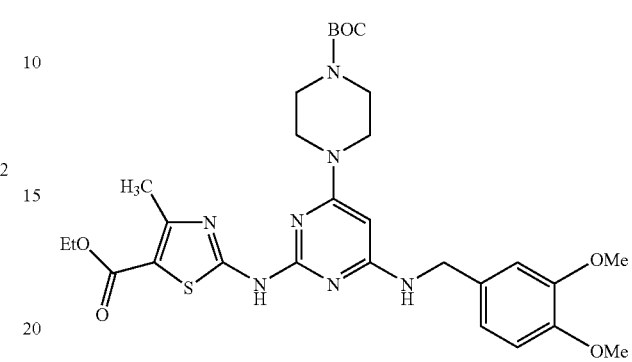

A solution of A2.1 (40.0 mg, 0.08 mmol) and veratrylamine (30.0 mg, 0.18 mmol) in n-butanol (0.5 ml) was heated to 130° C. overnight. After cooling to room temperature, the precipitated solid was collected by filtration and washed with methanol to yield A2.2 (37.2 mg, 73%). $^1$H-NMR (DMSO-$d_6$) δ: 6.99 (1H, s), 6.88 (2H, s), 5.39 (1H, s), 4.48 (1H, br. s),4.18 (2H, q, J=7 Hz), 3.72 (3H, s), 3.71 (3H, s), 3.51 (4H, br. s), 3.40 (4H, br. s), 2.50 (3H, merge with DMSO), 1.42 (9H, s), 1.24 (3H, t, J=7 Hz). HPLC: 95%, ret. time=3.080 min., LC/MS (M+H)$^+$=614.

A2.3: 2-[[4-[[(3,4-Dimethoxyphenyl)methyl]amino]-6-(1-piperazinyl)-2-pyrimidinyl]amino]-4-methyl-5-thiazolecarboxylic acid ethyl ester trifluoroacetate salt Trifluoroacetic acid (10% solution in dichloromethane, 0.6 ml) was added in one portion to a stirred solution of compound A2.2 (21.3 mg, 0.035 mmol). After stirring for 2 hours at room temperature, diethyl ether was added (2 ml) and the solution was concentrated in vacuo. Two subsequent additions of diethyl ether (2×2 ml) followed by concentration in vacuo left the trifluoroacetic acid salt of compound A2. HPLC: 95%, ret. time=2.020 min., LC/MS (M+H)$^+$=514.

Examples A3–A214

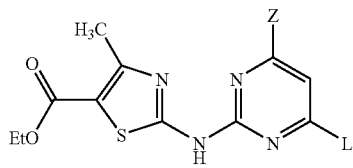

Examples A3 to A214 were prepared in a similar manner to that used for Example A1 or A2 utilizing the appropriate amines. Examples A61 and A62 used only a single amine addition step as in A2.1, substituting the appropriate amine. Example A63 was prepared in a manner similar to step A1.5 except that sodium ethoxide was used in place of an amine.

TABLE A

| Ex. | L | Z | Name | HPLC Retention[a] (min) | MS Reported |
|---|---|---|---|---|---|
| A3 | 4-aminosulfonylbenzyl-NH- | piperazinyl | 2-[[4-[[[4-(Aminosulfonyl)phenyl]methyl]amino]-6-(1-piperazinyl)-2-pyrimidinyl]amino]-4-methyl-5-thiazolecarboxylic acid ethyl ester | 1.98 | 533.18 |
| A4 | 4-methylsulfonylbenzyl-NH- | piperazinyl | 4-Methyl-2-[[4-[[[4-(methylsulfonyl)phenyl]methyl]amino]-6-(1-piperazinyl)-2-pyrimidinyl]amino]-5-thiazolecarboxylic acid ethyl ester | 1.05 | 532.36 |
| A5 | 4-methoxybenzyl-NH- | piperazinyl | 2-[[4-[[(4-Methoxyphenyl)methyl]amino]-6-(1-piperazinyl)-2-pyrimidinyl]amino]-4-methyl-5-thiazolecarboxylic acid ethyl ester | 2.15 | 484.56 |
| A6 | 3-methoxybenzyl-NH- | piperazinyl | 2-[[4-[[(3-Methoxyphenyl)methyl]amino]-6-(1-piperazinyl)-2-pyrimidinyl]amino]-4-methyl-5-thiazolecarboxylic acid ethyl ester | 1.50 | 484.16 |
| A7 | 2-methoxybenzyl-NH- | piperazinyl | 2-[[4-[[(2-Methoxyphenyl)methyl]amino]-6-(1-piperazinyl)-2-pyrimidinyl]amino]-4-methyl-5-thiazolecarboxylic acid ethyl ester | 1.51 | 484.16 |
| A8 | 3,4,5-trimethoxybenzyl-NH- | piperazinyl | 4-Methyl-2-[[4-(1-piperazinyl)-6-[[(3,4,5-trimethoxyphenyl)methyl]amino]-2-pyrimidinyl]amino]-5-thiazolecarboxylic acid ethyl ester | 1.44 | 544.19 |
| A9 | 2-ethoxybenzyl-NH- | piperazinyl | 2-[[4-[[(2-Ethoxyphenyl)methyl]amino]-6-(1-piperazinyl)-2-pyrimidinyl]amino]-4-methyl-5-thiazolecarboxylic acid ethyl ester | 2.29 | 498.64 |
| A10 | 2,5-dimethoxybenzyl-NH- | piperazinyl | 2-[[4-[[(2,5-Dimethoxyphenyl)methyl]amino]-6-(1-piperazinyl)-2-pyrimidinyl]amino]-4-methyl-5-thiazolecarboxylic acid ethyl ester | 2.22 | 514.59 |
| A11 | 3,5-dimethoxybenzyl-NH- | piperazinyl | 2-[[4-[[(3,5-Dimethoxyphenyl)methyl]amino]-6-(1-piperazinyl)-2-pyrimidinyl]amino]-4-methyl-5-thiazolecarboxylic acid ethyl ester | 1.54 | 514.18 |

TABLE A-continued

| Ex. | L | Z | Name | HPLC Retention[a] (min) | MS Reported |
|---|---|---|---|---|---|
| A12 | 2,6-dimethylbenzyl-NH- | piperazinyl | 2-[[4-[[(2,6-Dimethylphenyl)methyl]amino]-6-(1-piperazinyl)-2-pyrimidinyl]amino]-4-methyl-5-thiazolecarboxylic acid ethyl ester | 1.65 | 482.15 |
| A13 | 4-(methoxycarbonyl)benzyl-NH- | piperazinyl | 2-[[4-[[[4-(Methoxycarbonyl)phenyl]methyl]amino]-6-(1-piperazinyl)-2-pyrimidinyl]amino]-4-methyl-5-thiazolecarboxylic acid ethyl ester | 1.53 | 512.17 |
| A14 | 3-bromobenzyl-NH- | piperazinyl | 2-[[4-[[(3-Bromophenyl)methyl]amino]-6-(1-piperazinyl)-2-pyrimidinyl]amino]-4-methyl-5-thiazolecarboxylic acid ethyl ester | 1.68 | 532.04 |
| A15 | 1,3-benzodioxol-5-ylmethyl-NH- | piperazinyl | 2-[[4-[(1,3-Benzodioxol-5-ylmethyl)amino]-6-(1-piperazinyl)-2-pyrimidinyl]amino]-4-methyl-5-thiazolecarboxylic acid ethyl ester | 2.13 | 498.48 |
| A16 | 3-pyridinylmethyl-N(CH3)- | piperazinyl | 4-Methyl-2-[[4-[methyl(3-pyridinylmethyl)amino]-6-(1-piperazinyl)-2-pyrimidinyl]amino]-5-thiazolecarboxylic acid ethyl ester | 1.71 | 469.55 |
| A17 | 4-(1,2,3-thiadiazol-4-yl)benzyl-NH- | piperazinyl | 4-Methyl-2-[[4-(1-piperazinyl)-6-[[[4-(1,2,3-thiadiazol-4-yl)phenyl]methyl]amino]-2-pyrimidinyl]amino]-5-thiazolecarboxylic acid ethyl ester | 2.18 | 538.42 |
| A18 | 3-(cyclopentyloxy)-4-methoxybenzyl-NH- | piperazinyl | 2-[[4-[[[3-(Cyclopentyloxy)-4-methoxyphenyl]methyl]amino]-6-(1-piperazinyl)-2-pyrimidinyl]amino]-4-methyl-5-thiazolecarboxylic acid ethyl ester | 2.46 | 568.56 |
| A19 | benzyl-NH- | piperazinyl | 4-Methyl-2-[[4-[(phenylmethyl)amino]-6-(1-piperazinyl)-2-pyrimidinyl]amino]-5-thiazolecarboxylic acid ethyl ester | 2.13 | 454.53 |

TABLE A-continued

| Ex. | L | Z | Name | HPLC Retention[a] (min) | MS Reported |
|---|---|---|---|---|---|
| A20 | 3,4,5-trimethoxybenzyl-NH- | 4-methylpiperazin-1-yl | 4-Methyl-2-[[4-(4-methyl-1-piperazinyl)-6-[[(3,4,5-trimethoxyphenyl)methyl]amino]-2-pyrimidinyl]amino]-5-thiazolecarboxylic acid ethyl ester | 1.19 | 558.49 |
| A21 | piperazin-1-yl | 4-hydroxypiperidin-1-yl | 2-[[4-(4-Hydroxy-1-piperidinyl)-6-[[[4-(methylsulfonyl)phenyl]methoxy]-amino]-2-pyrimidinyl]-amino]-4-methyl-5-thiazolecarboxlic acid ethyl ester | 1.27 | 547.20 |
| A22 | 4-(methylsulfonyl)benzyl-NH- | (1-ethylpyrrolidin-2-yl)methyl-NH- | 4-Methyl-2-[[4-[[2-(1-methylethoxy)ethyl]amino]-6-[[[4-(methylsulfonyl)phenyl]-methyl]amino]-2-pyrimidinyl]-amino]-5-thiazolecarboxylic acid ethyl ester | 1.13 | 574.39 |
| A23 | 4-(methylsulfonyl)benzyl-NH- | 3-(aminocarbonyl)piperidin-1-yl | 2-[[4-[3-(Aminocarbonyl)-1-piperidinyl]-6-[[[4-(methylsulfonyl)phenyl]methyl]-amino]-2-pyrimidinyl]amino]-4-methyl-5-thiazolecarboxylic acid ethyl ester | 1.26 | 574.33 |
| A24 | 4-(methylsulfonyl)benzyl-NH- | 2-(1H-imidazol-4-yl)ethyl-NH- | 2-[[4-[[2-(1H-imidazol-4-yl)ethyl]amino]-6-[[[4-(methylsulfonyl)phenyl]methyl]-amino]-2-pyrimidinyl]amino]-4-methyl-5-thiazolecarboxylic acid ethyl ester | 1.13 | 557.32 |
| A25 | 4-(methylsulfonyl)benzyl-NH- | 3-(morpholin-4-yl)propyl-NH- | 4-Methyl-2-[[4-[[[4-(methylsulfonyl)phenyl]methyl]-amino]-6-[[3-(4-morpholinyl)propyl]amino]-2-pyrimidinyl]amino]-5-thiazolecarboxylic acid ethyl ester | 1.13 | 590.37 |
| A26 | 4-(methylsulfonyl)benzyl-NH- | 2-methoxy-1-methylethyl-NH- | 2-[[4-[(2-Methoxy-1-methylethyl)amino]-6-[[[4-(methylsulfonyl)phenyl]methyl]-amino]-2-pyrimidinyl]amino]-4-methyl-5-thiazolecarboxylic acid ethyl ester | 1.34 | 535.35 |
| A27 | 4-(methylsulfonyl)benzyl-NH- | (tetrahydrofuran-2-yl)methyl-NH- | 4-Methyl-2-[[4-[[[4-(methylsulfonyl)phenyl]methyl]-amino]-6-[[(tetrahydro-2-furanyl)methyl]amino]-2-pyrimidinyl]amino]-5-thiazolecarboxylic acid ethyl ester | 1.35 | 547.36 |

TABLE A-continued

| Ex. | L | Z | Name | HPLC Retention[a] (min) | MS Reported |
|---|---|---|---|---|---|
| A28 | H3C-S(O)(O)-C6H4-CH2-NH- | 4-(2-hydroxyethyl)piperazin-1-yl | 2-[[4-[4-(2-Hydroxyethyl)-1-piperazinyl]-6-[[[4-(methylsulfonyl)phenyl]methyl]amino]-4-methyl-5-thiazolecarboxylic acid ethyl ester | 1.60[a] | 575.21 |
| A29 | H3C-S(O)(O)-C6H4-CH2-NH- | 2-(aminocarbonyl)pyrrolidin-1-yl | 2-[[4-[2-(Aminocarbonyl)-1-pyrrolidinyl]-6-[[[4-(methylsulfonyl)phenyl]methyl]amino]-2-pyrimidinyl]amino]-4-methyl-5-thiazolecarboxylic acid ethyl ester | 1.41[a] | 560.14 |
| A30 | H3C-S(O)(O)-C6H4-CH2-NH- | N-methyl-N-(pyridin-3-ylmethyl)amino | 4-Methyl-2-[[4-[methyl(3-pyridinylmethyl)amino]-6-[[[4-(methylsulfonyl)phenyl]methyl]amino]-2-pyrimidinyl]amino]-5-thiazolecarboxylic acid ethyl ester | 1.28[a] | 568.14 |
| A31 | H3C-S(O)(O)-C6H4-CH2-NH- | 4-(hydroxymethyl)piperidin-1-yl | 2-[[4-[4-(Hydroxymethyl)-1-piperidinyl]-6-[[[4-(methylsulfonyl)phenyl]methyl]amino]-2-pyrimidinyl]amino]-4-methyl-5-thiazolecarboxylic acid ethyl ester | 1.33 | 561.35 |
| A32 | H3C-S(O)(O)-C6H4-CH2-NH- | N-[2-(diethylamino)ethyl]-N-methylamino | 2-[[4-[[2-(Diethylamino)ethyl]methylamino]-6-[[[4-(methylsulfonyl)phenyl]methyl]amino]-2-pyrimidinyl]amino]-4-methyl-5-thiazolecarboxylic acid ethyl ester | 1.33 | 576.17 |
| A33 | H3C-S(O)(O)-C6H4-CH2-NH- | [3-(2-oxo-1-pyrrolidinyl)propyl]amino | 4-Methyl-2-[[4-[[[4-(methylsulfonyl)phenyl]methyl]amino]-6-[[3-(2-oxo-1-pyrrolidinyl)propyl]amino]-2-pyrimidinyl]amino]-5-thiazolecarboxylic acid ethyl ester | 1.51 | 588.12 |
| A34 | H3C-S(O)(O)-C6H4-CH2-NH- | 3-(hydroxymethyl)piperidin-1-yl | 2-[[4-[3-(Hydroxymethyl)-1-piperidinyl]-6-[[[4-(methylsulfonyl)phenyl]methyl]amino]-2-pyrimidinyl]amino]-4-methyl-5-thiazolcarboxylic acid ethyl ester | 1.58[a] | 561.18 |
| A35 | H3C-S(O)(O)-C6H4-CH2-NH- | 4-methylpiperazin-1-yl | 4-Methyl-2-[[4-(4-methyl-1-piperazinyl)-6-[[[4-(methylsulfonyl)phenyl]methyl]amino]-2-pyrimidinyl]amino]-5-thiazolecarboxylic acid ethyl ester | 1.28[a] | 546.18 |

TABLE A-continued

| Ex. | L | Z | Name | HPLC Retention[a] (min) | MS Reported |
|---|---|---|---|---|---|
| A36 | H3C-S(O)2-C6H4-CH2-NH- | -NH-CH2CH2-NH-C(O)CH3 | 2-[[4-[[2-[(Acetylamino)ethyl]amino]-6-[[[4-(methylsulfonyl)phenyl]methyl]amino]-2-pyrimidinyl]amino]-4-methyl-5-thiazolecarboxylic acid ethyl ester | 1.27[a] | 548.16 |
| A37 | H3C-S(O)2-C6H4-CH2-NH- | 4-ethyl-piperazin-1-yl | 2-[[4-(4-Ethyl-1-piperazinyl)-6-[[[4-(methylsulfonyl)phenyl]methyl]amino]-2-pyrimidinyl]amino]-4-methyl-5-thiazolecarboxylic acid ethyl ester | 1.26[a] | 559.73 |
| A38 | H3C-S(O)2-C6H4-CH2-NH- | 4-acetyl-piperazin-1-yl | 2-[[4-(4-Acetyl-1-piperazinyl)-6-[[[4-(methylsulfonyl)phenyl]methyl]amino]-2-pyrimidinyl]amino]-4-methyl-5-thiazolecarboxylic acid ethyl ester | 1.45[a] | 573.69 |
| A39 | H3C-S(O)2-C6H4-CH2-NH- | -NH-CH2CH2-NMe2 | 2-[[4-[[2-(Dimethylamino)ethyl]amino]-6-[[[4-(methylsulfonyl)phenyl]methyl]amino]-2-pyrimidinyl]amino]-4-methyl-5-thiazolecarboxylic acid ethyl ester | 1.21 | 534.11 |
| A40 | H3C-S(O)2-C6H4-CH2-NH- | 3-(aminocarbonyl)-piperazin-1-yl | 2-[[4-[3-(Aminocarbonyl)-1-piperazinyl]-6-[[[4-(methylsulfonyl)-phenyl]methyl]-amino]-2-pyrimidinyl]amino]-4-methyl-5-thiazolecarboxylic acid ethyl ester | 1.07[a] | 575.42 |
| A41 | H3C-S(O)2-C6H4-CH2-NH- | 3-hydroxy-pyrrolidin-1-yl | 2-[[4-(3-Hydroxy-1-pyrrolidinyl)-6-[[[4-(methylsulfonyl)phenyl]methyl]amino]-2-pyrimidinyl]amino]-4-methyl-5-thiazolecarboxylic acid ethyl ester | 1.07[a] | 574.15 |
| A42 | H3C-S(O)2-C6H4-CH2-NH- | -NH-(CH2)4-OH | 2-[[4-[(4-Hydroxybutyl)amino]-6-[[[4-(methylsulfonyl)phenyl]methyl]amino]-2-pyrimidinyl]amino]-4-methyl-5-thiazolecarboxylic acid ethyl ester | 1.46 | 463.13 |
| A43 | H3C-S(O)2-C6H4-CH2-NH- | -NH-CH2-CH(OH)-CH2OH | 2-[[4-[(2,3-Dihydroxypropyl)amino]-6-[[[4-(methylsulfonyl)phenyl]methyl]amino]-2-pyrimidinyl]amino]-4-methyl-5-thiazolecarboxylic acid ethyl ester | 1.35 | 537.12 |

TABLE A-continued

| Ex. | L | Z | Name | HPLC Retention<sup>a</sup> (min) | MS Reported |
|---|---|---|---|---|---|
| A44 | 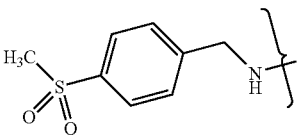 | 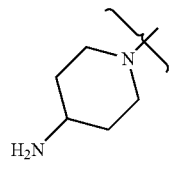 | 2-[[4-(4-Amino-1-piperidinyl)-6-[[[4-(methylsulfonyl)-phenyl]methyl]amino]-2-pyrimidinyl]amino]-4-methyl-5-thiazolecarboxylic acid ethyl ester | 1.25 | 546.12 |
| A45 | 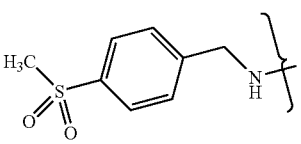 | 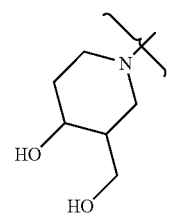 | 2-[[4-[4-Hydroxy-3-(hydroxymethyl)-1-piperidinyl]-6-[[[4-(methylsulfonyl)-phenyl]methyl]amino]-2-pyrimidinyl]amino]-4-methyl-5-thiazolecarboxylic acid ethyl ester | 1.24 | 577.46 |
| A46 | 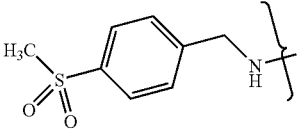 | 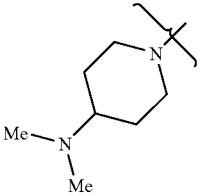 | 2-[[4-(4-Dimethylamino-1-piperidinyl)-6-[[[4-(methylsulfonyl)-phenyl]methyl]amino]-2-pyrimidinyl]amino]-4-methyl-5-thiazolecarboxylic acid ethyl ester | 1.31 | 574.30 |
| A47 | 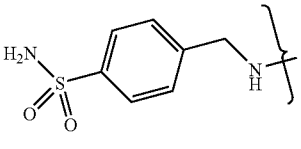 | —NHMe | 2-[[4-[[[4-(Aminosulfonyl)phenyl]methyl]-amino]-6-(methylamino)-2-pyrimidinyl]amino]-4-methyl-5-thiazolecarboxylic acid, ethyl ester | 2.42 | 478.42 |
| A48 | 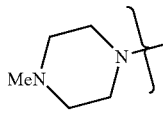 | 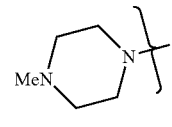 | 2-[4,6-Bis-(4-methyl-piperzin-1-yl)-pyrimidin-2-ylamino]-4-methyl-thiazole-5-carboxylic acid ethyl ester | 1.11 | 461.20 |
| A49 | 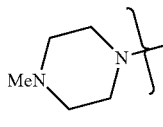 | 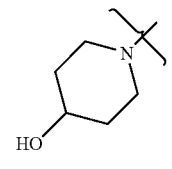 | 2-[4-(4-Hydroxy-piperidin-1-yl)-6-(4-methyl-piperzin-1-yl)-pyrimidin-2-ylamino]-4-methyl-thiazole-5-carboxylic acid ethyl ester | 1.20 | 462.25 |
| A50 | 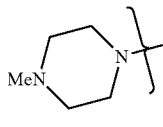 | 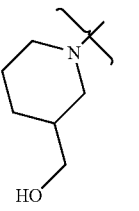 | 2-[4-(3-Hydroxymethyl-piperidin-1-yl)-6-(4-methyl-piperazin-1-yl)-pyrimidin-2-ylamino]-4-methyl-thiazole-5-carboxylic acid ethyl ester | 1.33 | 476.20 |
| A51 | 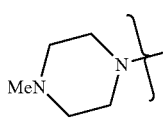 | 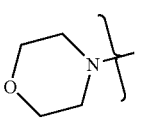 | 4-Methyl-2-[4-(4-methyl-piperazin-1-yl)-6-morpholin-4-yl-pyrimidin-2-ylamino]-thiazole-5-carboxylic acid ethyl ester | 1.30 | 448.22 |

TABLE A-continued

| Ex. | L | Z | Name | HPLC Retention[a] (min) | MS Reported |
|---|---|---|---|---|---|
| A52 | MeN-piperazinyl | 4-amino-piperidin-1-yl | 2-[4-(4-Amino-piperidin-1-yl)-6-(4-methyl-piperazin-1-yl)-pyrimidin-2-ylamino]-4-methyl-thiazole-5-carboxylic acid ethyl ester | 0.94 | 461.36 |
| A53 | 4-hydroxy-piperidin-1-yl | 4-hydroxy-piperidin-1-yl | 2-[4,6-Bis-(4-hydroxy-piperidin-1-yl)-pyrimidin-2-ylamino]-4-methyl-thiazole-5-carboxylic acid ethyl ester | 1.43[b] | 463.35 |
| A54 | 4-oxo-piperidin-1-yl | 4-methyl-piperazin-1-yl | 2-[4-(4-oxo-piperidin-1-yl)-6-(4-methyl-piperazin-1-yl)-pyrimidin-2-ylamino]-4-methyl-thiazole-5-carboxylic acid ethyl ester | 1.11[a] | 461.38 |
| A55 | 4-methyl-4-hydroxy-piperidin-1-yl | 4-methyl-piperazin-1-yl | 2-[4-(4-methyl-4-hydroxy-piperidin-1-yl)-6-(4-methyl-piperazin-1-yl)-pyrimidin-2-ylamino]-4-methyl-thiazole-5-carboxylic acid ethyl ester | 1.31[c] | 476.31 |
| A56 | 4-hydroxy-piperidin-1-yl | 4-dimethylamino-piperidin-1-yl | 2-[4-(4-hydroxy-piperidin-1-yl)-6-(4-dimethylmethyl-piperazin-1-yl)-pyrimidin-2-ylamino]-4-methyl-thiazole-5-carboxylic acid ethyl ester | 1.23[c] | 490.39 |
| A57 | 4-hydroxymethyl-piperidin-1-yl | 4-dimethylamino-piperidin-1-yl | 2-[4-(4-hydroxymethyl-piperidin-1-yl)-6-(4-dimethylmethyl-piperazin-1-yl)-pyrimidin-2-ylamino]-4-methyl-thiazole-5-carboxylic acid ethyl ester | 1.27[c] | 504.41 |
| A58 | 3-hydroxymethyl-piperidin-1-yl | 4-dimethylamino-piperidin-1-yl | 2-[4-(3-hydroxymethyl-piperidin-1-yl)-6-(4-dimethylmethyl-piperazin-1-yl)-pyrimidin-2-ylamino]-4-methyl-thiazole-5-carboxylic acid ethyl ester | 1.31[c] | 504.32 |

TABLE A-continued

| Ex. | L | Z | Name | HPLC Retention[a] (min) | MS Reported |
|---|---|---|---|---|---|
| A59 | 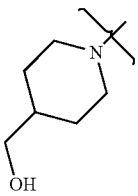 | 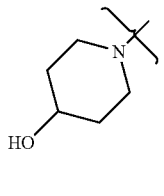 | 2-[4-(4-hydroxymethyl-piperidin-1-yl)-6-(4-hydroxy-piperazin-1-yl)-pyrimidin-2-ylamino]-4-methyl-thiazole-5-carboxylic acid ethyl ester | 1.52[c] | 476.93 |
| A60 | 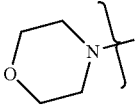 | 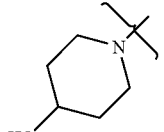 | 4-Methyl-2-[4-(4-hydroxy-piperazin-1-yl)-6-morpholin-4-yl-pyrimidin-2-ylamino]-thiazole-5-carboxylic acid ethyl ester | 1.51[c] | 448.92 |
| A61 | 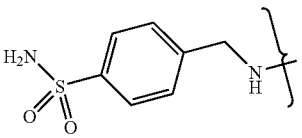 | —Cl | 2-[[4-[[[4-(Methylsulfonyl)phenyl]methyl]-amino]-6-chloro-2-pyrimidinyl]amino]-4-methyl-5-thiazolecarboxylic acid, ethyl ester | 1.43[b] | 482.21 |
| A62 | 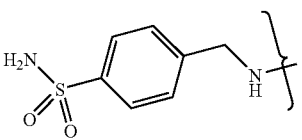 | —Cl | 2-[[4-[[[4-(Aminosulfonyl)phenyl]methyl]-amino]-6-chloro-2-pyrimidinyl]amino]-4-methyl-5-thiazolecarboxylic acid, ethyl ester | 3.23 | 483.11 |
| A63 | 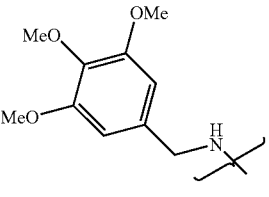 | 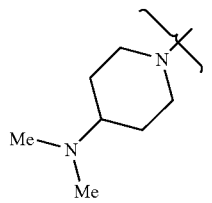 | 2-[[4-[4-(Dimethylamino)-1-piperidinyl]-6-[[[(3,4,5-trimethoxyphenyl)methyl]amino]-2-pyrimidinyl]amino]-4-methyl-5-thiazolecarboxylic acid, ethyl ester | 1.38[b] | 586.21 |
| A64 | 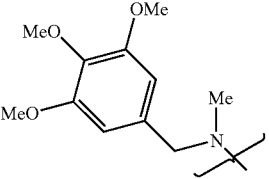 | 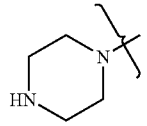 | 2-[[4-[1-piperizinyl]-6-methyl-6-[[[(3,4,5-trimethoxyphenyl)methyl]amino]-2-pyrimidinyl]amino]-4-methyl-5-thiazolecarboxylic acid, ethyl ester | 1.48[c] | 558.30 |
| A65 | 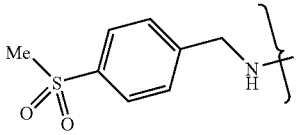 | 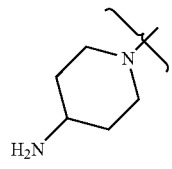 | 2-[[4-(4-Amino-1-piperidinyl)-6-[[[4-(methylsulfonyl)phenyl]methyl]-amino]-2-pyrimidinyl]amino]-4-methyl-5-thiazolecarboxylic acid, ethyl ester. | 1.25 | 546.12 |
| A66 | 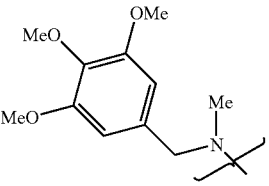 | 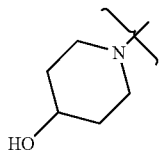 | 2-[[4-[4-hydroxy-1-piperidinyl]-6-methyl-6-[[[(3,4,5-trimethoxyphenyl)methyl]amino]-2-pyrimidinyl]amino]-4-methyl-5-thiazolecarboxylic acid, ethyl ester | 1.55 | 600.54 |

TABLE A-continued

| Ex. | L | Z | Name | HPLC Retention[a] (min) | MS Reported |
|---|---|---|---|---|---|
| A67 | (3,4,5-trimethoxybenzyl)(methyl)amine group | 4-(hydroxymethyl)piperidin-1-yl | 2-[[4-[4-(Hydroxymethyl)-1-piperidinyl]-6-methyl-6-[[(3,4,5-trimethoxyphenyl)methyl]amino]-2-pyrimidinyl]amino]-4-methyl-5-thiazolecarboxylic acid, ethyl ester | 1.52 | 587.32 |
| A68 | 3-oxopiperazin-1-yl | 4-hydroxypiperidin-1-yl | 2-[4-(4-Hydroxypiperidin-1-yl)-6-(3-oxo-piperzin-1-yl)-pyrimidin-2-ylamino]-4-methyl-thiazole-5-carboxylic acid ethyl ester | 1.36[c] | 462.19 |
| A69 | (3,4,5-trimethoxybenzyl)(methyl)amine group | 3-(aminocarbonyl)piperazin-1-yl | 2-[[4-[3-(Aminocarbonyl)-1-piperizinyl]-6-methyl-6-[[(3,4,5-trimethoxyphenyl)methyl]amino]-2-pyrimidinyl]amino]-4-methyl-5-thiazolecarboxylic acid, ethyl ester | 1.55[c] | 601.34 |
| A70 | (3,4,5-trimethoxybenzyl)(methyl)amine group | morpholin-4-yl | 2-[[4-[1-morpholinyl]-6-methyl-6-[[(3,4,5-trimethoxyphenyl)methyl]amino]-2-pyrimidinyl]amino]-4-methyl-5-thiazolecarboxylic acid, ethyl ester | 1.67[c] | 559.32 |
| A71 | (1,1-dioxido-3-oxo-1,2-benzisothiazol-2(3H)-yl)methyl-NH | 3-oxopiperazin-1-yl | 2-[[4-[3-Oxo-1-piperizinyl]-6-[[(1,1-dioxido-3-oxo-1,2-benzisothiazol-2-(3H)-yl)methyl]amino]-2-pyrimidinyl]amino]-4-methyl-5-thiazolecarboxylic acid, ethyl ester | 1.29 | 573.08 |
| A72 | 4-(ethylsulfonylamino)benzyl-NH | 3-oxopiperazin-1-yl | 2-[[4-[3-Oxo1-piperizinyl]-6-[[(4-(ethylsulfonylamino)phenyl)methyl]-amino]-2-pyrimidinyl]-amino]-4-methyl-5-thiazolecarboxylic acid, ethyl ester | 1.43 | 574.69 |

TABLE A-continued

| Ex. | L | Z | Name | HPLC Retention[a] (min) | MS Reported |
|---|---|---|---|---|---|
| A73 | | | 2-[[4-[3-Oxo-1-piperizinyl]-6-[[(4-(hydroxysulfonyl)phenyl)methyl]-amino]-2-pyrimidinyl]-amino]-4-methyl-5-thiazolecarboxylic acid, ethyl ester | 1.29[c] | 548.42 |
| A74 | | | 2-[4-(4-Hydroxypiperidin-1-yl)-6-(4-methyl-3-oxo-piperazin-1-yl)-pyrimidin-2-ylamino]-4-methyl-thiazole-5-carboxylic acid ethyl ester | 1.43[c] | 476.53 |
| A75 | | | 2-[4-(4(Dimethylamino)-piperazin-1-yl)-6-(4-((1-pyrrolidinyl)carbonylmethyl)piperazin-1-yl)-pyrimidin-2-ylamino]-4-methyl-thiazole-5-carboxylic acid ethyl ester | 1.17[c] | 586.35 |
| A76 | | | 2-[[4-[3-(Aminocarbonyl)-1-piperazinyl]-6-[[(3,4,5-trimethoxyphenyl)methyl]amino]-2-pyrimidinyl]amino]-4-methyl-5-thiazolecarboxylic acid, ethyl ester | 1.36[b] | 587.17 |
| A77 | | | 2-[[4-(4-Amino-1-piperidinyl)-6-[[(3,4,5-trimethoxyphenyl)methyl]amino]-2-pyrimidinyl]amino]-4-methyl-5-thiazolecarboxylic acid, ethyl ester | 1.38[b] | 558.21 |
| A78 | | | 2-[[4-[4-(Hydroxymethyl)-1-piperidinyl]-6-[4-tetrazol-5-yl]-4-hydroxypiperidin-1-yl]2-pyrimidinyl]amino]-4-methyl-5-thiazolecarboxylic acid, ethyl ester | 2.62 | 544.98 |

TABLE A-continued

| Ex. | L | Z | Name | HPLC Retention[a] (min) | MS Reported |
|---|---|---|---|---|---|
| A79 | (3,4,5-trimethoxybenzyl)(methyl)amino | 4-methylpiperazin-1-yl | 2-[[4-[4-methyl-1-piperazinyl]-6-[N-methyl-N-[(3,4,5-trimethoxyphenyl)methyl]amino]-2-pyrimidinyl]amino]-4-methyl-5-thiazolecarboxylic acid, ethyl ester | 1.55[c] | 572.35 |
| A80 | (4-(hydroxysulfonyl)benzyl)amino | 4-hydroxypiperidin-1-yl | 2-[[4-[4-Hydroxy-1-piperidinyl]-6-[[(4-(hydroxysulfonyl)phenyl)methyl]-amino]-2-pyrimidinyl]amino]-4-methyl-5-thiazolecarboxylic acid, ethyl ester | 1.39[c] | 549.43 |
| A81 | (4-cyanobenzyl)amino | piperazin-1-yl | 2-[[4-[[(4-Cyanophenyl)methyl]amino]-6-(1-piperazinyl)-2-pyrimidinyl]amino]4-methyl-5-thiazolecarboxylic acid, ethyl ester, trifluroacetate (1:1) | 1.36 | 479.14 |
| A82 | (4-(aminosulfonyl)benzyl)amino | morpholin-4-yl | 2-[[4-[[[4-(Aminosulfonyl)phenyl]methyl]-amino]-6-(4-morpholinyl)-2-pyrimidinyl]amino]-4-methyl-5-thiazolecarboxylic acid, ethyl ester. | 2.67 | 534.17 |
| A83 | 1-oxa-3,8-diazaspiro[4.5]decane-2,4-dione-8-yl | 4-hydroxypiperidin-1-yl | 2-[[4-[4-Hydroxy-1-piperidinyl]-6-[(1-oxa-3,8-diazaspiro[4.5]decan-2,4-dion-8-yl]-2-pyrimidinyl]amino]-4-methyl-5-thiazolecarboxylic acid, ethyl ester | 1.49 | 532.52 |
| A84 | 4-methylpiperazin-1-yl | 4-(2-(dimethylamino)ethyl)piperazin-1-yl | 2-[4-(2-(Dimethylamino)ethyl)-piperazin-1-yl)-6-(4-methyl piperazin-1-yl)-pyrimidin-2-ylamino]-4-methyl-thiazole-5-carboxylic acid ethyl ester | 1.12[c] | 518.43 |

TABLE A-continued

| Ex. | L | Z | Name | HPLC Retention[a] (min) | MS Reported |
|---|---|---|---|---|---|
| A85 | (N-Me, CH2-3-pyridinyl) | 4-hydroxypiperidin-1-yl | 2-[[4-(4-Hydroxy-1-piperidinyl)-6-[methyl(3-pyridinylmethyl)amino]-2-pyrimidinyl]amino]-4-methyl-5-thiazolecarboxylic acid, ethyl ester | 1.31[c] | 484.37 |
| A86 | (3,4,5-trimethoxybenzyl)NH | 4-hydroxy-3-(hydroxymethyl)piperidin-1-yl | 2-[[4-[4-Hydroxy-3-hydroxymethylpiperidin-1-yl]-6-[[(3,4,5-trimethoxyphenyl)methyl]amino]-2-pyrimidinyl]amino]-4-methyl-5-thiazolecarboxylic acid, ethyl ester | 1.54 | 589.23 |
| A87 | 6,7-dihydroxy-3,4-dihydroisoquinolin-2(1H)-yl | 4-methylpiperazin-1-yl | 2-[[4-(3,4-Dihydro-6,7-dihydroxy-2(1H)-isoquinolinyl)-6-(4-methyl-1-piperazinyl)-2-pyrimidinyl]amino]-4-methyl-5-thiazolecarboxylic acid, ethyl ester, trifluoroacetate (1:1) | 1.45 | 526.19 |
| A88 | (4-(methylsulfonyl)benzyl)NH | 4-[(methoxyacetyl)amino]piperidin-1-yl | 2-[[4-[4-[(Methoxyacetyl)amino]-1-piperidinyl]-6-[[[4-(methylsulfonyl)phenyl]methyl]amino]-2-pyrimidinyl]amino]-4-methyl-5-thiazolecarboxylic acid, ethyl ester | 1.45[b] | 618.16 |
| A89 | (3,4-dimethoxybenzyl)NH | 4-(dimethylamino)piperidin-1-yl | 2-[[4-[[(3,4-Dimethoxyphenyl)methyl]amino]-6-[4-(dimethylamino)-1-piperidinyl]-2-pyrimidinyl]amino]-4-methyl-5-thiazolecarboxylic acid, ethyl ester | 1.36[b] | 556.19 |
| A90 | 4-(2-hydroxyethyl)piperidin-1-yl | 4-(dimethylamino)piperidin-1-yl | 2-[[4-[4-(Hydroxyethyl)piperidin-1-yl]-6-[4-(dimethylamino)-1-piperidinyl]-2-pyrimidinyl]amino]-4-methyl-5-thiazolecarboxylic acid, ethyl ester | 1.10[c] | 519.34 |

TABLE A-continued

| Ex. | L | Z | Name | HPLC Retention[a] (min) | MS Reported |
|---|---|---|---|---|---|
| A91 | (3-pyridinylmethyl)(methyl)amino group | 4-(dimethylamino)-1-piperidinyl | 2-[[4-[4-(Dimethylamino)-1-piperidinyl]-6-[methyl(3-pyridinylmethyl)amino]-2-pyrimidinyl]amino]-4-methyl-5-thiazolecarboxylic acid, ethyl ester | 1.10[b] | 511.15 |
| A92 | 4-(methoxycarbonyl)-1-piperidinyl | 4-hydroxy-1-piperidinyl | 2-[[4-[4-(Hydroxy)piperidin-1-yl]-6-[4-(methoxycarbonyl)-1-piperidinyl]-2-pyrimidinyl]amino]-4-methyl-5-thiazolecarboxylic acid, ethyl ester | 1.57[c] | 505.22 |
| A93 | 4-methyl-4-hydroxy-1-piperidinyl | 4-hydroxy-1-piperidinyl | 2-[[4-[4-(Hydroxy)piperidin-1-yl]-6-[4-(methyl)-4-(hydroxy)-1-piperidinyl]-2-pyrimidinyl]amino]-4-methyl-5-thiazolecarboxylic acid, ethyl ester | 1.56[c] | 477.54 |
| A94 | 3-oxopiperazin-1-yl | 4-methylpiperazin-1-yl | 2-[4-(3-oxopiperazin-1-yl)-6-(4-methylpiperazin-1-yl)-pyrimidin-2-ylamino]-4-methyl-thiazole-5-carboxylic acid ethyl ester | 1.23[c] | 461.26 |
| A95 | 3-oxopiperazin-1-yl | (4-cyanophenyl)methylamino | 2-[[4-[[(4-Cyanophenyl)methyl]amino]-6-[4-(dimethylamino)-1-piperidinyl]-2-pyrimidinyl]amino]-4-methyl-5-thiazolecarboxylic acid, ethyl ester | 1.47 | 493.10 |
| A96 | 1-piperazinyl | (3-nitrophenyl)methylamino | 4-Methyl-2-[[4-[[(3-nitrophenyl)methyl]amino]-6-(1-piperazinyl)-2-pyrimidinyl]amino]-5-thiazolecarboxylic acid, ethyl ester, trifluoroacetate (1:1) | 2.15 | 499.55 |

TABLE A-continued

| Ex. | Name | HPLC Retention[a] (min) | MS Reported |
|---|---|---|---|
| A97 | 2-[[4-(4-Hydroxy-1-piperidinyl)-6-[[(3,4,5-trimethoxyphenyl)methyl]amino]-2-pyrimidinyl]amino]-4-methyl-5-thiazolecarboxylic acid, ethyl ester | 1.59 | 559.18 |
| A98 | 2-[4-(Dimethylamino)-piperazin-1-yl)-6-(4-methyl piperazin-1-yl)-pyrimidin-2-ylamino]-4-methyl-thiazole-5-carboxylic acid ethyl ester | 1.11[c] | 489.17 |
| A99 | 2-[4-(Dimethylamino)-piperidin-1-yl)-6-(3-(aminocarbonyl)-1-piperazinyl)-pyrimidin-2-ylamino]-4-methyl-thiazole-5-carboxylic acid ethyl ester | 1.17[c] | 518.65 |
| A100 | 2-[4-(2-Hydroxyethyl)-piperazin-1-yl)-6-(4-methyl-1-piperazinyl)-pyrimidin-2-ylamino]-4-methyl-thiazole-5-carboxylic acid ethyl ester | 1.10[c] | 491.38 |
| A101 | 2-[[4-[4-(Aminocarbonyl)-1-piperidinyl]-6-[[[4-(methylsulfonyl)phenyl]methyl]-amino]-2-pyrimidinyl]amino]-4-methyl-5-thiazolecarboxylic acid, ethyl ester | 1.36[b] | 574.17 |
| A102 | 2-[[4-[4-(Hydroxymethyl)-1-piperidinyl]-6-[N-methyl-N-(3-pyridinylmethyl)amino]-2-pyrimidinyl]amino]-4-methyl-5-thiazolecarboxylic acid, ethyl ester | 1.34[c] | 498.39 |

TABLE A-continued

| Ex. | L | Z | Name | HPLC Retention[a] (min) | MS Reported |
|---|---|---|---|---|---|
| A103 | (3,4-dimethoxybenzyl)amino | 4-methylpiperazin-1-yl | 2-[[4-[4-Methylpiperazin-1-yl]-6-[[(3,4-dimethoxyphenyl)methyl]amino]-2-pyrimidinyl]amino]-4-methyl-5-thiazolecarboxylic acid, ethyl ester | 1.34 | 528.15 |
| A104 | (4-carboxybenzyl)amino | piperazin-1-yl | 2-[[4-[piperazin-1-yl]-6-[[(4-carboxyphenyl)methyl]amino]-2-pyrimidinyl]amino]-4-methyl-5-thiazolecarboxylic acid, ethyl ester | 1.30[b] | 512.19 |
| A105 | N-methyl-N-(3,4,5-trimethoxybenzyl)amino | 3-hydroxymethylpiperidin-1-yl | 2-[[4-[3-Hydroxymethylpiperidin-1-yl]-6-[[N-[(3,4,5-trimethoxyphenyl)methyl]]-N-(methyl)amino]-2-pyrimidinyl]amino]-4-methyl-5-thiazolecarboxylic acid, ethyl ester | 1.62[c] | 587.37 |
| A106 | 4-carboxypiperidin-1-yl | 4-hydroxypiperidin-1-yl | 2-[4-[4-Hydroxypiperidin-1-yl]-6-(4-carboxypiperidin-1-yl)-pyrimidin-2-ylamino]-4-methyl-thiazole-5-carboxylic acid ethyl ester | 1.52[c] | 491.20 |
| A107 | (3,4-dimethoxybenzyl)amino | piperazin-1-yl | 2-[[4-[Piperazin-1-yl]-6-[[(3,4-dimethoxyphenyl)methyl]amino]-2-pyrimidinyl]amino]-4-methyl-5-thiazolecarboxylic acid, ethyl ester | 2.90 | 514.55 |
| A108 | (4-methylsulfonylbenzyl)amino | 4-formylpiperazin-1-yl | 2-[[4-(4-Formyl-1-piperazinyl)-6-[[[4-(methylsulfonyl)phenyl]methyl]amino]-2-pyrimidinyl]amino]-4-methyl-5-thiazolecarboxylic acid, ethyl ester | 1.40[b] | 560.13 |

TABLE A-continued

| Ex. | L | Z | Name | HPLC Retention[a] (min) | MS Reported |
|---|---|---|---|---|---|
| A109 | | | 2-[4-(4-Hydroxypiperidin-1-yl)-6-(4-(hydroxy)-4-(4-chlorophenyl)piperidin-1-yl)-pyrimidin-2-ylamino]-4-methyl-thiazole-5-carboxylic acid ethyl ester | 1.83[c] | 573.20 |
| A110 | | | 4-Methyl-2-[[4-[4-dimethylamino-1-piperidinyl]-6-[[(tetrahydro-2-furanyl)methyl]amino]-2-pyrimidinyl]amino]-5-thiazolecarboxylic acid ethyl ester | 1.29[c] | 490.39 |
| A111 | | | 2-[[4-[Piperazin-1-yl]-6-[[N-methyl-N-(5-tetrazolylmethyl]amino]-2-pyrimidinyl]amino]-4-methyl-5-thiazolecarboxylic acid, ethyl ester | 1.32 | 459.54 |
| A112 | | | 2-[[4-[4-Morpholinyl]-6-[4-[tetrazol-5-yl]-4-hydroxypiperidin-1-yl]2-pyrimidinyl]amino]-4-methyl-5-thiazolecarboxylic acid, ethyl ester | 1.23 | 516.97 |
| A113 | | | 2-[[4-[4-Hydroxy-1-piperidinyl]-6-[[(1,1-dioxido-3-oxo-1,2-benzisothiazol-2-(3H)-yl)methyl]amino]-2-pyrimidinyl]amino]-4-methyl-5-thiazolecarboxylic acid, ethyl ester | 1.41 | 574.10 |
| A114 | | | 2-[4-(4-Hydroxypiperidin-1-yl)-6-(4-(1-methyl-hydroxyethyl)piperidin-1-yl)-pyrimidin-2-ylamino]-4-methyl-thiazole-5-carboxylic acid ethyl ester | 1.64[c] | 505.51 |

TABLE A-continued

| Ex. | L | Z | Name | HPLC Retention[a] (min) | MS Reported |
|---|---|---|---|---|---|
| A115 | | | 2-[[4-[3-(Aminocarbonyl)-1-piperidinyl]-6-[[N-methyl-N-(3-pyridinylmethyl)]amino]-2-pyrimidinyl]amino]-4-methyl-5-thiazolecarboxylic acid, ethyl ester | 1.21[b] | 511.16 |
| A116 | | | 2-[[4-[4-Hydroxymethyl-1-piperidinyl]-6-[[(4-(ethylsufonylamino)phenyl)-methyl]amino]-2-pyrimidinyl]amino]-4-methyl-5-thiazolecarboxylic acid, ethyl ester | 1.58 | 589.74 |
| A117 | | | 2-[[4-[4-Hydroxy-1-piperidinyl]-6-[4-[tetrazol-5-yl]-4-hydroxypiperidin-1-yl]2-pyrimidinyl]amino]-4-methyl-5-thiazolecarboxylic acid, ethyl ester | 1.20 | 531.32 |
| A118 | | | 2-[[4-[4-tertButyloxycarbonylamino-1-piperidinyl]-6-[[N-[(3,4,5-trimethoxyphenyl)methyl]]-N-(methyl)amino]-2-pyrimidinyl]amino]-4-methyl-5-thiazolecarboxylic acid, ethyl ester | 1.76[c] | 672.70 |
| A119 | | | 2-[[4-[[(4-Cyanophenyl)methyl]amino]-6-(4-methyl-1-piperazinyl)-2-pyrimidinyl]amino]-4-methyl-5-thiazolecarboxylic acid, ethyl ester, trifluoroacetate (1:1) | 1.40 | 397.12 |

TABLE A-continued

| Ex. | L | Z | Name | HPLC Retention[a] (min) | MS Reported |
|---|---|---|---|---|---|
| A120 | 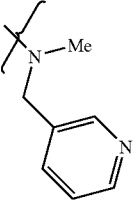 | 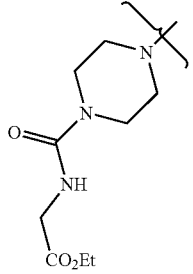 | 2-[[4-[4-[[(2-Ethoxy-2-oxoethyl)amino]carbonyl]-1-piperazinyl]-6-[methyl(3-pyridinylmethyl)amino]-2-pyrimidinyl]amino]-4-methyl-5-thiazolecarboxylic acid, ethyl ester, trifluoroacetate (1:1) | 1.36 | 598.28 |
| A121 | 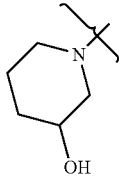 | 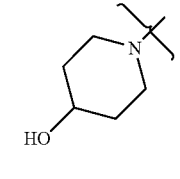 | 2-[4-(4-Hydroxypiperidin-1-yl)-6-(3-hydroxypiperidin-1-yl)-pyrimidin-2-ylamino]-4-methyl-thiazole-5-carboxylic acid ethyl ester | 1.48[c] | 463.21 |
| A122 | 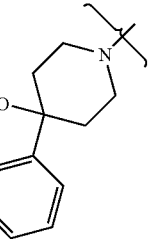 | 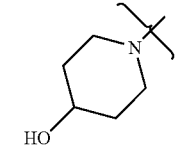 | 2-[4-(4-Hydroxypiperidin-1-yl)-6-(4-hydroxy-4-phenyl-1-piperidinyl)-pyrimidin-2-ylamino]-4-methyl-thiazole-5-carboxylic acid ethyl ester | 1.76[c] | 539.20 |
| A123 | 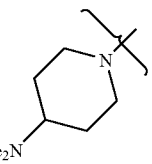 | 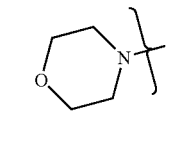 | 4-Methyl-2-[[4-[4-morpholinyl]-6-[[(tetrahydro-2-furanyl)methyl]amino]-2-pyrimidinyl]amino]-5-thiazolecarboxylic acid ethyl | 1.38[c] | 476.58 |
| A124 | 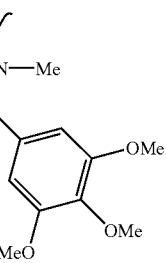 | 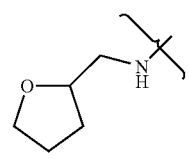 | 2-[[4-[(Tetrahydro-2-furanyl)methyl]amino]-6-[[N-[(3,4,5-trimethoxyphenyl)methyl]]-N-(methyl)amino]-2-pyrimidinyl]amino]-4-methyl-5-thiazolecarboxylic acid, ethyl ester | 1.30[c] | 573.31 |
| A125 | 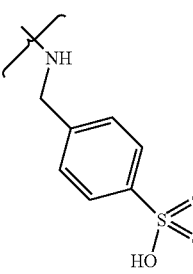 | 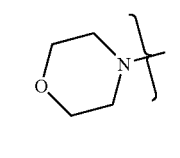 | 2-[[4-[4-Morpholinyl]-6-[[(4-(hydroxysulfonyl)phenyl)methyl]-amino]-2-pyrimidinyl]amino]-4-methyl-5-thiazolecarboxylic acid, ethyl ester | 1.44[c] | 535.40 |

TABLE A-continued

| Ex. | L | Z | Name | HPLC Retention[a] (min) | MS Reported |
|---|---|---|---|---|---|
| A126 | 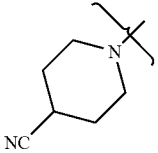 | 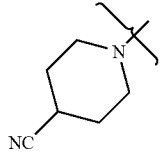 | 2-[Bis-4,6-(4-Cyano-1-piperidinyl)-pyrimidin-2-ylamino]-4-methyl-thiazole-5-carboxylic acid ethyl ester | 2.86 | 480.91 |
| A127 | 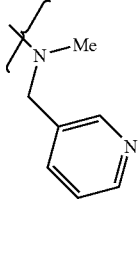 | 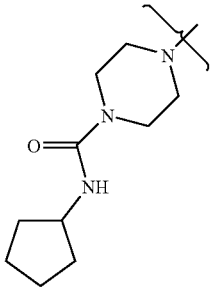 | 2-[[-4-[4-(Cyclopentylaminocarbonyl)-1-piperazinyl]-6-[N-methyl-N-(3-pyridinylmethyl)amino]-2-pyrimidinyl]amino]-4-methyl-5-thiazolecarboxylic acid, ethyl ester | 1.55 | 580.25 |
| A128 | 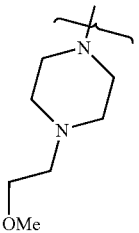 | 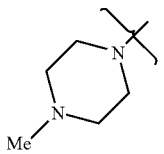 | 2-[4-(2-Methoxyethyl)-piperazin-1-yl)-6-(4-methyl-1-piperazinyl)-pyrimidin-2-ylamino]-4-methyl-thiazole-5-carboxylic acid ethyl ester | 1.15[c] | 505.39 |
| A129 | 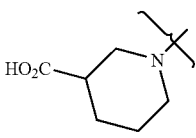 | 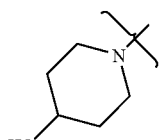 | 2-[4-(4-Hydroxypiperidin-1-yl)-6-(3-carboxypiperidin-1-yl)-pyrimidin-2-ylamino]-4-methyl-thiazole-5-carboxylic acid ethyl ester | 1.55[c] | 491.14 |
| A130 | 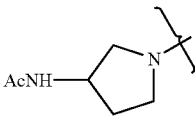 | 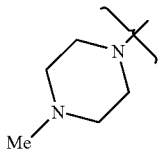 | 2-[[4-[4-Methylpiperazin-1-yl]-6-[3-(acetylamino)-1-pyrrolidinyl]-2-pyrimidinyl]amino]-4-methyl-5-thiazolecarboxylic acid, ethyl ester | 1.14[c] | 489.31 |
| A131 | 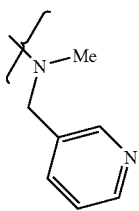 | 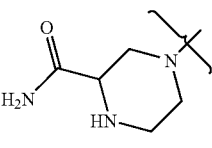 | 2-[[4-[3-(Aminocarbonyl)-1-piperazinyl]-6-[[N-methyl-N-(3-pyridinylmethyl)]amino]-2-pyrimidinyl]amino]-4-methyl-5-thiazolecarboxylic acid, ethyl estr | 1.13[b] | 512.13 |
| A132 | 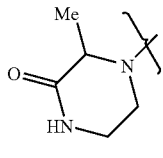 | 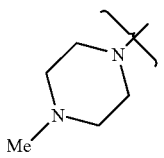 | 2-[[4-[2-Methyl-3-oxo1-piperizinyl]-6-[4-methyl-1-piperazinyl]-2-pyrimidinyl]amino]-4-methyl-5-thiazolecarboxylic acid, ethyl ester | 1.32[c] | 475.36 |

TABLE A-continued

| Ex. | L | Z | Name | HPLC Retention[a] (min) | MS Reported |
|---|---|---|---|---|---|
| A133 | (structure) | (structure) | 2-[[4-[3-(Aminocarbonyl)-1-piperizinyl]-6-(4-methyl-1-piperazinyl)-2-pyrimidinyl]amino]-4-methyl-5-thiazolecarboxylic acid, ethyl ester | 1.09[b] | 490.16 |
| A134 | (structure) | (structure) | 2-[[4-[3-(Aminocarbonyl)-1-piperidinyl]-6-(4-methyl-dimethylamino-1-piperidinyl)-2-pyrimidinyl]amino]-4-methyl-5-thiazolecarboxylic acid, ethyl ester | 1.21[c] | 517.39 |
| A135 | (structure) | (structure) | 2-[[4-[1-piperazinyl]-6-[[N-methyl-N-(2-furylmethyl)]amino]-2-pyrimidinyl]amino]-4-methyl-5-thiazolecarboxylic acid, ethyl ester | 1.51 | 458.13 |
| A136 | (structure) | (structure) | 2-[[4-[[(4-Methoxycarbonylphenyl)methyl]-amino]-6-(4-dimethyl-1-piperidinyl)-2-pyrimidinyl]amino]-4-methyl-5-thiazolecarboxylic acid, ethyl ester, trifluoroacetate (1:1) | 1.42[b] | 554.20 |
| A137 | (structure) | (structure) | 2-[[4-[3-Oxo-1-piperazinyl]-6-[[(4-(methylsufonylamino)phenyl)methyl]amino]-2-pyrimidinyl]amino]-4-methyl-5-thiazolecarboxylic acid, ethyl ester | 1.30 | 560.66 |
| A138 | (structure) | (structure) | 2-[[4-[3-Oxo-1-piperazinyl]-6-[[(4-(propylsufonylamino)phenyl)methyl]amino]-2-pyrimidinyl]amino]-4-methyl-5-thiazolecarboxylic acid, ethyl ester | 1.49 | 588.71 |

TABLE A-continued

| Ex. | L | Z | Name | HPLC Retention[a] (min) | MS Reported |
|---|---|---|---|---|---|
| A139 | (3,4,5-trimethoxybenzyl)amino-CH2 | 3-aminocarbonyl-piperidin-1-yl | 2-[[4-[3-(Aminocarbonyl)-1-piperidinyl]-6-[[(3,4,5-trimethoxyphenyl)methyl]amino]-2-pyrimidinyl]amino]-4-methyl-5-thiazolecarboxylic acid, ethyl ester | 1.54[b] | 586.20 |
| A140 | 4-hydroxy-4-methyl-piperidin-1-yl | 4-hydroxy-4-methyl-piperidin-1-yl | 2-[Bis-4,6-(4-Hydroxy-4-methyl-1-piperidinyl)-pyrimidin-2-ylamino]-4-methyl-thiazole-5-carboxylic acid ethyl ester | 1.65[c] | 491.53 |
| A141 | 3-(2-oxopyrrolidin-1-yl)propylamino | 4-dimethylamino-piperidin-1-yl | 4-Methyl-2-[[4-[4-dimethylamino-1-piperidinyl]-6-[[(2-oxo-1-pyrrolidinyl)propyl]amino]-2-pyrimidinyl]amino]-5-thiazolecarboxylic acid ethyl | 1.32[c] | 531.58 |
| A142 | 4-(1-isopropylsulfonylamino)benzyl-amino | 3-oxopiperazin-1-yl | 2-[[4-[3-Oxo-1-piperazinyl]-6-[[(4-iso-propylsufonylamino)phenyl)-methyl]amino]-2-pyrimidinyl]amino]-4-methyl-5-thiazolecarboxylic acid, ethyl ester | 1.47 | 588.71 |
| A143 | 3-hydroxymethyl-piperidin-1-yl | 4-hydroxy-piperidin-1-yl | 2-[4-(4-Hydroxypiperidin-1-yl)-6-(3-hydroxymethyl-1-piperidinyl)-pyrimidin-2-ylamino]-4-methyl-thiazole-5-carboxylic acid ethyl ester | 1.54[c] | 477.19 |
| A144 | 2-morpholinoethylamino | 4-hydroxy-piperidin-1-yl | 4-Methyl-2-[[4-[4-hydroxy-1-piperidinyl]-6-[[(2-(4-morpholinyl)ethyl]amino]-2-pyrimidinyl]amino]-5-thiazolecarboxylic acid ethyl | 1.08[c] | 491.37 |

TABLE A-continued

| Ex. | L | Z | Name | HPLC Retention[a] (min) | MS Reported |
|---|---|---|---|---|---|
| A145 | 4-(ethylaminosulfonyl)benzyl-NH- | —OMe | 2-[[4-[[[4-(Ethylaminosulfonyl)phenyl]-methyl]amino]-6-methoxy-2-pyrimidinyl]amino]-4-methyl-5-thiazolecarboxylic acid, methyl ester, trifluoroacetate (1:1) | 3.81 | 506.81 |
| A146 | 1-oxa-3,8-diazaspiro[4.5]decan-2,4-dion-8-yl | morpholinyl | 2-[[4-[4-Morpholinyl]-6-[(1-oxa-3,8-diazaspiro[4.5]decan-2,4-dion-8-yl]-2-pyrimidinyl]amino]-4-methyl-5-thiazolecarboxylic acid, ethyl ester | 1.58 | 518.46 |
| A147 | 4-(ethylsulfonylamino)benzyl-NH- | 4-hydroxy-1-piperidinyl | 2-[[4-[4-Hydroxy-1-piperidinyl]-6-[[(4-(ethylsufonylamino)phenyl)methyl]-amino]-2-pyrimidinyl]amino]-4-methyl-5-thiazolecarboxylic acid, ethyl ester | 1.51 | 575.71 |
| A148 | 3,4,5-trimethoxybenzyl-NH- | 4-Boc-piperazinyl | 2-[[4-[tertButyloxycarbonyl-1-piperazinyl]-6-[[(3,4,5-trimethoxyphenyl)methyl]amino]-2-pyrimidinyl]amino]-4-methyl-5-thiazolecarboxylic acid, ethyl ester | 4.00[d] | 644.65 |
| A149 | 3,4-dimethoxybenzyl-NH- | 3-(aminocarbonyl)-1-piperidinyl | 2-[[4-[3-(Aminocarbonyl)-1-piperidinyl]-6-[[(3,4-dimethoxyphenyl)methyl]amino]-2-pyrimidinyl]amino]-4-methyl-5-thiazolecarboxylic acid, ethyl ester | 1.54[b] | 556.14 |

TABLE A-continued

| Ex. | L | Z | Name | HPLC Retention[a] (min) | MS Reported |
|---|---|---|---|---|---|
| A150 | | | 2-[[4-[4-ethoxycarbonyl-1-piperazinyl]-6-[[N-methyl-N-(5-tetrazolylmethyl]amino]-2-pyrimidinyl]amino]-4-methyl-5-thiazolecarboxylic acid, ethyl ester | 1.61 | 531.60 |
| A151 | | | 2-[[4-[3-Oxo1-piperizinyl]-6-[[(4-(cyclopropylsufonylamino)phenyl)-methyl]amino]-2-pyrimidinyl]amino]-4-methyl-5-thiazolecarboxylic acid, ethyl ester | 1.44 | 586.70 |
| A152 | | | 2-[[4-[4-Hydroxymethyl-1-piperidinyl]-6-[[(4-(methylsufonylamino)phenyl)methyl]amino]-2-pyrimidinyl]amino]-4-methyl-5-thiazolecarboxylic acid, ethyl ester | 1.51 | 575.71 |
| A153 | | | 2-[4-(4-Dimethylamino-1-piperazinyl)-6-(4-tertbutyloxycarbonylamino-1-piperidinyl)-pyrimidin-2-ylamino]-4-methyl-thiazole-5-carboxylic acid ethyl ester | 1.55[c] | 589.44 |
| A154 | | | 2-[4-(4-Hydroxypiperidin-1-yl)-6-(4-methoxymethyl-1-piperidinyl)-pyrimidin-2-ylamino]-4-methyl-thiazole-5-carboxylic acid ethyl ester | 1.58[c] | 477.19 |
| A155 | | | 2-[4-(4-Hydroxypiperidin-1-yl)-6-(4-hydroxyethyl-1-piperidinyl)-pyrimidin-2-ylamino]-4-methyl-thiazole-5-carboxylic acid ethyl ester | 1.58[c] | 491.00 |

TABLE A-continued

| Ex. | L | Z | Name | HPLC Retention[a] (min) | MS Reported |
|---|---|---|---|---|---|
| A156 | | | 2-[4-(4-Hydroxypiperidin-1-yl)-6-(4-(hydroxy)-4-(3-trifluoromethylphenyl)piperidin-1-yl)-pyrimidin-2-ylamino]-4-methyl-thiazole-5-carboxylic acid ethyl ester | 1.85[c] | 607.25 |
| A157 | | | 2-[[4-[4-morpholinyl]-6-[4-[1-methyl-1-hydroxyethyl]-1-piperidinyl]-2-pyrimidinyl]amino]-4-methyl-5-thiazolecarboxylic acid, ethyl ester | 1.57[a] | 491.22 |
| A158 | | | 2-[[4-[3-Oxo-1-piperizinyl]-6-[[3-pyridyl]oxy]-2-pyrimidinyl]amino]-4-methyl-5-thiazolecarboxylic acid, ethyl ester | 1.35[c] | 456.19 |
| A159 | | | 2-[[4-[4-Methyl-1-piperazinyl]-6-[(1,4-dioxaspiro[4.5]decan-8-yl]-2-pyrimidinyl]amino]-4-methyl-5-thiazolecarboxylic acid, ethyl ester | 1.43[b] | 504.25 |
| A160 | | | 2-[[4-[4-Morpholinyl]-6-[[(4-(methylsufonylamino)phenyl)methyl]amino]-2-pyrimidinyl]amino]-4-methyl-5-thiazolecarboxylic acid, ethyl ester | 1.53 | 547.66 |
| A161 | | | 2-[[4-[3-Oxo-1-piperazinyl]-6-[(1-oxa-3,8-diazaspiro[4.5]decan-2,4,dion-8-yl]-2-pyrimidinyl]amino]-4-methyl-5-thiazolecarboxylic acid, ethyl ester | 1.46 | 531.47 |

TABLE A-continued

| Ex. | L | Z | Name | HPLC Retention[a] (min) | MS Reported |
|---|---|---|---|---|---|
| A162 | | | 2-[[4-[4-Hydroxy-1-piperidinyl]-6-[[(4-(carboxy)phenyl)methyl]amino-2-pyrimidinyl]amino]-4-methyl-5-thiazolecarboxylic acid, ethyl ester | 2.37 | 513.31 |
| A163 | | | 2-[4-(4-Hydroxypiperidin-1-yl)-6-(4-(hydroxy)-4-(4-bromophenyl)piperidin-1-yl)-pyrimidin-2-ylamino]-4-methyl-thiazole-5-carboxylic acid ethyl ester | 1.76[a] | 619.42 |
| A164 | | | 2-[[4-[4-Morpholinyl]-6-[[(4-(ethylsufonylamino)phenyl)methyl]-amino]-2-pyrimidinyl]amino]-4-methyl-5-thiazolecarboxylic acid, ethyl ester | 1.55 | 561.69 |
| A165 | | | 2-[[4-[3-(Aminocarbonyl)-1-piperazinyl]-6-[[(3,4-dimethoxyphenyl)methyl]amino]-2-pyrimidinyl]amino]-4-methyl-5-thiazolecarboxylic acid, ethyl ester | 1.35 | 557.14 |
| A166 | | | 2-[[4-[4-Formyl-1-piperazinyl]-6-[[(3-(5-(1H)tetrazolyl)phenyl)methyl]amino]-2-pyrimidinyl]amino]-4-methyl-5-thiazolecarboxylic acid, ethyl ester | 1.47 | 549.62 |
| A167 | | | 2-[[4-[4-(Hydroxymethyl)-1-Piperidinyl]-6-[[N-methyl-N-(5-tetrazolylmethyl]amino]-2-pyrimidinyl]amino]-4-methyl-5-thiazolecarboxylic acid, ethyl ester | 1.35 | 489.23 |

TABLE A-continued

| Ex. | L | Z | Name | HPLC Retention[a] (min) | MS Reported |
|---|---|---|---|---|---|
| A168 | 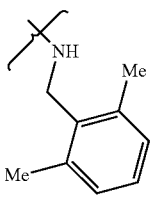 | 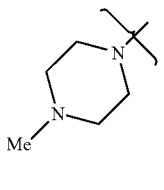 | 2-[[4-[4-Methyl-1-piperazinyl]-6-[[(2,5-dimethyl)phenyl)methyl]amino]-2-pyrimidinyl]amino]-4-methyl-5-thiazolecarboxylic acid, ethyl ester | 1.58[b] | 496.17 |
| A169 | H | 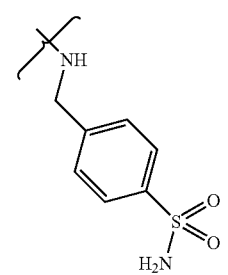 | 2-[[2-[[[4-(Aminosulfonyl)phenyl]methyl]-amino]-4-methyl-5-thiazolecarboxylic acid, ethyl ester | 2.56 | 449.08 |
| A170 | H | 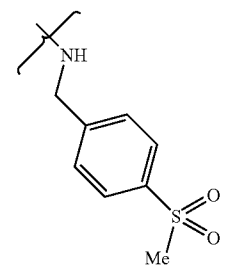 | 2-[[2-[[[4-(Methylsulfonyl)phenyl]methyl]-amino]-4-methyl-5-thiazolecarboxylic acid, ethyl ester | 2.82 | 448.02 |
| A171 | 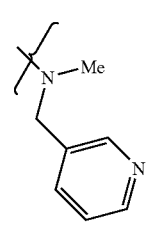 | 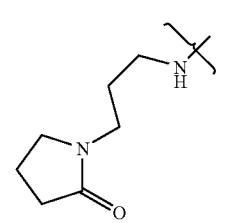 | 2-[[4-[3-(2-oxo-1-pyrrolidinyl)propyl]amino]-6-[N-methyl-N-(3-pyridinylmethyl)amino]-2-pyrimidinyl]amino]-4-methyl-5-thiazolecarboxylic acid, ethyl ester | 1.60[c] | 614.38 |
| A172 | 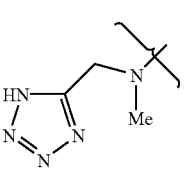 | 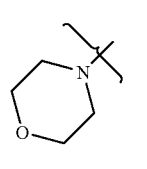 | 2-[[4-[(1-Morpholinyl)]-6-[[N-methyl-N-(5-tetrazolylmethyl]amino]-2-pyrimidinyl]amino]-4-methyl-5-thiazolecarboxylic acid, ethyl ester | 1.59 | 460.52 |
| A173 | 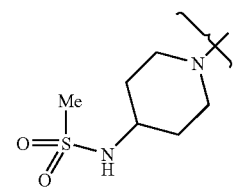 | 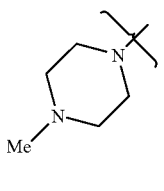 | 2-[[4-[4-methyl-1-piperazinyl]-6-[4-[methylsulfonylamino]-1-piperidinyl]-2-pyrimidinyl]amino]-4-methyl-5-thiazolecarboxylic acid, ethyl ester | 1.25[b] | 539.41 |

TABLE A-continued

| Ex. | L | Z | Name | HPLC Retention[a] (min) | MS Reported |
|---|---|---|---|---|---|
| A174 | | | 2-[[4-[4-hydroxy-1-piperidinyl]-6-[[(2,5-dimethyl)phenyl)methyl]amino]-2-pyrimidinyl]amino]-4-methyl-5-thiazolecarboxylic acid, ethyl ester | 1.80[b] | 497.13 |
| A175 | | | 4-Methyl-2-[[4-(4-morpholinyl)-6-[[(3,4,5-trimethoxyphenyl)methyl]amino]-2-pyrimidinyl]amino]-5-thiazolecarboxylic acid, ethyl ester | 1.43[b] | 545.50 |
| A176 | | | 2-[4-(4-Hydroxypiperidin-1-yl)-6-(3-hydroxy-1-piperidinyl)-pyrimidin-2-ylamino]-4-methyl-thiazole-5-carboxylic acid ethyl ester | 1.42[c] | 449.21 |
| A177 | | | 4-Methyl-2-[[4-(4-methyl-1-piperazinyl)-6-[methyl(3-pyridinylmethyl)amino]-2-pyrimidinyl]amino]-5-thiazolecarboxylic acid, ethyl ester | 1.12[b] | 483.18 |
| A178 | | | 2-[[4-[3-Oxo-1-piperazinyl]-6-[[(2-(5-(1H)tetrazolyl)phenyl)methyl]amino]-2-pyrimidinyl]amino]-4-methyl-5-thiazolecarboxylic acid, ethyl ester | 1.52 | 535.59 |
| A179 | | | 2-[[4-[(2-Furanylmethyl)amino]-6-(1-piperazinyl)-2-pyrimidinyl]amino]-4-methyl-5-thiazolecarboxylic acid, ethyl ester, trifluoroacetate (1:1) | 1.32 | 444.15 |

TABLE A-continued

| Ex. | L | Z | Name | HPLC Retention[a] (min) | MS Reported |
|---|---|---|---|---|---|
| A180 | (3,4-dimethoxybenzyl)amino- methyl linker | morpholinyl | 2-[[4-[[(3,4-Dimethoxyphenyl)methyl]amino]-6-(4-morpholinyl)-2-pyrimidinyl]amino]-4-methyl-5-thiazolecarboxylic acid, ethyl ester | 1.65[b] | 515.13 |
| A181 | N-methyl-N-(3-pyridinylmethyl)amino | (tetrahydro-2-furanyl)methylamino | 4-Methyl-2-[[4-[methyl(3-pyridinylmethyl)amino]-6-[[(tetrahydro-2-furanyl)methyl]amino]-2-pyrimidinyl]amino]-5-thiazolecarboxylic acid, ethyl ester | 1.36[c] | 484.37 |
| A182 | N-methyl-N-(1H-tetrazol-5-ylmethyl)amino | 4-hydroxy-1-piperidinyl | 2-[[4-[(4-hydroxy-1-piperidinyl)]-6-[[N-methyl-N-(5-tetrazolylmethyl)amino]-2-pyrimidinyl]amino]-4-methyl-5-thiazolecarboxylic acid, ethyl ester | 1.30 | 475.20 |
| A183 | 4-hydroxy-4-(phenylmethyl)piperidin-1-yl | 4-hydroxy-1-piperidinyl | 2-[4-(4-Hydroxypiperidin-1-yl)-6-[(4-(hydroxy)-4-(phenylmethyl)piperidin-1-yl)]-pyrimidin-2-ylamino]-4-methyl-thiazole-5-carboxylic acid ethyl ester | 1.66[a] | 553.35 |
| A184 | 2-(morpholin-4-yl)ethylamino | 4-dimethylamino-1-piperidinyl | 2-[4-(4-Dimethylamino-1-piperazinyl)-6-[[2-(1-morpholinyl)ethyl]amino] pyrimidin-2-ylamino]-4-methyl-thiazole-5-carboxylic acid ethyl ester | 1.04[c] | 519.35 |
| A185 | (3-pyridinylmethyl)oxy | 4-hydroxy-1-piperidinyl | 2-[[4-[4-hydroxy-1-piperidinyl]-6-[[(3-pyridinylmethyl)]oxy]-2-pyrimidinyl]amino]-4-methyl-5-thiazolecarboxylic acid, ethyl ester | 1.50[c] | 471.05 |

TABLE A-continued

| Ex. | L | Z | Name | HPLC Retention[a] (min) | MS Reported |
|---|---|---|---|---|---|
| A186 | (2,6-dimethylbenzyl)amino group | 3-(aminocarbonyl)piperidin-1-yl | 2-[[4-[3-(Aminocarbonyl)-1-piperidinyl]-6-[[(2,6-dimethylphenyl)methyl]amino]-2-pyrimidinyl]amino]-4-methyl-5-thiazolecarboxylic acid, ethyl ester | 1.74[b] | 524.14 |
| A187 | [4-(methylsulfonylamino)benzyl]amino group | 4-hydroxypiperidin-1-yl | 2-[[4-[4-hydroxy-1-piperidinyl]-6-[[(4-(methylsufonylamino)phenyl)methyl]amino]-2-pyrimidinyl]amino]-4-methyl-5-thiazolecarboxylic acid, ethyl ester | 1.49 | 561.69 |
| A188 | [4-(propylsulfonylamino)benzyl]amino group | 4-hydroxypiperidin-1-yl | 2-[[4-[4-hydroxy-1-piperidinyl]-6-[[(4-(propylsufonylamino)phenyl)methyl]amino]-2-pyrimidinyl]amino]-4-methyl-5-thiazolecarboxylic acid, ethyl ester | 1.60 | 589.74 |
| A189 | 3-(aminocarbonyl)piperidin-1-yl | 4-methylpiperazin-1-yl | 2-[[4-[3-(Aminocarbonyl)-1-piperidinyl]-6-(4-methyl-1-piperazinyl)-2-pyrimidinyl]amino]-4-methyl-5-thiazolecarboxylic acid, ethyl ester | 1.10[b] | 489.43 |
| A190 | 6,7-dimethoxy-3,4-dihydroisoquinolin-2(1H)-yl | 4-methylpiperazin-1-yl | 2-[[4-(3,4-Dihydro-6,7-dimethoxy-2(1H)-isoquinolinyl)-6-(4-methyl-1-piperazinyl)-2-pyrimidinyl]amino]-4-methyl-5-thiazolecarboxylic acid, ethyl ester | 2.53[b] | 554.42 |
| A191 | N-methyl-N-[(1H-tetrazol-5-yl)methyl]amino | 4-formylpiperazin-1-yl | 2-[[4-[4-Formyl-1-piperazinyl]-6-[[N-methyl-N-(5-tetrazolylmethyl)amino]-2-pyrimidinyl]amino]-4-methyl-5-thiazolecarboxylic acid, ethyl ester | 1.34 | 487.55 |

TABLE A-continued

| Ex. | L | Z | Name | HPLC Retention[a] (min) | MS Reported |
|---|---|---|---|---|---|
| A192 | | | 2-[[4-[[(4-Carboxyphenyl)methyl]amino]-6-[4-(hydroxymethyl)-1-piperidinyl]-2-pyrimidinyl]amino]-4-methyl-5-thiazolecarboxylic acid, ethyl ester | 1.57[b] | 527.16 |
| A193 | | | 2-[[4-[[(4-Carboxyphenyl)methyl]amino]-6-[(4-methyl-1-piperazinyl)-2-pyrimidinyl]amino]-4-methyl-5-thiazolecarboxylic acid, ethyl ester, monohydrochloride | 1.30[b] | 512.19 |
| A194 | | | 4-Methyl-2-[[4-(4-methyl-1-piperazinyl)-6-[[(tetrahydro-2-furanyl)methyl]amino]-2-pyrimidinyl]amino]-5-thiazolecarboxylic acid, ethyl ester | 1.28[b] | 462.18 |
| A195 | | | 2-[[4-[[(4-Carboxyphenyl)methyl]amino]-6-[3-(hydroxymethyl)-1-piperidinyl]-2-pyrimidinyl]amino]-4-methyl-5-thiazolecarboxylic acid, ethyl ester | 1.61[b] | 527.13 |
| A196 | | | 2-[[4-[[[4-[[(2-Methoxyethyl)amino]carbonyl]-phenyl]methyl]amino]-6-(4-methyl-1-piperazinyl)-2-pyrimidinyl]amino]-4-methyl-5-thiazolecarboxylic acid, ethyl ester, trifluoroacetate (1:1) | 1.27 | 569.26 |
| A197 | | | 2-[4,6-Bis-(1-morpholinyl)-pyrimidin-2-ylamino]-4-methyl-thiazole-5-carboxylic acid ethyl ester | 1.35[b] | 435.31 |

TABLE A-continued

| Ex. | L | Z | Name | HPLC Retention[a] (min) | MS Reported |
|---|---|---|---|---|---|
| A198 | (1H-tetrazol-5-ylmethyl)(methyl)amino- | 3-(aminocarbonyl)piperidin-1-yl | 2-[[4-[3-(Aminocarbonyl)-1-piperidinyl]-6-[[N-methyl-N-(5-tetrazolylmethyl)amino]-2-pyrimidinyl]amino]-4-methyl-5-thiazolecarboxylic acid ethyl ester | 1.28 | 502.22 |
| A199 | methyl(pyridin-3-ylmethyl)amino- | morpholin-4-yl | 4-Methyl-2-[[4-[methyl(3-pyridinylmethyl)amino]-6-[4-morpholinyl]-2-pyrimidinyl]amino]-5-thiazolecarboxylic acid, ethyl ester | 1.35[b] | 470.12 |
| A200 | [4-(methoxycarbonyl)benzyl]amino- | 3-(aminocarbonyl)piperazin-1-yl | 2-[[4-[3-(Aminocarbonyl)-1-piperazinyl]-6-[[[4-(methoxycarbonyl)phenyl]methyl]amino]-2-pyrimidinyl]amino]-4-methyl-5-thiazolecarboxylic acid, ethyl ester | 1.47[b] | 555.15 |
| A201 | 4-hydroxypiperidin-1-yl | —Cl | 2-[[4-[4-hydroxy-1-piperidinyl]-6-chloro-4-methyl-5-thiazolecarboxylic acid, ethyl ester | 1.50[c] | 398.18 |
| A202 | 1-oxa-3,8-diazaspiro[4.5]decan-2,4-dion-8-yl | —Cl | 2-[[4-Chloro-6-[(1-oxa-3,8-diazaspiro[4.5]decan-2,4-dion-8-yl]-2-pyrimidinyl]amino]-4-methyl-5-thiazolecarboxylic acid, ethyl ester | 1.80 | 467.41 |
| A203 | (3,4,5-trimethoxybenzyl)amino- | 4-(hydroxymethyl)piperidin-1-yl | 2-[[4-[4-(Hydroxymethyl)-1-piperidinyl]-6-[[(3,4,5-trimethoxyphenyl)methyl]amino]-2-pyrimidinyl]amino]-4-methyl-5-thiazolecarboxylic acid, ethyl ester | 1.63 | 573.21 |

TABLE A-continued

| Ex. | L | Z | Name | HPLC Retention[a] (min) | MS Reported |
|---|---|---|---|---|---|
| A204 | | | 2-[[4-[3-(Hydroxymethyl)-1-Piperidinyl]-6-[[N-methyl-N-(5-tetrazolylmethyl)amino]-2-pyrimidinyl]amino]-4-methyl-5-thiazolecarboxylic acid, ethyl ester | 1.40 | 489.23 |
| A205 | | | 2-[[4-[3-(Hydroxymethyl)-1-pyrrolidinyl]-6-[[N-methyl-N-(5-tetrazolylmethyl)amino]-2-pyrimidinyl]amino]-4-methyl-5-thiazolecarboxylic acid, ethyl ester | 1.42 | 474.55 |
| A206 | | | 4-Methyl-2-[[4-[methyl(phenylmethyl)amino]-6-(4-methyl-1-piperazinyl)-2-pyrimidinyl]amino]-5-thiazolecarboxlic acid, ethyl ester | 2.37 | 482.45 |
| A207 | | Me$_2$N— | 2-[[4-(Dimethylamino)-6-[[[4-(methylsulfonyl)phenyl]methyl]amino]-2-pyrimidinyl]amino]-4-methyl-5-thiazolecarboxylic acid, ethyl ester | 1.31[b] | 491.45 |
| A208 | | | 2-[[4-[4-Hydroxy-1-piperidinyl]-6-[[(3-(5-(1H)tetrazolyl)phenyl)methyl]amino]-2-pyrimidinyl]amino]-4-methyl-5-thiazolecarboxylic acid, ethyl ester | 1.43 | 536.62 |
| A209 | | | 2-[[4-[4-hydroxymethyl-1-piperidinyl]-6-[[(4-(propylsufonylamino)phenyl)methyl]amino]-2-pyrimidinyl]amino]-4-methyl-5-thiazolecarboxylic acid, ethyl ester | 1.61 | 603.77 |

TABLE A-continued

| Ex. | L | Z | Name | HPLC Retention[a] (min) | MS Reported |
|---|---|---|---|---|---|
| A210 | (4-cyclopropylsulfonylamino-benzyl-NH-) | (4-hydroxymethyl-piperidin-1-yl) | 2-[[4-[4-hydroxymethyl-1-piperidinyl]-6-[[(4-(cyclopropylsufonylamino)phenyl)-methyl]amino]-2-pyrimidinyl]amino]-4-methyl-5-thiazolecarboxylic acid, ethyl ester | 1.56 | 601.75 |
| A211 | (3,4,5-trimethoxybenzyl-NH-) | (3-hydroxymethyl-piperidin-1-yl) | 2-[[4-[3-(Hydroxymethyl)-1-piperidinyl]-6-[[(3,4,5-trimethoxyphenyl)methyl]amino]-2-pyrimidinyl]amino]-4-methyl-5-thiazolecarboxylic acid, ethyl ester | 1.48[b] | 573.47 |
| A212 | (3,4,5-trimethoxybenzyl-N(Me)-) | (tetrahydropyran-4-yloxy) | 2-[[4-[4-tetrahydropyranyl]oxy-6-[[N-[(3,4,5-trimethoxyphenyl)methyl]]-N-(methyl)amino]-2-pyrimidinyl]amino]-4-methyl-5-thiazolecarboxylic acid, ethyl ester | 1.95[c] | 574.26 |
| A213 | (piperazin-1-yl) | —NH$_2$ | 2-[[4-[1-piperazinyl]-6-amino-4-methyl-5-thiazolecarboxylic acid, ethyl ester | 1.07 | 364.14 |
| A214 | (4-methoxyphenoxy) | (4-methyl-piperazin-1-yl) | 2-[[4-[4-Methyl-1-piperazinyl]-6-[(4-methoxyphenyl)oxy]-2-pyrimidinyl]amino]-4-methyl-5-thiazolecarboxylic acid, ethyl ester | 1.63[c] | 485.23 |

[a]HPLC conditions used to determine retention times; 4 min gradient 0–100% B in A(A; 0.1% TFA in 90/10 water/methanol; B; 0.1% TFA in 10/90 water/methanol) using a YMC turbopack column at 254 nm. Waters Xterra 4.6 × 30 5μ C18 4 min gradient 0–100% B in A(A; 0.2% H$_3$PO$_4$ in 90/10 water/methanol; B; 0.2% H$_3$PO$_4$ in 10/90 water/methanol)[a]. YMC ODS-A 4.6 × 33 (2 min)[b]. Phenomenox 4.6 × 30 5μ (2min)[c]. Phenomenex Primesphere S5 C18 4.6 × 50 (4 min)[d].

Examples B1

4-Methyl-2-{4-(4-methyl-piperazin-1-yl)-6-[[[4-(aminosulfonyl)phenyl]methyl]amino]pyrimidin-2-ylamino}-thiazole-5-carboxylic acid ethyl ester

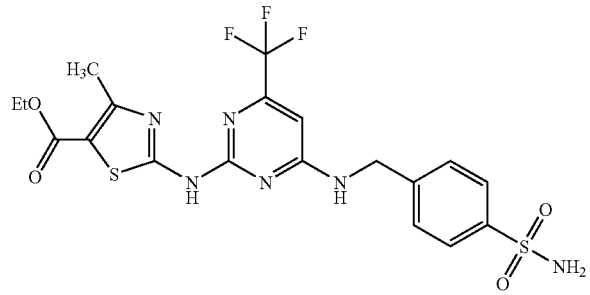

B1

B1.1: 4-Methyl-2-(6-oxo-4-trifluoromethyl-1,6-dihydro-pyrimidin-2-ylamino)-thiazole-5-carboxylic acid ethyl ester

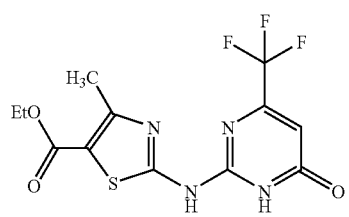

B1.1

A solution of A1.1 (125 mg, 0.731 mmol), ethyl trifluoroacetoacetate (167 mg, 0.731 mmol) and sodium ethoxide (21% in ethanol, 0.989 ml, 2.65 mmol) in DMA was heated to 100° C. for 1 hr and then it was cooled down to RT. The reaction mixture was diluted with 2 mL of water, and neutralized with 1 N HCl. The solid was collected by filtration and dried to yield B1.1 (150 mg, 59%).

B1.2: 2-(4-Chloro-6-trifluoromethyl-pyrimidin-2-ylamino)-4-methyl-thiazole-5-carboxylic acid ethyl ester

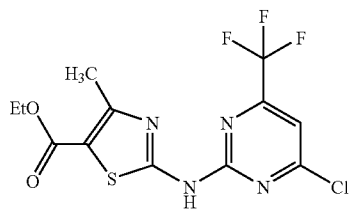

B1.2

A solution of B1.1 (150 mg, 0.429 mmol) in POCl$_3$ (1 ml) was heated to 100° C. for 2 hours and then it was cooled down to RT which was poured into 10 ml of ice-water. It was neutralized with NaOH to pH about 9. The solid was collected with filtration and then it was added to 10 ml of methanol and stirred about 10 minutes. The solid was filtered off. The mother solution was concentrated to yield the desired product B1.2 (70 mg, 44.3%). LC/MS (M+H)$^+$ =368.

B1.3: 4-Methyl-2-{4-(4-methyl-piperazin-1-yl)-6-[[[4-(aminosulfonyl)phenyl]methyl]amino]pyrimidin-2-ylamino}-thiazole-5-carboxylic acid ethyl ester A solution of B1.2 (70 mg, 0.19 mmol) and 4-methylsulfonylbenzylamine hydrochloric salt (66 mg, 0.285 mmol), diisopropylethylamine (111 mg, 0.855 mmol) in N-methyl-2-pyrrolidine (2 mL) was heated to 120 to 130° C. for two hours. The reaction mixture was concentrated to yield a crude product which was purified with prep. HPLC (reverse phase) to yield B1 (38 mg, 32%). $^1$H-NMR (CD$_3$OD) δ: 7.78 (2H, d, J=8 Hz), 7.52 (2H, d, J=8 Hz), 4.92 (2H, s), 4.17 (2H, q, JJ=7 Hz), 4.03 (2H, m), 3.45 (2H, m), 2.93–2.98 (8H, m), 2.40 (3H, s), 1.18 (3H, t, J=7 Hz). HPLC: 98%, ret. time=1.58 min., LC/MS (M+H)$^+$=517.

Examples B2–B4

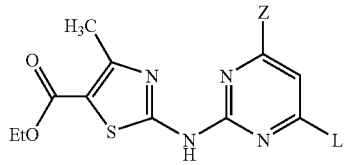

Examples B2–B3 were prepared in a similar manner to that used for Example B1, with the use of the appropriate beta-ketoester in step B1.1, and the appropriate amine in step B1.3.

TABLE B

| Ex. | L | Z | Name | HPLC Retention[a] (min) | MS Reported |
|---|---|---|---|---|---|
| B2 | ![H2N-SO2-C6H4-CH2-NH-] | (CH$_3$)$_2$CH— | 2-[4-Isopropyl-6-(4-sulfamoyl-benzylamino)-pyrimidin-2-ylamino]-4-methyl-thiazole-5-carboxylic acid ethyl ester | 2.55 | 491.18 |

TABLE B-continued

| Ex. | L | Z | Name | HPLC Retention[a] (min) | MS Reported |
|---|---|---|---|---|---|
| B3 | ![H2N-SO2-C6H4-CH2-NH-] | CH$_3$— | 4-Methyl-2-[4-(4-sulfamoyl-benzylamino)-6-methyl-pyrimidin-2-ylamino]-thiazole-5-carboxylic acid ethyl ester | 2.23 | 463.18 |
| B4 | ![H2N-SO2-C6H4-CH2-NH-] | HOCH$_2$— | 4-Methyl-2-[4-(4-sulfamoyl-benzylamino)-6-hydroxymethyl-pyrimidin-2-ylamino]-thiazole-5-carboxylic acid ethyl ester | 1.35 | 479 |

[a] HPLC conditions used to determine retention times; 4 min gradient 0–100% B in A(A; 0.1% TFA in 90/10 water/methanol; B; 0.1% TFA in 10/90 water/methanol) using a YMC turbopack column at 254 nm.
*Waters Xterra 4.6 × 30 5 u C18 (2 min) Solvent A and B as above.

Example B5

1-Acetyl-5-{4-(4-methyl-piperazin-1-yl)-6-[[[4-(aminosulfonyl)phenyl]methyl]amino]pyrimidin-2-ylamino}-2,3-dihydro-1H-tetrahyroindole

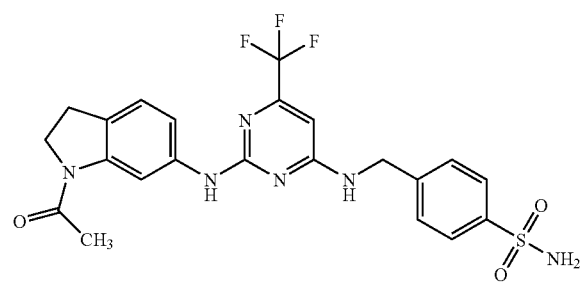

B5

B5.1: 4-Chloro-2-methylthio-6-trifluoromethylpyrimidine

B5.1

A mixture of commercially available 4-hydroxy-2-methylthio-6-trifluoromethylpyrimidine (2.00 g, 9.52 mmol) and POCl$_3$ (10 mL) was heated at reflux for 1.5 h. The excess POCl$_3$ was removed under vacuum. The residue was dissolved in AcOEt, washed with cold water, saturated NaHCO$_3$ solution, cold water, and brine. The solution was then dried over anhydrous MgSO$_4$. Evaporation of solvent provided B5.1 (1.31 g, 60% yield) as a colorless oil.

B5.2: 4-[[[4-(Aminosulfonyl)phenyl]methyl]amino]-2-methylthio-6-trifluoromethylpyrimidine

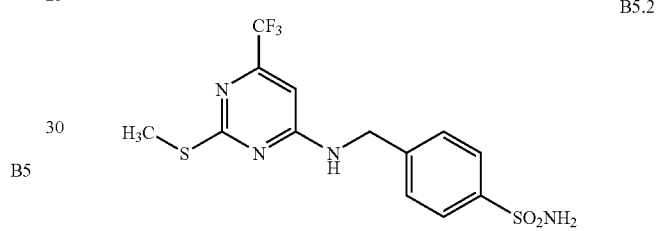

B5.2

A mixture of B5.1 (1.28 g, 5.60 mmol), 4-aminomethyl-benzenesulfonamide hydrochloride (1.97 g, 8.85 mmol), and triethylamine (1.76 mL, 12.6 mmol) in ethanol (15 mL) was heated at 85° C. in a sealed tube for 1 h. The mixture was concentrated under vacuum. The residue was diluted with AcOEt, washed with water, 1N AcOH (twice), saturated NaHCO$_3$ solution (twice), and brine. The solution was then dried over anhydrous MgSO$_4$. Evaporation of solvent provided B5.2 (2.10 g, 99% yield) as a white solid.

B5.3: 4-[[[4-(Aminosulfonyl)phenyl]methyl]amino]-2-methylsulfonyl-6-trifluoromethylpyrimidine

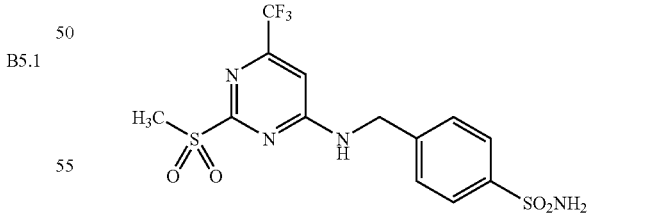

B5.3

To a solution of B5.2 (1.88 g, 4.97 mmol) in MeOH (130 mL) was added mCPBA (75%, 3.42 g, 14.9 mmol) at rt in one portion. The resulting mixture was stirred at rt for 16 h before it was concentrated under vacuum. The residue was diluted with AcOEt, washed with 5% NaS$_2$O$_3$ solution (twice), saturated NaHCO$_3$ solution (twice), and brine. The solution was then dried over anhydrous MgSO$_4$. Evaporation of solvent provided B5.3 (2.00 g, 98% yield) as a white solid.

B5.5: 1-Acetyl-5-{4-(4-methyl-piperazin-1-yl)-6-[[[4(aminosulfonyl)phenyl]methyl]amino]pyrimidin-2-ylamino}-2,3-dihydro-1H-tetrahyroindole A mixture of B5.3 (20 mg, 0.048 mmol) and commercially available 1-Acetyl-5-amino-2,3-dihydro-(1H)indole (84 mg, 0.48 mmol) was fused at 175° C. for 20 min. After cooling to rt, the mixture was dissolved in a minimum amount of DMSO, diluted with MeOH, and applied to preparative HPLC. B5 (16 mg, 46% yield) was obtained as a lyophilized powder as a 2 eq. TFA salt. $(M+H)^+$=507.09.

Examples C1

4-Methyl-2-{4-(4-methyl-piperazin-1-yl)-6-[4-(1H-tetrazol-5-yl)-benzylamino]-pyrimidin-2-ylamino}-thiazole-5-carboxylic acid ethyl ester

C1

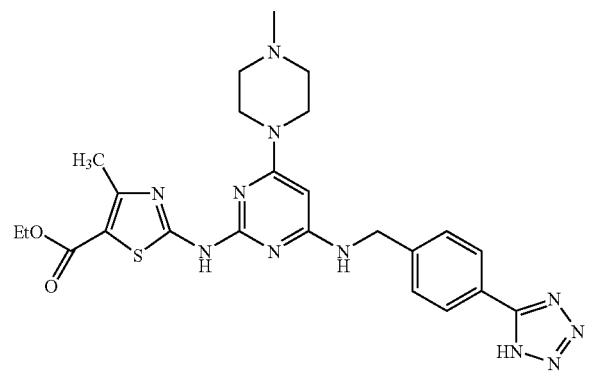

C1.1: 2-[4-Chloro-6-(4-methyl-piperazin-1-yl)-pyrimidin-2-ylamino]-4-methyl-thiazole-5-carboxylic acid ethyl ester

C1.1

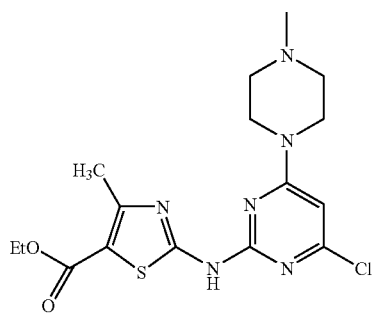

A suspension of A1.1 (600 mg, 1.8 mmol), 1-methyl-piperazine (0.22 mL, 2.0 mmol) and diisopropylethylamine (1.4 mL, 7.9 mmol) in n-butanol (12 mL) was heated to 110° C. for 3 hours. After cooling to room temperature, the precipitated solid was collected by filtration and washed with methanol to yield C1.1 (670 mg, 94%). HPLC: 95%, ret. time=1.403 min., LC/MS $M^+$=397.

C1.2: 2-[4-(4-Cyano-benzylamino)-6-(4-methyl-piperazin-1-yl)-pyrimidin-2-ylamino]-4-methyl-thiazole-5-carboxylic acid ethyl ester

C1.2

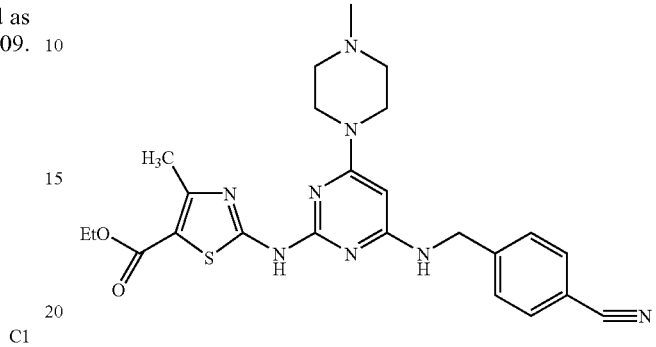

A solution of compound C1.1 (117.0 mg, 0.3 mmol) and 4-cyanobenzylamine (86.0 mg, 0.65 mmol) in n-butanol (2.0 ml) was heated to 130° C. overnight. After cooling to room temperature, the precipitated solid was collected by filtration and purified by preparative HPLC to yield C1.2 (118.0 mg, 81%). HPLC: 95%, ret. time=1.947 min., LC/MS $M^+$=493.

C1.3  4-Methyl-2-{4-(4-methyl-piperazin-1-yl)-6-[4-(1H-tetrazol-5-yl)-benzylamino]-pyrimidin-2-ylamino}-thiazole-5-carboxylic acid ethyl ester Azidotrimethyltin (42.0 mg, 0.21 mmol) was added in one portion to a stirred suspension of compound C1.2 (53.4 mg, 0.11 mmol) in o-xylene (0.5 mL) and heated to 115° C. overnight. After cooling to room temperature the solid was filtered, washed with hot toluene and purified by preparative HPLC to yield C1 (37.0 mg, 64%). $^1$H-NMR (MeOH-d$_4$) □: 8.24 (2H, d, J=8.5 Hz), 7.82 (2H, d, J=8.0 Hz), 5.11 (3H, br. s), 4.96 (1H, br. s), 4.52 (2H, q, J=7.0 Hz), 3.57 (4H, br. s), 3.53 (4H, br. s), 3.18 (3H, s), 2.78 (3H, s), 1.56 (3H, t, J=7.0 Hz). HPLC: 95%, ret. time=1.847 min., LC/MS $(M+H)^+$=536.

Examples 2–C12

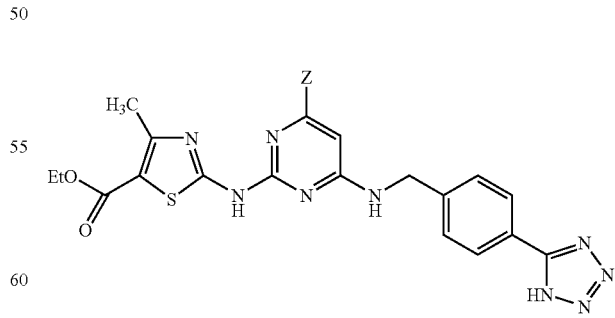

Examples C2–C12 were prepared in a similar manner to that used for Example C1, with the use of the appropriate amine in step C1.1.

TABLE C

| Ex. | Z | Name | HPLC Retention[a] (min) | MS Reported |
|---|---|---|---|---|
| C2 | 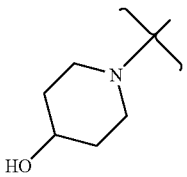 | 2-{4-(4-Hydroxy-piperidin-1-yl)-6-[4-(1H-tetrazol-5-yl)-benzylamino]-pyrimidin-2-ylamino}-4-methyl-thiazole-5-carboxylic acid ethyl ester | 1.30 | 537.57 |
| C3 | 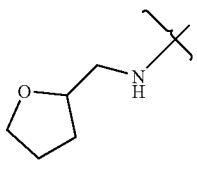 | 4-Methyl-2-{4-[(tetrahydro-furan-2-ylmethyl)-amino]-6-[4-(1H-tetrazol-5-yl)-benzylamino]-pyrimidin-2-ylamino}-thiazole-5-carboxylic acid ethyl ester | 1.58 | 537.34 |
| C4 | 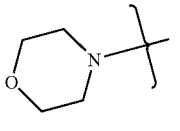 | 4-Methyl-2-{4-morpholin-4-yl-6-[4-(1H-tetrazol-5-yl)-benzylamino]-pyrimidin-2-ylamino}-thiazole-5-carboxylic acid ethyl ester | 1.55 | 523.22 |
| C5 | 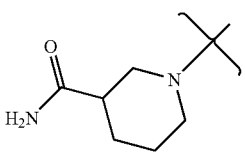 | 2-{4-(3-Carbamoyl-piperidin-1-yl)-6-[4-(1H-tetrazol-5-yl)-benzylamino]-pyrimidin-2-ylamino}-4-methyl-thiazole-5-carboxylic acid ethyl ester | 1.427 | 564.36 |
| C6 | 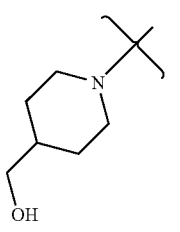 | 2-{4-(4-Hydroxymethylpiperidin-1-yl)-6-[4-(1H-tetrazol-5-yl)-benzylamino]-pyrimidin-2-ylamino}-4-methyl-thiazole-5-carboxylic acid ethyl ester | 1.443 | 551.36 |
| C7 | 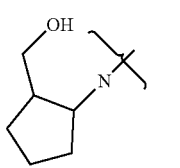 | 2-{4-(2-Hydroxymethyl-1-pyrrolidinyl)-6-[4-(1H-tetrazol-5-yl)-benzylamino]-pyrimidin-2-ylamino}-4-methyl-thiazole-5-carboxylic acid ethyl ester | 1.55 | 536.62 |
| C8 | 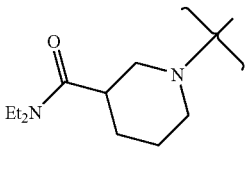 | 2-{4-(3-N,N-Diethylcarbamoyl-1-piperidinyl)-6-[4-(1H-tetrazol-5-yl)-benzylamino]-pyrimidin-2-ylamino}-4-methyl-thiazole-5-carboxylic acid ethyl ester | 1.73 | 619.75 |
| C9 | 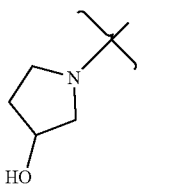 | 2-{4-(3-Hydroxy-1-pyrrolidinyl)-6-[4-(1H-tetrazol-5-yl)-benzylamino]-pyrimidin-2-ylamino}-4-methyl-thiazole-5-carboxylic acid ethyl ester | 1.59 | 522.59 |

TABLE C-continued

| Ex. | Z | Name | HPLC Retention[a] (min) | MS Reported |
|---|---|---|---|---|
| C10 | 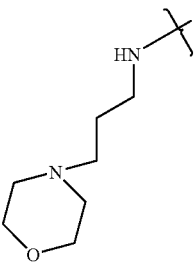 | 4-Methyl-2-{[[2-[4-morpholin-4-yl]ethyl]amino-6-[4-(1H-tetrazol-5-yl)-benzylamino]-pyrimidin-2-ylamino}-thiazole-5-carboxylic acid ethyl ester | 1.42 | 579.69 |
| C11 | 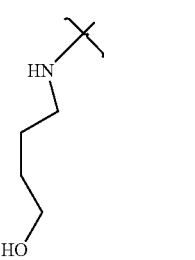 | 4-Methyl-2-{[[4-hydroxy]butyl]amino-6-[4-(1H-tetrazol-5-yl)-benzylamino]-pyrimidin-2-ylamino}-thiazole-5-carboxylic acid ethyl ester | 1.507 | 524.61 |
| C12 | 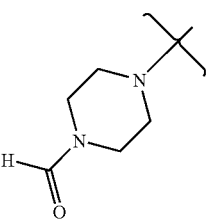 | 2-{4-(4-Formyl-1-piperazinyl)-6-[4-(1H-tetrazol-5-yl)-benzylamino]-pyrimidin-2-ylamino}-4-methyl-thiazole-5-carboxylic acid ethyl ester | 1.46 | 549.62 |

[a]HPLC conditions used to determine retention times; 4 min gradient 0–100% B in A(A; 0.1% TFA in 90/10 water/methanol; B; 0.1% TFA in 10/90 water/methanol) using a YMC turbopack column at 254 nm.
*Waters Xterra 4.6 × 30 5 u C18 (2 min) Solvent A and B as above.

Example D1

2-[[4-[[(4-Chlorophenyl)methyl]amino]-6-(5-oxazolyl)-2-pyrimidinyl]amino]-4-methyl-5-thiazole-carboxylic acid ethyl ester

D1

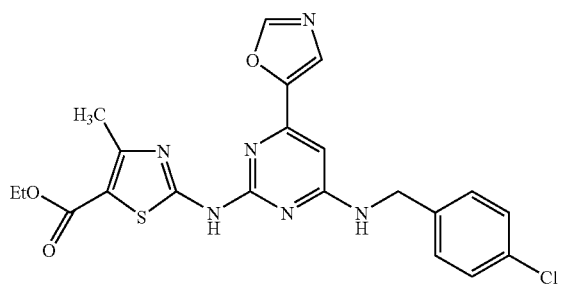

D1.1: 2-Amino-6-diethoxymethyl-3H-pyrimidin-4-one

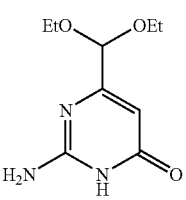

D1.1

A solution of 4,4-diethoxy-3-oxo-butyric acid ethyl ester [Johnson, T. B. and Mikeska, L. A. J. Am. Chem. Soc. 41, 810 (1919)] (18.0 g, 82.5 mol) in ethanol (300 mL) was treated with guanidine carbonate (14.8 g, 82.5 mol) and this was stirred under reflux until no solid remained (~4 hours). The mixture was concentrated, diluted with water and the solid was collected by filtration to give D1.1 (13.1 g, 74%) as a beige solid. $^1$H-NMR (DMSO-$d_6$) δ: 10.78 (1H, br s), 6.61 (2H, br s), 5.63 (1H, s), 4.90 (1H, s), 3.51 (4H, m), 1.13 (6H, t, J=7.1 Hz). LC/MS$^c$: ret. time: 0.757 min. (M+H)$^+$: 214. M.p.: 198.0–202.7° C.

D1.2 (4-Diethoxymethyl-6-oxo-1,6-dihydro-pyrimidin-2-yl)-thiourea

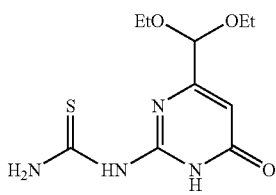

A solution of D1.1 (1.0 g, 4.69 mmol) in dioxane (18 mL) was treated with ethoxycarbonyl isothiocyanate (0.553 mL, 4.69 mmol) and refluxed for 30 minutes. The mixture was then freeze dried to afford the crude (4-diethoxymethyl-6-oxo-1,6-dihydro-pyrimidin-2-yl)-(ethoxycarbonyl)-thiourea (1.6 g, 100%). LC/MS$^c$: ret. time: 1.527 min. (M+H)$^+$: 345.40.

The residue was dissolved in sodium hydroxide (2N, 50 mL) and stirred at 100° C. for 30 minutes. The mixture was then cooled in an ice-bath and acidified with concentrated hydrochloric acid. The solid was collected by filtration and dried under vacuum to give D1.2 (0.740 g, 59%). HPLC$^b$: 96.6%, ret. time: 0.844 min.

D1.3 2-[(4-Diethoxymethyl-6-oxo-1,6-dihydro-pyrimidin-2-yl)-amino]-4-methyl-5-thiazolecarboxylic acid ethyl ester

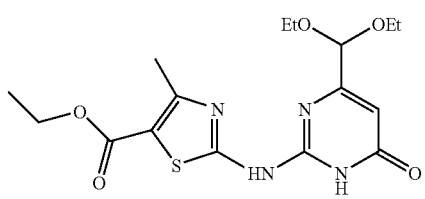

A mixture of D1.2 (3.62 g, 13.29 mmol) and ethyl 2-chloroacetate (1.86 mL, 13.29 mmol) in ethanol (250 mL) was refluxed for 20 hours. The mixture was then diluted with water and the solid collected by filtration to afford D1.3 (3.9 g, 76%). $^1$H-NMR (DMSO-d$_6$) δ: 11.84 (2H, br s), 5.24 (1H, br s), 4.23 (2H, q, J=7.1 Hz), 3.64 (4H, m), 1.27 (3H, t, J=7.2 Hz), 1.20 (6H, t, J=7.0 Hz). LC/MS$^c$: ret. time: 1.663 min. (M+H)$^+$: 383.

D1.4 2-[(4-Formyl-6-chloro-pyrimidin-2-yl)-amino]-4-methyl-5-thiazolecarboxylic acid ethyl ester

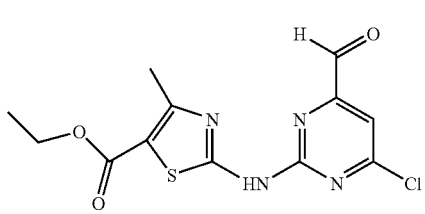

A solution of D1.3 (0.500 g, 1.31 mmol) in phosphorous oxychloride (5 mL) was stirred at 60° C. for 2 hours. The mixture was then added to ice/water and stirred for 30 minutes. Saturated sodium carbonate was then added and this was diluted with ethyl acetate/tetrahydrofuran. The aqueous layer was separated and extracted with ethyl acetate. The combined organic layers were dried over anhydrous magnesium sulfate, filtered and concentrated to give D1.4 (0.330 g, 77%). $^1$H-NMR (DMSO-d$_6$) δ: 11.92 (1H, br s), 9.95 (1H, s), 7.66 (1H, s), 4.33 (2H, q, J=7.1 Hz), 2.63 (3H, s), 1.36 (3H, t, J=7.1 Hz). LC/MS$^c$: 86.1%, ret. time: 1.413 min. (M+H$_2$O+H)$^+$: 345.33.

D1.5 2-[(4-Oxazol-5-yl-6-chloro-pyrimidin-2-yl)-amino]-4-methyl-5-thiazolecarboxylic acid ethyl ester

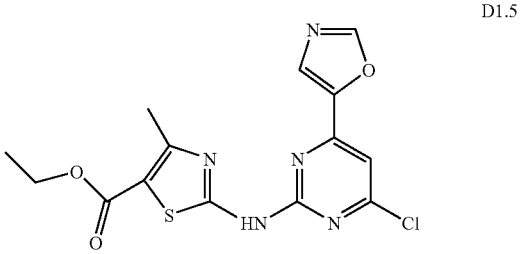

A mixture of D1.4 (0.515 g, 1.57 mmol), TOSMIC (0.307 g, 1.57 mmol) and potassium carbonate (0.217 g, 1.57 mmol) in ethanol (30 mL) was refluxed for 2 hours. The mixture was then cooled to room temperature and diluted with water. The precipitated solid was collected by filtration and dried under vacuum to provide D1.5 (0.482 g, 75%). $^1$H-NMR (DMSO-d$_6$) δ: 12.68 (1H, br s), 8.82 (1H, s), 8.15 (1H, s), 7.66 (1H, s), 4.29 (2H, q, J=7.1 Hz), 2.56 (3H, s), 1.34 (3H, t, J=7.2 Hz). LC/MS$^c$: ret. time: 1.807 min. (M+H)$^+$: 366.28.

D1.6 2-[[4-[[(4-Chlorophenyl)methyl]amino]-6-(5-oxazolyl)-2-pyrimidinyl]amino]-4-methyl-5-thiazolecarboxylic acid ethyl ester A mixture of D1.5 (0.048 g, 0.131 mmol) and 4-chlorobenzylamine (0.032 mL, 0.262 mmol) in N-methylpyrrolidinone was stirred at 60° C. for 2 hours. The mixture was then concentrated, dissolved in DMF and purified by Prep HPLC (Acetonitrile/water/0.1% TFA, column Xterra C8 20×100 mm). The residue was then triturated in methanol to yield D1 (0.049 g, 65%) as a beige solid. $^1$H-NMR (DMSO-d$_6$) δ: 11.72 (1H, br s), 8.56 (1H, s), 8.39 (1H, br s), 7.66 (1H, s), 7.36 (4H, m), 6.51 (1H, s), 4.68 (2H, br s), 4.18 (2H, q, J=7.1 Hz), 1.22 (3H, t, J=7.1 Hz). LC/MS$^c$: ret. time: 1.703 min. (M+H)$^+$: 471.30.

Examples D2 to D17

Examples D2 to D17 were prepared in a similar manner to that used for Example D1 utilizing the appropriate amines and N,N-dimethylformamide as the solvent instead of N-methylpyrrolidinone.

TABLE D

| Ex. | L | Name | HPLC Retention[a] (min) | % Purity | MS Reported |
|---|---|---|---|---|---|
| D2 | 4-aminosulfonylphenyl-methylamino group | 2-[[4-[[(4-Aminosylfonylphenyl)methyl]amino]-6-(5-oxazolyl)-2-pyrimidinyl]amino]-4-methyl-5-thiazolecarboxylic acid ethyl ester | 1.28 | 95 | 516.33 |
| D3 | morpholino | 2-[[4-Morpholino-6-(5-oxazolyl)-2-pyrimidinyl]amino]-4-methyl-5-thiazolecarboxylic acid ethyl ester | 1.3 | 100 | 417.32 |
| D4 | (3,4-dimethoxyphenyl)methylamino | 2-[[4-[[(3,4-Dimethoxyphenyl)methyl]amino]-6-(5-oxazolyl)-2-pyrimidinyl]amino]-4-methyl-5-thiazolecarboxylic acid ethyl ester | 1.39 | 89 | 497.34 |
| D5 | 1,4-dioxa-8-azaspiro[4.5]dec-8-yl | 2-[[4-(1,4-Dioxa-8-aza-spiro[4.5]dec-8-yl)-6-(5-oxazolyl)-2-pyrimidinyl]amino]-4-methyl-5-thiazolecarboxylic acid ethyl ester | 1.37 | 100 | 473.39 |
| D6 | 4-hydroxy-4-phenylpiperidinyl | 2-[[4-[4-Hydroxy-4-phenyl-piperidinyl]-6-(5-oxazolyl)-2-pyrimidinyl]amino]-4-methyl-5-thiazolecarboxylic acid ethyl ester | 1.47 | 89 | 507.39 |
| D7 | (4-methylsulfonylphenyl)methylamino | 2-[[4-[[(4-Methylsulfonylphenyl)methyl]amino]-6-(5-oxazolyl)-2-pyrimidinyl]amino]-4-methyl-5-thiazolecarboxylic acid ethyl ester | 1.32 | 97 | 515.29 |
| D8 | 4-hydroxypiperidinyl | 2-[[4-[4-Hydroxy-piperidinyl]-6-(5-oxazolyl)-2-pyrimidinyl]amino]-4-methyl-5-thiazolecarboxylic acid ethyl ester | 1.19 | 100 | 431.35 |

TABLE D-continued

| Ex. | L | Name | HPLC Retention[a] (min) | % Purity | MS Reported |
|---|---|---|---|---|---|
| D9 | 4-(ethoxycarbonyl)piperidin-1-yl | 2-[[4-[4-Ethoxycarbonyl-piperidinyl]-6-(5-oxazolyl)-2-pyrimidinyl]amino]-4-methyl-5-thiazolecarboxylic acid ethyl ester | 1.47 | 94 | 487.35 |
| D10 | piperidin-1-yl | 2-[[4-Piperidinyl-6-(5-oxazolyl)-2-pyrimidinyl]amino]-4-methyl-5-thiazolecarboxylic acid ethyl ester | 1.42 | 97 | 415.36 |
| D11 | 4-methylpiperazin-1-yl | 2-[[4-[N-Methylpiperazinyl-6-(5-oxazolyl)-2-pyrimidinyl]amino]-4-methyl-5-thiazolecarboxylic acid ethyl ester | 1.11 | 94 | 430.37 |
| D12 | 4-(furan-2-carbonyl)piperazin-1-yl | 2-[[4-[N-(2-Furylcarbonyl)piperazinyl-6-(5-oxazolyl)-2-pyrimidinyl]amino]-4-methyl-5-thiazolecarboxylic acid ethyl ester | 1.35 | 91 | 510.33 |
| D13 | 4-acetyl-1,4-diazepan-1-yl | 2-[[4-[N-Acetyl-[1,4]-diazepyl]-6-(5-oxazolyl)-2-pyrimidinyl]amino]-4-methyl-5-thiazolecarboxylic acid ethyl ester | 1.2 | 100 | 472.34 |

TABLE D-continued

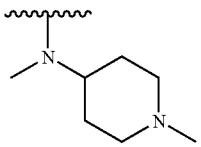

| Ex. | L | Name | HPLC Retention[a] (min) | % Purity | MS Reported |
|---|---|---|---|---|---|
| D14 | 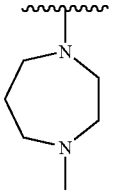 | 2-[[4-[N-Methyl-N-(N-methyl-4-piperidinyl)-amino]-6-(5-oxazolyl)-2-pyrimidinyl]amino]-4-methyl-5-thiazolecarboxylic acid ethyl ester | 1.07 | 93 | 458.37 |
| D15 | 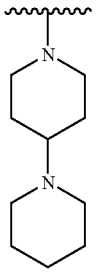 | 2-[[4-[N-Methyl-[1,4]-diazepyl]-6-(5-oxazolyl)-2-pyrimidinyl]amino]-4-methyl-5-thiazolecarboxylic acid ethyl ester | 1.07 | 100 | 444.34 |
| D16 | —N(CH$_2$CH$_2$OMe)$_2$ | 2-[[4-N,N-Dimethoxyethylamino-6-(5-oxazolyl)-2-pyrimidinyl]amino]-4-methyl-5-thiazolecarboxylic acid ethyl ester | 1.34 | 96 | 463.4 |
| D17 | | 2-[[4-[(1',4)-Bipiperidinyl]-6-(5-oxazolyl)-2-pyrimidinyl]amino]-4-methyl-5-thiazolecarboxylic acid ethyl ester | 1.13 | 99 | 498.38 |

[a]HPLC conditions used to determine retention times; 2 min gradient 0–100% B in A; (A; 0.05% TFA in 90/10 water/acetonitrile; B; 0.05% TFA in 10/90 water/acetonitrile) using a X-terra C-8 4.6 × 30 mm column at 254 nm

Examples E1

2-[4-(4-Hydroxy-piperidin-1-yl)-6-(3,4,5-tri-methoxy-phenyl)-pyrimidin-2-ylamino]-4-methylthiazole-5-carboxylic acid ethyl ester

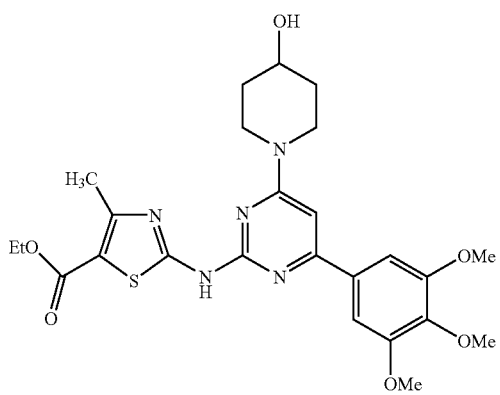

E1

E1.1 2-[4-(4-Hydroxy-piperidin-1-yl)-6-(3,4,5-trimethoxy-phenyl)-pyrimidin-2-ylamino]-4-methylthiazole-5-carboxylic acid ethyl ester

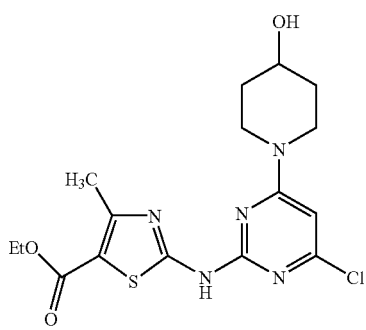

E1.1

A suspension solution of A1.3 (6.04 g, 18.1 mmol), 4-hydroxypiperidine (1.84 g, 18.2 mmol) and diisopropylethylamine (6.3 ml, 36.2 mmol) in ethanol (30 mL) was heated to 50° C. for 16 hours. After cooling to room temperature, the precipitated solid was collected by filtration and washed with ethanol to yield E1.1 (4.72 g, 65%). $^1$H-NMR (DMSO-d$_6$) δ: 11.82 (1H, bs), 6.59 (1H, s), 4.82 (1H, d, J=4.0 Hz), 4.20 (2H, q, J=7.1 Hz), 3.79 (1H, m), 3.40 (2H, m), 2.50 (3H, s), 1.80 (2H, m), 1.40 (2H, m), 1.26 (3H, t, J=7.1 Hz); HPLC: 95%, ret. time$^a$=1.50 min., LC/MS (M+H)$^+$=398.

E1.2 2-[4-(4-Hydroxy-piperidin-1-yl)-6-(3,4,5-trimethoxy-phenyl)-pyrimidin-2-ylamino]-4-methylthiazole-5-carboxylic acid ethyl ester

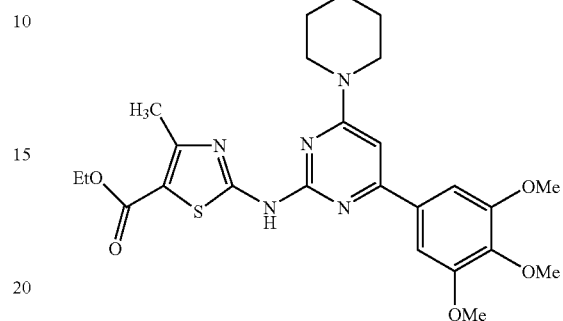

E1.2

A solution of E1.1 (147 mg, 0.370 mmol), 3,4,5-trimethoxyphenylboronic acid (130 mg, 0.613 mmol), Pd(PPh$_3$)$_4$ (21 mg, 0.018 mmol) and K$_2$CO$_3$ (2 mL of 2M aqueous solution) in 1,2-dimethoxyethane (10 mL) and ethanol (3 mL) under argon atmosphere was heated at reflux for 16 h. The reaction was concentrated, the residue dissolved in DMF, filtered through cotton and a plug C-18 silica gel. The resulting solution was directly purified on the preparative HPLC. Fractions containing the product was slightly concentrated and the resulting precipitate collected by filtration, washed with water, to afford E1 (89 mg, 45%) as a light pink solid. $^1$H-NMR (DMSO-d$_6$) δ: 11.55 (1H, s), 7.58 (2H, s), 7.02 (1H, s), 4.80 (1H, d, J=4.0 Hz), 4.22 (2H, q, J=7.1 Hz), 4.22 (2H, m), 3.93 (6H, s), 3.77 (1H, m), 3.72 (3H, s), 3.36 (2H, m), 2.52 (3H, s), 1.80 (2H, m), 1.40 (2H, m), 1.25 (3H, t, J=7.1 Hz); HPLC: 95%, ret. time$^a$=1.44 min., LC/MS (M+H)$^+$=530.

Example E2

2-{4-(4-Hydroxy-piperidin-1-yl)-6-[4-(1H-tetrazol-5-yl)-phenyl]-pyrimidin-2-ylamino}-4-methylthiazole-5-carboxylic acid ethyl ester

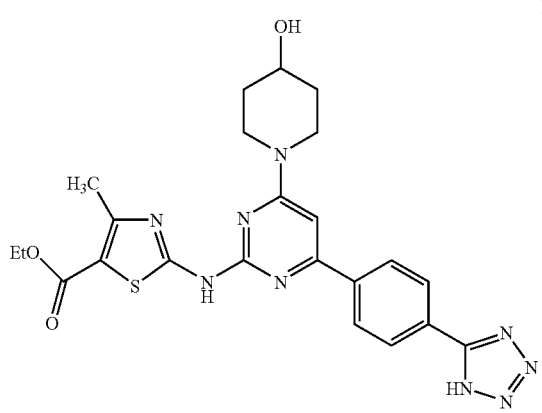

E2

A solution of E6 (52 mg, 0.1119 mmol), sodium azide (92 mg, 1.415 mmol) and ammonium chloride (85 mg, 1.586 mmol) in DMF (2 mL) in a quartz microwave reactor was irradiated for 15 min at 300W so as to maintain a reactive temperature of 175° C. Upon cooling, the reaction was filtered and purified by preparative HPLC to afford E2 (25 mg, 44%). $^1$H-NMR (DMSO-$d_6$) δ: 11.66 (1H, bs), 8.41 (2H, d, J=8.2 Hz), 8.15 (2H, d, J=8.2 Hz), 7.13 (1H, s), 4.81 (1H, bs), 4.23 (2H, q, J=7.1 Hz), 4.22 (2H, m), 3.81 (1H, bs), 3.43 (2H, m), 2.53 (3H, s), 1.84 (2H, m), 1.40 (2H, m), 1.30 (3H, t, J=7.1 Hz); HPLC: 100%, ret. time$^a$=1.30 min., LC/MS (M+H)$^+$=508.

Examples E3–E30

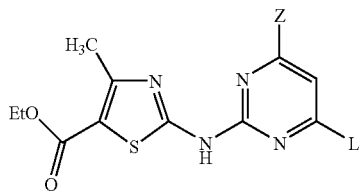

Examples E3 to E30 were prepared in a similar manner to that used for Example E1 utilizing the appropriate amines and organometallic coupling partner.

TABLE E

| Ex. | Z | L | Name | HPLC Retention$^a$ (min) | MS Reported |
|---|---|---|---|---|---|
| E3 | 4-hydroxy-piperidin-1-yl | pyridin-3-yl | 2-[4-(4-Hydroxy-piperidin-1-yl)-6-pyridin-3-yl-pyrimidin-2-ylamino]-4-methylthiazole-5-carboxylic acid ethyl ester | 1.21 | 441 |
| E4 | 4-methanesulfonyl-benzylamino | pyridin-3-yl | 2-[4-(4-Methanesulfonyl-benzylamino)-6-pyridin-3-yl-pyrimidin-2-ylamino]-4-methylthiazole-5-carboxylic acid ethyl ester | 1.54$^b$ | 525 |
| E5 | 4-hydroxy-piperidin-1-yl | pyridin-4-yl | 2-[4-(4-Hydroxy-piperidin-1-yl)-6-pyridin-4-yl-pyrimidin-2-ylamino]-4-methylthiazole-5-carboxylic acid ethyl ester | 1.14 | 441 |
| E6 | 4-hydroxy-piperidin-1-yl | 4-cyano-phenyl | 2-[4-(4-Cyano-phenyl)-6-(4-hydroxy-piperidin-1-yl)-pyrimidin-2-ylamino]-4-methylthiazole-5-carboxylic acid ethyl ester | 1.43 | 465 |
| E7 | 4-hydroxy-piperidin-1-yl | 4-acetyl-phenyl | 2-[4-(4-Acetyl-phenyl)-6-(4-hydroxy-piperidin-1-yl)-pyrimidin-2-ylamino]-4-methylthiazole-5-carboxylic acid ethyl ester | 1.37 | 482 |
| E8 | 4-hydroxy-piperidin-1-yl | 4-hydroxymethyl-phenyl | 2-[4-(4-Hydroxymethyl-phenyl)-6-(4-hydroxy-piperidin-1-yl)-pyrimidin-2-ylamino]-4-methylthiazole-5-carboxylic acid ethyl ester | 1.29 | 470 |
| E9 | 4-hydroxy-piperidin-1-yl | 4-hydroxy-phenyl | 2-[4-(4-Hydroxy-phenyl)-6-(4-hydroxy-piperidin-1-yl)-pyrimidin-2-ylamino]-4-methylthiazole-5-carboxylic acid ethyl ester | 1.32 | 456 |

TABLE E-continued

| Ex. | Z | L | Name | HPLC Retention[a] (min) | MS Reported |
|---|---|---|---|---|---|
| E10 | 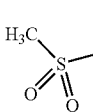 | 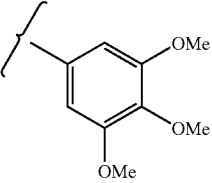 | 2-[4-(4-Methanesulfonyl-benzylamino)-6-(3,4,5-trimethoxy-phenyl)-pyrimidin-2-ylamino]-4-methylthiazole-5-carboxylic acid ethyl ester | 1.51 | 614 |
| E11 | 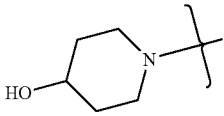 | 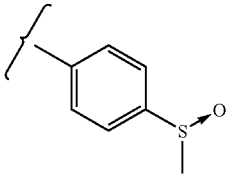 | 2-[4-(4-Methanesulfinylphenyl)-6-(4-hydroxypiperidin-1-yl)-pyrimidin-2-ylamino]-4-methylthiazole-5-carboxylic acid ethyl ester | 1.26 | 502 |
| E12 | 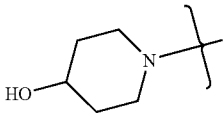 | 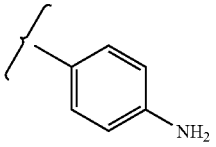 | 2-[4-(4-(Amino)phenyl)-6-(4-hydroxy-piperidin-1-yl)-pyrimidin-2-ylamino]-4-methylthiazole-5-carboxylic acid ethyl ester | 1.54 | 455 |
| E13 | 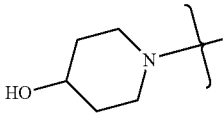 | 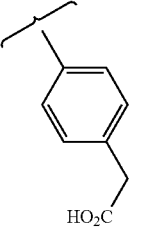 | 2-[4-(4-Carboxymethyl-phenyl)-6-(4-hydroxy-piperidin-1-yl)-pyrimidin-2-ylamino]-4-methylthiazole-5-carboxylic acid ethyl ester | 1.31 | 498 |
| E14 | 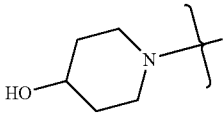 | 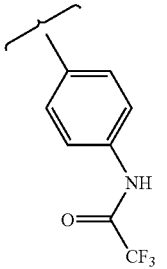 | 2-[4-(4-(Trifluoromethylcarbonylamino)phenyl)-6-(4-hydroxy-piperidin-1-yl)-pyrimidin-2-ylamino]-4-methylthiazole-5-carboxylic acid ethyl ester | 1.50 | 551 |
| E15 | 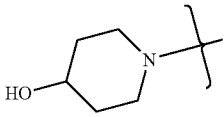 | 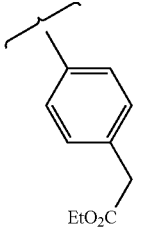 | 2-[4-(4-(Ethoxycarbonylmethyl)phenyl)-6-(4-hydroxy-piperidin-1-yl)-pyrimidin-2-ylamino]-4-methylthiazole-5-carboxylic acid ethyl ester | 1.50 | 526 |
| E16 | 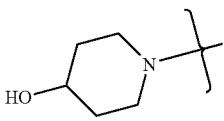 | 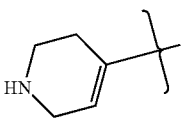 | 2-[4-(1,2,3,6-Tetrahydropyridin-4-yl)-6-(4-hydroxy-piperidin-1-yl)-pyrimidin-2-ylamino]-4-methylthiazole-5-carboxylic acid ethyl ester | 1.16 | 445 |

TABLE E-continued

| Ex. | Z | L | Name | HPLC Retention[a] (min) | MS Reported |
|---|---|---|---|---|---|
| E17 | 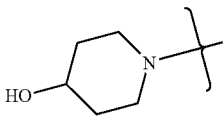 | 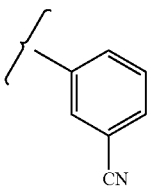 | 2-[4-(3-(cyano)phenyl)-6-(4-hydroxy-piperidin-1-yl)-pyrimidin-2-ylamino]-4-methylthiazole-5-carboxylic acid ethyl ester | 1.43 | 465 |
| E18 | 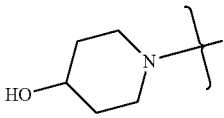 | 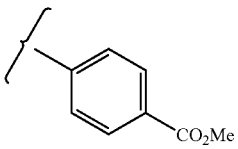 | 2-[4-(4-(Methoxycarbonyl)phenyl)-6-(4-hydroxy-piperidin-1-yl)-pyrimidin-2-ylamino]-4-methylthiazole-5-carboxylic acid ethyl ester | 1.73 | 498 |
| E19 | 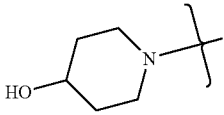 | 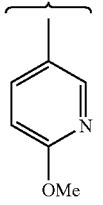 | 2-[4-(2-(Methoxy)-5-pyridinyl)-6-(4-hydroxy-piperidin-1-yl)-pyrimidin-2-ylamino]-4-methylthiazole-5-carboxylic acid ethyl ester | 1.66 | 471 |
| E20 | 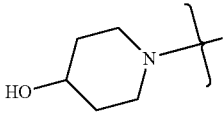 | 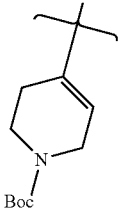 | 2-[4-(4-tertButyloxycarbonyl-1,2,3,6-Tetrahydropyridin-4-yl)-6-(4-hydroxy-piperidin-1-yl)-pyrimidin-2-ylamino]-4-methylthiazole-5-carboxylic acid ethyl ester | 1.83 | 545 |
| E21 | 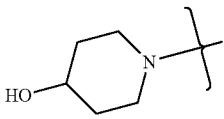 | 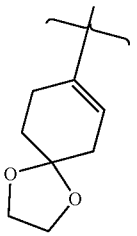 | 2-[4-(1,4-Dioxaspiro[4.5]dec-7-en-8-yl)-6-(4-hydroxy-piperidin-1-yl)-pyrimidin-2-ylamino]-4-methylthiazole-5-carboxylic acid ethyl ester | 1.27 | 502 |
| E22 | 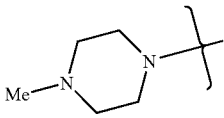 | 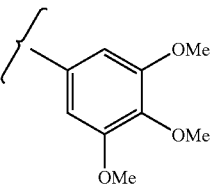 | 2-[4-(4-Methyl-1-piperazin-yl)-6-(3,4,5-trimethoxy-phenyl)-pyrimidin-2-ylamino]-4-methylthiazole-5-carboxylic acid ethyl ester | 2.20 | 528 |
| E23 | 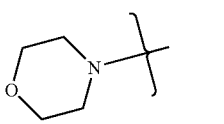 | 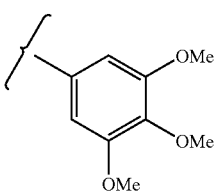 | 2-[4-(4-Morpholinyl)-6-(3,4,5-trimethoxy-phenyl)-pyrimidin-2-ylamino]-4-methylthiazole-5-carboxylic acid ethyl ester | 2.04 | 515 |

TABLE E-continued

| Ex. | Z | L | Name | HPLC Retention[a] (min) | MS Reported |
|---|---|---|---|---|---|
| E24 | 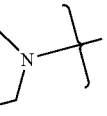 | 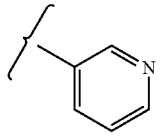 | 2-[4-(4-Morpholinyl)-6-(3-pyridinyl)-pyrimidin-2-ylamino]-4-methylthiazole-5-carboxylic acid ethyl ester | 1.29 | 427 |
| E25 | 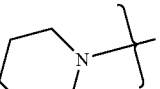 | 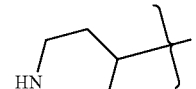 | 2-[4-(Piperadin-4-yl)-6-(4-hydroxy-piperidin-1-yl)-pyrimidin-2-ylamino]-4-methylthiazole-5-carboxylic acid ethyl ester | 1.23 | 447 |
| E26 | 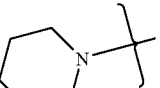 | 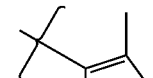 | 2-[[4-[4-Hydroxy-piperidinyl]-6-(3,5-dimethyl-4-isoxazolyl)-2-pyrimidinyl]amino]-4-methyl-5-thiazolecarboxylic acid ethyl ester | 1.31 | 459 |
| E27 | 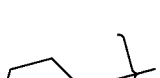 | 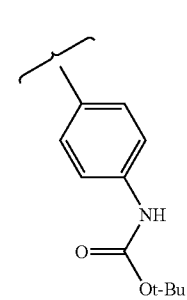 | 2-[4-(4-tert-Butoxycarbonylamino-phenyl)-6-(4-hydroxy-piperidin-1-yl)-pyrimidin-2-ylamino]-4-methyl-5-thiazolecarboxylic acid ethyl ester | 1.87 | 555 |
| E28 | 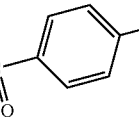 | 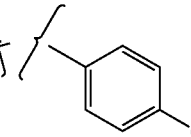 | 2-[4-(4-Cyano-phenyl)-6-(4-methanesulfonyl-benzylamino)-pyrimidin-2-ylamino]-4-methyl-5-thiazolecarboxylic acid ethyl ester | 1.79 | 549 |
| E29 | 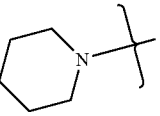 | 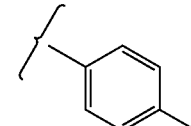 | 2-[4-(4-Methanesulfonylphenyl)-6-(4-hydroxypiperidin-1-yl)-pyrimidin-2-ylamino]-4-methylthiazole-5-carboxylic acid ethyl ester | 1.35 | 518 |
| E30 |  | 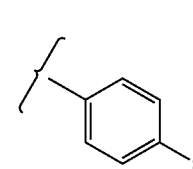 | 2-[4-(4-Methanesulfanylphenyl)-6-(4-hydroxypiperidin-1-yl)-pyrimidin-2-ylamino]-4-methylthiazole-5-carboxylic acid ethyl ester | 1.65 | 486 |

[a] HPLC conditions used to determine retention times: 2 min gradient 0–100% B in A(A; 0.05% TFA in 90/10 water/acetonitrile; B; 0.05% TFA in 10/90 water/acetonitrile) using a Primesphere C4 4.6 × 30 mm column at 254 nm.

[b] 2 min gradient 0–100% B in A(A; 5 mM NH$_4$OAc in 90/10 water/acetonitrile; B; 5 mM NH$_4$OAc in 10/90 water/acetonitrile) using a Primesphere C4 4.6 × 30 mm column at 254 nm.

Examples F1

2-[4-[4-Carboxy-phenyl)-6-(4-hydroxy-piperidin-1-yl)-pyrimidin-2-ylamino]-4-methyl-thiazole-5-carboxylic acid ethyl ester

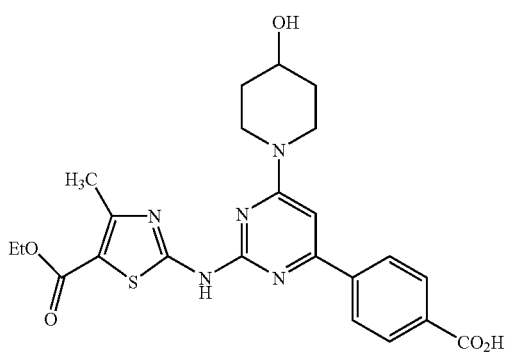

F1.1: 4-(2-Amino-6-hydroxy-pyrimidin-4-yl)-benzoic acid ethyl ester

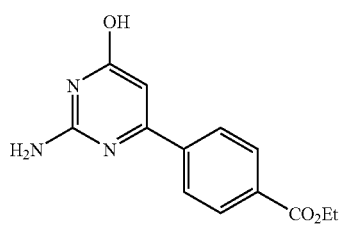

A solution of 4-methoxycarbonylbenzoylacetic acid methyl ester (5.0 g, 21.2 mmol) and guanidine carbonate (3.82 g, 21.2 mmol) in ethanol (150 mL) was heated at reflux for 4 hours. The reaction was cooled to rt then 2N HCl (40 mL) was added. The resulting solid was collected by filtration to afford F1.1 (7.1 g) as a carbonate salt which was used as is in the subsequent step. HPLC: 90%; ret. time$^b$=1.30 min.; LC/MS (M+H)$^+$=261.

F1.2: 4-(2-Amino-6-chloro-pyrimidin-4-yl)-benzoic acid ethyl ester

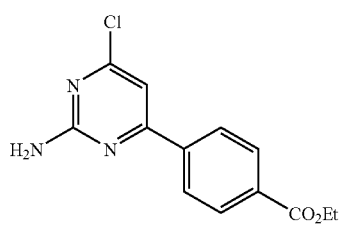

A solution of F1.1 (4.0 g, 12.5 mmol) in POCl$_3$ (15 mL) was heated at 100° C. for 4 hours. The reaction was cooled to RT, partitioned between EtOAc and NaHCO$_3$, the organic phase was dried (MgSO$_4$), filtered and concentrated. The residue was purified by flash chromatography (10%→4100% EtOAc/hexane) to afford F1.2 (1.183 g).

$^1$H-NMR (DMSO-d$_6$) δ: 8.22 (2H, d, J=8.6 Hz), 8.06 (2H, d, J=8.6 Ha), 7.32 (1H, s), 7.26 (2H, bs), 4.34 (2H, q, J=7.1 Hz), 1.33 (3H, t, J=7.1 Hz); HPLC: 92%; ret. time$^b$=1.87 min.; LC/MS (M+H)$^+$=278.

F1.3: 4-(6-Chloro-2-ethoxycarbonylthioureido-pyrimidin-4-yl)-benzoic acid ethyl ester

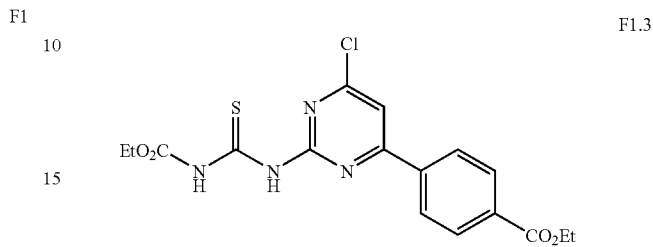

A solution of F1.2 (1.18 g, 4.26 mmol) and ethoxycarbonylisothiocyanate (1.12 g, 8.52 mmol) in dioxane (40 mL) was heated at 100° C. for 16 hours. The reaction was cooled to rt and Et$_2$O and hexane were added. The resulting precipitate was collected by filtration to afford F1.3 (1.36 g, 78%). $^1$H-NMR (DMSO-d$_6$) δ: 12.43 (1H, s), 12.08 (1H, s), 8.37 (2H, d, J=8.6 Hz), 8.13 (1H, s), 8.10 (2H, d, J=8.6 Hz), 4.36(2H, q, J=7.1 Hz), 4.18 (2H, q, J=7.1 Hz), 1.34 (3H, t, J=7.1 Hz), 1.24 (3H, t, J=7.1 Hz); HPLC: 95% ret. time$^b$=2.15 min.; LC/MS (M+H)$^+$=409.

F1.4: 4-(6-Chloro-2-thioureido-pyrimidin-4-yl)-benzoic acid

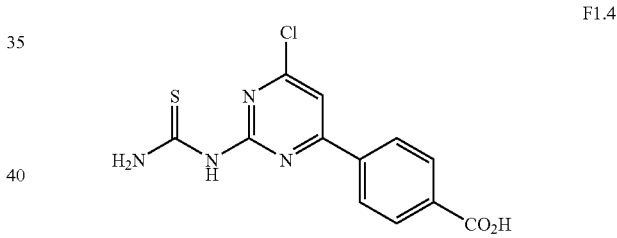

A solution of F1.3 (1.3 g, 3.2 mmol) in 2N NaOH (25 mL) was stirred at rt for 2 hours. The reaction was acidified with 2N HCl. The resulting precipitate was collected by filtration to obtain F1.4 (982 mg, 100%). $^1$H-NMR (DMSO-d$_6$) δ: 11.07 (1H, s), 9.93 (1H, d, J=3.0 Hz), 9.38 (1H, s), 8.31 (2H, d, J=8.5 Hz), 8.15 (2H, d, J=8.5 Hz), 8.14 (1H, s); HPLC: 95%; ret. time$^b$=1.05 min.; LC/MS (M−H)$^-$=307.

F1.5: 2-[4-(4-Carboxy-phenyl)-6-chloro-pyrimidin-2-ylamino]-4-methylthiazole-5-carboxylic acid ethyl ester

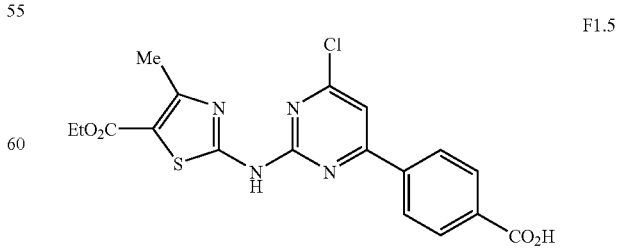

A solution of F1.4 (980 mg, 3.2 mmol) and ethyl 2 chloroacetoacetate (630 mg, 3.84 mmol) in EtOH (45 mL)

was heated at 100° C. for 16 hours. The reaction was cooled and the resulting precipitate was collected by filtration to afford F1.5 (570 mg, 43%). $^1$H-NMR (DMSO-d$_6$) δ: 8.42 (2H, d, J=8.4 Hz), 8.11 (2H, d, J=8.3 Hz), 7.95 (1H, s), 4.26 (2H, q, J=7.1 Hz), 1.31 (3H, t, J=7.1 Hz); HPLC: 95%; ret. time$^b$=1.87 min.; LC/MS (M+H)$^+$=419.

F1.6  2-[4-(4-Carboxy-phenyl)-6-(4-hydroxy-piperidin-1-yl)-pyrimidin-2-ylamino]-4-methylthiazole-5-carboxylic acid ethyl ester

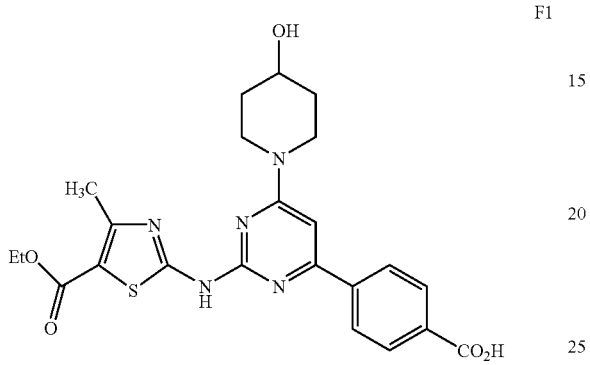

A solution of F1.5 (21 mg, 50 µmol), 4-hydroxypiperidine (200 µL, 0.5M in DMF, 100 µmol) and Et$_3$N (20 µL) in DMF (1.5 mL) was heated to 80° C. for 4 hours. The reaction was diluted to 2 mL with DMF, filtered then the filtrate subjected to purification by preparative HPLC to obtained F1 (5.7 mg, 24%). $^1$H-NMR (DMSO-d$_6$) δ: 8.31 (2H, d, J=8.3 Hz), 8.03 (2H, d, J=8.3 Hz), 7.10 (1H, s), 4.80 (1H, bs), 4.22 (2H, q, J=7.1 Hz), 4.22 (2H, m), 1.38 (1H, m), 3.42 (2H, m), 2.52 (3H, s), 1.83 (2H, m), 1.41 (2H, m), 1.29 (3H, t, J=7.1 Hz); HPLC: 100%; ret. time$^c$=1.32 min.; LC/MS (M+H)$^+$=484.

Examples F2–F11

Examples F2 to F11 were prepared in a similar manner to that used for Example F1 utilizing the appropriate amines.

TABLE F

| Ex. | Z | Name | HPLC Retention$^a$ (min) | MS Reported |
|---|---|---|---|---|
| F2 | (3-oxo-piperazin-1-yl) | 2-[4-(4-Carboxy-phenyl)-6-(3-oxo-piperazin-1-yl)-pyrimidin-2-ylamino]-4-methylthiazole-5-carboxylic acid ethyl ester | 1.25 | 483.31 |
| F3 | (4-methyl-piperazin-1-yl) | 2-[4-(4-Carboxy-phenyl)-6-(4-methyl-piperazin-1-yl)-pyrimidin-2-ylamino]-4-methylthiazole-5-carboxylic acid ethyl ester | 1.21 | 483.37 |
| F4 | morpholin-4-yl | 2-[4-(4-Carboxy-phenyl)-6-morpholin-4-yl-pyrimidin-2-ylamino]-4-methylthiazole-5-carboxylic acid ethyl ester | 1.28 | 470.05 |
| F5 | (4-methyl-[1,4]diazepan-1-yl) | 2-[4-(4-Carboxy-phenyl)-6-(4-methyl-[1,4]diazepan-1-yl)-pyrimidin-2-ylamino]-4-methylthiazole-5-carboxylic acid ethyl ester | 1.17 | 497.34 |

TABLE F-continued

| Ex. | Z | Name | HPLC Retention[a] (min) | MS Reported |
|---|---|---|---|---|
| F6 | 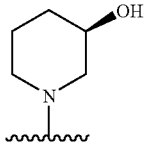 | 2-[4-(4-Carboxy-phenyl)-6-(3-R-hydroxy-piperidin-1-yl)-pyrimidin-2-ylamino]-4-methylthiazole-5-carboxylic acid ethyl ester | 1.37 | 484.35 |
| F7 | 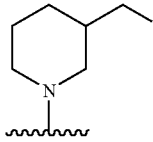 | 2-[4-(4-Carboxy-phenyl)-6-(3-hydroxymethyl-piperidin-1-yl)-pyrimidin-2-ylamino]-4-methylthiazole-5-carboxylic acid ethyl ester | 1.40 | 498.32 |
| F8 | 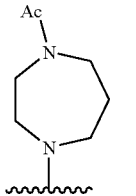 | 2-[4-(4-Acetyl-[1,4]diazepan-1-yl)-6-(4-carboxy-phenyl)-pyrimidin-2-ylamino]-4-methylthiazole-5-carboxylic acid ethyl ester | 1.32 | 525.34 |
| F9 | 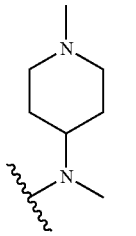 | 2-{4-(4-Carboxy-phenyl)-6-[N-methyl-N-(1-N-methyl-piperidin-4-yl)-amino]-pyrimidin-2-ylamino}-4-methylthiazole-5-carboxylic acid ethyl ester | 1.17 | 511.37 |
| F10 | 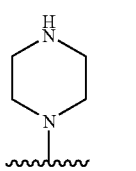 | 2-[4-(4-Carboxy-phenyl)-6-piperazin-1-yl-pyrimidin-2-ylamino]-4-methylthiazole-5-carboxylic acid ethyl ester | 1.19 | 469.34 |
| F11 | 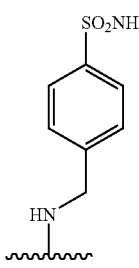 | 2-[4-(4-Carboxy-phenyl)-6-(4-sulfamoyl-benzylamino)-pyrimidin-2-ylamino]-4-methylthiazole-5-carboxylic acid ethyl ester | 1.36 | 569.26 |

[a]HPLC conditions used to determine retention times: 2 min gradient 0–100% B in A(A; 0.05% TFA in 90/10 water/acetonitrile; B; 0.05% TFA in 10/90 water/acetonitrile) using a Primesphere C18 4.6 × 30 mm column at 220 nm.

Examples G1

2-[[4-[[5-Allyl[4-(aminosulfonyl)phenyl]methyl]amino]-6-chloro-2-pyrimidinyl]amino]-4-methyl-5-thiazolecarboxylic acid, ethyl ester

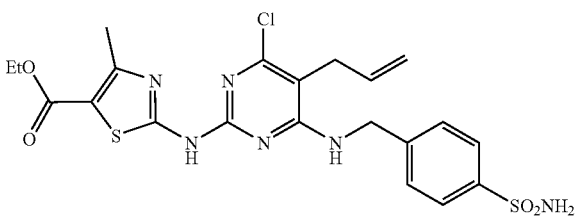

G1

G1.1: 2-[(5-Allyl-4,6-(1H,5H)pyrimidinedion-2yl)amino-4-methyl-5-thiazolecarboxylic acid ethyl ester

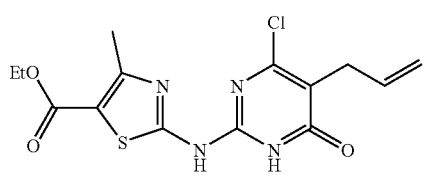

G1.1

A solution of NaOEt in EtOH was prepared by stirring Na (88 mg, 3.83 mmol) with absolute EtOH (15 mL) at room temperature until the mixture became homogeneous. A1.1 (350 mg, 1.53 mmol) was then added and the mixture was stirred for 20 min. Diethyl allylmalonate (0.30 mL, 1.53 mmol) was added dropwise, the reaction mixture was heated at reflux for 22 hr, and then cooled and poured onto a mixture of 10% aqueous $H_2SO_4$ and ice. The solid was collected by filtration, washed with water and dried to afford 346 mg (67% yield) of G1.1 as a tan solid. LC/MS: 337.58 [M+H]$^+$ G1.2: 2-[(5-Allyl-4,6-dichloropyrimidin-2-yl)amino]-4-methyl-5-thiazolecarboxylic acid ethyl ester

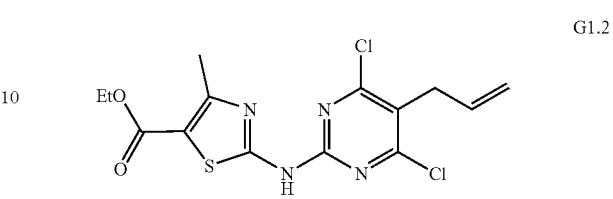

G1.2

A mixture of G1.1 (346 mg, 1.03 mmol) and POCl$_3$ (5 mL) was heated at 100° C. for 19 hr. The reaction mixture was poured slowly onto a mixture of ethyl acetate, 2 N NaOH and ice. The layers were separated and the organic phase was washed with sat. NaHCO$_3$, water and brine, dried over MgSO$_4$ and concentrated. Afforded 285 mg (74% yield) of G1.2 as a yellow solid. LC/MS: 373.49 [M+H]$^+$; $^1$H NMR (400 MHz, d$_6$-DMSO): δ 5.90 (m, 1H), 5.10 (m, 2H), 4.27 (q, J=7.1 Hz, 2H), 3.51 (m, 2H), 2.5 (s, 3H), 1.29 (t, J=7.1 Hz, 3H).

G1.3: 2-[[4-[[5-Allyl[4-(aminosulfonyl)phenyl]methyl]amino]-6-chloro-2-pyrimidinyl]amino]-4-methyl-5-thiazolecarboxylic acid ethyl ester A mixture of G1.2 (51 mg, 0.137 mmol), 4-aminomethylbenzenesulfonamide hydrochloride (32 mg, 0.143 mmol), (iPr)$_2$NEt (70 μL, 0.411 mmol) and iPrOH (0.6 mL) was heated at 105° C. in a sealed tube for 24 hr. The reaction mixture was cooled to room temperature and the precipitated solid was collected by filtration and washed with water, iPrOH, and ether. Afforded 63 mg (88% yield) of G1 as a tan solid: LC/MS: 523.49 [M+H]$^+$

Examples G2–G16

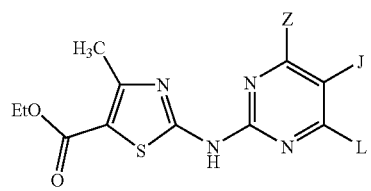

Examples G2 to G16 were prepared in a similar manner to that used for Example G1 utilizing the appropriate replacement for diethyl allylmalonate in step G1.1.

TABLE G

| Ex. | Z | L | J | Name | HPLC Retention[a] (min) | MS Reported |
|---|---|---|---|---|---|---|
| G2 | 4-(aminosulfonyl)benzyl-NH- | piperazinyl (HN-) | —CH₃ | 2-[[4-[[[4-(Aminosulfonyl)phenyl]methyl]amino]-5-methyl-6-(1-piperazinyl)-2-pyrimidinyl]amino]-4-methyl-5-thiazolecarboxylic acid, ethyl ester, trifluoroacetate (1:3) | 2.31 | 547.23 |
| G3 | 4-(aminosulfonyl)benzyl-NH- | morpholinyl | —CH₃ | 2-[[4-[[[4-(Aminosulfonyl)phenyl]methyl]amino]-5-methyl-6-(4-morpholinyl)-2-pyrimidinyl]amino]-4-methyl-5-thiazolecarboxylic acid, ethyl ester. | 2.84 | 548.22 |
| G4 | 4-(aminosulfonyl)benzyl-NH- | 4-methylpiperazinyl | allyl | 2-[[4-[[5-Allyl[4-(aminosulfonyl)phenyl]methyl]amino]-6-(4-methylpiperazinyl)-2-pyrimidinyl]amino]-4-methyl-5-thiazolecarboxylic acid, ethyl ester | 2.47 | 587.51 |
| G5 | 4-(aminosulfonyl)benzyl-NH- | 4-methylpiperazinyl | 2-methylprop-3-enyl (CMe₂-CH=CH₂) | 2-[[4-[[5-[2-[2-Methylprop-3-en]]-4-[4-(aminosulfonyl)phenyl]methyl]amino]-6-(4-methylpiperazinyl)-2-pyrimidinyl]amino]-4-methyl-5-thiazolecarboxylic acid, ethyl ester | 2.93 | 615.50 |

TABLE G-continued

| Ex. | Z | L | J | Name | HPLC Retention[a] (min) | MS Reported |
|---|---|---|---|---|---|---|
| G6 | 3,4,5-trimethoxybenzyl-NH | piperazinyl (HN) | —CH₃ | 2-[[4-[[[3,4,5-(Trimethoxy)phenyl]methyl]amino]-5-methyl-6-(1-piperazinyl)-2-pyrimidinyl]amino]-4-methyl-5-thiazolecarboxylic acid, ethyl ester, trifluoroacetate | 1.64[b] | 572.26 |
| G7 | 4-(aminosulfonyl)benzyl-NH | 4-methylpiperazinyl | 2,3-propandiol (HOCH₂-CH(OH)-) | 2-[[4-[[5-[2,3-propandiol][4-(aminosulfonyl)phenyl]methyl]amino]-6-(4-methylpiperazinyl)-2-pyrimidinyl]amino]-4-methyl-5-thiazolecarboxylic acid, ethyl ester | 2.29 | 621.50 |
| G8 | 3,4,5-trimethoxybenzyl-NH | 4-methylpiperazinyl | —CH₃ | 2-[[4-[[[3,4,5-(Trimethoxy)phenyl]methyl]amino]-5-methyl-6-(4-methyl-1-piperazinyl)-2-pyrimidinyl]amino]-4-methyl-5-thiazolecarboxylic acid, ethyl ester, trifluoroacetate | 1.35[c] | 572.31 |
| G9 | 4-(aminosulfonyl)benzyl-NH | —Cl | 2-methylprop-3-en-dimethyl | 2-[[4-[[5-[2-[2-Methylprop-3-en]]-4-[4-(aminosulfonyl)phenyl]methyl]amino]-6-chloro-2-pyrimidinyl]amino]-4-methyl-5-thiazolecarboxylic acid, ethyl ester | 3.47 | 551.35 |
| G10 | 4-(aminosulfonyl)benzyl-NH | N-Boc-piperazinyl | —CH₃ | 2-[[4-[[[4-(Aminosulfonyl)phenyl]methyl]amino]-5-methyl-6-(4-tertbutyloxycarbonyl-1-piperazinyl)-2-pyrimidinyl]amino]-4-methyl-5-thiazolecarboxylic acid, ethyl ester | 3.60 | 647.32 |

TABLE G-continued

| Ex. | Z | L | J | Name | HPLC Retention[a] (min) | MS Reported |
|---|---|---|---|---|---|---|
| G11 | 3,5-dimethoxy-4-methoxybenzyl-N(Me)- | 4-methylpiperazin-1-yl | —CH₃ | 2-[[4-[N-[[3,4,5-(Trimethoxy)phenyl]methyl]-N-methylamino]-5-methyl-6-(4-methyl-1-piperazinyl)-2-pyrimidinyl]amino]-4-methyl-5-thiazolecarboxylic acid, ethyl ester | 1.64[b] | 586.34 |
| G12 | 4-hydroxypiperidin-1-yl | 4-hydroxypiperidin-1-yl | —CH₃ | 2-[4,6-Bis-(4-hydroxy-piperidin-1-yl)-5-methylpyrimidin-2-ylamino]-4-methyl-thiazole-5-carboxylic acid ethyl ester | 1.55[b] | 477.20 |
| G13 | 3-oxopiperazin-1-yl | 3-oxopiperazin-1-yl | —CH₂CO₂Et | 2-[4,6-Bis-(3-oxo-piperazin-1-yl)-5-[ethoxycarbonylmethyl]pyrimidin-2-ylamino]-4-methyl-thiazole-5-carboxylic acid ethyl ester | 2.89 | 547.29 |
| G14 | 4-hydroxypiperidin-1-yl | 4-hydroxypiperidin-1-yl | —OMe | 2-[4,6-Bis-(4-hydroxy-piperidin-1-yl)-5-methoxypyrimidin-2-ylamino]-4-methyl-thiazole-5-carboxylic acid ethyl ester | 1.62[b] | 493.21 |
| G15 | 3,5-dimethoxy-4-methoxybenzyl-N(Me)- | 4-methylpiperazin-1-yl | —OMe | 2-[[4-[N-[[3,4,5-(Trimethoxy)phenyl]methyl]-N-methylamino]-5-methoxy-6-(4-methyl-1-piperazinyl)-2-pyrimidinyl]amino]-4-methyl-5-thiazolecarboxylic acid, ethyl ester | 1.65[b] | 602.18 |
| G16 | (pyridin-3-yl)methoxy | morpholin-4-yl | —CH₂CH=CH₂ | 2-[[4-[[3-pyridyl]methyloxy]-5-(2-propenyl)-6-(4-morpholinyl)-2-pyrimidinyl]amino]-4-methyl-5-thiazolecarboxylic acid, ethyl ester | 3.29 | 497.07 |

[a] HPLC conditions used to determine retention times; 4 min gradient 0–100% B in A(A; 0.1% TFA in 90/10 water/methanol; B; 0.1% TFA in 10/90 water/methanol) using a YMC turbopack column at 254 nm.
[b] YMC ODS 5 μm C18 column 4.6 × 30 mm (2 min)
[c] Waters Xterra 4.6 × 30 5μ C18, 4 min gradient, 0–100% B in A(A; 0.2% H₃PO₄ in 90/10 water/methanol; B; 0.2% H₃PO₄ in 10/90 water/methanol) at 220 nm

Example H3

2-[(4-Ethoxycarbonylmethyl-6-morpholin-4-yl-pyrimidin-2-yl)-amino]-4-methyl-5-thiazolecarboxylic acid ethyl ester

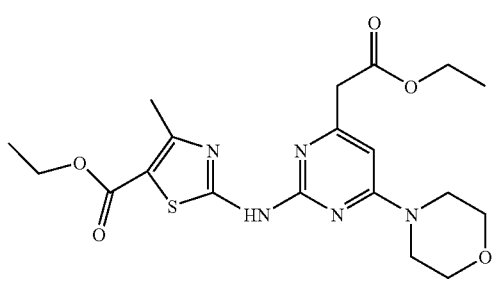

H1.1 2-[(4-Chloro-6-ethoxycarbonylmethyl-pyrimidin-2-yl-amino]-4-methyl-5-thiazolecarboxylic acid ethyl ester

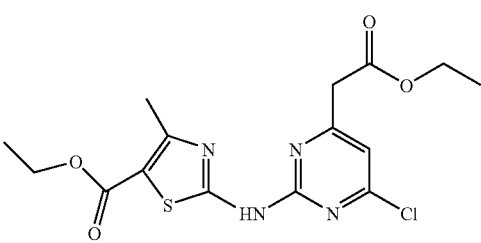

A1.1 (3.0 g, 13.14 mmol) was added to a solution of sodium ethoxide in ethanol (705 mg of sodium, 30 mmol in 100 mL of ethanol). The reaction mixture was heated in an oil bath at 100° C. for 30 minutes during which time most, but not all, of the material had dissolved, and diethyl-3-oxoglutarate (4.00 g, 19.74 mmol) was added dropwise over 30 minutes. The reaction mixture was maintained in an oil bath to 100° C. for 16 hours. An additional 2.4 mL of diethyl-3-oxoglutarate were added and the reaction mixture refluxed for an additional 4 hours after which HPLC analysis indicated only a trace amount of starting material remained. The reaction mixture was allowed to cool to room temperature, added to 300 mL of ice/10% sulfuric acid, stirred 30 minutes and the solid was collected by filtration and dried to give a brown solid.

The residue was dissolved in phosphorous oxychloride (15 mL) and stirred at 55° C. for 3 hours. The mixture was then added to ice/water. After the ice melted the solid was collected by filtration and, dried under vacuum and purified by flash chromatography (Hexane/ethyl acetate 30% to 100%) to yield H1.1 as a light yellow foam (1.63 g, 32%). $^1$H-NMR (CDCl$_3$) δ: 7.02 (1H, s), 4.37 (2H, q, J=7 Hz), 4.28 (2H, q, J=7 Hz), 3.83 (2H, s), 2.74 (3H, s), 1.42 (3H, t, J=7 Hz), 1.33 (3H, t, J=7 Hz). HPLC: 96.4%, ret. time=1.990 min., LC/MS (M+H)$^+$=385.

H1.2 2-[(4-Ethoxycarbonylmethyl-6-morpholin-4-yl-pyrimidin-2-yl)-amino]-4-methyl-5-thiazolecarboxylic acid ethyl ester A mixture of H1.1 (0.229 g, 0.59 mmol) and morpholine (0.100 mL, 1.18 mmol) in tetrahydrofuran was stirred at 50° C. for 2.5 hours. The mixture was then concentrated, and purified by flash chromatographiy (Dichloromethane/Methanol 2% to 10%) to give pure H1 as a white solid (0.249 g, 97%). $^1$H-NMR (CDCl$_3$) δ: 6.20 (1H, s) 4.32 (2H, q, J=7 Hz), 4.22 (2H, q, J=7 Hz), 3.83 (4H, m), 3.73 (4H, br, s), 3.68 (2H, s) 2.66 (3H, s), 1.38 (3H, t, J=7 Hz), 1.19 (3H, t, J=7 Hz). HPLC: 96.2%, ret. time=1.387 min., LC/MS (M+H)$^+$=436.

Example H2

2-[(4-Ethoxycarbonylmethyl-6-[3-oxo-1-piperazinyl]-pyrimidin-2-yl)-amino]-4-methyl-5-thiazolecarboxylic acid ethyl ester

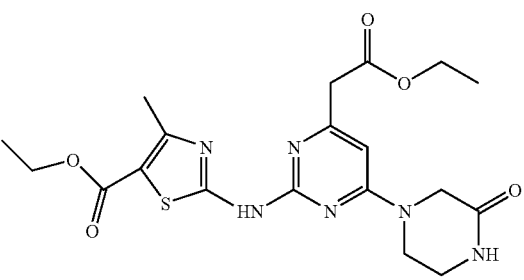

Example H2 was prepared in an analogous manner to example H1 with the exception that morpholine was replaced by 2-piperazinone. HPLC: 95.7%, ret. time=1.487 min., LC/MS (M+H)$^+$=449.

Example H3

2-[(4-Carboxymethyl-6-morpholin-4-yl-pyrimidin-2-yl)-amino]-4-methyl-5-thiazolecarboxylic acid

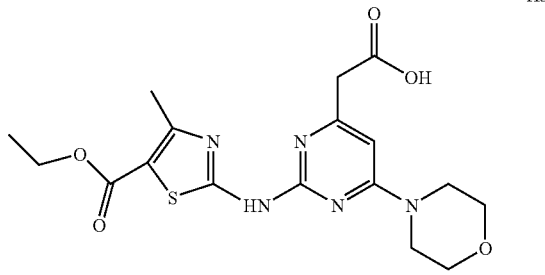

H1.2 (0.036 g, 0.083 mmol) was added to a solution made of ethanol (5 mL) and sodium hydroxide (1N, 0.1 mL) and stirred at 23° C. for 15 minutes. The mixture was then acidified to pH 4 with hydrogen chloride (1N), concentrated, dissolved in DMF and purified by Prep HPLC (Acetonitrile/water/5 mM ammonium acetate, column Primesphere C18 21×100 mm) to yield H3 as a white solid (0.029 g, 86%). $^1$H-NMR (DMSO-d$_6$) δ: 12.40 (1H, br, s), 11.50 (1H, br, s), 6.35 (1H, s), 4.09 (2H, q, J=7 Hz), 3.58 (8H, m), 3.42 (2H, s), 2.39 (3H, s), 1.16 (3H, t, J=7 Hz). HPLC: 95.2%, ret time=1.250 min., LC/MS (M+H)$^+$=408.

Example H4

2-[4-Morpholin-4-yl-6-[(3 4,5-trimethoxy-phenyl-carbamoyl)-methyl]-pyrimidin-2-ylamino]-4-methyl-5-thiazolecarboxylic acid ethyl ester

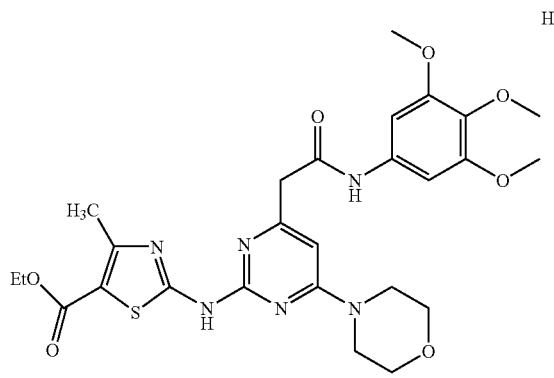

To a solution of H3 (0.025 g, 0.061 mmol) in DMF was added 3,4,5-trimethoxyaniline (0.013 g, 0.073 mmol), a solution of containing EDC/hydroxybenzotriazole in DMF (0.25M, 0.370 mL, 0.092 mmol) and N,N-diisopropylethylamine (32 μL, 0.183 mmol). Stirred at 23° C. for 20 hors. The mixture was then acidified with acetic acid (0.100 mL) and purified by Prep HPLC (Acetonitrile/water/5 mM ammonium acetate, column Primesphere C18 21×100 mm) to yield H4 as a white solid (0.024 g, 68%). $^1$H-NMR (DMSO-d$_6$) δ: 11.58 (1H, br, s), 10.10 (1H, s), 6.98 (2H, s), 6.48 (1H, s), 4.15 (2H, q, J=7 Hz), 3.66 (19H, m), 1.21 (3H, t, J=7 Hz). HPLC: 93.0%, ret. time=1.450 min., LC/MS (M+H)$^+$=573.

Examples H5 to H19

Examples H2 to H19 were prepared in a similar manner to that used for Example H1 utilizing the appropriate amines.

TABLE H

| Ex. | Q | Name | HPLC Retention[a] (min) | % Purity | MS Reported (M + H)$^+$ |
|---|---|---|---|---|---|
| H5 | (3-oxopiperazin-1-yl) | 2-[[4-[2-oxo-2-(3-oxo-piperazin-1-yl)-ethyl]-6-(4-sulfamoyl-benzylamino)-2-pyrimidinyl]amino]-4-methyl-5-thiazolecarboxylic acid ethyl ester | 1.163 | 100 | 589 |
| H6 | (4-sulfamoylbenzylamino) | 2-[[4-(4-sulfamoyl-benzylamino)-6-[(4-sulfamoyl-benzylcarbamoyl)-methyl]-2-pyrimidinyl]amino]-4-methyl-5-thiazolecarboxylic acid ethyl ester | 1.270 | 100 | 675 |
| H7 | (1,4-dioxa-8-azaspiro[4.5]dec-8-yl) | 2-[4-[2-(1,4-Dioxa-8-aza-spiro[4.5]dec-8-yl)-2-oxo-ethyl]-6-(4-sulfamoyl-benzylamino)-2-pyrimidinyl]amino]-4-methyl-5-thiazolecarboxylic acid ethyl ester | 1.277 | 91 | 632 |

TABLE H-continued

| Ex. | Q | Name | HPLC Retention[a] (min) | % Purity | MS Reported (M + H)+ |
|---|---|---|---|---|---|
| H8 | 4-chloro-N-methylanilino | 2-[[4-[[(4-Chloro-phenyl)-methyl-carbamoyl]-methyl]-6-(4-sulfamoyl-benzylamino)2-pyrimidinyl]amino]-4-methyl-5-thiazolecarboxylic acid ethyl ester | 1.483 | 100 | 630 |
| H9 | 4-hydroxypiperidin-1-yl | 2-[[4-[2-(4-Hydroxy-piperidin-1-yl)-2-oxo-ethyl]-6-(4-sulfamoyl-benzylamino)-2-pyrimidinyl]amino]-4-methyl-5-thiazolecarboxylic acid ethyl ester | 1.193 | 100 | 590 |
| H10 | 4-(ethoxycarbonyl)piperidin-1-yl | 2-[[4-[2-(4-Ethoxycarbonyl-piperidin-1-yl)-2-oxo-ethyl]-6-(4-sulfamoyl-benzylamino)-2-pyrimidinyl]amino]-4-methyl-5-thiazolecarboxylic acid ethyl ester | 1.377 | 100 | 646 |
| H11 | piperidin-1-yl | 2-[[4-(2-oxo-2-piperidin-1-yl-ethyl)-6-(4-sulfamoyl-benzylamino)2-pyrimidinyl]amino]-4-methyl-5-thiazolecarboxylic acid ethyl ester | 1.310 | 100 | 574 |
| H12 | 4-(furan-2-carbonyl)piperazin-1-yl | 2-[[4-[2-[4-(Furan-2-carbonyl)-piperazin-1-yl]-2-oxo-ethyl]-6-(4-sulfamoyl-benzylamino)2-pyrimidinyl]amino]-4-methyl-5-thiazolecarboxylic acid ethyl ester | 1.280 | 95 | 669 |

TABLE H-continued

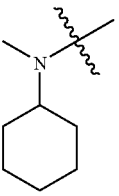

| Ex. | Q | Name | HPLC Retention[a] (min) | % Purity | MS Reported (M + H)[+] |
|---|---|---|---|---|---|
| H13 | 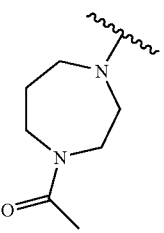 | 2-[[4-[(Cyclohexyl-methyl-carbamoyl)-methyl]-6-(4-sulfamoyl-benzylamino)2-pyrimidinyl]amino]-4-methyl-5-thiazolecarboxylic acid ethyl ester | 1.460 | 89 | 601 |
| H14 | 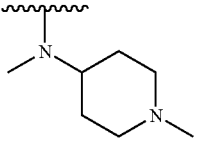 | 2-[[4-[2-(4-Acetyl-[1,4]diazepan-1-yl)-2-oxo-ethyl]-6-(4-sulfamoyl-benzylamino)-2-pyrimidinyl]amino]-4-methyl-5-thiazolecarboxylic acid ethyl ester | 1.207 | 100 | 631 |
| H15 | 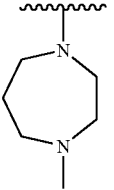 | 2-[[4-[[Methyl-(1-methyl-piperidin-4-yl)-carbamoyl]-methyl]-6-(4-sulfamoyl-benzylamino)-2-pyrimidinyl]amino]-4-methyl-5-thiazolecarboxylic acid ethyl ester | 1.130 | 100 | 617 |
| H16 | | 2-[[4-[2-(4-methyl-[1,4]diazepan-1-yl)-2-oxo-ethyl]-6-(4-sulfamoyl-benzylamino)-2-pyrimidinyl]amino]-4-methyl-5-thiazolecarboxylic acid ethyl ester | 1.127 | 100 | 603 |
| H17 | —N(CH$_2$CH$_2$OMe)$_2$ | 2-[[4-[[Bis-(2-methoxy-ethyl)-carbamoyl]-methyl]-6-(4-sulfamoyl-benzylamino)-2-pyrimidinyl]amino]-4-methyl-5-thiazolecarboxylic acid ethyl ester | 1.293 | 87 | 622 |

TABLE H-continued

| Ex. | Q | Name | HPLC Retention[a] (min) | % Purity | MS Reported (M + H)+ |
|---|---|---|---|---|---|
| H18 | (4-piperidinyl-piperidine structure) | 2-[[4-(2-[1,4']Bipiperidinyl-1'-yl-2-oxo-ethyl)-6-(4-sulfamoyl-benzylamino)-2-pyrimidinyl]amino]-4-methyl-5-thiazolecarboxylic acid ethyl ester | 1.153 | 100 | 657 |
| H19 | (4-hydroxy-4-phenylpiperidine structure) | 2-[[4-[2-(4-Hydroxy-4-phenyl-piperidin-1-yl)-2-oxo-ethyl]-6-(4-sulfamoyl-benzylamino)-2-pyrimidinyl]amino]-4-methyl-5-thiazolecarboxylic acid ethyl ester | 1.370 | 100 | 666 |

[a]HPLC conditions used to determine retention times; 2 min gradient 0–100% B in A; (A; 0.05% TFA in 90/10 water/acetonitrile; B; 0.05% TFA in 10/90 water/acetonitrile) using a Primesphere C-18 4.6 × 30 mm column at 254 nm.

To avoid confusion in enumeration of the examples the letter "I" has been intentionally omitted. Thus there are no examples such as I1, etc. The example numbering proceeds directly from H#, to J#.

Example J1

2-[[4-Ethoxycarbonyl-6-(4-sulfamoyl-benzylamino)-2-pyrimidinyl]amino]-4-methyl-5-thiazole carboxylic acid ethyl ester

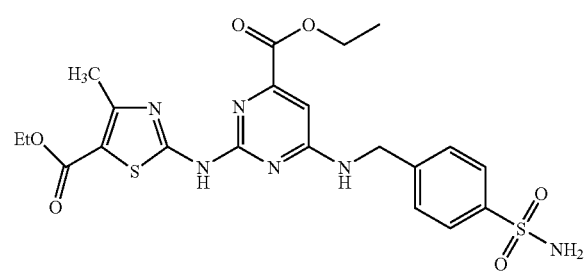

J1

J1.1: 2-Amino-6-oxo-1,6-dihydro-pyrimidine-4-carboxylic acid ethyl ester

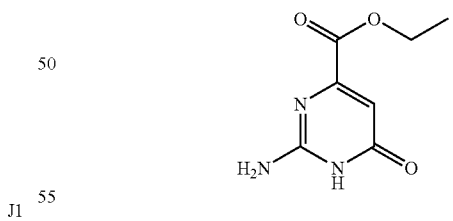

J1.1

A solution of oxalacetic acid diethyl ester (8.5 g, 45.2 mmol) in ethanol (100 mL) was treated with guanidine carbonate (8.1 g, 45.2 mmol) and this was stirred under reflux for 2 hours. The mixture was diluted with water, concentrated to removed ethanol, and the solid was collected by filtration. The solid was then suspended in ethanol (40 mL) and concentrated hydrochloric acid (1 mL) and refluxed for 15 minutes. The mixture was then cooled, basified with potassium carbonate, diluted with water and concentrated to removed ethanol. The white solid was collected by filtration and vacuum dried to give J1.1 (1.67 g, 20%). $^1$H-NMR (DMSO-d$_6$) δ: 10.34 (1H, br s), 8.92 (1H, br s), 7.46 (1H, br, s), 5.42 (1H, s), 4.18 (2H, q, J=7 Hz), 1.24 (3H, t, J=7 Hz).

J1.2 4-(6-Oxo-2-ethoxycarbonylthioureido-1,6-dihydro-pyrimidin-4-yl)-carboxylic acid ethyl ester

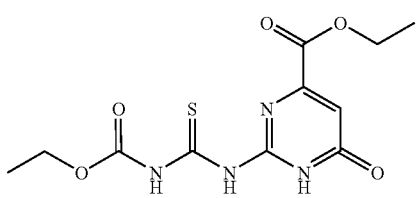

J1.2

A solution of J1.1 (1.67 g, 9.11 mmol) in dioxane (20 mL) was treated with ethoxycarbonyl isothiocyanate (1.07 mL, 9.11 mmol) and refluxed for 30 minutes. The mixture was then freeze dried to afford J1.2 (2.86 g, 100%). $^1$H-NMR (DMSO-d$_6$) δ: 12.25 (1H, br s), 12.15 (1H, br s), 11.40 (1H, br, s), 5.72 (1H, s), 4.22 (2H, q, J=7 Hz), 4.12 (2H, q, J=7 Hz), 1.27 (3H, t, J=7 Hz), 1.22 (3H, t, J=7 Hz). LC/MS$^c$: ret. time: 1.470 min. (M+H)$^+$: 315.

J1.3 2-[[4-Ethoxycarbonyl-6-chloro-2-pyrimidinyl]amino]-4-methyl-5-thiazole carboxylic acid ethyl ester

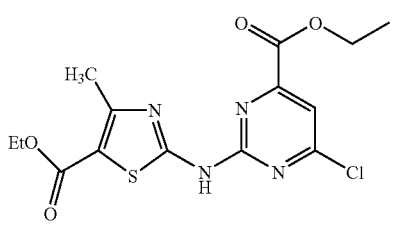

J1.3

J1.2 (2.6 g, 8.27 mmol) was dissolved in aqueous sodium hydroxide (2N, 20 mL) and stirred at 90° C. for 30 minutes. The mixture was then cooled in an ice-bath, acidified with concentrated hydrochloric acid and concentrated to dryness. The solid was suspended in an ethanolic hydrochloric acid solution (2M, 30 mL) and heated at 80° C. for 2 hours. The mixture was concentrated, diluted with water and the white solid was collected by filtration. The thiourea and ethyl-2-chloroacetate (0.6 mL, 4.33 mmol) in ethanol (5 mL) were stirred at reflux 24 hours, to give an insoluble product which after dilution with water, was collected by filtration and vacuum dried. The resulting solid was suspended in phosphorous oxychloride (30 mL) and stirred at 100° C. for 2 hours. The mixture was then cooled to room temperature and added to ice/water and stirred for 2 hours. The beige solid which precipitated out was collected by filtration and dried under vacuum to yield J1.3 (0.719 g, 23%). $^1$H-NMR (DMSO-d$_6$) δ: 7.64 (1H, s), 4.40 (2H, q, J=7 Hz), 4.25 (2H, q, J=7 Hz), 2.55 (3H, s), 1.40 (3H, t, J=7 Hz), 1.29 (3H, t, J=7 Hz), LC/MS$^c$: ret. time: 1.980 min. (M+H)$^+$: 371.

J1.4 2-[[4-Ethoxycarbonyl-6-(4-sulfamoyl-benzylamino)-2-pyrimidinyl]amino]-4-methyl-5-thiazole carboxylic acid ethyl ester A solution made of J1.3 (0.719 g, 1.9 mmol), 4-aminomethylbenzenesulfonamide hydrochloride (0.520 g, 2.3 mmol) and triethylamine (530 µL, 3.8 mmol) in N-methylpyrrolidinone (20 mL) was stirred at 90° C. for 1 hour. The mixture was then cooled to room temperature, diluted with water and the white solid was collected by filtration to give pure J1 (0.937 g, 95%). $^1$H-NMR (DMSO-d$_6$) δ: 11.78 (1H, br, s), 8.58 (1H, br, s), 7.71 (2H, d, J=8 Hz), 7.48 (2H, d, J=8 Hz), 7.25 (2H, s), 6.80 (1H, s), 4.73 (2H, br, s), 4.26 (2H, q, J=7 Hz), 4.15 (2H, q, J=7 Hz), 2.43 (3H, merge with DMSO), 1.27 (3H, t, J=7 Hz), 1.19 (3H, t, J=7 Hz). HPLC: 91.3%, ret. time=1.363 min., LC/MS (M+H)$^+$=521.

Example J2

2-[[4-Carboxyl-6-(4-sulfamoyl-benzylamino)-2-pyrimidinyl]amino]-4-methyl-5-thiazole carboxylic acid ethyl ester

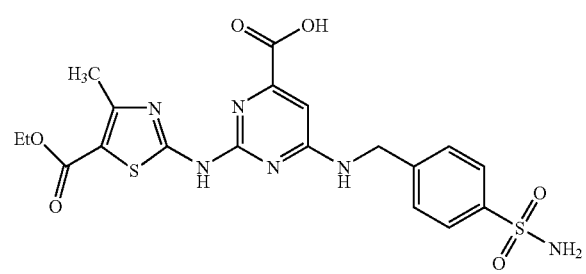

J2

A solution of J1 (0.880 g, 1.7 mmol) in ethanol (10 mL) and sodium hydroxide (20%, 5 mL) was stirred at room temperature for 90 minutes. The mixture was then acidified with acetic acid to precipitate the salt, which is collected by filtration. The product is dissolved in DMF and purified by Prep HPLC (Acetonitrile/water/5 mM ammonium acetate, column Xterra C8 20×10 mm) to give J2 (820 mg, 98%) as a white solid. $^1$H-NMR (DMSO-d$_6$) δ: 13.33 (1H, br, s), 11.81 (1H, br, s), 8.63 (1H, br, s), 7.77 (2H, d, J=8 Hz), 7.54 (2H, d, J=8 Hz), 7.31 (2H, s), 6.84 (1H, s), 4.82 (2H, br, s), 4.22 (2H, q, J=7 Hz), 2.49 (3H, merge with DMSO), 1.05 (3H, t, J=7 Hz). HPLC: 96.9%, ret. time=1.213 min., LC/MS (M+H)$^+$=493.

Example J3

2-[[4-(Carboxymethyl-carbamoyl)-6-(4-sulfamoyl-benzylamino)-2-pyrimidinyl]amino]-4-methyl-5-thiazolecarboxylic acid ethyl ester

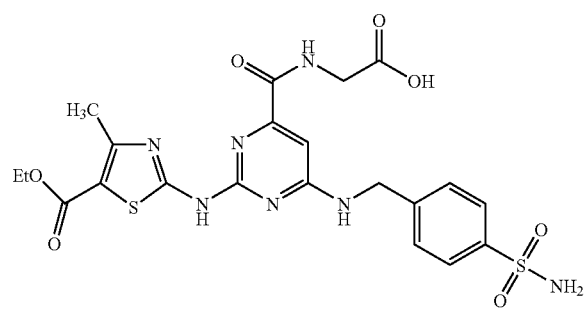

J3

To a solution of J2 (0.100 g, 0.2 mmol) in DMF (3 mL) was added Glycine methyl ester hydrochloride (38 mg, 0.30 mmol), triethylamine (85 µL, 0.60 mmol) and benzothiazole-1-yl-oxy-tris-pyrrolidino-phosphonium hexafluorophosphate (158 mg, 0.30 mmol). The mixture was stirred at 23° C. for half an hour, then diluted with water and the precipitate was collected by filtration. The ester was sasponified in ethanol (5 mL) and sodium hydroxide (0.5 mL) at 23° C. in 1 hour. The mixture was then acidified with acetic acid, concentrated to remove ethanol and freeze dried. The resulting solid was triturated with water, filtered and vacuum dried to give pure J3 (44 mg, 76%) as a white solid. $^1$H-NMR (DMSO-d$_6$) δ: 11.84 (1H, br, s), 8.61 (1H, br, s), 8.22 (1H, br, s), 7.70 (2H, d, J=8 Hz), 7.47 (2H, d, J=8 Hz), 7.24 (2H, s), 6.80 (1H, s), 4.78 (2H, m), 4.15 (2H, q, J=7 Hz), 3.71 (2H, br s), 2.43 (3H, merge with DMSO), 1.19 (3H, t, J=7 Hz). HPLC: 94.8%, ret. time=1.330 min., LC/MS (M+H)$^+$=550.

Example K1

2-[4-(4-Hydroxy-piperidin-1-yl)-6-(4-methylsulfanyl-benzyl)-pyrimidin-2-ylamino]-4-methyl-5-thiazolecarboxylic acid ethyl ester

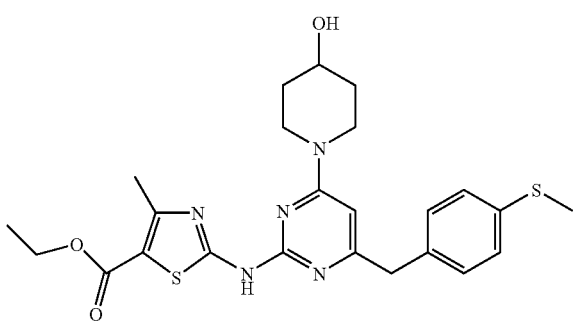

K1.1: 2-Amino-6-(4-methylsulfanyl-benzyl)-3H-pyrimidin-4-one

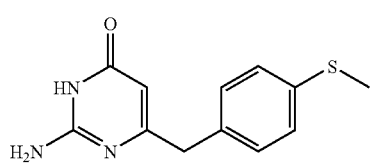

A solution of guanidine carbonate (0.785 g, 4.36 mmol), 4-(4-methylsulfanyl-phenyl)-3-oxo-butyric acid ethyl ester ((28 g, 0.17 mol) {prepared following the method described by Becher in J. Org. Chem, 64, pp. 2814–2820, (1999)}) in ethanol (50 mL) was heated to 90° C. for 1 hour. The reaction mixture was concentrated, diluted with water and ethyl acetate, then neutralized with HCl conc. The beige solid which precipitated out was collected by filtration and dried under vacuum to yield K1.1 (0.420 g, 39%). $^1$H-NMR (DMSO-d$_6$) δ: 7.21 (4H, s), 6.94 (1H, s), 6.52 (2H, br, s), 5.36 (1H, s), 3.53 (2H, s), 2.45 (3H, s). HPLC: 100%, ret. time=1.293 min., LC/MS (M+H)$^+$=248.

K1.2: 2-[4-Chloro-6-(4-methylsulfanyl-benzyl)-pyrimidin-2-ylamino]-4-methyl-5-thiazolecarboxylic acid ethyl ester

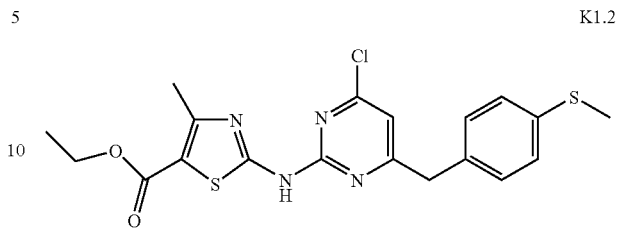

To a solution of K1.1 (0.3 g, 1.21 mmol) in dry dioxane (20 mL) was added ethyl isothiocyanatoformate (0.143 mL, 1.21 mmol). The reaction mixture was heated in an oil bath at 120° C. for 1 hour and then concentrated to dryness to give an orange paste. The residue was then dissolved in aqueous sodium hydroxide (1N, 15 mL) and heated to 80° C. for 1 hour. The reaction mixture was allowed to cool to room temperature, the pH adjusted to 7 with aqueous HCl and the solid which precipitated out was collected by filtration and dried under vacuum. The thiourea was then suspended in ethanol and 2-chloroacetoacetate (0.130 mL, 0.92 mmol), and the resulting mixture was maintained at 100° C. for 3 hours, cooled down to room temperature and diluted with water. The resulting off-white solid was collected by filtration and vacuum dried. The solid was finally added to phosphorous oxychloride (5 mL) and stirred at 85° C. for 3 hours and then it was cooled down to room temperature and poured into 50 g of ice. After the ice melted, the aqueous phase was extracted with a 7:3 mixture of ethyl acetate/THF. The organic phase was dried with sodium sulphate, filtered and concentrated. The residue was purified on flash chromatographiy with ethyl acetate to give a yellow solid which was triturated with methanol to give pure K1.2 (0.108 g, 20%). $^1$H-NMR (DMSO-d$_6$) δ: 12.45 (1H, br s) 7.26 (5H, m), 4.27 (2H, q, J=7 Hz), 4.05 (2H, s) 2.54 (3H, s), 2.44 (3H, s), 1.32 (3H, t, J=7 Hz). HPLC: 95.8%, ret. time=2.350 min., LC/MS (M+H)$^+$=435.

K1.3: 2-[4-(4-Hydroxy-piperidin-1-yl)-6-(4-methylsulfanyl-benzyl)-pyrimidin-2-ylamino]-4-methyl-5-thiazolecarboxylic acid ethyl ester A solution of K1.2 (95 mg, 0.21 mmol) and 4-hydroxypiperidine (26 mg, 0.26 mmol) in N-methylpyrrolidinone (3.0 mL) was heated to 60° C. for an hour. An additional portion of 4-hydroxypiperidine (26 mg, 0.26 mmol) was added and the mixture was stirred for 15 minutes. The reaction mixture was allowed to cool to room temperature, diluted with water and extracted with ethyl acetate. The organic phase was washed with water, brine, dried with magnesium sulphate, filtered and concentrated. The residue was purified on flash chromatography using ethyl acetate to give K1 which crystallized from methanol (98 mg, 93%). $^1$H-NMR (DMSO-d$_6$) δ: 11.49 (11H, s), 7.29 (2H, d, J=8 Hz), 7.19 (21H, d, J=8 Hz), 6.47 (1H, s), 4.79 (1H, d, J=4.22 (2H, q, J=7 Hz), 4.10 (2H, m), 3.78 (3H, m), 3.31 (1H, Merge with H$_2$O), 3.17 (1H, d, J=5 Hz), 2.50 (3H, merge with DMSO), 2.44 (3H, s), 1.79 (2H, m), 1.37 (2H, m), 1.29 (3H, t, J=7 Hz). HPLC: 100%, ret. time=1.720 min., LC/MS (M+H)$^+$=500.

Example K2

2-[4-(4-Hydroxy-piperidin-1-yl)-6-(4-methanesulfinyl-benzyl)-pyrimidin-2-ylamino]-4-methyl-5-thiazolecarboxylic acid ethyl ester

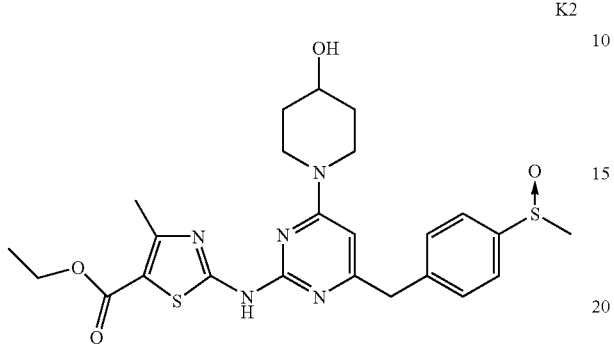

To a solution of K1 (43 mg, 0.086 mmol) in dichloromethane (3 mL) was added peracetic acid (32% solution in acetic acid, 24 µL, 0.112 mmol) and the mixture was stirred at 23° C. for half an hour after which HPLC analysis indicated no trace of starting material. Dimethylsulfide was added and the mixture was concentrated. The residue which crystallized from methanol gave pure K2 as a cream solid (44 mg, 100%). $^1$H-NMR (DMSO-$d_6$) δ: 11.58 (1H, br, s), 7.92 (2H, d, J=8 Hz), 7.68 (2H, d, J=8 Hz), 6.63 (1H, s), 4.86 (1H, br, s), 4.28 (2H, q, J=7 Hz), 4.00 (5H, m), 2.76 (3H, s), 2.56 (3H, merge with DMSO), 1.98 (2H, s), 1.86 (2H, m), 1.44 (2H, m), 1.35 (3H, t, J=7 Hz). HPLC: 91.3%, ret. time=1.270 min., LC/MS (M+H)$^+$=516.

Example K3

2-[[4-(4-Hydroxy-piperidin-1yl)-6-(4-methanesulfonyl-benzyl)-2-pyrimidinyl]amino]-4-methyl-5-thiazolecarboxylic acid ethyl ester

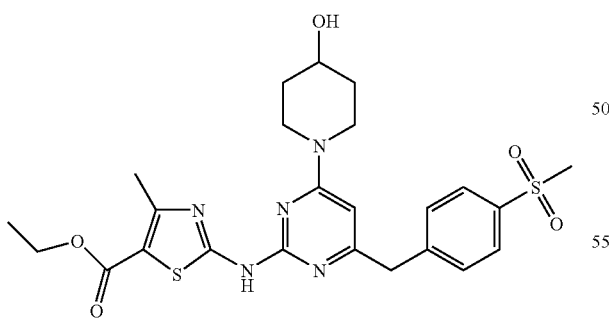

To a solution of K2 (28 mg, 0.054 mmol) in dichloromethane (2 mL) was added peracetic acid (32% solution in acetic acid, 50 µL, 0.233 mmol) and the mixture was stirred at 23° C. for half an hour after which HPLC analysis indicated no trace of starting material. Dimethylsulfide was added and the mixture was concentrated. The residue was stripped 2 times with methanol, triturated with ethyl acetate to give K3 as a light yellow solid (21 mg, 72%). $^1$H-NMR (CD$_3$OD) δ: 7.94 (2H, d, J=8 Hz), 7.64 (2H, d, J=8 Hz), 6.51 (1H, s), 4.34 (2H, q, J=7 Hz), 4.27 (2H, m), 4.08 (2H, s), 4.00 (1H, m), 3.57 (2H, m), 3.12 (3H, s), 2.58 (3H, s), 2.02 (2H, m), 1.62 (2H, m), 1.38 (3H, t, J=7 Hz). HPLC: 91.1%, ret. time=1.586 min., LC/MS (M+H)$^+$=532.

Examples L1

2-[[4-[4-methyl-1-piperazinyl]-6-[N-methyl-N-[(3,4,5-trimethoxyphenyl)methyl]amino]-2-pyrimidinyl]amino]-4-trifluoromethyl-5-thiazolecarboxylic acid, ethyl ester

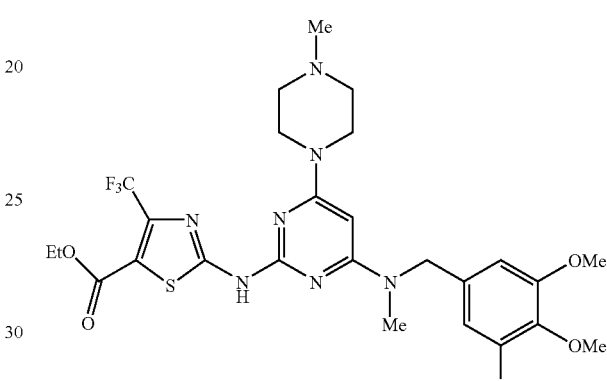

L1.1; 2-Amino-4-[4-methyl-1-piperazinyl]-6-[N-methyl-N-[[3,4,5-trimethoxyphenyl]methyl]pyrimidine

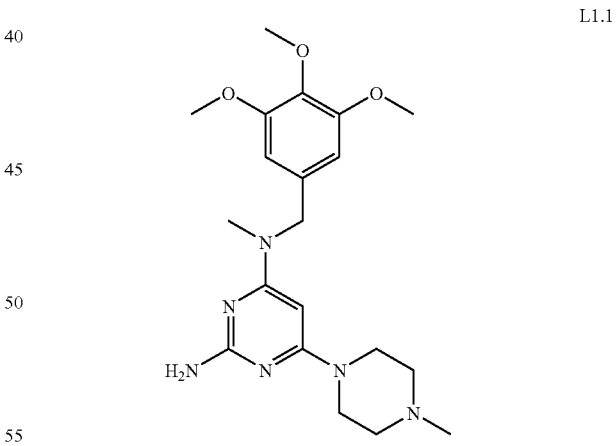

A mixture of 2-amino-4,6-dichloropyrimidine (1.5 g, 9.146 mmol, 1.0 eq), N-methyl-3,4,5-trimethoxybenzylamine (2.03 g, 9.604 mmol, 1.05 eq), and diisopropylethylamine (4.8 mL, 27.438 mmol, 3.0 eq) in n-butanol (20 mL) was heated in a sealed tube at 110° C. for 43 h. After cooling to rt, N-methylpiperazine (1.52 mL, 13.719 mmol, 1.5 eq) was added. The reaction mixture was heated at 125° C. for 48 h, and then cooled and concentrated in vacuo. The residue was passed through a plug of silica gel using, 5% methanol/dichloromethane to provide L1.1 a tan semisolid which was used in subsequent reactions without further purification. LC/MS: 403.59 [M+H]+; HPLC: 90% at 1.42 min (YMC ODS 5 μm C18 column 4.6×50 mm, 10–90% aqueous methanol over 4 min containing 0.1% TFA, 4 mL/min, monitoring at 254 nm).

L1.2; 2-[Ethoxycarbonylaminothiocarbonylamino]-4-[4-methyl-1-piperazinyl]-6-[N-methyl-N-[[3,4,5-trimethoxyphenyl]methyl]pyrimidine

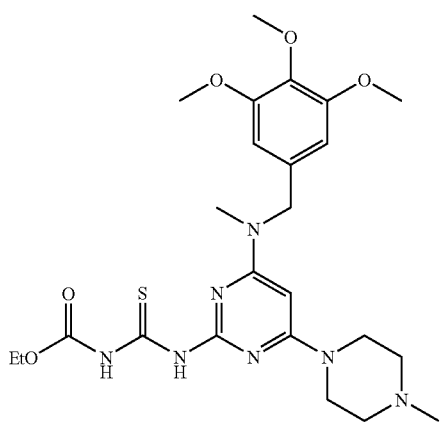

L1.2

A solution of L1 (0.5 g) and ethyl isothiocyanatoformate (0.15 mL, 1.242 mmol) in 1,4-dioxane (5 mL) was heated at reflux for 1.5 h during which time a solid formed. The reaction mixture was cooled and the solid was collected by filtration, washed with ether and dried to afford 445 mg (67% yield) of L1.2 as a beige solid. LC/MS: 534.55 [M+H]+; HPLC: 100% at 2.31 min (YMC ODS 5 μm C18 column 4.6×50 mm, 10–90% aqueous methanol over 4 min containing 0.1% TFA, 4 mL/min, monitoring at 254 nm).

L1.3; 2-[Aminothiocarbonylamino]-4-[4-methyl-1-piperazinyl]-6-[N-methyl-N-[[3,4,5-trimethoxyphenyl]methyl]pyrimidine

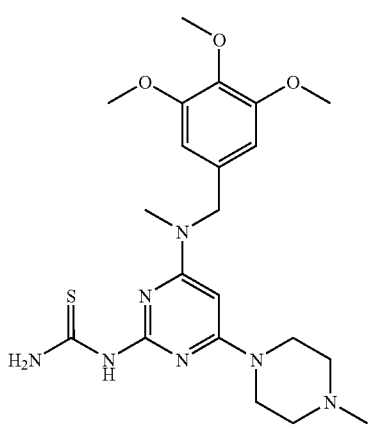

L1.3

A solution of L1.2 (438 mg, 0.821 mmol, 1.0 eq) in 2 N NaOH (8 mL) was stirred at rt for 19 h and then heated at reflux for 15 min. The reaction mixture was cooled in an ice/water bath and the solid was collected by filtration, washed with water and dried to afford 299 mg (79% yield) of product as an off-white solid. LC/MS: 462.47 [M+H]+; HPLC: >95% at 1.98 min (YMC ODS 5 μm C18 column 4.6×50 mm, 10–90% aqueous methanol over 4 min containing 0.1% TFA, 4 mL/min, monitoring at 254 nm).

L1.4; 2-[[4-[4-methyl-1-piperazinyl]-6-[N-methyl-N-[(3,4,5-trimethoxyphenyl)methyl]amino]-2-pyrimidinyl]amino]-4-trifluoromethyl-5-thiazolecarboxylic acid, ethyl ester A mixture of L1.3 (30 mg, 0.065 mmol, 1.0 eq) and ethyl 2-chloro-4,4,4,-trifluoroacetoacetate (90%, 15.8 mg, 0.065, 1.0 eq) in ethanol (0.5 mL) was heated in a sealed tube at 100° C. After 19 h, the mixture was cooled to rt, poured into saturated NaHCO₃ (5 mL) and extracted with ethyl acetate (3×10 mL). The combined extracts were washed with brine, dried over Na₂SO₄ and concentrated. The residue was purified by preparative TLC (0.5 mm, 5% methanol/dichloromethane, eluted 2×) to afford 14.6 mg (36% yield) of L1 as a glass. LC/MS: 626.19 [M+H]+; HPLC: >95% at 1.51 min (Xterra 5 μm C18 column 4.6×30 mm, 10–90% aqueous methanol over 2 min containing 0.2% H₃PO₄, 5 mL/min, monitoring at 254 nm).

Example L2

2-[[4-[4-Methylpiperazin-1-yl]-6-[N-methyl-N-[[(3,4,5-trimethoxyphenyl)methyl]amino]-2-pyrimidinyl]amino]-4-methyl-5-cyanothiazole

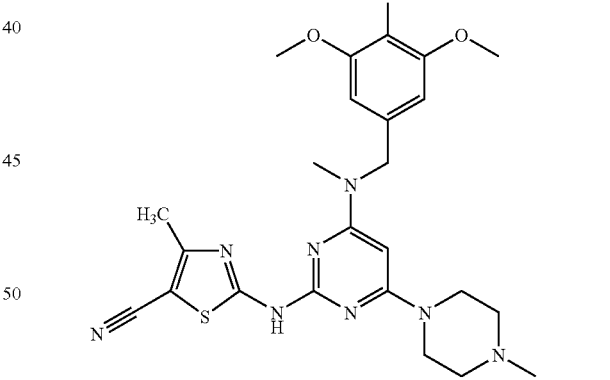

L2

A mixture of L1.3 (30 mg, 0.065 mmol, 1.0 eq) and 2-chloroacetoacetonitrile (prepared from 5-methyl-isoxazole by the method of Blount et al. *J. Org. Chem.* 1978, 43, 3821) (8.0 mg, 0.0682 mmol, 1.05 eq) in ethanol (0.5 mL) was heated in a sealed tube at 80° C. After 7 h, the reaction mixture was cooled to rt, and the precipitated solid was collected by filtration, washed with ether and dried. Gave 23 mg (63% yield) of L2 as the HCl salt. Off-white solid; LC/MS: 525.22 [M+H]+; HPLC: 87% at 1.28 min (Xterra 5 μm C18 column 4.6×30 mm, 10–90% aqueous methanol over 2 min containing 0.2% H₃PO₄, 5 mL/min, monitoring at 254 nm).

Example L3

2-[[4-[4-Methylpiperazin-1-yl]-6-methyl-6-[[(3,4,5-trimethoxyphenyl)methyl]amino]-2-pyrimidinyl]amino]-4-methyl-5-thiazolecarboxylic acid, 2-methoxyethyl ester

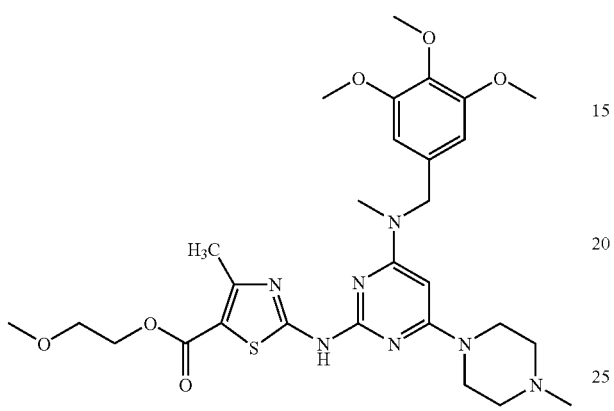

A mixture of L1.3 (50 mg, 0.108 mmol, 1.0 eq) and 2-chloro-3-oxo-butyric acid 2-methoxy-ethyl ester (21.2 mg, 0.108 mmol, 1.0 eq) in ethanol (0.5 mL) was heated in a sealed tube at 100° C. After 1.5 h, the reaction mixture was cooled to rt and methyl t-butyl ether (1 ml) was added. The precipitated solid was collected by filtration, washed with methyl t-butyl ether and dried to afford 42.8 mg (62% yield) of product as the HCl salt. Beige solid; LC/MS: 602.20 [M+H]$^+$; HPLC: 92.8% at 1.24 min (Xterra 5 μm C18 column 4.6×30 mm, 10–90% aqueous methanol over 2 min containing 0.2% $H_3PO_4$, 5 mL/min, monitoring at 254 nm).

Examples L4–15

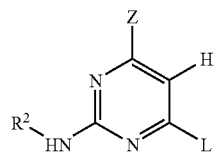

Examples L4 to L5 were prepared in a similar manner to that used for Example L1 utilizing the appropriate replacement for ethyl 2-chloro-4,4,4,-trifluoroacetoacetate in step L1.4.

TABLE L

| Ex. | Z | L | R² | Name | HPLC Retention[a] (min) | MS Reported |
|---|---|---|---|---|---|---|
| L4 | Me, N, OMe, OMe, MeO (trimethoxybenzyl-N-Me) | 4-hydroxypiperidin-1-yl | Me-thiazole-C(O)O-Bu | 2-[[4-[4-Hydroxy-piperidin-1-yl]-6-[N-methyl[[N-[(3,4,5-trimethoxyphenyl)methyl][-N-methyl]amino]-2-pyrimidinyl]amino]-4-methyl-5-thiazolecarboxylic acid, butyl ester | 1.56[b] | 600.54 |
| L5 | NH with ethyl-morpholine | morpholin-4-yl | Me-thiazole-C(O)O-Bu | 2-[[4-[1-morpholinyl]-6-[[2-[1-morpholinyl]ethyl]amino]-2-pyrimidinyl]amino]-4-methyl-5-thiazolecarboxylic acid, butyl ester | 1.30[b] | 506.32 |
| L6 | Me, N, OMe, OMe, MeO (trimethoxybenzyl-N-Me) | 4-methylpiperazin-1-yl | Me-isopropyl-thiazole-C(O)O-Et | 2-[[4-[4-methyl-1-piperazinyl]-6-[[N-[(3,4,5-trimethoxyphenyl)methyl]]-N-(methyl)amino]-2-pyrimidinyl]amino]-4-isopropyl-5-thiazolecarboxylic acid, ethyl ester | 3.07 | 600.16 |

TABLE L-continued

| Ex. | Z | L | R² | Name | HPLC Retention[a] (min) | MS Reported |
|---|---|---|---|---|---|---|
| L7 | 3,5-dimethoxy-4-methoxybenzyl-N-methyl group | methylpiperazinyl | 4-methyl-N-methyl-thiazole-5-carboxamide | 2-[[4-[4-methyl-1-piperazinyl]-6-[[N-[(3,4,5-trimethoxyphenyl)methyl]]-N-(methyl)amino]-2-pyrimidinyl]amino]-4-methyl-5-thiazolecarboxylic acid, methyl amide | 2.00 | 557.61 |

[a] HPLC conditions used to determine retention times; 4 min gradient 0–100% B in A(A; 0.1% TFA in 90/10 water/methanol; B; 0.1% TFA in 10/90 water/methanol) using a YMC turbopack column at 254 nm.
[b] YMC ODS 5 μm C18 column 4.6 × 30 mm (2 min).

Examples M1–M13

Exampes M1 to M13 were prepared in the following manner using the appropriate amines:

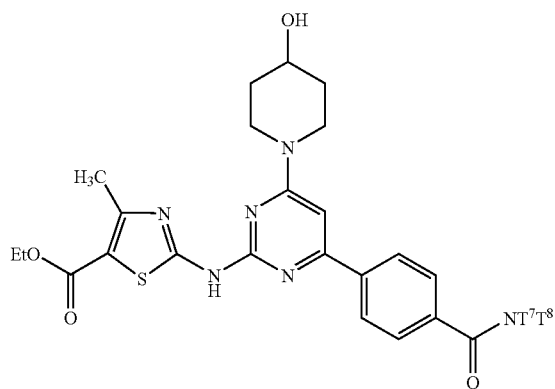

A solution of F1 (425 mg in 17 mL DMF) was dispensed into vials. To each vial was added the appropriate amines (155 μL, 0.5M in DMF, 1.5 equiv.), EDAC/HOBT (40 μL, 0.25 M in DMF, 2 equiv.) followed by diisopropylethylamine (27 μL, 3 equiv.). The reactions were stirred at room temperature overnight. Purification by preparative HPLC ($C_{18}$, water/acetonitrile containing 5 mM $NH_4OAc$) afforded the desired products.

TABLE M

| Ex. | NT⁷T⁸ | Name | Yield, % | HPLC Retention[a] (min) | MS Reported |
|---|---|---|---|---|---|
| M1 | N-(2-diisopropylaminoethyl) | 2-[4-[4-(2-Diisopropylamino-ethylcarbamoyl)-phenyl]-6-(4-hydroxy-piperidin-1-yl)-pyrimidin-2-ylamino]-4-methyl-5-thiazolecarboxylic acid ethyl ester | 80 | 1.60 | 610 |
| M2 | N-(3-dimethylaminopropyl) | 2-[4-[4-(3-Dimethylamino-propylcarbamoyl)-phenyl]-6-(4-hydroxy-piperidin-1-yl)-pyrimidin-2-ylamino]-4-methyl-5-thiazolecarboxylic acid ethyl ester | 92 | 1.48 | 568 |
| M3 | N-(cyclohexylmethyl) | 2-[4-[4-(Cyclohexylmethylcarbamoyl)-phenyl]-6-(4-hydroxy-piperidin-1-yl)-pyrimidin-2-ylamino]-4-methyl-5-thiazolecarboxylic acid ethyl ester | 9 | 2.01 | 579 |

TABLE M-continued

| Ex. | NT⁷T⁸ | Name | Yield, % | HPLC Retention[a] (min) | MS Reported |
|---|---|---|---|---|---|
| M4 | | 2-[4-[4-(Pyridin-4-ylmethylcarbamoyl)-phenyl]-6-(4-hydroxy-piperidin-1-yl)-pyrimidin-2-ylamino]-4-methyl-5-thiazolecarboxylic acid ethyl ester | 79 | 1.55 | 574 |
| M5 | | 2-[4-[4-(Isobutylcarbamoyl)-phenyl]-6-(4-hydroxy-piperidin-1-yl)-pyrimidin-2-ylamino]-4-methyl-5-thiazolecarboxylic acid ethyl ester | 47 | 1.79 | 539 |
| M6 | | 2-[4-[4-(N-Cyclohexyl-N-methylcarbamoyl)-phenyl]-6-(4-hydroxy-piperidin-1-yl)-pyrimidin-2-ylamino]-4-methyl-5-thiazolecarboxylic acid ethyl ester | 91 | 1.97 | 579 |
| M7 | | 2-[4-[4-(N-Cyclopropylmethyl-N-propylcarbamoyl)-phenyl]-6-(4-hydroxy-piperidin-1-yl)-pyrimidin-2-ylamino]-4-methyl-5-thiazolecarboxylic acid ethyl ester | 96 | 1.98 | 579 |
| M8 | | 2-[4-[4-(4-Ethoxycarbonylpyperidine-1-carbamoyl)-phenyl]-6-(4-hydroxy-piperidin-1-yl) pyrimidin-2-ylamino]-4-methyl-5-thiazolecarboxylic acid ethyl ester | 83 | 1.78 | 623 |
| M9 | | 2-[4-[4-(3-Hydroxymethyl-piperidine-1-carbonyl)-phenyl]-6-(4-hydroxy-piperidin-1-yl)-pyrimidin-2-ylamino]-4-methyl-5-thiazolecarboxylic acid ethyl ester | 79 | 1.54 | 581 |
| M10 | | 2-[4-[4-(N-2-Hydroxyethyl-N-ethylcarbamoyl)-phenyl]-6-(4-hydroxy-piperidin-1-yl)-pyrimidin-2-ylamino]-4-methyl-5-thiazolecarboxylic acid ethyl ester | 74 | 1.51 | 555 |
| M11 | | 2-[4-[4-(Thiomorpholine-1-carbonyl)-phenyl]-6-(4-hydroxy-piperidin-1-yl)-pyrimidin-2-ylamino]-4-methyl-5-thiazolecarboxylic acid ethyl ester | 77 | 1.74 | 569 |
| M12 | | 2-[4-[4-(Morpholine-1-carbonyl)-phenyl]-6-(4-hydroxy-piperidin-1-yl)-pyrimidin-2-ylamino]-4-methyl-5-thiazolecarboxylic acid ethyl ester | 86 | 1.57 | 553 |

TABLE M-continued

| Ex. | NT⁷T⁸ | Name | Yield, % | HPLC Retention[a] (min) | MS Reported |
|---|---|---|---|---|---|
| M13 | (structure: N-H linked phenyl with Cl para) | 2-[4-[4-(4-Chloro-phenylcarbamoyl)-phenyl]-6-(4-hydroxy-piperidin-1-yl)-pyrimidin-2-ylamino]-4-methyl-5-thiazolecarboxylic acid ethyl ester | 13 | 2.08 | 593 |

[a]HPLC conditions used to determine retention times: 2 min gradient 0–100% B in A (A; 5 mM NH₄OAc in 90/10 water/acetonitrile; B; 5 mM NH₄OAc in 10/90 water/acetonitrile) using a Primesphere C4 4.6 × 30 mm column at 254 nm.

We claim:

1. A compound of formula III

[Structure III shown]

or a stereoisomer, or a pharmaceutically acceptable salt, or a hydrate, thereof, wherein:

$R^{1a}$ is hydrogen or alkyl;

$R^{2a}$ is

[Structure shown with X¹, X², W]

W is S;
X¹ is alkoxy; and
X² is alkyl;
Z* is halogen, haloalkyl, oxazolyl, —NR³ᵃR⁴ᵃ, —C(O)—N(H)-alkylene-COOH, or phenyl which is unsubstituted or substituted with heteroaryl, CO_tH, or CO_tT⁶;
$R^{3a}$ is hydrogen or alkyl;
$R^{4a}$ is alkyl, alkoxy, unsubstituted or substituted (heteroaryl)alkyl, unsubstituted or substituted heterocyclo, unsubstituted or substituted (heterocyclo)alkyl, or (aryl)alkyl wherein the aryl group is substituted with one or two groups T¹* and/or T²* and/or further substituted with a group T³*;
or $R^{3a}$ and $R^{4a}$ together with the nitrogen atom to which they are attached combine to form an unsubstituted or substituted heterocyclo ring;
$R^{5a}$ is an unsubstituted or substituted (heteroaryl)alkyl, or (aryl)alkyl wherein the aryl group is substituted with one or two groups T¹* and/or T²* and/or further substituted with a group T³*;
or $R^{5a}$ and $R^{6a}$ together with the nitrogen atom to which they are attached combine to form an unsubstituted or substituted heterocyclo ring;

$R^{6a}$ is hydrogen or alkyl;
J* is hydrogen or alkyl;
T¹* and T²* are independently alkoxy, alkoxycarbonyl, heteroaryl, SO₃H, or SO₂R⁸ᵃ where R⁸ᵃ is alkyl, amino, alkylamino or dialkylamino;
or T¹* and T²* together with the aryl ring to which they are attached combine to form a bicyclic ring;
T³* is H, alkyl, halo, haloalkyl, or cyano;
t is 1 or 2; and
T⁶ is alkyl, haloalkyl, cycloalkyl, alkoxy, or heteroaryl.

2. A compound of claim 1, or a stereoisomer, or a pharmaceutically acceptable salt, or a hydrate, thereof, wherein
$R^{1a}$ is hydrogen;
Z* is halogen, alkyl, haloalkyl, NR³ᵃR⁴ᵃ, —C(O)—N(T¹⁰)-T⁵-H, or —C(O)—N(T¹⁰)-T⁵-T⁶;
$R^{3a}$ is hydrogen;
$R^{4a}$ is alkyl, alkoxy, haloalkyl, or unsubstituted or substituted (heterocyclo)alkyl;
or $R^{3a}$ and $R^{4a}$ together with the nitrogen atom to which they are attached combine to form an unsubstituted or substituted heterocyclo ring;
$R^{5a}$ is
 a) (phenyl)alkyl where the phenyl group is substituted with one or two alkoxy, alkoxycarbonyl, heteroaryl, or —SO₂R⁸ᵃ;
 b) unsubstituted or substituted (heteroaryl)alkyl; or
 c) unsubstituted or substituted (benzodioxole)alkyl;
$R^{6a}$ is hydrogen;
or $R^{5a}$ and $R^{6a}$ together with the nitrogen atom to which they are attached combine to form an unsubstituted or substituted heterocyclo ring; and
J* is hydrogen or alkyl.

3. A compound of claim 2, or a stereoisomer, or a pharmaceutically acceptable salt, or a hydrate, thereof, wherein
$R^{1a}$ is hydrogen;
$R^{3a}$ is hydrogen;
$R^{4a}$ is alkyl, alkoxy, unsubstituted or substituted (morpholinyl)alkyl, unsubstituted or substituted (pyrrolidinyl)alkyl, or unsubstituted or substituted (tetrahydrofuranyl)alkyl;
or $R^{3a}$ and $R^{4a}$ together with the nitrogen atom to which they are attached combine to form a piperazine, piperadine, or morpholine ring, any of which is unsubstituted or substituted with one or more more alkyl, (hydroxy)alkyl, hydroxy, —C(O)NH₂, cyano, oxo, —CO_tH, or —CO_tT⁶;

$R^{5a}$ is
a) (phenyl)alkyl where the phenyl group is substituted with one or more alkoxy, alkoxycarbonyl, heteroaryl, or —SO$_2$R$^{8a}$;
b) (tetrazolyl)alkyl, or (pryidyl)alkyl;
c) unsubstituted or substituted (benzodioxole)alkyl;
$R^{6a}$ is hydrogen;
or $R^{5a}$ and $R^{6a}$ together with the nitrogen atom to which they are attached combine to form a piperazine, piperadine or morpholine ring any of which is unsubstituted or substituted with one or more alkyl, (hydroxy)alkyl, hydroxy, —C(O)NH$_2$, cyano, oxo, —CO$_r$H, or —CO$_r$T$^6$; and
J* is hydrogen or alkyl.

4. A compound selected from the following:
(i) 2-[[4-[[[4-(Aminosulfonyl)phenyl]methy]amino]-6-(4-methyl-1-piperazinyl)-2-pyrimidinyl]amino]-4-methyl-5-thiazolecarboxylic acid ethyl ester;
2-[[4-[[(3,4-Dimethoxyphenyl)methyl]amino]-6-(1-piperazinyl)-2-pyrimidinyl]amino]-4-methyl-5-thiazolecarboxylic acid ethyl ester trifluoroacetate salt;
2-[[4-[[[4-(Aminosulfonyl)phenyl]methyl]amino]-6-(1-piperazinyl)-2-pyrimidinyl]amino]-4-methyl-5-thiazolecarboxylic acid ethyl ester;
4-Methyl-2-[[4-[[[4-(methylsulfonyl)phenyl]methyl]amino]-6-(1-piperazinyl)-2-pyrimidinyl]amino]-5-thiazolecarboxylic acid ethyl ester;
2-[[4-[[(4-Methoxyphenyl)methyl]amino]-6-(1-piperazinyl)-2-pyrimidinyl]amino]-4-methyl-5-thiazolecarboxylic acid ethyl ester;
2-[[4-[[(3-Methoxyphenyl)methyl]amino]-6-(1-piperazinyl)-2-pyrimidinyl]amino]-4-methyl-5-thiazolecarboxylic acid ethyl ester;
2-[[4-[[(2-Methoxyphenyl)methyl]amino]-6-(1-piperazinyl)-2-pyrimidinyl]amino]-4-methyl-5-thiazolecarboxylic acid ethyl ester;
4-Methyl-2-[[4-(1-piperazinyl)-6-[[(3,4,5-trimethoxyphenyl)methyl]amino]-2-pyrimidinyl]amino]-5-thiazolecarboxylic acid ethyl ester;
2-[[4-[[(2-Ethoxyphenyl)methyl]amino]-6-(1-piperazinyl)-2-pyrimidinyl]amino]-4-methyl-5-thiazolecarboxylic acid ethyl ester;
2-[[4-[[(2,5-Dimethoxyphenyl)methyl]amino]-6-(1-piperazinyl)-2-pyrimidinyl]amino]-4-methyl-5-thiazolecarboxylic acid ethyl ester;
2-[[4-[[(3,5-Dimethoxyphenyl)methyl]amino]-6-(1-piperazinyl)-2-pyrimidinyl]amino]-4-methyl-5-thiazolecarboxylic acid ethyl ester;
2-[[4-[[(2,6-Dimethylphenyl)methyl]amino]-6-(1-piperazinyl)-2-pyrimidinyl]amino]-4-methyl-5-thiazolecarboxylic acid ethyl ester;
2-[[4-[[[4-(Methoxycarbonyl)phenyl]methyl]amino]-6-(1-piperazinyl)-2-pyrimidinyl]amino]-4-methyl-5-thiazolecarboxylic acid ethyl ester;
2-[[4-[[(3-Bromophenyl)methyl]amino]-6-(1-piperazinyl)-2-pyrimidinyl)amino]-4-methyl-5-thiazolecarboxylic acid ethyl ester;
2-[[4-[(1,3-Benzodioxol-5-ylmethyl)amino]-6-(1-piperazinyl)-2-pyrimidinyl]amino]-4-methyl-5-thiazolecarboxylic acid ethyl ester;
4-Methyl-2-[[4-[methyl(3-pyridinylmethyl)amino]-6-(1-piperazinyl)-2-pyrimidinyl]amino]-5-thiazolecarboxylic acid ethyl ester;
4-Methyl-2-[[4-(1-piperazinyl)-6-[[[4-(1,2,3-thiadiazol-4-yl)phenyl]methyl]amino]-2-pyrimidinyl]amino]-5-thiazolecarboxylic acid ethyl ester;
2-[[4-[[[3-(Cyclopentyloxy)-4-methoxyphenyl]methyl]amino]-6-(1-piperazinyl)-2-pyrimidinyl]amino]-4-methyl-5-thiazolecarboxylic acid ethyl ester;
4-Methyl-2-[[4-[(phenylmethyl)amino]-6-(1-piperazinyl)-2-pyrimidinyl]amino]-5-thiazolecarboxylic acid ethyl ester;
4-Methyl-2-[[4-(4-methyl-1-piperazinyl)-6-[[(3,4,5-trimethoxyphenyl)methyl]amino]-2-pyrimidinyl]amino]-5-thiazolecarboxylic acid ethyl ester;
2-[[4-(4-Hydroxy-1-piperidinyl)-6-[[[4-(methylsulfonyl)phenyl]methyl]amino]-2-pyrimidinyl]amino]-4-methyl-5-thiazolecarboxylic acid ethyl ester;
4-Methyl-2-[[4-[[2-(1-methylethoxy)ethyl]amino]-6-[[[4-(methylsulfonyl)phenyl]methyl]amino]-2-pyrimidinyl]amino]-5-thiazolecarboxylic acid ethyl ester;
2-[[4-[3-(Aminocarbonyl)-1-piperidinyl]-6-[[[4-(methylsulfonyl)phenyl]methyl]amino]-2-pyrimidinyl]amino]-4-methyl-5-thiazolecarboxylic acid ethyl ester;
2-[[4-[[[2-(1H-imidazol-4-yl)ethyl]amino]-6-[[[4-(methylsulfonyl)phenyl]methyl]amino]-2-pyrimidinyl]amino]-4-methyl-5-thiazolecarboxylic acid ethyl ester;
4-Methyl-2-[[4-[[[4-(methylsulfonyl)phenyl]methyl]amino]-6-[[3-(4-morpholinyl)propyl]amino]-2-pyrimidinyl]amino]-5-thiazolecarboxylic acid ethyl ester;
2-[[4-[(2-Methoxy-1-methylethyl)amino]-6-[[[4-(methylsulfonyl)phenyl]methyl]amino]-2-pyrimidinyl]amino]-4-methyl-5-thiazolecarboxylic acid ethyl ester;
4-Methyl-2-[[4-[[[4-(methylsulfonyl)phenyl]methyl]amino]-6-[[(tetrahydro-2-furanyl)methyl]amino]-2-pyrimidinyl]amino]-5-thiazolecarboxylic acid ethyl ester;
2-[[4-[4-(2-Hydroxyethyl)-1-piperazinyl]-6-[[[4-(methylsulfonyl)phenyl]methyl]amino]-2-pyrimidinyl]amino]-4-methyl-5-thiazolecarboxylic acid ethyl ester;
2-[[4-[2-(Aminocarbonyl)-1-pyrrolidinyl]-6-[[[4-(methylsulfonyl)phenyl]methyl]amino]-2-pyrimidinyl]amino]-4-methyl-5-thiazolecarboxylic acid ethyl ester;
4-Methyl-2-[[4-[methyl(3-pyridinylmethyl)amino]-6-[[[4-(methylsulfonyl)phenyl]methyl]amino]-2-pyrimidinyl]amino]-5-thiazolecarboxylic acid ethyl ester;
2-[[4-[4-(Hydroxymethyl)-1-piperidinyl]-6-[[[4-(methylsulfonyl)phenyl]methyl]amino]-2-pyrimidinyl]amino]-4-methyl-5-thiazolecarboxylic acid ethyl ester;
2-[[4-[[2-(Diethylamino)ethyl]methylamino]-6-[[[4-(methylsulfonyl)phenyl]methyl]amino]-2-pyrimidinyl]amino]-4-methyl-5-thiazolecarboxylic acid ethyl ester;
4-Methyl-2-[[4-[[[4-(methylsulfonyl)phenyl]methyl]amino]-6-[[3-(2-oxo-1-pyrrolidinyl)propyl]amino]-2-pyrimidinyl]amino]-5-thiazolecarboxylic acid ethyl ester;
2-[[4-[3-(Hydroxymethyl)-1-piperidinyl]-6-[[[4-(methylsulfonyl)phenyl]methyl]amino]-2-pyrimidinyl]amino]-4-methyl-5-thiazolecarboxylic acid ethyl ester;

4-Methyl-2-[[4-(4-methyl-1-piperazinyl)-6-[[[(4-(methylsulfonyl)phenyl]methyl]amino]-2-pyrimidinyl]amino]-5-thiazolecarboxylic acid ethyl ester;

2-[[4-[[2-[(Acetylamino)ethyl]amino]-6-[[[(4-(methylsulfonyl)phenyl]methyl]amino]-2-pyrimidinyl]amino]-4-methyl-5-thiazolecarboxylic acid ethyl ester;

2-[[4-(4-Ethyl-1-piperazinyl)-6-[[[4-(methylsulfonyl)phenyl]methyl]amino]-2-pyrimidinyl]amino]-4-methyl-5-thiazolecarboxylic acid ethyl ester;

2-[[4-(4-Acetyl-1-piperazinyl)-6-[[[4-(methylsulfonyl)phenyl]methyl]amino]-2-pyrimidinyl]amino]-4-methyl-5-thiazolecarboxylic acid ethyl ester;

2-[[4-[[2-(Dimethylamino)ethyl]amino]-[[[4-(methylsulfonyl)phenyl]methyl]amino]-2-pyrimidinyl]amino]-4-methyl-5-thiazolecarboxylic acid ethyl ester;

2-[[4-[3-(Aminocarbonyl)-1-piperazinyl]-6-[[[4-(methylsulfonyl)phenyl]methyl]amino]-2-pyrimidinyl]amino]-4-methyl-5-thiazolecarboxylic acid ethyl ester;

2-[[4-(3-Hydroxy-1-pyrrolidinyl)-6-[[[4-(methylsulfonyl)phenyl]methyl]amino]-2-pyrimidinyl]amino]-4-methyl-5-thiazolecarboxylic acid ethyl ester;

2-[[4-[(4-Hydroxybutyl)amino]-6-[[[4-(methylsulfonyl)phenyl]methyl]amino]-2-pyrimidinyl]amino]-4-methyl-5-thiazolecarboxylic acid ethyl ester;

2-[[4-[(2,3-Dihydroxypropyl)amino]-6-[[[4-(methylsulfonyl)phenyl]methyl]amino]-2-pyrimidinyl]amino]-4-methyl-5-thiazolecarboxylic acid ethyl ester;

2-[[4-[(4-Amino-1-piperidinyl)-6-[[[4-(methylsulfonyl)phenyl]methyl]amino]-2-pyrimidinyl]amino]-4-methyl-5-thiazolecarboxylic acid ethyl ester;

2-[[4-[4-Hydroxy-3-(hydroxymethyl)-1-piperidinyl]-6-[[[4-(methylsulfonyl)phenyl]methyl]amino]-2-pyrimidinyl]amino]-4-methyl-5-thiazolecarboxylic acid ethyl ester;

2-[[4-(4-Dimethylamino-1-piperidinyl)-6-[[[4-(methylsulfonyl)phenyl]methyl]amino]-2-pyrimidinyl]amino]-4-methyl-5-thiazolecarboxylic acid ethyl ester;

2-[[4-[[[4-(Aminosulfonyl)phenyl]methyl]amino]-6-(methylamino)-2-pyrimidinyl]amino]-4-methyl-5-thiazolecarboxylic acid, ethyl ester;

2-[4,6-Bis-(4-methyl-piperazin-1-yl)-pyrimidin-2-ylamino]-4-methyl-thiazole-5-carboxylic acid ethyl ester;

2-[4-(4-Hydroxy-piperidin-1-yl)-6-(4-methyl-piperazin-1-yl)-pyrimidin-2-ylamino]-4-methyl-thiazole-5-carboxylic acid ethyl ester;

2-[4-(3-Hydroxymethyl-piperidin-I-yl)-6-(4-methyl-piperazin-1-yl)-pyrimidin-2-ylamino]-4-methyl-thiazole-5-carboxylic acid ethyl ester;

4-Methyl-2-[4-(4-methyl-piperazin-1-yl)-6-morpholin-4-yl-pyrimidin-2-ylamino]-thiazole-5-carboxylic acid ethyl ester;

2-[4-(4-Amino-piperidin-1-yl)-6-(4-methyl-piperazin-1-yl)-pyrimidin-2-ylamino]-4-methyl-thiazole-5-carboxylic acid ethyl ester;

2-[4,6-Bis-(4-hydroxy-piperidin-1-yl)-pyrimidin-2-ylamino]-4-methyl-thiazole-5-carboxylic acid ethyl ester;

2-[4-(4-oxo-piperidin-1-yl)-6-(4-methyl-piperazin-1-yl)-pyrimidin-2-ylamino]-4-methyl-thiazole-5-carboxylic acid ethyl ester;

2-[4-(4-methyl-4-hydroxy-piperidin-1-yl)-6-(4-methyl-piperazin-1-yl)-pyrimidin-2-ylamino]-4-methyl-thiazole-5-carboxylic acid ethyl ester;

2-[-(4-hydroxy-piperidin-1-yl)-6-(4-dimethylmethyl-piperazin-1-yl)-pyrimidin-2-ylamino]-4-methyl-thiazole-5-carboxylic acid ethyl ester;

2-[4-(4-hydroxymethyl-piperidin-1-yl)-6-(4-dimethylmethyl-piperazin-1-yl)-pyrimidin-2-ylamino]-4-methyl-thiazole-5-carboxylic acid ethyl ester;

2-[4-(3-hydroxymethyl-piperidin-1-yl)-6-(4-dimethyl-methyl-piperazin-1-yl)-pyrimidin-2-ylamino]-4-methyl-thiazole-5-carboxylic acid ethyl ester;

2-[4-(4-hydroxymethyl-piperidin-1-yl)-6-(4-hydroxy-piperazin-1-yl)-pyrimidin-2-ylamino]-4-methyl-thiazole-5-carboxylic acid ethyl ester;

4-Methyl-2-[4-(4-hydroxy-piperazin-1-yl)-6-morpholin-4-yl-pyrimidin-2-ylamino]-thiazole-5-carboxylic acid ethyl ester;

2-[[(4-[[[4-(Methylsulfonyl)phenyl]methyl]amino]-6-chloro-2-pyrimidinyl]amino]-4-methyl-5-thiazolecarboxylic acid, ethyl ester;

2-[[4-[[[4-(Aminosulfonyl)phenyl]methyl]amino]-6-chloro-2-pyrimidinyl]amino]-4-methyl-5-thiazolecarboxylic acid, ethyl ester;

2-[[4-[4-(Dimethylamino)-1-piperidinyl]-6-[[(3,4,5-trimethoxyphenyl)methyl]amino]-2-pyrimidinyl]amino]-4-methyl-5-thiazolecarboxylic acid, ethyl ester;

2-[[4-[1-piperizinyl]-6-methyl-6-[[(3,4,5-trimethoxyphenyl)methyl]amino]-2-pyrimidinyl]amino]-4-methyl-5-thiazolecarboxylic acid, ethyl ester;

2-[[4-(4-Amino-1-piperidinyl)-6-[[[4-(methylsulfonyl)phenyl]methyl]amino]-2-pyrimidinyl]amino]-4-methyl-5-thiazolecarboxylic acid, ethyl ester;

2-[[4-[4-hydroxy-1-piperidinyl]-6-methyl-6-[[(3,4,5-trimethoxyphenyl)methyl]amino]-2-pyrimidinyl]amino]-4-methyl-5-thiazolecarboxylic acid, ethyl ester;

2-[[4-[4-(Hydroxymethyl)-1-piperidinyl]-6-methyl-6-[[(3,4,5-trimethoxyphenyl)methyl]amino]-2-pyrimidinyl]amino]-4-methyl-5-thiazolecarboxylic acid, ethyl ester;

2-[4-(4-Hydroxypiperidin-1-yl)-6-(3-oxo-piperazin-1-yl)-pyrimidin-2-ylamino]-4-methyl-thiazole-5-carboxylic acid ethyl ester;

2-[[4-[3-(Aminocarbonyl)-1-piperizinyl]-6-methyl-6-[[(3,4,5-trimethoxyphenyl)methyl]amino]-2-pyrimidinyl]amino]-4-methyl-5-thiazolecarboxylic acid, ethyl ester;

2-[[4-[1-morpholinyl]-6-methyl-6-[[(3,4,5-trimethoxyphenyl)methyl]amino]-2-pyrimidinyl]amino]-4-methyl-5-thiazolecarboxylic acid, ethyl ester;

2-[[4-[3-Oxo-1-piperizinyl]-6-[[(1,1-dioxido-3-oxo-1,2-benzisothiazol-2-(3H)-yl)methyl]amino]-2-pyrimidinyl]amino]-4-methyl-5-thiazolecarboxylic acid, ethyl ester;

2-[[4-[3-Oxo1-piperizinyl]-6-[[[4-(ethylsufonylamino)phenyl)methyl]amino]-2-pyrimidinyl]amino]-4-methyl-5-thiazolecarboxylic acid, ethyl ester;

2-[[4-[3-Oxo-1-piperizinyl]-6-[[(4-(hydroxysulfonyl)phenyl)methyl]amino]-2-pyrimidinyl]amino]-4-methyl-5-thiazolecarboxylic acid, ethyl ester;

2-[4-(4-Hydroxypiperidin-1-yl)-6-(4-methyl-3-oxo-piperazin-1-yl)-pyrimidin-2-ylamino]-4-methyl-thiazole-5-carboxylic acid ethyl ester;

2-[4-(4(Dimethylamino)-piperizin-1-yl)-6-(4-((1-pyrrolidinyl)carbonylmethyl)piperazin-1-yl)-pyrimidin-2-ylamino]-4-methyl-thiazole-5-carboxylic acid ethyl ester;

2-[[4-[3-(Aminocarbonyl)-1-piperazinyl]-6-[[(3,4,5-trimethoxyphenyl)methyl]amino]-2-pyrimidinyl]amino]-4-methyl-5-thiazolecarboxylic acid, ethyl ester;

2-[[4-(4-Amino-1-piperidinyl)-6-[[(3,4,5-trimethoxyphenyl)methyl]amino]-2-pyrimidinyl]amino]-4-methyl-5-thiazolecarboxylic acid, ethyl ester;

2-[[4-[4-(Hydroxymethyl)-1-piperidinyl]-6-[4-[tetrazol-5-yl]-4-hydroxypiperidin-1-yl]2-pyrimidinyl]amino]-4-methyl-5-thiazolecarboxylic acid, ethyl ester;

2-[[4-[4-methyl-1-piperazinyl]-6-[N-methyl-N-[(3,4,5-trimethoxyphenyl)methyl]amino]-2-pyrimidinyl]amino]-4-methyl-5-thiazolecarboxylic acid, ethyl ester;

2-[[4-[4-Hydroxy-1-piperidinyl]-6-[[(4-(hydroxysulfonyl)phenyl)methyl]amino]-2-pyrimidinyl]amino]-4-methyl-5-thiazolecarboxylic acid, ethyl ester;

2-[[4-[[(4-Cyanophenyl)methyl]amino]-6-(1-piperazinyl)-2-pyrimidinyl]amino]-4-methyl-5-thiazolecarboxylic acid, ethyl ester; trifluoroacetate (1:1);

2-[[4-[[[4-(Aminosulfonyl)phenyl]methyl]amino]-6-(4-morpholinyl)-2-pyrimidinyl]amino]-4-methyl-5-thiazolecarboxylic acid, ethyl ester;

2-[[4-[4-Hydroxy-1-piperidinyl]-6-[(1-oxa-3,8-diazaspiro[4.5]decan-2,4,dion-8-yl]-2-pyrimidinyl]amino]-4-methyl-5-thiazolecarboxylic acid, ethyl ester;

2-[4-(2-(Dimethylamino)ethyl)-piperazin-1-yl)-6-(4-methylpiperazin-1-yl)-pyrimidin-2-ylamino]-4-methyl-thiazole-5-carboxylic acid ethyl ester;

2-[[4-(4-Hydroxy-1-piperidinyl)-6-[methyl(3-pyridinylmethyl)amino]-2-pyrimidinyl]amino]-4-methyl-5-thiazolecarboxylic acid, ethyl ester;

2-[[4-[4-Hydroxy-3-hydroxymethylpiperidin-1-yl]-6-[[(3,4,5-trimethoxyphenyl)methyl]amino]-2-pyrimidinyl]amino]-4-methyl-5-thiazolecarboxylic acid, ethyl ester;

2-[[4-(3,4-Dihydro-6,7-dihydroxy-2(1H)-isoquinolinyl)-6-(4-methyl-1-piperazinyl)-2-pyrimidinyl]amino]-4-methyl-5-thiazolecarboxylic acid, ethyl ester, trifluoroacetate 1:1);

2-[[4-[4-[(Methoxyacetyl)amino]-1-piperidinyl]-6-[[4-(methylsulfonyl)phenyl]methyl]amino]-2-pyrimidinyl]amino]-4-methyl-5-thiazolecarboxylic acid, ethyl ester;

2-[[4-[[(3,4-Dimethoxyphenyl)methyl]amino]-6-[4-(dimethylamino)-1-piperidinyl]-2-pyrimidinyl]amino]-4-methyl-thiazolecarboxylic acid, ethyl ester;

2-[[4-[4-(Hydroxyethyl)piperidin-1-yl]-6-[4-(dimethylamino)-1-piperidinyl]-2-pyrimidinyl]amino]-4-methyl-5-thiazolecarboxylic acid, ethyl ester;

2-[[4-[4-(Dimethylamino)-1-piperidinyl]-6-[methyl(3-pyridinylmethyl)amino]-2-pyrimidinyl]amino]-4-methyl-5-thiazolecarboxylic acid, ethyl ester;

2-[[4-[4-(Hydroxy)piperidin-1-yl]-6-[4-(methycarbonyl)-1-piperidinyl]-2-pyrimidinyl]amino]-4-methyl-5-thiazolecarboxylic acid, ethyl ester;

2-[[4-[4-(Hydroxy)piperidin-1-yl]-6-[4-(methyl)-4-(hydroxy)-1-piperidinyl]-2-pyrimidinyl]amino]-4-methyl-5-thiazolecarboxylic acid, ethyl ester;

2-[4-(3-oxopiperazin-1-yl)-6-(4-methylpiperazin-1-yl)-pyrimidin-2-ylamino]-4-methyl-thiazole-5-carboxylic acid ethyl ester;

2-[[4-[[(4-Cyanophenyl)methyl]amino]-6-[4-dimethylamino)-1-piperidinyl]-2-pyrimidinyl]amino]-4-methyl-5-thiazolecarboxylic acid, ethyl ester;

4-Methyl-2-[[4-[[(3-nitrophenyl)methyl]amino]-6-(1-piperazinyl)-2-pyrimidinyl]amino]-5-thiazolecarboxylic acid, ethyl ester, trifluoroacetate (1:1);

2-[[4-(4-Hydroxy-1-piperidinyl)-6-[[(3,4,5-trimethoxyphenyl)methyl]amino]-2-pyrimidinyl]amino]-4-methyl-5-thiazolecarboxylic acid, ethyl ester;

2-[4-(Dimethylamino)-piperazin-1-yl)-6-(4-methyl piperazin-1-yl)-pyrimidin-2-2-ylamino]-4-methyl-thiazole-5-carboxylic acid ethyl ester;

2-[4-(Dimethylamino)-piperidin-1-yl)-6-(3-(aminocarbonyl)-1-piperazinyl)-pyrimidin-2-ylamino]-4-methyl-thiazole-5-carboxylic acid ethyl ester;

2-[4-(2-Hydroxyethyl)-piperazin-1-yl)-6-(4-methyl-1-piperazinyl)-pyrimidin-2-ylamino]-4-methyl-thiazole-5-carboxylic acid ethyl ester;

2-[[4-[4-(Aminocarbonyl)-1-piperidinyl]-6-[[[4-(methylsulfonyl)phenyl]methyl]amino]-2-pyrimidinyl]amino]-4-methyl-5-thiazolecarboxylic acid, ethyl ester;

2-[[4-[4-(Hydroxymethyl)-1-piperidinyl]-6-[N-methyl-N-(3-pyridinylmethyl)amino]-2-pyrimidinyl]amino]-4-methy-5-thiazolecarboxylic acid, ethyl ester;

2-[[4-[4-Methylpiperazin-1-yl]-6-[[(3,4-dimethoxyphenyl)methyl]amino]-2-pyrimidinyl]amino]-4-methyl-5-thiazolecarboxylic acid, ethyl ester;

2-[[4-[piperazin-1-yl]-6-[[(4-carboxyphenyl)methyl]amino]-2-pyrimidinyl]amino]-4-methyl-5-thiazolecarboxylic acid, ethyl ester;

2-[[4-[3-Hydroxymethylpiperidin-1-yl]-6-[[N-[(3,4,5-trimethoxyphenyl)methyl]]-N-(methyl)amino]-2-pyrimidinyl]amino]-4-methyl-5-thiazolecarboxylic acid, ethyl ester;

2-[4-(4-Hydroxypiperidin-1-yl)-6-(4-carboxypiperidin-1-yl)-pyrimidin-2-ylamino]-4-methyl-thiazole-5-carboxylic acid ethyl ester;

2-[[4-[Piperazin-1-yl]-6-[[(3,4-dimethoxyphenyl)methyl]amino]-2-pyrimidinyl]amino]-4-methyl-5-thiazolecarboxylic acid, ethyl ester;

2-[[4-(4-Formyl-1-piperazinyl)-6-[[[4-(methylsulfonyl)phenyl]methyl]amino]-2-pyrimidinyl]amino]-4-methyl-5-thiazolecarboxylic acid, ethyl ester;

2-[4-(4-Hydroxypiperidin-1-yl)-6-(4-(hydroxy)-4-(4-chlorophenyl)piperidin-1-yl)-pyrimidin-2-ylamino]-4-methyl-thiazole-5-carboxylic acid ethyl ester;

4-Methyl-2-[[4-[4-dimethylamino-1-piperidinyl]-6-[[(tetrahydro-2-furanyl)methyl]amino]-2-pyrimidinyl]amino]-5-thiazolecarboxylic acid ethyl ester;

2-[[4-[Piperazin-1-yl]-6-[[N-methyl-N-(5-tetrazolylmethyl]amino]-2-pyrimidinyl]amino]-4-methyl-5-thiazolecarboxylic acid, ethyl ester;

2-[[4-[4-Morpholinyl]-6-[4-[tetrazol-5-yl]-4-hydroxypiperidin-1-yl]-2-pyrimidinyl]amino]-4-methyl-5-thiazolecarboxylic acid, ethyl ester;

2-[[4-[4-Hydroxy-1-piperidinyl]-6-[[(1,1-dioxido-3-oxo-1,2-benzisothiazol-2-(3H)-yl)methyl]amino]-2-pyrimidinyl]amino]-4-methyl-5-thiazolecarboxylic acid, ethyl ester;

2-[4-(4-Hydroxypiperidin-1-yl)-6-(4-(1-methyl-1-hydroxyethyl)piperidin-1-yl)-pyrimidin-2-ylamino]-4-methyl-thiazole-5-carboxylic acid ethyl ester;

2-[[4-[3-(Aminocarbonyl)-1-piperidinyl]-6-[[N-methyl-N-(3-pyridinylmethyl)]amino]-2-pyrimidinyl]amino]-4-methyl-5-thiazolecarboxylic acid, ethyl ester;

2-[[4-[4-Hydroxymethyl-1-piperidinyl]-6-[[(4-(ethylsufonylamino)phenyl)methyl]amino]-2-pyrimidinyl]amino]-4-methyl-5-thiazolecarboxylic acid, ethyl ester;

2-[[4-[4-Hydroxy-1-piperidinyl]-6-[4-[tetrazol-5-yl]-4-hydroxypiperidin-1-yl]2-pyrimidinyl]amino]-4-methyl-5-thiazolecarboxylic acid, ethyl ester;

2-[[4-[4-tertButyloxycarbonylamino-1-piperidinyl]-6-[[N-[(3,4,5-trimethoxyphenyl)methyl]]-N-(methyl)amino]-2-pyrimidinyl]amino]-4-methyl-5-thiazolecarboxylic acid, ethyl ester;

2-[[4-[[(4-Cyanophenyl)methyl]amino]-6-(4-methyl-1-piperazinyl)-2-pyrimidinyl]amino]-4-methyl-5-thiazolecarboxylic acid, ethyl ester, trifluoroacetate (1:1);

2-[[4-[4-[[(2-Ethoxy-2-oxoethyl)amino]carbonyl]-1-piperazinyl]-6-[methyl(3-pyridinylmethy)amino]-2-pyrimidinyl]amino]-4-methyl-5-thiazolecarboxylic acid, ethyl ester, trifluoroacetate (1:1);

2-[4-(4-Hydroxypiperidin-1-yl)-6-(3-hydroxypiperidin-1-yl)-pyrimidin-2-ylamino]-4-methyl-thiazole-5-carboxylic acid ethyl ester;

2-[4-(4-Hydroxypiperidin-1-yl)-6-(4-hydroxy-4-phenyl-1-piperidinyl)-pyrimidin-2-ylamino]-4-methyl-thiazole-5-carboxylic acid ethyl ester;

4-Methyl-2-[[4-[4-morpholinyl]-6-[[(tetrahydro-2-furanyl)methyl]amino]-2-pyrimidinyl]amino]-5-thiazolecarboxylic acid ethyl ester;

2-[[4-[(Tetrahydro-2-furanyl)methyl]amino]-6-[[N-[(3,4,5-trimethoxyphenyl)methyl]]-N-(methyl)amino]-2-pyrimidinyl]amino]-4-methyl-5-thiazolecarboxylic acid, ethyl ester;

2-[[4-[4-Morpholinyl]-6-[[(4-(hydroxysulfonyl)phenyl)methyl]amino]-2-pyrimidinyl]amino]-4-methyl-5-thiazolecarboxylic acid, ethyl ester;

2-[Bis-4,6-(4-Cyano-1-piperidinyl)-pyrimidin-2-ylamino]-4-methyl-thiazole-5-carboxylic acid ethyl ester;

2-[[4-[4-(Cyclopentylaminocarbonyl)-1-piperazinyl]-6-[N-methyl-N-(3-pyridinylmethyl)amino]-2-pyrimidinyl]amino]-4-methyl-5-thiazolecarboxylic acid, ethyl ester;

2-[4-(2-Methoxyethyl)-piperazin-1-yl)-6-(4-methyl-1-piperzinyl)-pyrimidin-2-ylamino]-4-methyl-thiazole-5-carboxylic acid ethyl ester;

2-[4-(4-Hydroxypiperidin-1-yl)-6-(3-carboxypiperidin-1-yl)-pyrimidin-2-ylamino]-4-methyl-thiazole-5-carboxylic acid ethyl ester;

2-[[4-[4-Methylpiperazin-1-yl]-6-[3-(acetylamino)-1-pyrrolidinyl]-2-pyrimidinyl]amino]-4-methyl-5-thiazolecarboxylic acid, ethyl ester;

2-[[4-[3-(Aminocarbonyl)-1-piperazinyl]-6-[[N-methyl-N-(3-pyridinylmethyl)]amino]-2-pyrimidinyl]amino]-4-methyl-5-thiazolecarboxylic acid, ethyl ester;

2-[[4-[2-Methyl-3-oxol-piperizinyl]-6-[4-methyl-1-piperazinyl]-2-pyrimidinyl]amino]-4-methyl-5-thiazolecarboxylic acid, ethyl ester;

2-[[4-[3-(Aminocarbonyl)-1-piperazinyl]-6-(4-methyl-1-piperazinyl)-2-pyrimidinyl]amino]-4-methyl-5-thiazolecarboxylic acid, ethyl ester;

2-[[4-[3-(Aminocarbonyl)-1-piperidinyl]-6-(4-dimethylamino-1-piperidinyl)-2-pyrimidinyl]amino]-4-methyl-5-thiazolecarboxylic acid, ethyl ester;

2-[[4-[1-piperazinyl]-6-[[N-methyl-N-(2-furylmethyl)]amino]-2-pyrimidinyl]amino]-4-methyl-5-thiazolecarboxylic acid, ethyl ester;

2-[[4-[[(4-Methoxycarbonylphenyl)methyl]amino]-6-(4-dimethyl-1-piperidinyl)-2-pyrimidinyl]amino]-4-methyl-5-thiazolecarboxylic acid, ethyl ester, trifluoroacetate (1:1);

2-[[4-[3-Oxo-1-piperazinyl]-6-[[(4-(methylsufonylamino)phenyl)methyl]amino]-2-pyrimidinyl]amino]-4-methyl-5-thiazolecarboxylic acid, ethyl ester;

2-[[4-[3-Oxo-1-piperazinyl]-6-[[(4-(propylsufonylamino)phenyl)methyl]amino]-2-pyrimidinyl]amino]-4-methyl-5-thiazolecarboxylic acid, ethyl ester;

2-[[4-[3-(Aminocarbonyl)-1-piperidinyl]-6-[[(3,4,5-trimethoxyphenyl)methyl]amino]-2-pyrimidinyl]amino]-4-methyl-5-thiazolecarboxylic acid, ethyl ester;

2-[Bis-4,6-(4-Hydroxy-4-methyl-1-piperidinyl)-pyrimidin-2-ylamino]-4-methyl-thiazole-5-carboxylic acid ethyl ester;

4-Methyl-2-[[4-[4-dimethylamino-1-piperidinyl]-6-[[(2-oxo-1-pyrrolidinyl)propyl]amino]-2-pyrimidinyl]amino]-5-thiazolecarboxylic acid ethyl ester;

2-[[4-[3-Oxo-1-piperazinyl]-6-[[(4-(iso-propylsufonylamino)phenyl)methyl]amino]-2-pyrimidinyl]amino]-4-methyl-5-thiazolecarboxylic acid, ethyl ester;

2-[4-(4-Hydroxypiperidin-1-yl)-6-(3-hydroxymethyl-1-piperidinyl)-pyrimidin-2-ylamino]-4-methyl-thiazole-5-carboxylic acid ethyl ester;

4-Methyl-2-[[4-[4-hydroxy-1-piperidinyl]-6-[[(2-(4-morpholinyl)ethyl]amino]-2-pyrimidinyl]amino]-5-thiazolecarboxylic acid ethyl ester;

2-[[4-[[[4-(Ethylaminosulfonyl)phenyl]methyl]amino]-6-methoxy-2-pyrimidinyl]amino]-4-methyl-5-thiazolecarboxylic acid, methyl ester, trifluoroacetate (1:1);

2-[[4-[4-Morpholinyl]-6-[(1-oxa-3,8-diazaspiro[4.5]decan-2,4,dion-8-yl]-2-pyrimidinyl]amino]-4-methyl-5-thiazolecarboxylic acid, ethyl ester;

2-[[4-[4-Hydroxy-1-piperidinyl]-6-[[(4-(ethylsufonylamino)phenyl)methyl]amino]-2-pyrimidinyl]amino]-4-methyl-5-thiazolecarboxylic acid, ethyl ester;

2-[[4-[tertButyloxycarbonyl-1-piperazinyl]-6-[[(3,4,5-trimethoxyphenyl)methyl]amino]-2-pyrimidinyl]amino]-4-methyl-5-thiazolecarboxylic acid, ethyl ester;

2-[[4-[3-(Aminocarbonyl)-1-piperidinyl]-6-[[(3,4-dimethoxyphenyl)methyl]amino]-2-pyrimidinyl]amino]-4-methyl-5-thiazolecarboxylic acid, ethyl ester;

2-[[4-[4-ethoxycarbonyl-1-piperazinyl]-6-[[N-methyl-N-(5-tetrazolylmethyl)amino]-2-pyrimidinyl]amino]-4-methyl-5-thiazolecarboxylic acid, ethyl ester;

2-[[4-[3-Oxo1-piperizinyl]-6-[[(4-(cyclopropylsufonylamino)phenyl)methyl]amino]-2-pyrimidinyl]amino]-4-methyl-5-thiazolecarboxylic acid, ethyl ester;

2-[[4-[4-Hydroxymethyl-1-piperidinyl]-6-[[(4-(methylsufonylamino)phenyl)methyl]amino]-2-pyrimidinyl]amino]-4-methyl-5-thiazolecarboxylic acid, ethyl ester;

2-[4-(4-Dimethylamino-1-piperazinyl)-6-(4-tertbutyloxycarbonylamino-1-piperidinyl)-pyrimidin-2-ylamino]-4-methyl-thiazole-5-carboxylic acid ethyl ester;

2-[4-(4-Hydroxypiperidin-1-yl)-6-(4-methoxymethyl-1-piperidinyl)-pyrimidin-2-ylamino]-4-methyl-thiazole-5-carboxylic acid ethyl ester;

2-[4-(4-Hydroxypiperidin-1-yl)-6-(4-hydroxyethyl-1-piperidinyl)-pyrimidin-2-ylamino]-4-methyl-thiazole-5-carboxylic acid ethyl ester;

2-[4-(4-Hydroxypiperidin-1-yl)-6-(4-(hydroxy)-4-(3-trifluoromethylphenyl)piperidin-1-yl)-pyrimidin-2-ylamino]-4-methyl-thiazole-5-carboxylic acid ethyl ester;

2-[[4-[4-morpholinyl]-6-[4-[1-methyl-1-hydroxyethyl]-1-piperidinyl]-2-pyrimidinyl]amino]-4-methyl-5-thiazolecarboxylic acid, ethyl ester;

2-[[4-(3-Oxo-1-piperizinyl)-6-[[3-pyridyl]oxy]-2-pyrimidinyl]amino]-4-methyl-5-thiazolecarboxylic acid, ethyl ester;

2-[[4-[4-Methyl-1-piperazinyl]-6-[(1,4-dioxaspiro[4.5]decan-8-yl]-2-pyrimidinyl]amino]-4-methyl-5-thiazolecarboxylic acid, ethyl ester;

2-[[4-[4-Morpholinyl]-6-[[(4-(methylsufonylamino)phenyl)methyl]amino]-2-pyrimidinyl]amino]-4-methyl-5-thiazolecarboxylic acid, ethyl ester;

2-[[4-[3-Oxo-1-piperazinyl]-6-[(1-oxa-3,8-diazospiro[4.5]decan-2,4,dion-8-yl]-2-pyrimidinyl]amino]-4-methyl-5-thiazolecarboxylic acid, ethyl ester;

2-[[4-[4-Hydroxy-1-piperidinyl]-6-[[(4-(carboxy)phenyl)methyl]amino]-2-pyrimidinyl]amino]-4-methyl-5-thiazolecarboxylic acid, ethyl ester;

2-[4-(4-Hydroxypiperidin-1-yl)-6-(4-(hydroxy)-4-(4-bromophenyl)piperidin-1-yl)-pyrimidin-2-ylamino]-4-methyl-thiazole-5-carboxylic acid ethyl ester;

2-[[4-[4-Morholinyl]-6-[[(4-ethylsufonylamino)phenyl)methyl]amino]-2-pyrimidinyl]amino]-4-methyl]-5-thiazolecarboxylic acid, ethyl ester;

2-[[4-[3-(Aminocarbonyl)-1-piperazinyl]-6-[[(3,4-dimethoxyphenyl)methyl]amino]-2-pyrimidinyl] amino]-4-methyl-5-thiazolecarboxylic acid, ethyl ester;

2-[[4-[4-Formyl-1-piperazinyl]-6-[[(3-(5-(1H)tetrazolyl)phenyl)methyl]amino]-2-pyrimidinyl]amino]-4-methyl-5-thiazolecarboxylic acid, ethyl ester;

2-[[4-[4-(Hydroxymethyl)-1-Piperidinyl]-6-[[N-methyl-N-(5-tetrazolylmethyl]amino]-2-pyrimidinyl] amino]-4-methyl-5-thiazolecarboxylic acid, ethyl ester;

2-[[4-[4-Methyl-1-piperazinyl]-6-[[(2,5-dimethyl)phenyl)methyl]amino]-2-pyrimidinyl]amino]-4-methyl-5-thiazolecarboxylic acid, ethyl ester;

2-[[4-[3-(2-oxo-1-pyrrolidinyl)propyl]amino]-6-[N-methyl-N-(3-pyridinylmethyl)amino]-2-pyrimidinyl]amino]-4-methyl-5-thiazolecarboxylic acid, ethyl ester;

2-[[4-[(1-Morpholinyl)]-6-[[N-methyl-N-(5-tetrazolylmethyl]amino]-2-pyrimidinyl]amino]-4-methyl-5-thiazolecarboxylic acid, ethyl ester;

2-[[4-[4-methyl-1-piperazinyl]-6-[4-[methylsulfonylamino]-1-piperidinyl]-2-pyrimidinyl]amino]-4-methyl-5-thiazolecarboxylic acid, ethyl ester;

2-[[4-[4-hydroxy-1-piperidinyl]-6-[[(2,5-dimethyl)phenyl)methyl]amino]-2-pyrimidinyl]amino]-4-methyl-5-thiazolecarboxylic acid, ethyl ester;

4-Methyl-2-[[4-(4-morpholinyl)-6-[[(3,4,5-trimethoxyphenyl)methyl]amino-2-pyrimidinyl]amino]-5-thiazolecarboxylic acid, ethyl ester;

2-[4-(4-Hydroxypiperidin-1-yl)-6-(3-hydroxy-1-piperidinyl)-pyrimidin-2-ylamino]-4-methyl-thiazole-5-carboxylic acid ethyl ester;

4-Methyl-2-[[4-(4-methyl-1-piperazinyl)-6-[methyl(3-pyridinylmethyl)amino]-2-pyrimidinyl]amino]-5-thiazolecarboxylic acid, ethyl ester;

2-[[4-[3-Oxo-1-piperazinyl]-6-[[(2-(5-(1H)tetrazolyl)phenyl)methyl]amino]-2-pyrimidinyl]amino]-4-methyl-4-thiazolecarboxylic acid, ethyl ester;

2-[[4-[(2-Furanylmethyl)amino]-6-(1-piperazinyl)-2-pyrimidinyl]amino]-4-methyl-5-thiazolecarboxylic acid, ethyl ester, trifluoroacetate (1:1);

2-[[4-[[(3,4-Dimethoxyphenyl)methyl]amino]-6-(4-morpholinyl)-2-pyrimidinyl]amino]-4-methyl-5-thiazolecarboxylic acid, ethyl ester;

4-Methyl-2-[[4-[methyl(3-pyridinylmethyl)amino]-6-[[(tetrahydro-2-furanyl)methyl]amino]-2-pyrimidinyl]amino]-5-thiazolecarboxylic acid, ethyl ester;

2-[[4-[(4-hydroxy-1-piperidinyl)]-6-[[N-methyl-N-(5-tetrazolylmethyl]amino]-2-pyrimidinyl]amino]-4-methyl-5-thiazolecarboxylic acid, ethyl ester;

2-[4-(4-Hydroxypiperidin-1-yl)-6-[(4-(hydroxy)-4-(phenylmethyl)piperidin-1-yl)]-pyrimidin-2-ylamino]-4-methyl-thiazole-5-carboxylic acid ethyl ester;

2-[4-(4-Dimethylamino-1-piperazinyl)-6-[[2-(1-morpholinyl)ethyl]amino]pyrimidin-2-ylamino]-4-methyl-thiazole-5-carboxylic acid ethyl ester;

2-[[4-[4-hydroxy-1-piperidinyl]-6-[[(3-pyridinylmethyl)]oxy]-2-pyrimidinyl]amino]-4-methyl-5-thiazolecarboxylic acid, ethyl ester;

2-[[4-[3-(Aminocarbonyl)-1-piperidinyl]-6-[[(2,6-dimethylphenyl)methyl]amino]-2-pyrimidinyl]amino]-4-methyl-5-thiazolecarboxylic acid, ethyl ester;

2-[[4-[4-hydroxy-1-piperidinyl]-6-[[(4-(methylsufonylamino)phenyl)methyl]amino]-2-pyrimidinyl] amino]-4-methyl-5-thiazolecarboxylic acid, ethyl ester;

2-[[4-[4-hydroxy-1-piperidinyl]-6-[[(4-(propylsufonylamino)phenyl)methyl]amino]-2-pyrimidinyl] amino]-4-methyl-5-thiazolecarboxylic acid, ethyl ester;

2-[[4-[3-(Aminocarbonyl)-1-piperidinyl]-6-(4-methyl-1-piperazinyl)-2-pyrimidinyl]amino]-4-methyl-5-thiazolecarboxylic acid, ethyl ester;

2-[[4-(3,4-Dihydro-6,7-dimethoxy-2(1H)-isoquinolinyl)-6-(4-methyl-1-piperazinyl)-2-pyrimidinyl] amino]-4-methyl-5-thiazolecarboxylic acid, ethyl ester;

2-[[4-[4-Formyl-1-piperazinyl]-6-[[N-methyl-N-(5-tetrazolylmethyl]amino]-2-pyrimidinyl]amino]-4-methyl-5-thiazolecarboxylic acid, ethyl ester;

2-[[4-[[(4-Carboxyphenyl)methyl]amino]-6-[4-(hydroxymethyl)-1-piperidinyl]-2-pyrimidinyl]amino]-4-methyl-5-thiazolecarboxylic acid, ethyl ester;

2-[[4-[[(4-Carboxyphenyl)methyl]amino]-6-(4-methyl-1-piperazinyl)-2-pyrimidinyl]amino]-4-methyl-5-thiazolecarboxylic acid, ethyl ester, monohydrochloride;

4-Methyl-2-[[4-(4-methyl-1-piperazinyl)-6-[[(tetrahydro-2-furanyl)methyl]amino]-2-pyrimidinyl]amino]-5-thiazolecarboxylic acid, ethyl ester;

2-[[4-[[(4-Carboxyphenyl)methyl]amino]-6-[3-(hydroxymethyl)-1-piperidinyl]-2-pyrimidinyl]amino]-4-methyl-5-thiazolecarboxylic acid, ethyl ester;

2-[[4-[[[4-[[(2-Methoxyethyl)amino]carbonyl]phenyl]methyl]amino]-6-(4-methyl-1-piperazinyl)-2-pyrimidinyl]amino]-4-methyl-5-thiazolecarboxylic acid, ethyl ester, trifluoroacetate (1:1);

2-[4,6-Bis-(1-morpholinyl)-pyrimidin-2-ylamino]-4-methyl-thiazole-5-carboxylic acid ethyl ester;

2-[[4-[3-(Aminocarbonyl)-1-piperazinyl]-6-[[N-methyl-N-(5-tetrazolylmethyl)amino]-2-pyrimidinyl]amino]-4-methyl-5-thiazolecarboxylic acid ethyl ester;

4-Methyl-2-[[4-[-methyl(3-pyridinylmethyl)amino]-6-[4-morpholinyl]-2-pyridinylmethyl]amino]-5-thiazolecarboxylic acid, ethyl ester;

2-[[4-[3-(Aminocarbonyl)-1-piperazinyl]-6-[[[4-(methoxycarbonyl)phenyl]methyl]amino]-2-pyrimidinyl]amino]-4-methyl-5-thiazolecarboxylic acid, ethyl ester;

2-[[4-Chloro-6-[(1-oxa-3,8-diazaspiro[4.5]decan-2,4,dion-8-yl]-2-pyrimidinyl]amino]-4-methyl-5-thiazolecarboxylic acid, ethyl ester;

2-[[4-[4-(Hydroxymethyl)-1-piperidinyl]-6-[[(3,4,5-trimethoxyphenyl)methyl]amino]-2-pyrimidinyl]amino]-4-methyl-5-thiazolecarboxylic acid, ethyl ester;

2-[[4-[3-(Hydroxymethyl)-1-Piperidinyl]-6-[[N-methyl-N-(5-tetrazolylmethyl)amino]-2-pyrimidinyl]amino]-4-methyl-5-thiazolecarboxylic acid, ethyl ester;

2-[[4-[3-(Hydroxymethyl)-1-pyrrolidinyl]-6-[[N-methyl-N-(5-tetrazolylmethyl)amino]-2-pyrimidinyl]amino]-4-methyl-5-thiazolecarboxylic acid, ethyl ester;

4-Methyl-2-[[4-[methyl(phenylmethyl)amino]-6-(4-methyl-1-piperazinyl)-2-pyrimidinyl]amino]-5-thiazolecarboxylic acid, ethyl ester;

2-[[4-(Dimethylamino)-6-[[[4-(methylsulfonyl)phenyl]methyl]amino]-2-pyrimidinyl]amino]-4-methyl-5-thiazolecarboxylic acid, ethyl ester;

2-[[4-[4-Hydroxy-1-piperidinyl]-6-[[(3-(5-(1H)tetrazolyl)phenyl)methyl]amino]-2-pyrimidinyl]amino]-4-methyl-5-thiazolecarboxylic acid, ethyl ester;

2-[[4-[4-hydroxymethyl-1-piperidinyl]-6-[[(4-(propylsufonylamino)phenyl)methyl]amino]-2-pyrimidinyl]amino]-4-methyl-5-thiazolecarboxylic acid, ethyl ester;

2-[[4-[4-hydroxymethyl-1-piperidinyl]-6-[[(4-(cyclopropylsufonylamino)phenyl)methyl]amino]-2-pyrimidinyl]amino]-4-methyl-5-thiazolecarboxylic acid, ethyl ester;

2-[[4-[3-(Hydroxymethyl)-1-piperidinyl]-6-[[(3,4,5-trimethoxyphenyl)methyl]amino]-2-pyrimidinyl]amino]-4-methyl-5-thiazolecarboxylic acid, ethyl ester;

2-[[4-[4-tetrahydropyranyl]oxy-6-[[N-[(3,4,5-trimethoxyphenyl)methyl]]-N-(methyl)amino]-2-pyrimidinyl]amino]-4-methyl-5-thiazolecarboxylic acid, ethyl ester;

2-[[4-[4-Methyl-1-piperazinyl]-6-[(4-methoxyphenyl)oxy]-2-pyrimidinyl]amino]-4-methyl-5-thiazolecarboxylic acid, ethyl ester;

4-Methyl-2-{4-(4-methyl-piperazin-1-yl)-6-[[[4-(aminosulfonyl)phenyl]methyl]amino]pyrimidin-2-ylamino}-thiazole-5-carboxylic acid ethyl ester;

2-[4-Isopropyl-6-(4-sulfamoyl-benzylamino)-pyrimidin-2-ylamino]-4-methyl-thiazole-5-carboxylic acid ethyl ester;

4-Methyl-2-[4-(4-sulfamoyl-benzylamino)-6-methyl-pyrimidin-2-ylamino]-thiazole-5-carboxylic acid ethyl ester;

4-Methyl-2-[4-(4-sulfamoyl-benzylamino)-6-hydroxymethyl-pyrimidin-2-ylamino]-thiazole-5-carboxylic acid ethyl ester;

4-Methyl-2-{4-(4-methyl-piperazin-1-yl)-6-[4-(1H-tetrazol-5-yl)-benzylamino]-pyrimidin-2-ylamino}-thiazole-5-carboxylic acid ethyl ester;

2-{4-(4-Hydroxy-piperidin-1-yl)-6-[4-(1H-tetrazol-5-yl)-benzylamino]-pyrimidin-2-ylamino}-4-methyl-thiazole-5-carboxylic acid ethyl ester;

4-Methyl-2-{4-[(tetrahydro-furan-2-ylmethyl)-amino]-6-[4-(1H-tetrazol-5-yl)-benzylamino]-pyrimidin-2-ylamino]-thiazole-5-carboxylic acid ethyl ester;

4-Methyl-2-{4-morpholin-4-yl-6-[4-(1H-tetrazol-5-yl)-benzylamino]-pyrimidin-2-ylamino}-thiazole-5-carboxylic acid ethyl ester;

2-{4-(3-Carbamoyl-piperidin-1-yl)-6-[4-(1H-tetrazol-5-yl)-benzylamino]-pyrimidin-2-ylamino})-4-methyl-thiazole-5-carboxylic acid ethyl ester;

2-{4-(4-Hydroxymethylpiperidin-1-yl)-6-[4-(1H-tetrazol-5-yl)-benzylamino]-pyrimidin-2-ylamino}-4-methyl-thiazole-5-carboxylic acid ethyl ester;

2-{4-(2-Hydroxymethyl-1-pyrrolidinyl)-6-[4-(1H-tetrazol-5-yl)-benzylamino]-pyrimidin-2-ylamino}-4-methyl-thiazole-5-carboxylic acid ethyl ester;

2-{4-(3-N,N-Diethylcarbamoyl-1-piperidinyl)-6-[4-(1H-tetrazol-5-yl)-benzylamino]-pyrimidin-2-ylamino}-4-methyl-thiazole-5-carboxylic acid ethyl ester;

2-{4-(3-Hydroxy-1-pyrrolidinyl)-6-[4-(1H-tetrazol-5-yl)-benzylamino]-pyrimidin-2-ylamino}-4-methyl-thiazole-5-carboxylic acid ethyl ester;

4-Methyl-2-{[[2-[4-morpholin-4-yl]ethyl]amino-6-[4-(1H-tetrazol-5-yl)-benzylamino]pyrimidin-2-ylamino}-thiazole-5-carboxylic acid ethyl ester;

4-Methyl-2-{[[4-hydroxyl]butyl]amino-6-[4-(1H-tetrazol-5-yl)-benzylamino]-pyrimidin-2-ylamino}-thiazole-5-carboxylic acid ethyl ester;

2-{4-(4-Formyl-1-piperazinyl)-6-[4-(1H-tetrazol-5-yl)-benzylamino]-pyrimidin-2-ylamino}-4-methyl-thiazole-5-carboxylic acid ethyl ester;

2-[[4-[[(4-Chlorophenyl)methyl]amino]-6-(5-oxazolyl)-2-pyrimidinyl]amino]-4-methyl-5-thiazolecarboxylic acid ethyl ester;

2-[[4-[[(4-Aminosylfonylphenyl)methyl]amino]-6-(5-oxazolyl)-2-pyrimidinyl]amino]-4-methyl-5-thiazolecarboxylic acid ethyl ester;

2-[[4-Morpholino-6-(5-oxazolyl)-2-pyrimidinyl]amino]-4-methyl-5-thiazolecarboxylic acid ethyl ester;

2-[[4-[[(3,4-Dimethoxyphenyl)methyl]amino]-6-(5-oxazolyl)-2-pyrimidinyl]amino]-4-methyl-5-thiazolecarboxylic acid ethyl ester;

2-[[4-(1,4-Dioxa-8-aza-spiro[4.5]dec-8-yl)-6-(5-oxazoly)-2-pyrimidinyl]amino]-4-methyl-5-thiazolecarboxylic acid ethyl ester;

2-[[4-[4-Hydroxy-4-phenyl-piperidinyl]-6-(5-oxazolyl)-2-pyrimidinyl]amino]-4-methyl-5-thiazolecarboxylic acid ethyl ester;

2-[[4-[[(4-Methylsulfonylphenyl)methyl]amino]-6-(5-oxazolyl)-2-pyrimidinyl]amino]-4-methyl-5-thiazolecarboxylic acid ethyl ester;

2-[[4-[4-Hydroxy-piperidinyl]-6-(5-oxazolyl)-2-pyrimidinyl]amino]-4-methyl-5-thiazolecarboxylic acid ethyl ester;

2-[[4-[4-Ethoxycarbonyl-piperidinyl]-6-(5-oxazolyl)-2-pyrimidinyl]amino]-4-methyl-5-thiazolecarboxylic acid ethyl ester;

2-[[4-Piperidinyl-6-(5-oxazolyl)-2-pyrimidinyl]amino]-4-methyl-5-thiazolecarboxylic acid ethyl ester;

2-[[4-[N-Methylpiperazinyl-6-(5-oxazolyl)-2-pyrimidinyl]amino]-4-methyl-5-thiazolecarboxylic acid ethyl ester;

2-[[4-[N-(2-Furylcarbonyl)piperazinyl-6-(5-oxazolyl)-2-pyrimidinyl]amino]-4-methyl-5-thiazolecarboxylic acid ethyl ester;

2-[[4-[N-Acetyl-[1,4-diazepyl]-6-(5-oxazolyl)-2-pyrimidinyl]amino]-4-methyl-5-thiazolecarboxylic acid ethyl ester;

2-[[4-[N-Methyl-N-(N-methyl-4-piperidinyl)-amino]-6-(5-oxazolyl)-2-pyrimidinyl]amino]-4-methyl-5-thiazolecarboxylic acid ethyl ester;

2-[[4-[N-Methyl-[1,4]-diazepyl]-6-(5-oxazolyl)-2-pyrimidinyl]amino]-4-methyl-5-thiazolecarboxylic acid ethyl ester;

2-[[4-N,N-Dimethoxyethylamino-6-(5-oxazolyl)-2-pyrimidinyl]amino]-4-methyl-5-thiazolecarboxylic acid ethyl ester;

2-[[4-[(1',4)-Bipiperidinyl]-6-(5-oxazolyl)-2-pyrimidinyl]amino]-4-methyl-5-thiazolecarboxylic acid ethyl ester;

2-[4-(4-Hydroxy-piperidin-1-yl)-6-(3,4,5-trimethoxyphenyl)-pyrimidin-2-ylamino]-4-methylthiazole-5-carboxylic acid ethyl ester;

2-{(4-(4-Hydroxy-piperidin-1-yl)-6-[4-(1H-tetrazol-5-yl)-phenyl]-pyrimidin-2-ylamino}-4-methylthiazole-5-carboxylic acid ethyl ester;

2-[4-(4-Hydroxy-piperidin-1-yl)-6-pyridin-3-yl-pyrimidin-2-ylamino]-4-methylthiazole-5-carboxylic acid ethyl ester;

2-[4-(4-Methanesulfonyl-benzylamino)-6-pyridin-3-yl-pyrimidin-2-ylamino]-4-methylthiazole-5-carboxylic acid ethyl ester;

2-[4-(4-Hydroxy-piperidin-1-yl)-6-pyrimidin-4-yl-pyrimidin-2-ylamino]-4-methylthiazole-5-carboxylic acid ethyl ester;

2-[4-(4-Cyano-phenyl)-6-(4-hydroxy-piperidin-1-yl)-pyrimidin-2-ylamino]-4-methylthiazole-5-carboxylic acid ethyl ester;

2-[4-(4-Acetyl-phenyl)-6-(4-hydroxy-piperidin-1-yl)-pyrimidin-2-ylamino]-4-methylthiazole-5-carboxylic acid ethyl ester;

2-[4-(4-Hydroxymethyl-phenyl)-6-(4-hydroxy-piperidin-1-yl)-pyrimidin-2-ylamino]-4-methylthiazole-5-carboxylic acid ethyl ester;

2-[4-(4-Hydroxy-phenyl)-6-(4-hydroxy-piperidin-1-yl)-pyrimidin-2-ylamino]-4-methylthiazole-5-carboxylic acid ethyl ester;

2-[4-(4-Methanesulfonyl-benzylamino)-6-(3,4,5-trimethoxy-phenyl)-pyrimidin-2-ylamino]-4-methylthiazole-5-carboxylic acid ethyl ester;

2-[4-(4-Methanesulfinylphenyl)-6-(4-hydroxypiperidin-1-yl)-pyrimidin-2-ylamino]-4-methylthiazole-5-carboxylic acid ethyl ester;

2-[4-(4-(Amino)phenyl)-6-(4-hydroxy-piperidin-1-yl)-pyrimidin-2-ylamino]-4-methylthiazole-5-carboxylic acid ethyl ester;

2-[4-(4-Carboxymethyl-phenyl)-6-(4-hydroxy-piperidin-1-yl)-pyrimidin-2-ylamino]-4-methylthiazole-5-carboxylic acid ethyl ester;

2-[4-(4-(Trifluoromethylcarbonylamino)phenyl)-6-(4-hydroxy-piperidin-1-yl)-pyrimidin-2-ylamino]-4-methylthiazole-5-carboxylic acid ethyl ester;

2-[4-(4-(Ethoxycarbonylmethyl)phenyl)-6-(4-hydroxy-piperidin-1-yl)-pyrimidin-2-ylamino]-4-methylthiazole-5-carboxylic acid ethyl ester;

2-[4-(1,2,3,6-Tetrahydropyridin-4-yl)-6-(4-hydroxy-piperidin-1-yl)-pyrimidin-2-ylamino]-4-methylthiazole-5-carboxylic acid ethyl ester;

2-[4-(3-(cyano)phenyl)-6-(4-hydroxy-piperidin-1-yl)-pyrimidin-2-ylamino]-4-methylthiazole-5-carboxylic acid ethyl ester;

2-[4-(4-(Methoxycarbonyl)phenyl)-6-(4-hydroxy-piperidin-1-yl)-pyrimidin-2-ylamino]-4-methylthiazole-5-carboxylic acid ethyl ester;

2-[4-(2-(Methoxy)-5-pyridinyl)-6-(4-hydroxy-piperidin-1-yl)-pyrimidin-2-ylamino]-4-methylthiazole-5-carboxylic acid ethyl ester;

2-[4-(4-tertButyloxycarbonyl-1,2,3,6-Tetrahydropyridin-4-yl)-6-(4-hydroxy-piperidin-1-yl)-pyrimidin-2-ylamino]-4-methylthiazole-5-carboxylic acid ethyl ester;

2-[4-(1,4-Dioxaspiro[4.5]dec-7-en-8-yl)-6-(4-hydroxy-piperidin-1-yl)-pyrimidin-2-ylamino]-4-methylthiazole-5-carboxylic acid ethyl ester;

2-[4-(4-Methyl-1-piperazin-yl)-6-(3,4,5-trimethoxyphenyl)-pyrimidin-2-ylamino]-4-methylthiazole-5-carboxylic acid ethyl ester;

2-[4-(4-Morpholinyl)-6-(3,4,5-trimethoxy-phenyl)-pyrimidin-2-ylamino]-4-methylthiazole-5-carboxylic acid ethyl ester;

2-[4-(4-Morpholinyl)-6-(3-pyridinyl)-pyrimidin-2-ylamino]-4-methylthiazole-5-carboxylic acid ethyl ester;

2-[4-(Piperadin-4-yl)-6-(4-hydroxy-piperidin-1-yl)-pyrimidin-2-ylamino]-4-methylthiazole-5-carboxylic acid ethyl ester;

2-[[4-[4-Hydroxy-piperidinyl]-6-(3,5-dimethyl-4-isoxazolyl)-2-pyrimidinyl]amino]-4-methyl-5-thiazolecarboxylic acid ethyl ester;

2-[4-(4-tert-Butoxycarbonylamino-phenyl)-6-(4-hydroxy-piperidin-1-yl)-pyrimidin-2-ylamino]-4-methyl-5-thiazolecarboxylic acid ethyl ester;

2-[4-(4-Cyano-phenyl)-6-(4-methanesulfonyl-benzylamino)-pyrimidin-2-ylamino]-4-methyl-5-thiazolecarboxylic acid ethyl ester;

2-[4-(4-Methanesulfonylphenyl)-6-(4-hydroxypiperidin-1-yl)-pyrimidin-2-ylamino]-4-methylthiazole-5-carboxylic acid ethyl ester;

2-[4-(4-Methanesulfanylphenyl)-6-(4-hydroxypiperidin-1-yl)-pyrimidin-2-ylamino]-4-methylthiazole-5-carboxylic acid ethyl ester;

2-[4-(4-Carboxy-phenyl)-6-(4-hydroxy-piperidin-1-yl)-pyrimidin-2-ylamino]-4-methyl-thiazole-5-carboxylic acid ethyl ester;

2-[4-(4-Carboxy-phenyl)-6-(3-oxo-piperazin-1-yl)-pyrimidin-2-ylamino]-4-methylthiazole-5-carboxylic acid ethyl ester;

2-[4-(4-Carboxy-phenyl)-6-(4-methyl-piperazin-1-yl)-pyrimidin-2-ylamino]-4-methylthiazole-5-carboxylic acid ethyl ester;

2-[4-(4-Carboxy-phenyl)-6-morpholin-4-yl-pyrimidin-2-ylamino]-4-methylthiazole-5-carboxylic acid ethyl ester;
2-[4-(4-Carboxy-phenyl)-6-(4-methyl-[1,4]diazepan-1-yl)-pyrimidin-2-ylamino]-4-methylthiazole-5-carboxylic acid ethyl ester;
2-[4-(4-Carboxy-phenyl)-6-(3-R-hydrox-piperidin-1-yl)-pyrimidin-2-ylamino]-4-methylthiazole-5-carboxylic acid ethyl ester;
2-[4-(4-Carboxy-phenyl)-6-(3-hydroxymethyl-piperidin-1-yl)-pyrimidin-2-ylamino]-4-methylthiazole-5-carboxylic acid ethyl ester;
2-[4-(4-Acetyl-[1,4]diazepan-1-yl)-6-(4-carboxy-phenyl)-pyrimidin-2-ylamino]-4-methylthiazole-5-carboxylic acid ethyl ester;
2-{4-(4-Carboxy-phenyl)-6-[N-methyl-N-(1-N-methyl-piperidin-4-yl)-amino]-pyrimidin-2-ylamino}-4-methylthiazole-5-carboxylic acid ethyl ester;
2-[4-(4-Carboxy-phenyl)-6-piperazin-1-yl-pyrimidin-2-ylamino]-4-methylthiazole-5-carboxylic acid ethyl ester;
2-[4-(4-Carboxy-phenyl)-6-(4-sulfamoyl-benzylamino)-pyrimidin-2-ylamino]-4-methylthiazole-5-carboxylic acid ethyl ester;
2-[[4-[[5-Allyl[4-(aminosulfonyl)phenyl]methyl]amino]-6-chloro-2-pyrimidinyl]amino]-4-methyl-5-thiazolecarboxylic acid, ethyl ester;
2-[[4-[[[4-(Aminosulfonyl)phenyl]methyl]amino]-5-methyl-6-(1-piperazinyl)-2-pyrimidinyl]amino]-4-methyl-5-thiazolecarboxylic acid, ethyl ester, trifluoroacetate (1:3);
2-[[4-[[[4-(Aminosulfonyl)phenyl]methyl]amino]-5-methyl-6-(4-morpholinyl)-2-pyrimidinyl]amino]-4-methyl-5-thiazolecarboxylic acid, ethyl ester;
2-[[4-[[5-Allyl[4-(aminosulfonyl)phenyl]methyl]amino]-6-(4-methylpiperazinyl)-2-pyrimidinyl]amino]-4-methyl-5-thiazolecarboxylic acid, ethyl ester;
2-[[4-[[5-[2-[2-Methylprop-3-en]]-4-[4-(aminosulfonyl)phenyl]methyl]amino]-6-(4-methylpiperazinyl)-2-pyrimidinyl]amino]-4-methyl-5-thiazolecarboxylic acid, ethyl ester;
2-[[4-[[[(3,4,5-Trimethoxy)phenyl]methyl]amino]-5-methyl-6-(1-piperazinyl)-2-pyrimidinyl]amino]-4-methyl-5-thiazolecarboxylic acid, ethyl ester, trifluoroacetate;
2-[[4-[[5-[2,3-propandiol][4-(aminosulfonyl)phenyl]methyl]amino]-6-(4-methylpiperazinyl)-2-pyrimidinyl]amino]-4-methyl-5-thiazolecarboxylic acid, ethyl ester;
2-[[4-[[[3,4,5-(Trimethoxy)phenyl]methyl]amino]-5-methyl-6-(4-methyl-1-piperazinyl)-2-pyrimidinyl]amino]-4-methyl-5-thiazolecarboxylic acid, ethyl ester, trifluoroacetate;
2-[[4-[[5-[2-[2-Methylprop-3-en]]-4-[4-(aminosulfonyl)phenyl]methyl]amino]-6-chloro-2-pyrimidinyl]amino]-4-methyl-5-thiazolecarboxylic acid, ethyl ester;
2-[[4-[[[4-(Aminosulfonyl)phenyl]methyl]amino]-5-methyl-6-(4-tertbutyloxycarbonyl-1-piperazinyl)-2-pyrimidinyl]amino]-4-methyl-5-thiazolecarboxylic acid, ethyl ester;
2-[[4-[N-[[3,4,5-(Trimethoxy)phenyl]methyl]-N-methylamino]-5-methyl-6-(4-methyl-1-piperazinyl)-2-pyrimidinyl]amino]-4-methyl-5-thiazolecarboxylic acid, ethyl ester;
2-[4,6-Bis-(4-hydroxy-piperidin-1-yl)-5-methylpyrimidin-2-ylamino]-4-methyl-thiazole-5-carboxylic acid ethyl ester;
2-[4,6-Bis-(3-oxo-piperazin-1-yl)-5-[ethoxycarbonylmethyl]pyrimidin-2-ylamino]-4-methyl-thiazole-5-carboxylic acid ethyl ester;
2-[4,6-Bis-(4-hydroxy-piperidin-1-yl)-5-methoxypyrimidin-2-ylamino]-4-methyl-thiazole-5-carboxylic acid ethyl ester;
2-[[4-[N-[[3,4,5-(Trimethoxy)phenyl]methyl]-N-methylamino]-5-methoxy-6-(4-methyl-1-piperazinyl)-2-pyrimidinyl]amino]-4-methyl-5-thiazolecarboxylic acid, ethyl ester;
2-[[4-[[3-pyridyl]methyloxy]-5-(2-propenyl-6-(4-morpholinyl)-2-pyrimidinyl]amino]-4-methyl-5-thiazolecarboxylic acid, ethyl ester;
2-[(4-Ethoxycarbonylmethyl-6-morpholin-4-yl-pyrimidin-2-yl)-amino]-4-methyl-5-thiazolecarboxylic acid ethyl ester;
2-[(4-Ethoxycarbonylmethyl-6-[3-oxo-1-piperazinyl]-pyrimidin-2-yl)-amino]-4-methyl-5-thiazolecarboxylic acid ethyl ester;
2-[(4-Carboxymethyl-6-morpholin-4-yl-pyrimidin-2-yl)-amino]-4-methyl-5-thiazolecarboxylic acid;
2-[4-Morpholin-4-yl-6-[(3,4,5-trimethoxy-phenylcarbamoyl)-methyl]-pyrimidin-2-ylamino]-4-methyl-5-thiazolecarboxylic acid ethyl ester;
2-[[4-[2-oxo-2-(3-oxo-piperazin-1-yl)-ethyl]-6-(4-sulfamoyl-benzylamino)-2-pyrimidinyl]amino]-4-methyl-5-thiazolecarboxylic acid ethyl ester;
2-[[4-(4-sulfamoyl-benzylamino)-6-[(4-sulfamoyl-benzylcarbamoyl)-methyl]-2-pyrimidinyl]amino]-4-methyl-5-thiazolecarboxylic acid ethyl ester;
2-[4-[2-(1,4-Dioxa-8-aza-spiro[4.5]dec-8-yl)-2-oxo-ethyl]-6-(4-sulfamoyl-benzylamino)-2-pyrimidinyl]amino]-4-methyl-5-thiazolecarboxylic acid ethyl ester;
2-[[4-[[(4-Chloro-phenyl)-methyl-carbamoyl]-methyl]-6-(4-sulfamoyl-benzylamino)2-pyrimidinyl]amino]-4-methyl-5-thiazolecarboxylic acid ethyl ester;
2-[[4-[2-(4-Hydroxy-piperidin-1-yl)-2-oxo-ethyl]-6-(4-sulfamoyl-benzylamino)-2-pyrimidinyl]amino]-4-methyl-5-thiazolecarboxylic acid ethyl ester;
2-[[4-[2-(4-Ethoxycarbonyl-piperidin-1-yl)-2-oxo-ethyl]-6-(4-sulfamoyl-benzylamino)-2-pyrimidinyl]amino]-4-methyl-5-thiazolecarboxylic acid ethyl ester;
2-[[4-(2-oxo-2-piperidin-1-yl-ethyl)-6-(4-sulfamoyl-benzylamino)2-pyrimidinyl]amino]-4-methyl-5-thiazolecarboxylic acid ethyl ester;
2-[[4-[2-[4-(Furan-2-carbonyl)-piperazin-1-yl]-2-oxo-ethyl]-6-(4-sulfamoyl-benzylamino)2-pyrimidinyl]amino]-4-methyl-5-thiazolecarboxylic acid ethyl ester;
2-[[4-[(Cyclohexyl-methyl-carbamoyl)-methyl]-6-(4-sulfamoyl-benzylamino)2-pyrimidinyl]amino]-4-methyl-5-thiazolecarboxylic acid ethyl ester;
2-[[4-[2-(4-Acetyl-[1,4]diazepan-1-yl)-2-oxo-ethyl]-6-(4-sulfamoyl-benzylamino)-2-pyrimidinyl]amino]-4-methyl-5-thiazolecarboxylic acid ethyl ester;
2-[[4-[[Methyl-(1-methyl-piperidin-4-yl)-carbamoyl]-methyl]-6-(4-sulfamoyl-benzylamino)-2-pyrimidinyl]amino]-4-methyl-5-thiazolecarboxylic acid ethyl ester;

2-[[4-[2-(4-methyl-[1,4]diazepan-1-yl)-2-oxo-ethyl]-6-(4-sulfamoyl-benzylamino)-2-pyrimidinyl]amino]-4-methyl-5-thiazolecarboxylic acid ethyl ester;

2-[[4-[[Bis-(2-methoxy-ethyl)-carbamoyl]-methyl]-6-(4-sulfamoyl-benzylamino)-2-pyrimidinyl]amino]-4-methyl-5-thiazolecarboxylic acid ethyl ester;

2-[[4-(2-[1,4']Bipiperidinyl-1'-yl-2-oxo-ethyl)-6-(4-sulfamoyl-benzylamino)-2-pyrimidinyl]amino]-4-methyl-5-thiazolecarboxylic acid ethyl ester;

2-[[4-[2-(4-Hydroxy-4-phenyl-piperidin-1-yl)-2-oxo-ethyl]-6-(4-sulfamoyl-benzylamino)-2-pyrimidinyl]amino]-4-methyl-5-thiazolecarboxylic acid ethyl ester;

2-[[4-Ethoxycarbonyl-6-(4-sulfamoyl-benzylamino)-2-pyrimidinyl]amino]-4-methyl-5-thiazolecarboxylic acid ethyl ester;

2-[[4-Carboxyl-6-(4-sulfamoyl-benzylamino)-2-pyrimidinyl]amino]-4-methyl-5-thiazolecarboxylic acid ethyl ester;

2-[[4-(Carboxymethyl-carbamoyl)-6-(4-sulfamoyl-benzylamino)-2-pyrimidinyl]amino]-4-methyl-5-thiazolecarboxylic acid ethyl ester;

2-[4-(4-Hydroxy-piperidin-1-yl)-6-(4-methylsulfanyl-benzyl)-pyrimidin-2-ylamino]-4-methyl-5-thiazolecarboxylic acid ethyl ester;

2-[4-(4-Hydroxy-piperidin-1-yl)-6-(4-methanesulfinyl-benzyl)-pyrimidin-2-ylamino]-4-methyl-5-thiazolecarboxylic acid ethyl ester;

2-[[4-(4-Hydroxy-piperidin-1-yl)-6-(4-methanesulfonyl-benzyl)-2-pyrimidinyl]amino]-4-methyl-5-thiazolecarboxylic acid ethyl ester;

2-[[4-[4-methyl-1-piperazinyl]-6-[N-methyl-N-[(3,4,5-trimethoxyphenyl)methyl]amino]-2-pyrimidinyl]amino]-4-trifluoromethyl-5-thiazolecarboxylic acid, ethyl ester;

2-[[4-[4-Methylpiperazin-1-yl]-6-(N-methyl-N-[[(3,4,5-trimethoxyphenyl)methyl]amino]-2-pyrimidinyl]amino]-4-methyl-5-cyanothiazole;

2-[[4-[4-Methylpiperazin-1-yl]-6-methyl-6-[[(3,4,5-trimethoxyphenyl)methyl]amino]-2-pyrimidinyl]amino]-4-methyl-5-thiazolecarboxylic acid, 2-methoxyethyl ester;

2-[[4-[4-Hydroxy-piperidin-1-yl]-6-[N-methyl[[N-[(3,4,5-trimethoxyphenyl)methyl][-N-methyl]amino]-2-pyrimidinyl]amino]-4-methyl-5-thiazolecarboxylic acid, butyl ester;

2-[[4-[1-morpholinyl]-6-[[2-[1-morpholinyl]ethyl]amino]-2-pyrimidinyl]amino]-4-methyl-5-thiazolecarboxylic acid, butyl ester;

2-[[4-[4-methyl-1-piperazinyl]-6-[[N-[(3,4,5-trimethoxyphenyl)methyl]]-N-(methyl)amino]-2-pyrimidinyl]amino]-4-isopropyl-5-thiazolecarboxylic acid, ethyl ester;

2-[[4-[4-methyl-1-piperazinyl]-6-[[N-[(3,4,5-trimethoxyphenyl)methyl]]-N-(methyl)amino]-2-pyrimidinyl]amino]-4-methyl-5-thiazolecarboxylic acid, methyl amide;

2-[4-[4-(2-Diisopropylamino-ethylcarbamoyl)-phenyl]-6-(4-hydroxy-piperidin-1-yl)-pyrimidin-2-ylamino]-4-methyl-5-thiazolecarboxylic acid ethyl ester;

2-[4-[4-(3-Dimethylamino-propylcarbamoyl)-phenyl]-6-(4-hydroxy-piperidin-1-yl)-pyrimidin-2-ylamino]-4-methyl-5-thiazolecarboxylic acid ethyl ester;

2-[4-[4-(Cyclohexylmethylcarbamoyl)-phenyl]-6-(4-hydroxy-piperidin-1-yl)-pyrimidin-2-ylamino]-4-methyl-5-thiazolecarboxylic acid ethyl ester;

2-[4-[4-(Pyridin-4-ylmethylcarbamoyl)-phenyl]-6-(4-hydroxy-piperidin-1-yl)-pyrimidin-2-ylamino]-4-methyl-5-thiazolecarboxylic acid ethyl ester;

2-[4-[4-(Isobutylcarbomoyl)-phenyl]-6-(4-hydroxy-piperidin-1-yl)-pyrimidin-2-ylamino]-4-methyl-5-thiazolecarboxylic acid ethyl ester;

2-[4-[4-(N-Cyclohexyl-N-methylcarbamoyl)-phenyl]-6-(4-hydroxy-piperidin-1-yl)-pyrimidin-2-ylamino]-4-methyl-5-thiazolecarboxylic acid ethyl ester;

2-[4-[4-(N-Cyclopropylmethyl-N-propylcarbamoyl)-phenyl]-6-(4-hydroxy-piperidin-1-yl)-pyrimidin-2-ylamino]-4-methyl-5-thiazolecarboxylic acid ethyl ester;

2-[4-[4-(4-Ethoxycarbonylpyperidine-1-carbamoyl)-phenyl]-6-(4-hydroxy-piperidin-1-yl)-pyrimidin-2-ylamino]-4-methyl-5-thiazolecarboxylic acid ethyl ester;

2-[4-[4-(3-Hydroxymethyl-piperidine-1-carbonyl)-phenyl]-6-(4-hydroxy-piperidin-1-yl)-pyrimidin-2-ylamino]-4-methyl-5-thiazolecarboxylic acid ethyl ester;

2-[4-[4-(N-2-Hydroxyethyl-N-ethylcarbamoyl)-phenyl]-6-(4-hydroxy-piperidin-1-yl)-pyrimidin-2-ylamino]-4-methyl-5-thiazolecarboxylic acid ethyl ester;

2-[4-[4-(Thiomorpholine-1-carbonyl)-phenyl]-6-(4-hydroxy-piperidin-1-yl)-pyrimidin-2-ylamino]-4-methyl-5-thiazolecarboxylic acid ethyl ester;

2-[4-[4-(Morpholine-1-carbonyl)-phenyl]-6-(4-hydroxy-piperidin-1-yl)-pyrimidin-2-ylamino]-4-methyl-5-thiazolecarboxylic acid ethyl ester; and 2-[4-[4-(4-Chloro-phenylcarbamoyl)-phenyl]-6-(4-hydroxy-piperidin-1-yl)-pyrimidin-2-ylamino]-4-methyl-5-thiazolecarboxylic acid ethyl ester; or (ii) a stereoisomer, a pharmaceutically acceptable salt, or a hydrate of (i), thereof.

5. A compound according to claim 4, selected from the following:

(i)

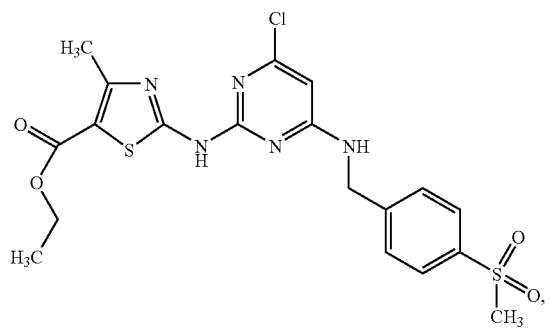

199
-continued
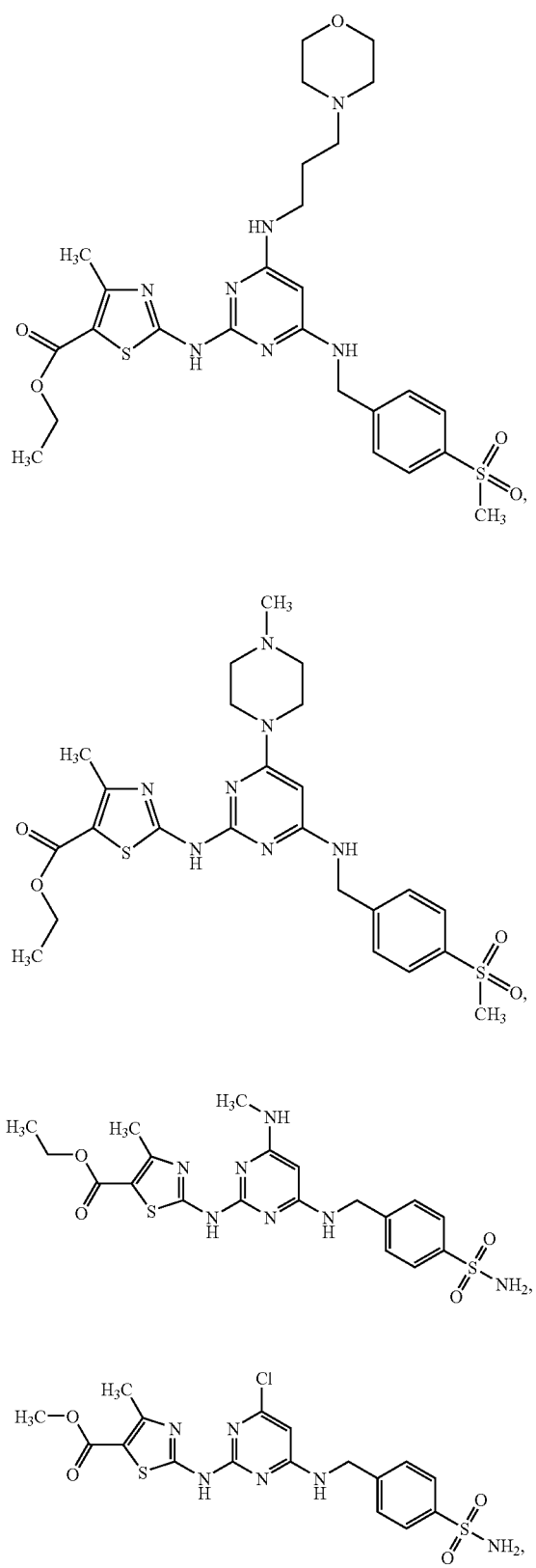
200
-continued
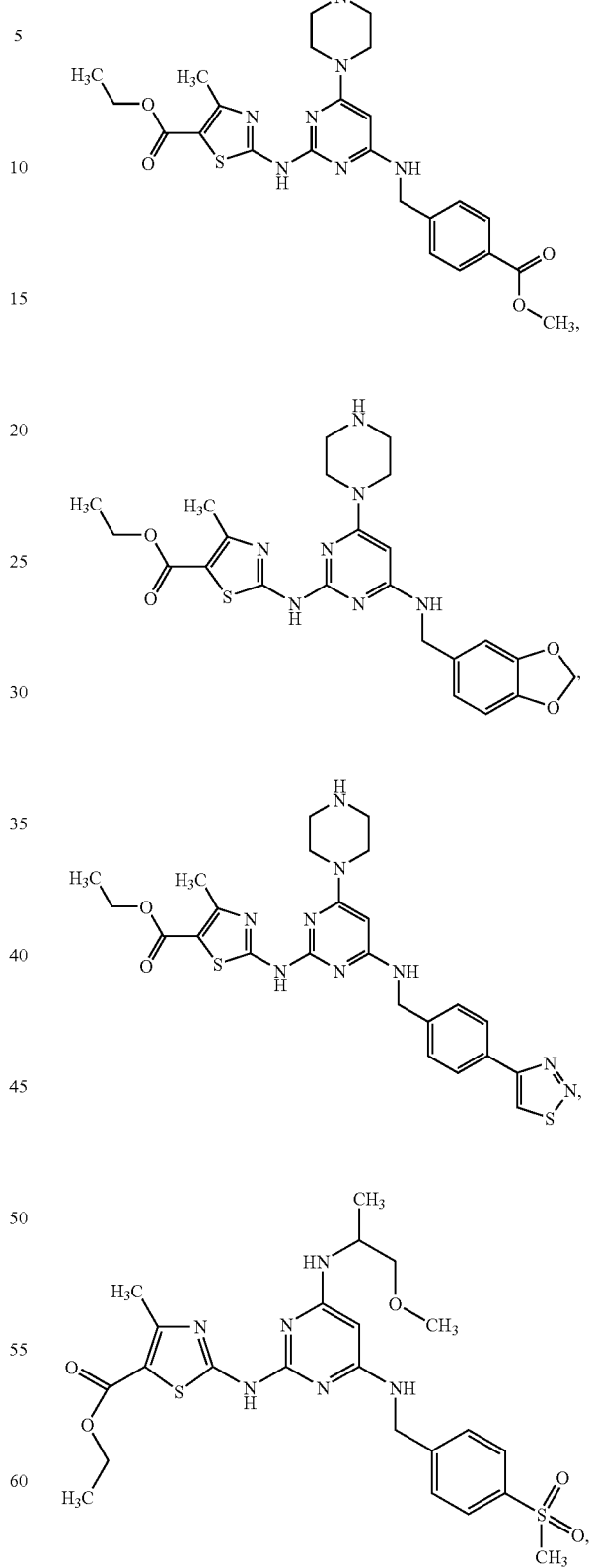

201
-continued
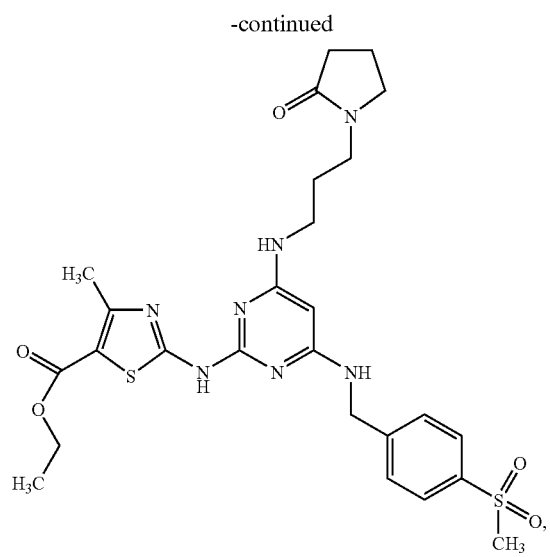
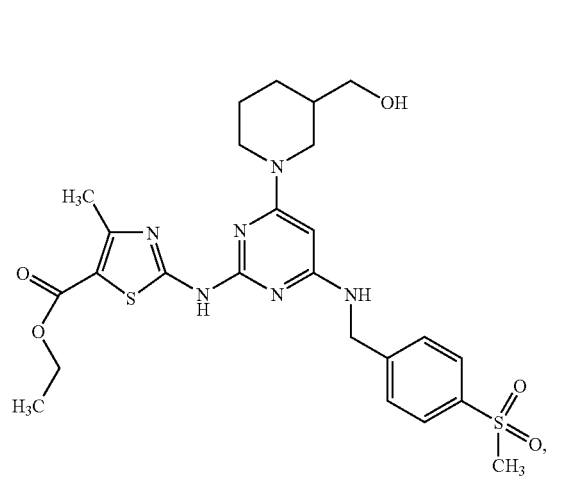
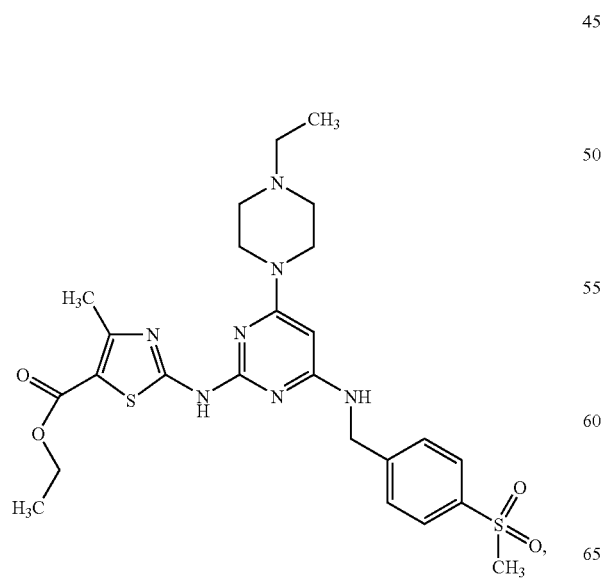
202
-continued
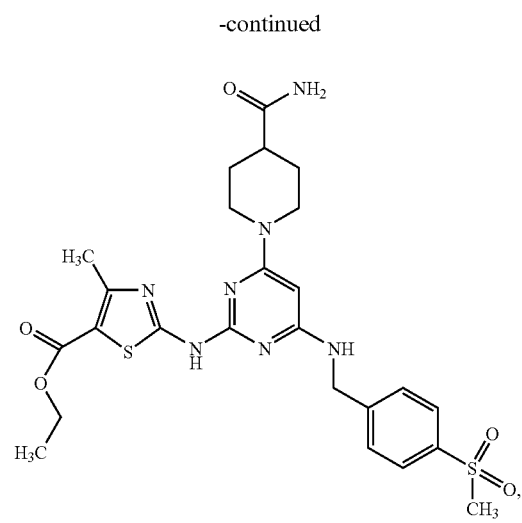
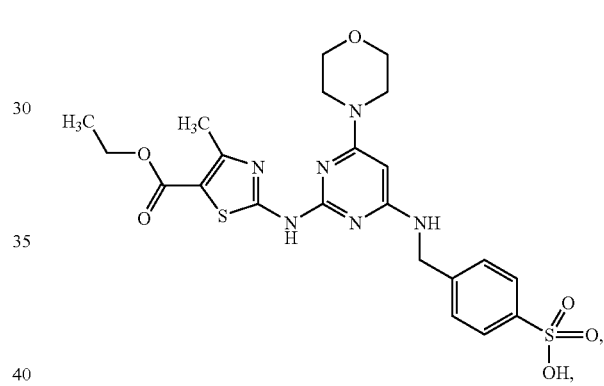
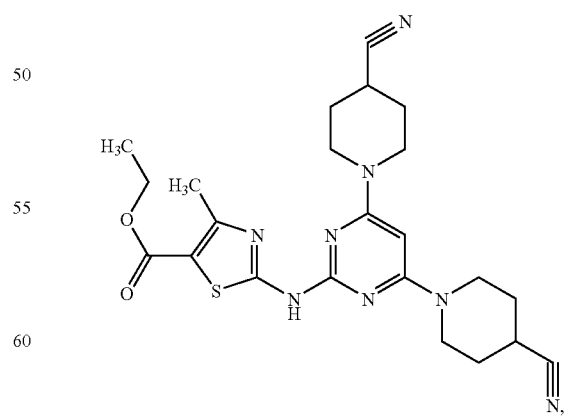

203
-continued
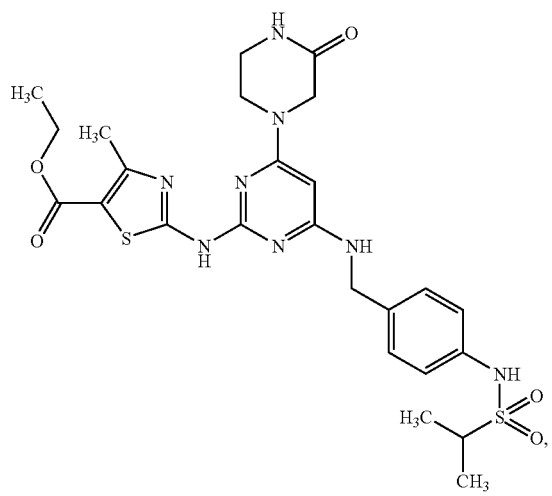
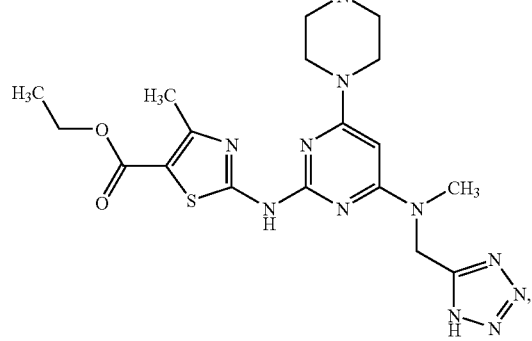
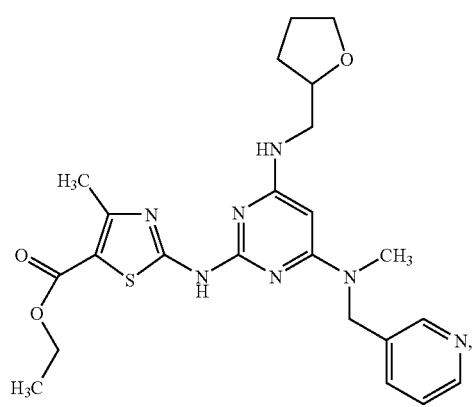
204
-continued
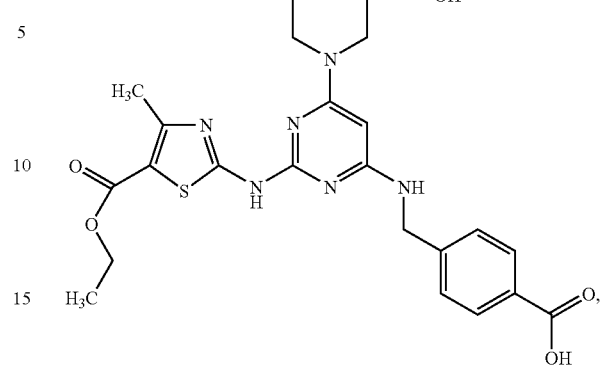
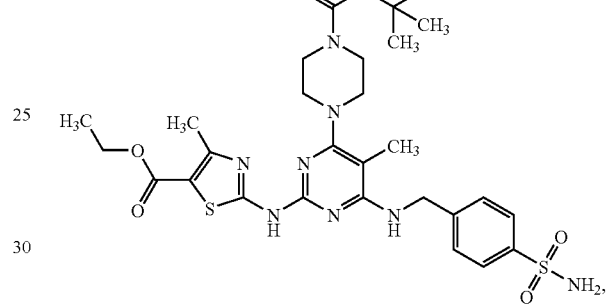
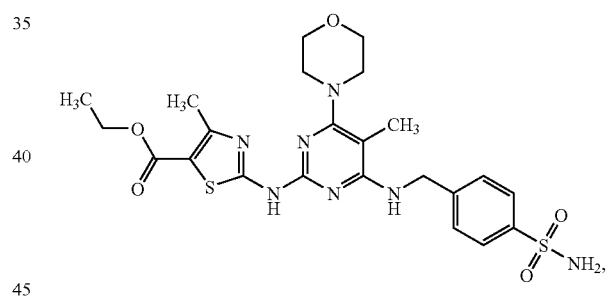

-continued

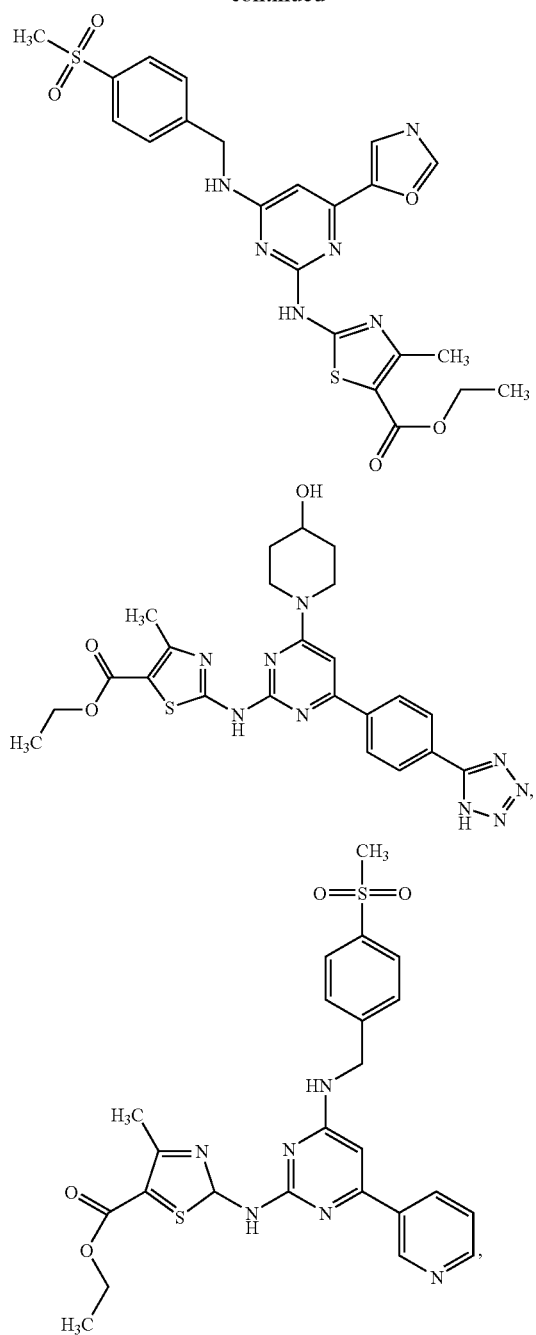

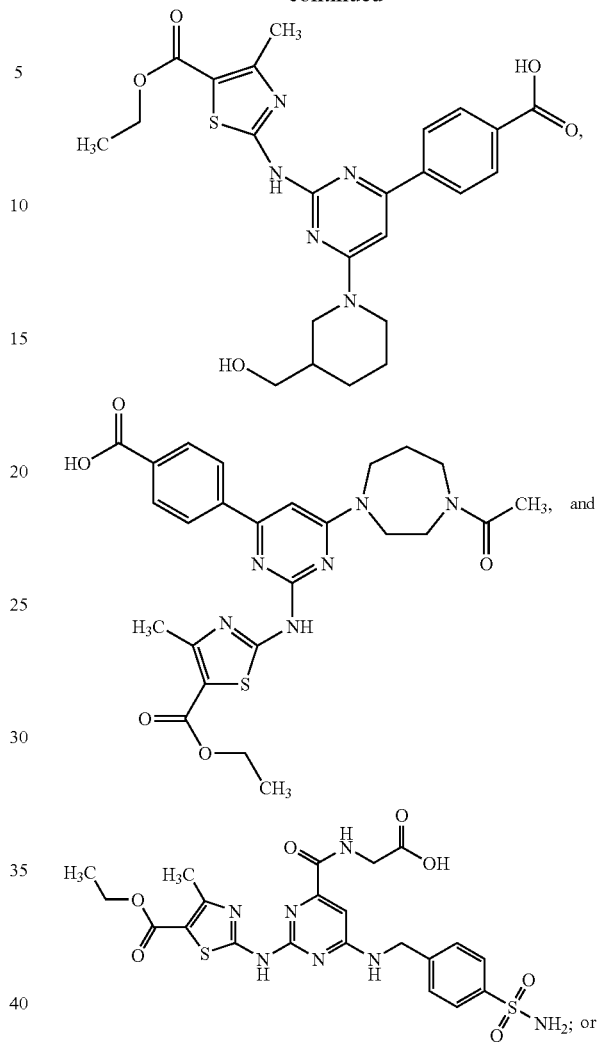

(ii) a stereoisomer, a pharmaceutically acceptable salt, or a hydrate of (i), thereof.

6. A pharmaceutical composition comprising at least one compound of claim 1 or 4, together with a pharmaceutically acceptable vehicle or carrier therefor.

7. A method of treating rheumatoid arthritis which comprises administering an effective amount of at least one compound claim 1 or 4 to a patient in need thereof.

* * * * *